(12) United States Patent
Edwards et al.

(10) Patent No.: US 7,393,663 B2
(45) Date of Patent: Jul. 1, 2008

(54) EXPRESSED SEQUENCE TAGS AND ENCODED HUMAN PROTEINS

(75) Inventors: Jean-Baptiste Dumas Milne Edwards, Paris (FR); Aymeric Duclert, Saint-Maur (FR); Bruno Lacroix, Saint-Genis Laval (FR)

(73) Assignee: Serono Genetics Institute S.A., Evry (FR)

( * ) Notice: Subject to any disclaimer, the term of this patent is extended or adjusted under 35 U.S.C. 154(b) by 973 days.

(21) Appl. No.: 10/631,441

(22) Filed: Jul. 30, 2003

(65) Prior Publication Data

US 2007/0027308 A1 Feb. 1, 2007

Related U.S. Application Data

(60) Division of application No. 09/547,599, filed on Apr. 11, 2000, now abandoned, which is a continuation-in-part of application No. 08/905,223, filed on Aug. 1, 1997, now Pat. No. 6,222,029, and a continuation-in-part of application No. 08/905,135, filed on Aug. 1, 1997, now abandoned, and a continuation-in-part of application No. 08/905,051, filed on Aug. 1, 1997, now abandoned, and a continuation-in-part of application No. 08/905,144, filed on Aug. 1, 1997, now abandoned, and a continuation-in-part of application No. 08/905,279, filed on Aug. 1, 1997, now abandoned, and a continuation-in-part of application No. 08/904,468, filed on Aug. 1, 1997, now abandoned, and a continuation-in-part of application No. 08/905,134, filed on Aug. 1, 1997, now abandoned, and a continuation-in-part of application No. 08/905,133, filed on Aug. 1, 1997, now abandoned.

(51) Int. Cl.
| | |
|---|---|
| C12P 21/02 | (2006.01) |
| C12P 19/34 | (2006.01) |
| C12N 15/00 | (2006.01) |
| C12N 15/11 | (2006.01) |
| C12N 15/12 | (2006.01) |

(52) U.S. Cl. .................. 435/69.8; 435/69.1; 435/69.7; 435/91.1; 435/320.1; 536/23.5

(58) Field of Classification Search .................. None
See application file for complete search history.

(56) References Cited

U.S. PATENT DOCUMENTS

| | | | |
|---|---|---|---|
| 5,605,817 A | 2/1997 | Coleman et al. | |
| 5,700,637 A | 12/1997 | Southern et al. | |
| 5,776,731 A | 7/1998 | Parnet et al. | |
| 5,932,549 A | 8/1999 | Allen et al. | |
| 5,985,863 A | 11/1999 | Su et al. | |
| 6,605,280 B1 | 8/2003 | Novick et al. | |

FOREIGN PATENT DOCUMENTS

| | | |
|---|---|---|
| EP | 0 625 572 A1 | 11/1994 |
| EP | 0 850 952 A1 | 7/1998 |
| EP | 0 864 585 A1 | 9/1998 |
| WO | WO 96/34981 A2 | 11/1996 |

OTHER PUBLICATIONS

Adams et al, Nature Genet. 4: 373 (1993).*
Schena, M. et al. "Quantitative Monitoring of Gene Expression Patterns with a Complementary DNA Microarray" *Science*, Oct. 20, 1995, pp. 467-470, vol. 270.
Adams et al. "Initial Assessment of Human Gene Diversity and Expression Patterns Based upon 83 Million Nucleotides of cDNA Sequence" *Nature*, 1995, vol. 377, pp. 3-17.
Carninci et al. "High-Efficiency Full-Length cDNA Cloning by Biotinylated CAP Trapper" *Genomics*, 1996, pp. 327-336, vol. 37.
Hillier et al. "Generation and Analysis of 280,000 Human Expressed Sequence Tags" *Genome Research*, 1996, pp. 807-828, vol. 6.
Kato et al. "Construction of a Human Full-Length cDNA Bank" *Gene*, 1994, pp. 243-250, vol. 150.
von Heijne et al. "A New Method for Predicting Signal Sequence Cleavage Sites" *Nucleic Acids Research*, 1986, pp. 4683-4690, vol. 14, No. 11.
Aizawa, Y., et al., "Cloning and expression of interleukin-18 binding protein", *FEBS Lett.* (1999), 445(2-3):338-342.
Car, B.D., et al., "Interferon γ Receptor Deficient Mice Are Resistant to Endotoxic Shock", *J. Exp. Med.* (1994), 179(5):1437-44.
Dao, T. et al., "Interferon-γ-inducing Factor, a Novel Cytokine, Enhances Fas Ligand-Mediated Cytotoxicity of Murine T Helper 1 Cells", *Cell Immunol.* (1996), 173(2):230-5.
Engelmann, H., et al., "A Tumor Necrosis Factor-binding Protein Purified to Homogeneity from Human Urine Protects Cells from Tumor Necrosis Factor Toxicity" *J. Biol. Chem.* (1989), 264(20):11974-80.
Engelmann, H., et al., "Two Tumor Necrosis Factor-binding Proteins Purified from Human Urine" *J. Biol. Chem.* (1989), 264(20):1531-6.
Ghayur, T., et al., "Caspase-1 processes IFN-γ-inducing factor and regulates LPS-induced IFN-γ production", *Nature* (1997), 386(6625):619-23.

(Continued)

*Primary Examiner*—James Martinell
(74) *Attorney, Agent, or Firm*—Saliwanchik, Lloyd & Saliwanchik

(57) ABSTRACT

The sequences of 5' ESTs derived from mRNAs encoding secreted proteins are disclosed. The 5' ESTs may be to obtain cDNAs and genomic DNAs corresponding to the 5' ESTs. The 5' ESTs may also be used in diagnostic, forensic, gene therapy, and chromosome mapping procedures. Upstream regulatory sequences may also be obtained using the 5' ESTs. The 5' ESTs may also be used to design expression vectors and secretion vectors.

27 Claims, 11 Drawing Sheets

OTHER PUBLICATIONS

Gu, Y., et al., "Activation of Interferon-γ Inducing Factor Mediated by Interleukin-1β Converting Enzyme", *Science* (1997), 275:206-9.

Heremans, H., et al., "Interferon-γ, A Mediator of Lethal Lipopolysaccharide-Induced Shwartzman-like Shock Reactions in Mice", *J. Exp. Med.* (1990), 171(6):1853-1869.

Kohno, K., et al., "IFN-γ-inducing Factor (IGIF) is a Costimulatory Factor on the Activation of TH1 but not Th2 Cells and Exerts its Effect Independently of IL-12", *J. Immunol.* (1997), 158(4):1541-50.

Maliszewski, C.R., et al., "Cytokine Receptors and B Cell Functions", *J. Immunol.* (1990), 144(8):3028-33.

Micallef, M.J., et al., "Interferon- γ-inducing factor enhances T helper 1 cytokine production by stimulated human T cells: synergism with interleukin-12 for interferon-γ production", *Eur. J. Immunol.* (1996), 26(7):1647-1651.

Nakamura, K., et al., "Endotoxin-Induced Serum Factor that Stiulates Gamma Interferon Production", *Infection and Immunity* (1989), 57(2):590-595.

Nakamura, K., et al., "Purification of a Factor Which Provides a Costimulatory Signal for Gamma Interferon Production", *Infection and Immunity* (1993), 61(1):64-70.

Novick, D., et al., "Soluble Cytokine Receptors are Present in Normal Human Urine", *J. Exp. Med.* (1989), 170(4):1409-1414.

Novick, D., et al., "Soluble interferon-α receptor molecules are present in body fluids", *FEBS Lett.* (1992), 314(3):445-8.

Novick, D., et al., "The human interferon alpha/beta receptor: characterization and molecular cloning", *Cell* (1994), 77(3):391-400.

Novick, et al., "Interleukin-18 binding protein: a novel modulator of the Th1 cytokine resonse", *Immunity* 1999), 10(1):127-136.

Okamura, et al., "Cloning of a new cytokine that induces IFN-gamma production by T cells", *Nature* (1995), 378(6552):88-91.

Parnet, et al., "IL-1Rrp is a novel receptor-like molecule similar to the type I interleukin-1 receptor and its homologues T1/ST2 and IL-1R AcP", *J. Biol. Chem.* (1996), 271(8):3967-70.

Rothe, et al., "Active stage of autoimmune diabetes is associated with the expression of a novel cytokine, IGIF, which is located near Idd2", *J. Clin. Invest.* (1997), 99(3):469-74.

Sarvetnick, "IFN-gamma, IGIF, and IDDM", *J. Clin. Invest.* (1997), 99(3):371-2.

Simonet, W.S., et al., "Osteoprotegerin: A Novel Secreted Protein Involved in the Regulation of Bone Density", *Cell* (1997), 89(2):309-319.

Tsutsui, H., et al., "IFN-gamma-induced fctor up-regulates Fas ligand-mediated cytotoxic activity of murine natural killer cell clones", *J. Immunol.* (1996), 157(9):3967-73.

Ushio, et al., "Cloning of the cDNA for human IFN-gamma-inducing factor, expression in *Escherichia coli*, and studies on the biologic activities of the protein", *J. Immunol.* (1996), 156(11):4274-9.

Xiang and Moss, "Identification of human and mouse homologs of the MC51L-53L-54L family of secreted glycoproteins encoded by the *Molluscum contagiosum* poxvirus", *Virology* (1999), 257(2):297-302.

Database SWISSPROT, Accession No. O95998; Interleukin-18 binding protein, created May 2000.

* cited by examiner

| Minimum signal peptide score | false positive rate | false negative rate | proba(0.1) | proba(0.2) |
|---|---|---|---|---|
| 3,5 | 0,121 | 0,036 | 0,467 | 0,664 |
| 4 | 0,096 | 0,06 | 0,519 | 0,708 |
| 4,5 | 0,078 | 0,079 | 0,565 | 0,745 |
| 5 | 0,062 | 0,098 | 0,615 | 0,782 |
| 5,5 | 0,05 | 0,127 | 0,659 | 0,813 |
| 6 | 0,04 | 0,163 | 0,694 | 0,836 |
| 6,5 | 0,033 | 0,202 | 0,725 | 0,855 |
| 7 | 0,025 | 0,248 | 0,763 | 0,878 |
| 7,5 | 0,021 | 0,304 | 0,78 | 0,889 |
| 8 | 0,015 | 0,368 | 0,816 | 0,909 |
| 8,5 | 0,012 | 0,418 | 0,836 | 0,92 |
| 9 | 0,009 | 0,512 | 0,856 | 0,93 |
| 9,5 | 0,007 | 0,581 | 0,863 | 0,934 |
| 10 | 0,006 | 0,679 | 0,835 | 0,919 |

FIG. 2

| Minimum signal peptide score | All ESTs | New ESTs | ESTs matching public EST closer than 40 bp from beginning | ESTs extending known mRNA more than 40 bp | ESTs extending public EST more than 40 bp |
|---|---|---|---|---|---|
| 3,5 | 2674 | 947 | 599 | 23 | 150 |
| 4 | 2278 | 784 | 498 | 23 | 126 |
| 4,5 | 1943 | 647 | 425 | 22 | 112 |
| 5 | 1657 | 523 | 353 | 21 | 96 |
| 5,5 | 1417 | 419 | 307 | 19 | 80 |
| 6 | 1180 | 340 | 238 | 18 | 68 |
| 6,5 | 1035 | 280 | 186 | 18 | 60 |
| 7 | 893 | 219 | 161 | 15 | 48 |
| 7,5 | 753 | 173 | 132 | 12 | 36 |
| 8 | 636 | 133 | 101 | 11 | 29 |
| 8,5 | 543 | 104 | 83 | 8 | 26 |
| 9 | 456 | 81 | 63 | 6 | 24 |
| 9,5 | 364 | 57 | 48 | 6 | 18 |
| 10 | 303 | 47 | 35 | 6 | 15 |

FIG. 4

| Tissue | All ESTs | New ESTs | ESTs matching public EST closer than 40 bp from beginning | ESTs extending known mRNA more than 40 bp | ESTs extending public EST more than 40 bp |
|---|---|---|---|---|---|
| Brain | 329 | 131 | 75 | 3 | 24 |
| Cancerous prostate | 134 | 40 | 37 | 1 | 6 |
| Cerebellum | 17 | 9 | 1 | 0 | 6 |
| Colon | 21 | 11 | 4 | 0 | 0 |
| Dystrophic muscle | 41 | 18 | 8 | 0 | 1 |
| Fetal brain | 70 | 37 | 16 | 0 | 1 |
| Fetal kidney | 227 | 116 | 46 | 1 | 19 |
| Fetal liver | 13 | 7 | 2 | 0 | 0 |
| Heart | 30 | 15 | 7 | 0 | 1 |
| Hypertrophic prostate | 86 | 23 | 22 | 2 | 2 |
| Kidney | 10 | 7 | 3 | 0 | 0 |
| Large intestine | 21 | 8 | 4 | 0 | 1 |
| Liver | 23 | 9 | 6 | 0 | 0 |
| Lung | 24 | 12 | 4 | 0 | 1 |
| Lung (cells) | 57 | 38 | 6 | 0 | 4 |
| Lymph ganglia | 163 | 60 | 23 | 2 | 12 |
| Lymphocytes | 23 | 6 | 4 | 0 | 2 |
| Muscle | 33 | 16 | 6 | 0 | 4 |
| Normal prostate | 131 | 61 | 45 | 7 | 11 |
| Ovary | 90 | 57 | 12 | 1 | 2 |
| Pancreas | 48 | 11 | 6 | 0 | 1 |
| Placenta | 24 | 5 | 1 | 0 | 0 |
| Prostate | 34 | 16 | 4 | 0 | 2 |
| Spleen | 56 | 28 | 10 | 0 | 1 |
| Substantia nigra | 108 | 47 | 27 | 1 | 6 |
| Surrenals | 15 | 3 | 3 | 1 | 0 |
| Testis | 131 | 68 | 25 | 1 | 8 |
| Thyroid | 17 | 8 | 2 | 0 | 2 |
| Umbilical cord | 55 | 17 | 12 | 1 | 3 |
| Uterus | 28 | 15 | 3 | 0 | 2 |
| Non tissue-specific | 568 | 48 | 177 | 2 | 28 |
| Total | 2677 | 947 | 601 | 23 | 150 |

FIG. 5

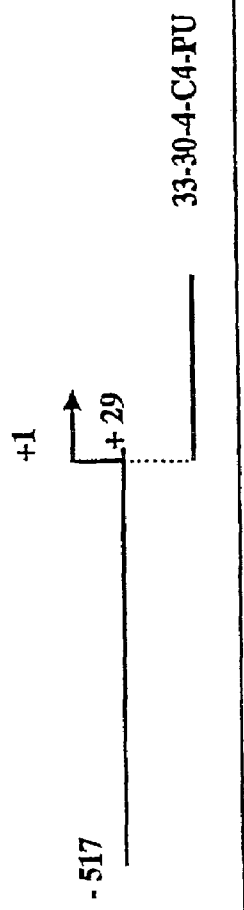
FIG. 6A  Promoter P13H2
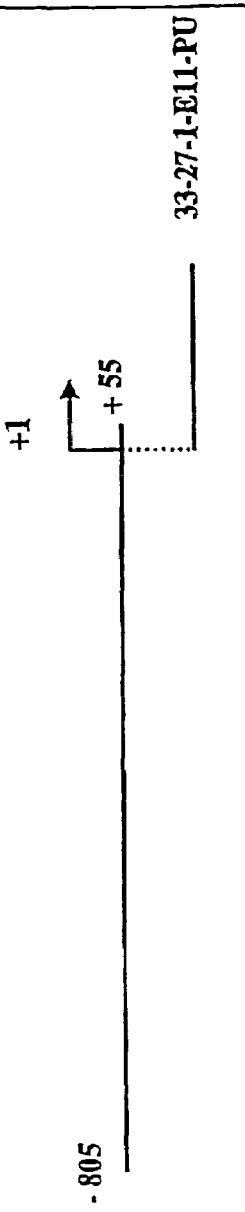
FIG. 6B  Promoter P15B4
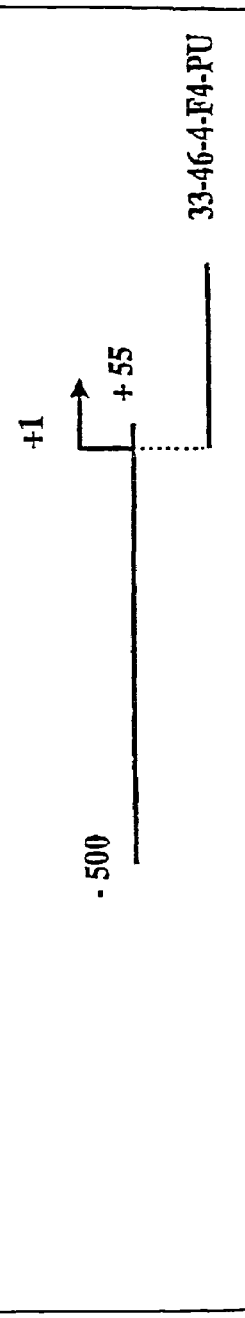
FIG. 6C  Promoter P29B6

Description of Transcription Factor Binding Sites present on promoters isolated from 5' EST sequences Promoter sequence P13H2 (546 bp):

| Matrix | Position | Orientation | Score | Length | Sequence | Location in: SEQ ID NO: 31 |
|---|---|---|---|---|---|---|
| CMYB_01 | -502 | + | 0.983 | 9 | TGTCAGTTG | 17-25 |
| MYOD_Q6 | -501 | - | 0.961 | 10 | CCCAACTGAC | complement of 18-27 |
| S8_01 | -444 | - | 0.960 | 11 | AATAGAATTAG | complement of 75-85 |
| S8_01 | -425 | + | 0.966 | 11 | AACTAAATTAG | 94-104 |
| DELTAEF1_01 | -390 | - | 0.960 | 11 | GCACACCTCAG | complement of 129-139 |
| GATA_C | -364 | - | 0.964 | 11 | AGATAAATCCA | complement of 155-165 |
| CMYB_01 | -349 | + | 0.958 | 9 | CTTCAGTTG | 170-178 |
| GATA1_02 | -343 | + | 0.959 | 14 | TTGTAGATAGGACA | 176-189 |
| GATA_C | -339 | + | 0.953 | 11 | AGATAGGACAT | 180-190 |
| TAL1ALPHAE47_01 | -235 | + | 0.973 | 16 | CATAACAGATGGTAAG | 284-299 |
| TAL1BETAE47_01 | -235 | + | 0.983 | 16 | CATAACAGATGGTAAG | 284-299 |
| TAL1BETAITF2_01 | -235 | + | 0.978 | 16 | CATAACAGATGGTAAG | 284-299 |
| MYOD_Q6 | -232 | - | 0.954 | 10 | ACCATCTGTT | complement of 287-296 |
| GATA1_04 | -217 | - | 0.953 | 13 | TCAAGATAAAGTA | complement of 302-314 |
| IK1_01 | -126 | + | 0.963 | 13 | AGTTGGGAATTCC | 393-405 |
| IK2_01 | -126 | + | 0.985 | 12 | AGTTGGGAATTC | 393-404 |
| CREL_01 | -123 | + | 0.962 | 10 | TGGGAATTCC | 396-405 |
| GATA1_02 | -96 | + | 0.950 | 14 | TCAGTGATATGGCA | 423-436 |
| SRY_02 | -41 | - | 0.951 | 12 | TAAAACAAAACA | complement of 478-489 |
| E2F_02 | -33 | + | 0.957 | 8 | TTTAGCGC | 486-493 |
| MZF1_01 | -5 | - | 0.975 | 8 | TGAGGGA | complement of 514-521 |

Promoter sequence P15B4 (861 bp):

| Matrix | Position | Orientation | Score | Length | Sequence | Location in: SEQ ID NO: 34 |
|---|---|---|---|---|---|---|
| NFY_Q6 | -748 | - | 0.956 | 11 | GGACCAATCAT | complement of 60-70 |
| MZF1_01 | -738 | + | 0.962 | 8 | CCTGGGGA | 70-77 |
| CMYB_01 | -684 | + | 0.994 | 9 | TGACCGTTG | 124-132 |
| VMYB_02 | -682 | - | 0.985 | 9 | TCCAACGGT | complement of 126-134 |
| STAT_01 | -673 | + | 0.968 | 9 | TTCCTGGAA | 135-143 |
| STAT_01 | -673 | - | 0.951 | 9 | TTCCAGGAA | complement of 135-143 |
| MZF1_01 | -556 | - | 0.956 | 8 | TTGGGGGA | complement of 252-259 |
| IK2_01 | -451 | + | 0.965 | 12 | GAATGGGATTTC | 357-368 |
| MZF1_01 | -424 | + | 0.986 | 8 | AGAGGGGA | 384-391 |
| SRY_02 | -398 | - | 0.955 | 12 | GAAAACAAAACA | complement of 410-421 |
| MZF1_01 | -216 | + | 0.960 | 8 | GAAGGGGA | 592-599 |
| MYOD_Q6 | -190 | + | 0.981 | 10 | AGCATCTGCC | 618-627 |
| DELTAEF1_01 | -176 | + | 0.958 | 11 | TCCCACCTTCC | 632-642 |
| S8_01 | 5 | - | 0.992 | 11 | GAGGCAATTAT | complement of 813-823 |
| MZF1_01 | 16 | - | 0.986 | 8 | AGAGGGGA | complement of 824-831 |

Promoter sequence P29B6 (555 bp):

| Matrix | Position | Orientation | Score | Length | Sequence | Location in: SEQ ID NO: 37 |
|---|---|---|---|---|---|---|
| ARNT_01 | -311 | + | 0.964 | 16 | GGACTCACGTGCTGCT | 191-206 |
| NMYC_01 | -309 | + | 0.965 | 12 | ACTCACGTGCTG | 193-204 |
| USF_01 | -309 | + | 0.985 | 12 | ACTCACGTGCTG | 193-204 |
| USF_01 | -309 | - | 0.985 | 12 | CAGCACGTGAGT | complement of 193-204 |
| NMYC_01 | -309 | - | 0.956 | 12 | CAGCACGTGAGT | complement of 193-204 |
| MYCMAX_02 | -309 | - | 0.972 | 12 | CAGCACGTGAGT | complement of 193-204 |
| USF_C | -307 | + | 0.997 | 8 | TCACGTGC | 195-202 |
| USF_C | -307 | - | 0.991 | 8 | GCACGTGA | complement of 195-202 |
| MZF1_01 | -292 | - | 0.968 | 8 | CATGGGGA | complement of 210-217 |
| ELK1_02 | -105 | + | 0.963 | 14 | CTCTCCGGAAGCCT | 397-410 |
| CETS1P54_01 | -102 | + | 0.974 | 10 | TCCGGAAGCC | 400-409 |
| AP1_Q4 | -42 | - | 0.963 | 11 | AGTGACTGAAC | complement of 460-470 |
| AP1FJ_Q2 | -42 | - | 0.961 | 11 | AGTGACTGAAC | complement of 460-470 |
| PADS_C | 45 | + | 1.000 | 9 | TGTGGTCTC | 547-555 |

FIG. 7

EXPRESSED SEQUENCE TAGS AND ENCODED HUMAN PROTEINS

RELATED APPLICATIONS

This application is divisional of U.S. patent application Ser. No. 09/547,599, filed Apr. 11, 2000 now anandoned, which is a continuation-in-part of U.S. patent applications Ser. No. 08/905,223, filed Aug. 1, 1997 now U.S. Pat. No. 6,222,029, Ser. No. 08/905,135, filed Aug. 1, 1997 now abandoned, Ser. No. 08/905,051, filed Aug. 1, 1997 now abandoned, Ser. No. 08/905,144, filed Aug. 1, 1997 now abandoned, Ser. No. 08/905,279, filed Aug. 1, 1997 now abandoned, Ser. No. 08/904,468, Aug. 1, 1997 now abandoned, Ser. No. 08/905,134, filed Aug. 1, 1997 now abandoned, Ser. No. 08/905,133, filed Aug. 1, 1997 now abandoned, the disclosures of which are incorporated herein by reference in their entireties.

BACKGROUND OF THE INVENTION

The estimated 50,000-100,000 genes scattered along the human chromosomes offer tremendous promise for the understanding, diagnosis, and treatment of human diseases. In addition, probes capable of specifically hybridizing to loci distributed throughout the human genome find applications in the construction of high resolution chromosome maps and in the identification of individuals.

In the past, the characterization of even a single human gene was a painstaking process, requiring years of effort. Recent developments in the areas of cloning vectors, DNA sequencing, and computer technology have merged to greatly accelerate the rate at which human genes can be isolated, sequenced, mapped, and characterized. Cloning vectors such as yeast artificial chromosomes (YACs) and bacterial artificial chromosomes (BACs) are able to accept DNA inserts ranging from 300 to 1000 kilobases (kb) or 100-400 kb in length respectively, thereby facilitating the manipulation and ordering of DNA sequences distributed over great distances on the human chromosomes. Automated DNA sequencing machines permit the rapid sequencing of human genes. Bio-informatics software enables the comparison of nucleic acid and protein sequences, thereby assisting in the characterization of human gene products.

Currently, two different approaches are being pursued for identifying and characterizing the genes distributed along the human genome. In one approach, large fragments of genomic DNA are isolated, cloned, and sequenced. Potential open reading frames in these genomic sequences are identified using bio-informatics software. However, this approach entails sequencing large stretches of human DNA which do not encode proteins in order to find the protein encoding sequences scattered throughout the genome. In addition to requiring extensive sequencing, the bio-informatics software may mischaracterize the genomic sequences obtained. Thus, the software may produce false positives in which non-coding DNA is mischaracterized as coding DNA or false negatives in which coding DNA is mislabeled as non-coding DNA.

An alternative approach takes a more direct route to identifying and characterizing human genes. In this approach, complementary DNAs (cDNAs) are synthesized from isolated messenger RNAs (mRNAs) which encode human proteins. Using this approach, sequencing is only performed on DNA which is derived from protein coding portions of the genome. Often, only short stretches of the cDNAs are sequenced to obtain sequences called expressed sequence tags (ESTs). The ESTs may then be used to isolate or purify extended cDNAs which include sequences adjacent to the EST sequences. The extended cDNAs may contain all of the sequence of the EST which was used to obtain them or only a portion of the sequence of the EST which was used to obtain them. In addition, the extended cDNAs may contain the full coding sequence of the gene from which the EST was derived or, alternatively, the extended cDNAs may include portions of the coding sequence of the gene from which the EST was derived. It will be appreciated that there may be several extended cDNAs which include the EST sequence as a result of alternate splicing or the activity of alternative promoters.

In the past, these short EST sequences were often obtained from oligo-dT primed cDNA libraries. Accordingly, they mainly corresponded to the 3' untranslated region of the mRNA. In part, the prevalence of EST sequences derived from the 3' end of the mRNA is a result of the fact that typical techniques for obtaining cDNAs, are not well suited for isolating cDNA sequences derived from the 5' ends of mRNAs. (Adams et al., *Nature* 377:174, 1996, Hillier et al., *Genome Res.* 6:807-828, 1996).

In addition, in those reported instances where longer cDNA sequences have been obtained, the reported sequences typically correspond to coding sequences and do not include the full 5' untranslated region of the mRNA from which the cDNA is derived. Such incomplete sequences may not include the first exon of the mRNA, particularly in situations where the first exon is short. Furthermore, they may not include some exons, often short ones, which are located upstream of splicing sites. Thus, there is a need to obtain sequences derived from the 5' ends of mRNAs.

While many sequences derived from human chromosomes have practical applications, approaches based on the identification and characterization of those chromosomal sequences which encode a protein product are particularly relevant to diagnostic and therapeutic uses. Of the 50,000-100,000 protein coding genes, those genes encoding proteins which are secreted from the cell in which they are synthesized, as well as the secreted proteins themselves, are particularly valuable as potential therapeutic agents. Such proteins are often involved in cell to cell communication and may be responsible for producing a clinically relevant response in their target cells.

In fact, several secretory proteins, including tissue plasminogen activator, G-CSF, GM-CSF, erythropoietin, human growth hormone, insulin, interferon-α, interferon-β, interferon-γ, and interleukin-2, are currently in clinical use. These proteins are used to treat a wide range of conditions, including acute myocardial infarction, acute ischemic stroke, anemia, diabetes, growth hormone deficiency, hepatitis, kidney carcinoma, chemotherapy induced neutropenia and multiple sclerosis. Thus, there is a need for the identification and characterization of secreted proteins and the nucleic acids encoding them.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. Because these signal peptides will direct the extracellular secretion of any protein to which they are operably linked, the signal sequences may be exploited to direct the efficient secretion of any protein by operably lining the signal sequences to a gene encoding the protein for which secretion is desired. This may prove beneficial in gene therapy strategies in which it is desired to deliver a particular gene product to cells other than the cell in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' portions of the genes for secretory proteins which encode signal peptides.

Public information on the number of human genes for which the promoters and upstream regulatory regions have been identified and characterized is quite limited. In part, this may be due to the difficulty of isolating such regulatory sequences. Upstream regulatory sequences such as transcription factor binding sites are typically too short to be utilized as probes for isolating promoters from human genomic libraries. Recently, some approaches have been developed to isolate human promoters. One of them consists of making a CpG island library (Cross, S. H. et al., Purification of CpG Islands using a Methylated DNA Binding Column, Nature Genetics 6: 236-244 (1994)). The second consists of isolating human genomic DNA sequences containing SpeI binding sites by the use of SpeI binding protein. (Mortlock et al., *Genome Res.* 6:327-335, 1996). Both of these approaches have their limits due to a lack of specificity or of comprehensiveness.

The present 5' ESTs may be used to efficiently identify and isolate upstream regulatory regions which control the location, developmental stage, rate, and quantity of protein synthesis, as well as the stability of the mRNA. (Theil, *BioFactors* 4:87-93, 1993). Once identified and characterized, these regulatory regions may be utilized in gene therapy or protein purification schemes to obtain the desired amount and locations of protein synthesis or to inhibit, reduce, or prevent the synthesis of undesirable gene products.

In addition, EST's containing the 5' ends of secretory protein genes may include sequences useful as probes for chromosome mapping and the identification of individuals. Thus, there is a need to identify and characterize the sequences upstream of the 5' coding sequences of genes encoding secretory proteins.

SUMMARY OF THE INVENTION

The present invention relates to purified, isolated, or recombinant ESTs which include sequences derived from the authentic 5' ends of their corresponding mRNAs. The term "corresponding mRNA" refers to the mRNA which was the template for the cDNA synthesis which produced the 5' EST. These sequences will be referred to hereinafter as "5' ESTs." As used herein, the term "purified" does not require absolute purity; rather, it is intended as a relative definition. Individual 5' EST clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$-$10^6$ fold purification of the native message. Purification of starting material or natural material to at least one order of magnitude, preferably two or three orders, and more preferably four or five orders of magnitude is expressly contemplated. As an alternative embodiment, purification of the polynucleotides of the present invention may be expressed as "at least" a percent purity relative to heterologous polynucleotides (DNA, RNA or both). As a preferred embodiment, the polynucleotides of the present invention are at least; 10%, 20%, 30%, 40%, 50%, 60%, 70%, 80%, 90%, 95%, 96%, 96%, 98%, 99%, or 100% pure relative to heterologous polynucleotides. As a further preferred embodiment the polynucleotides have a purity ranging from any integer, to the thousandth position, between 90% and 100% (e.g., 5' EST at least 99.995% pure) relative to either heterologous polynucleotides or as a weight/weight ratio relative to all compounds and molecules other than those existing in the carrier.

As used herein, the term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. Specifically excluded from the definition of "isolated" are: artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies, and further wherein the polynucleotide of the present invention makes up less than 5% (or alternatively 1%, 2%, 3%, 4%, 10%, 25%, 50%, 75%, or 90%, 95%, or 99%) of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

As used herein, the term "recombinant" means that the 5' EST is adjacent to "backbone" nucleic acid to which it is not adjacent in its natural environment. Additionally, to be "enriched" the 5' ESTs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched 5' ESTs represent 15% or more of the number of nucleic acid inserts in the population of recombinant backbone molecules. More preferably, the enriched 5' ESTs represent 50% or more of the number of nucleic acid inserts in the population of recombinant backbone molecules. In a highly preferred embodiment, the enriched 5' ESTs represent 90% or more (including any integer between 90 and 100%, to the thousandth position, e.g., 99.5%) of the number of nucleic acid inserts in the population of recombinant backbone molecules.

"Stringent", moderate," and "low" hybridization conditions are as defined in Example 29.

The term "polypeptide" refers to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included excluded as specific embodiments. Therefore, for example, modifications to polypeptides which include the covalent attachment of glycosyl groups, acetyl groups, phosphate groups, lipid groups and the like are expressly encompassed by the term polypeptide. Further, polyeptides with these modifications may be specified as individual species to be included or excluded from the present invention. The natural or other chemical modifications, such as those listed in example above, can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

As used interchangeably herein, the terms "nucleic acids", "oligonucleotides", and "polynucleotides" include RNA or DNA (either single or double stranded or antisense), or RNA/DNA hybrid sequences of more than one nucleotide in either single chain or duplex form (although each of the above species may be particularly specified). The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylarninomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. Methylenemethylimino linked oligonucleosides as well as mixed backbone compounds having, may be prepared as described in U.S. Pat. Nos. 5,378,825; 5,386,023; 5,489,677; 5,602,240; and 5,610,289. Formacetal and thioformacetal linked oligonucleosides may be prepared as described in U.S. Pat. Nos. 5,264,562 and 5,264,564. Ethylene oxide linked oligonucleosides may be prepared as described in U.S. Pat. No. 5,223,618. Phosphinate oligonucleotides may be prepared as described in U.S. Pat. No. 5,508,270. Alkyl phosphonate oligonucleotides may be prepared as described in U.S. Pat. No. 4,469,863. 3'-Deoxy-3'-methylene phosphonate oligonucleotides may be prepared as described in U.S. Pat. No. 5,610,289 or U.S. Pat. No. 5,625,050. Phosphoramidite oligonucleotides may be prepared as described in U.S. Pat. No. 5,256,775 or U.S. Pat. No. 5,366,878. Alkylphosphonothioate oligonucleotides may be prepared as described in published PCT applications WO 94/17093 and WO 94/02499. 3'-Deoxy-3'-amino phosphoramidate oligonucleotides may be prepared as described in U.S. Pat. No. 5,476,925. Phosphotriester oligonucleotides may be prepared as described in U.S. Pat. No. 5,023,243. Borano phosphate oligonucleotides may be prepared as described in U.S. Pat. Nos. 5,130,302 and 5,177,198.

The polynucleotide sequences of the invention may be prepared by any known method, including synthetic, recombinant, ex vivo generation, or a combination thereof, as well as utilizing any purification methods known in the art.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 genomic flanking gene(s).

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, *Biochemistry*, 4th edition, 1995).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Preferably, a "complementary" sequence is a sequence which an A at each position where there is a T on the opposite strand, a T at each position where there is an A on the opposite strand, a G at each position where there is a C on the opposite strand and a C at each position where there is a G on the opposite strand. Unless otherwise indicated, a "complementary" sequence is fully complementary.

Thus, 5' ESTs in cDNA libraries in which one or more 5' ESTs make up 5% or more of the number of nucleic acid inserts in the backbone molecules are "enriched recombinant 5' ESTs" as defined herein. Likewise, 5' ESTs in a population of plasmids in which one or more 5' EST of the present invention have been inserted such that they represent 5% or more of the number of inserts in the plasmid backbone are "enriched recombinant 5' ESTs" as defined herein. However, 5' ESTs in cDNA libraries in which 5' ESTs constitute less than 5% of the number of nucleic acid inserts in the population of backbone molecules, such as libraries in which backbone molecules having a 5' EST insert are extremely rare, are not "enriched recombinant 5' ESTs."

In particular, the present invention relates to 5' ESTs which are derived from genes encoding secreted proteins. As used herein, a "secreted" protein is one which, when expressed in a suitable host cell, is transported across or through a membrane, including transport as a result of signal peptides in its amino acid sequence. "Secreted" proteins include without limitation proteins secreted wholly (e.g. soluble proteins), or partially (e.g. receptors) from the cell in which they are expressed. "Secreted" proteins also include without limitation proteins which are transported across the membrane of the endoplasmic reticulum.

Such 5' ESTs include nucleic acid sequences, called signal sequences, which encode signal peptides which direct the extracellular secretion of the proteins encoded by the genes from which the 5' ESTs are derived. Generally, the signal peptides are located at the amino termini of secreted proteins. Polypeptides comprising these signal peptides (as delineated in the sequence listing), and polynucleotides encoding the same, are preferred embodiments of the present invention.

Secreted proteins are translated by ribosomes associated with the "rough" endoplasmic reticulum. Generally, secreted proteins are co-translationally transferred to the membrane of the endoplasmic reticulum. Association of the ribosome with the endoplasmic reticulum during translation of secreted proteins is mediated by the signal peptide. The signal peptide is typically cleaved following its co-translational entry into the endoplasmic reticulum. After delivery to the endoplasmic reticulum, secreted proteins may proceed through the Golgi apparatus. In the Golgi apparatus, the proteins may undergo post-translational modification before entering secretory vesicles which transport them across the cell membrane.

The 5' ESTs of the present invention have several important applications. For example, the 5' EST sequences of the sequence listing, and fragments thereof, may be used to distinguish human tissues/cells from non-human tissues/cells and to distinguish between human tissues/cells that do and do not express the polynucleotides comprising the 5' EST sequences. By knowing the tissue expression pattern of the 5' EST sequences, either through routine experimentation or by using the Tables herein, the polynucleotides of the present invention may be used in methods of determining the identity of an unknown tissue/cell sample. As part of determing the identity of an unknown tissue/cell sample, the 5' EST sequences may be used to determine what the unknown tissue/cell sample is and what it is not. For example, if a 5' EST is expressed in a particular tissue/cell type, as shown in the Tables below, and the unknown tissue/cell sample does not express the 5' EST, it may be inferred that the unknown tissue/cells are either not human or not the same human tissue/cell type as that which expresses the 5' EST. These methods of determining tissue/cell identity are are based on methods which detect the presence or absence of the 5' EST sequences in a tissue/cell sample using methods well know in the art (e.g., hybridization or PCR methods).

Another use of the polynucleotides of the present invention is to map open reading flumes from a genomic sequence. For example, the 5' ESTs can be used in combination with the sequence information from genome sequencing projects, such as the U.S. Human Genome Project or other public and private genome sequencing projects, to map regions of the genome that comprise expressed open reading frames. The polynucleotides of the present invention are particularly useful for mapping and identifying coding regions (regions containing expressed open reading frames) from a genomic sequence since the vast majority of the human genome does not encode expressed genes and since it is difficult to identify authentic open reading frames (open reading frames that encode expressed genes).

As described below, the polynucleotides of the present invention may also be used to design probes or primers which may be used to identify a cell containing a polynucleotide of the present invention, or a portion thereof, and to clone a nucleic acid comprising a polynucleotide of the present invention, or a portion thereof, which is contained in a nucleic acid library into a desired vector. For example, as described below, nucleic acids from cells containing a cDNA or genomic DNA library, such as the genomic fragments generated by the U.S. Human Genome Project or other public and private genome sequencing projects, may be contacted with a detectable probe comprising a polynucleotide of the present invention or a portion thereof under conditions in which the probe will specifically hybridize to complementary nucleic acids. In this way, clones in the library which contain sequences encoding secreted polypeptides may be identified and their inserts may be cloned into a desired vector. In some embodiment, inserts in a genomic library which contain sequences encoding the secreted polypeptides of the present invention may be obtained from the library by performing an amplification reaction, such as a PCR reaction, using one or more primers based on the polynucleotides of the present invention. The amplification product is then cloned into a desired vector. In some embodiments, the amplification product may be inserted into an expression vector such that a sequence which includes a coding region encoding the amino terminal region of a secreted polynucleotide is operably linked to a promoter. In some embodiments, a coding region encoding an entire secreted protein, or a desired portion thereof, is operably linked to the promoter. The expression vector is introduced into a suitable host cell and the protein encoded by the amplification product is produced.

In other useful applications, fragments of the 5' EST sequences encoding signal peptides as well as degenerate polynucleotides encoding the same, may be ligated to sequences encoding either the polypeptide from the same gene or to sequences encoding a heterologous polypeptide to facilitate secretion The 5' EST sequences, and fragments thereof, may also be used to obtain and express extended cDNAs encoding portions of the secreted protein. The portions may comprise the signal peptides of the secreted proteins or the mature proteins generated when the signal peptide is cleaved off. The portions may also comprise polypeptides having at least 6, 8, 10, 12, 15, 18, 20, 23, 25, 28, 30, 35, 40, or 50 consecutive amino acids encoded by the extended cDNAs or full length cDNAs.

Antibodies which specifically recognize the entire secreted proteins encoded by the extended cDNAs, full length cDNAs, or fragments thereof having at least 6, 8, 10, 12, 15, 18, 20, 23, 25, 28, 30, 35, 40, or 50 consecutive amino acids may also be obtained as described below. Antibodies which specifically recognize the mature protein generated when the signal peptide is cleaved may also be obtained as described below. Similarly, antibodies which specifically recognize the signal peptides encoded by the extended cDNAs or full length cDNAs may also be obtained. These antibodies are useful in determining the tissue type or species of origin of a biological sample. For example, to distinguish between human and non-human cells and tissues or to distinguish between human tissues that do and do not express the polypeptides.

In some embodiments, the extended cDNAs obtained using the 5' ESTs include the signal sequence. In other embodiments, the extended cDNAs obtained using the 5' ESTs may include the full coding sequence for the mature protein (i.e. the protein generated when the signal polypeptide is cleaved off). In addition, the extended cDNAs obtained using the 5' ESTs may include regulatory regions upstream of the translation start site or downstream of the stop codon which control the amount, location, or developmental stage of gene expression.

As discussed above, secreted proteins are therapeutically important. Thus, the proteins expressed from the extended cDNAs or full length cDNAs obtained using the 5' ESTs may be useful in treating or controlling a variety of human conditions.

The 5' ESTs (or cDNAs or genomic DNAs obtained therefrom) may be used in forensic procedures to identify individuals or in diagnostic procedures to identify individuals having genetic diseases resulting from abnormal expression of the genes corresponding to the 5' ESTs. In addition, the present invention is useful for constructing a high resolution map of the human chromosomes.

The present invention also relates to secretion vectors capable of directing the secretion of a protein of interest. Such vectors may be used in gene therapy strategies in which it is desired to produce a gene product in one cell which is to be delivered to another location in the body. Secretion vectors may also facilitate the purification of desired proteins. The secretion vectors may also be used to express a desired protein, such as a heterologous protein, such that the protein is secreted into the culture medium, thereby facilitating purification.

The present invention also relates to expression vectors capable of directing the expression of an inserted gene in a desired spatial or temporal manner or at a desired level. Such vectors may include sequences upstream of the 5' ESTs, such as promoters or upstream regulatory sequences. Preferred chimeric polypeptides, and vectors encoding the same, comprise a signal peptide set forth in the sequence listing below.

Finally, the present invention may also be used for gene therapy to control or treat genetic diseases. Signal peptides may also be fused to heterologous proteins to direct their extracellular secretion.

Bacterial clones containing Bluescript plasmids having inserts containing the 5' ESTs of the present invention (SEQ ID NOs: 38-1756) are presently stored at −80° C. in 4% (v/v) glycerol in the inventor's laboratories under the designations listed next tote SEQ ID NOs in Table II. The inserts may be recovered from the stored materials by growing the appropriate clones on a suitable medium. The Bluescript DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the EST insertion. The PCR product which corresponds to the 5' EST can then be manipulated using standard cloning techniques familiar to those skilled in the art.

One aspect of the present invention is a purified or isolated nucleic acid having the sequence of one of SEQ ID NOs: 38-1756 or having a sequence complementary thereto. In one embodiment, the nucleic acid is recombinant.

Another aspect of the present invention is a purified or isolated nucleic acid comprising at least 8, 10, 12, 15, 20, 23, 25, 28, 30, 35, 40, 50, 75, 100, 200, 300, 500, or more than 500 consecutive nucleotides, to the extent that sequences of these lengths are consistent with the specific sequence, of the sequence of one of SEQ ID NOs: 38-1756 or one of the sequences complementary thereto. In one embodiment, the nucleic acid is recombinant.

A further aspect of the present invention is a purified or isolated nucleic acid of at least 8, 10, 12, 15, 20, 23, 25, 28, 30, 35, 40, 50, 75, 100, 200, 300, 500, or more than 500 nucleotides which is capable of hybridizing under stringent conditions to the sequence of one of SEQ ID NOs: 38-1756 or one of the sequences complementary to the sequences of SEQ ID NOs: 38-1756. In one embodiment, the nucleic acid is recombinant.

Another aspect of the present invention is a purified or isolated nucleic acid encoding a human gene product, said human gene product having a sequence partially encoded by one of the sequences of SEQ ID NO: 38-1756.

Still another aspect of the present invention is a method of making a cDNA encoding a human secretory protein, said human secretory protein being partially encoded by one of SEQ ID NOs 38-1756, comprising the steps of contacting a collection of mRNA molecules from human cells with a primer comprising at least 8, 10, 15, 20, 25, 30, 35, 40 or more than 40 consecutive nucleotides of a sequence complementary to one of SEQ ID NOs: 38-1756; hybridizing said primer to an mRNA in said collection that encodes said protein; reverse transcribing said hybridized primer to make a first cDNA strand from said mRNA; making a second cDNA strand complementary to said first cDNA strand; and isolating the resulting cDNA encoding said protein comprising said first cDNA strand and said second cDNA strand.

Another aspect of the invention is an isolated or purified cDNA encoding a human secretory protein, said human secretory protein comprising the protein encoded by one of SEQ ID NOs 38-1756 or a fragment thereof of at least 6, 8, 10, 12, 15, 18, 20, 23, 25, 28, 30, 35, 40, or 50 amino acids, said cDNA being obtainable by the method described in the preceding paragraph.

In one embodiment, the cDNA comprises the full protein coding sequence of said protein which sequence is partially included in one of the sequences of SEQ ID NOs: 38-1756.

Another aspect of the present invention is a method of making a cDNA encoding a human secretory protein that is partially encoded by one of SEQ ID NOs 38-1756, comprising the steps of obtaining a cDNA comprising one of the sequences of SEQ ID NOs: 38-1756; contacting said cDNA with a detectable probe comprising at least 10, 15, 20, 25, 30, 35, 40 or more than 40 consecutive nucleotides of said sequence of SEQ ID NO: 38-1756 or a sequence complementary thereto under conditions which permit said probe to hybridize to said cDNA; identifying a cDNA which hybridizes to said detectable probe; and isolating said cDNA which hybridizes to said probe.

Another aspect of the present invention is an isolated or purified cDNA encoding a human secretory protein, said human secretory protein comprising the protein encoded by one of SEQ ID NOs 38-1756 or a fragment thereof of at least 6, 8, 10, 12, 15, 18, 20, 23, 25, 28, 30, 35, 40, or 50 amino acids, said cDNA being obtainable by the method described in the preceding paragraph. In one embodiment, the cDNA comprises the full protein coding sequence partially included in one of the sequences of SEQ ID NOs: 38-1756.

Another aspect of the present invention is a method of making a cDNA comprising the sequence of SEQ ID NOs: 38-1756, comprising the steps of contacting a collection of mRNA molecules from human cells with a first primer capable of hybridizing to the polyA tail of said mRNA; hybridizing said first primer to said polyA tail; reverse transcribing said mRNA to make a first cDNA strand; making a second cDNA strand complementary to said first cDNA strand using at least one primer comprising at least 15 nucleotides of one of the sequences of SEQ ID NOs 38-1756; and isolating the resulting cDNA comprising said first cDNA strand and said second cDNA strand. The term "capable of hybridizing to the polyA tail of said mRNA" refers to and embraces all primers containing stretches of thymidine residues, so-called oligo(dT) primers, that hybridize to the 3' end of eukaryotic poly(A)+ mRNAs to prime the synthesis of a first cDNA strand. Techniques for generating said oligo(dT) primers and hybridizing them to mRNA to subsequently prime the reverse transcription of said hybridized mRNA to generate a first cDNA strand are well known to those skilled in the art and are described in *Current Protocols in Molecular Biology*, John Wiley and Sons, Inc. 1997 and Sambrook et al., *Molecular Cloning: A Laboratory Manual*, Second Edition, Cold Spring Harbor Laboratory Press, 1989, the entire disclosures of which are incorporated herein by reference. Preferably, said oligo(dT) primers are present in a large excess in order to allow the hybridization of all mRNA 3' ends to at least one oligo(dT) molecule. The priming and reverse transcription step are preferably performed between 37° C. and 55° C. depending on the type of reverse transcriptase used.

Preferred oligo(dT) primers for priming reverse transcription of mRNAs are oligonucleotides containing a stretch of thymidine residues of sufficient length to hybridize specifically to the polyA tail of mRNAs, preferably of 12 to 18 thymidine residues in length. More preferably, such oligo(T) primers comprise an additional sequence upstream of the poly(dT) stretch in order to allow the addition of a given sequence to the 5' end of all first cDNA strands which may then be used to facilitate subsequent manipulation of the cDNA. Preferably, this added sequence is 8 to 60 residues in length. For instance, the addition of a restriction site in 5' of cDNAs facilitates subcloning of the obtained cDNA. Alternatively, such an added 5' end may also be used to design primers of PCR to specifically amplify cDNA clones of interest.

Another aspect of the present invention is an isolated or purified cDNA encoding a human secretory protein, said human secretory protein comprising the protein encoded by one of SEQ ID NOs 38-1756 or a fragment thereof of at least 6, 8, 10, 12, 15, 18, 20, 23, 25, 28, 30, 35, 40, or 50 amino acids, said cDNA being obtainable by the method described in the preceding paragraph. In one embodiment, the cDNA comprises the full protein coding sequence partially included in one of the sequences of SEQ ID NOs: 38-1756.

In one embodiment of the method described in the paragraph two paragraphs above, the second cDNA strand is made by contacting said first cDNA strand with a first pair of primers, said first pair of primers comprising a second primer comprising at least 10, 15, 20, 25, 30, 35, or 40 consecutive nucleotides of one of the sequences of SEQ ID NOs 38-1756 and a third primer having a sequence therein which is included within the sequence of said first primer; performing a first polymerase chain reaction with said first pair of nested primers to generate a first PCR product; contacting said first PCR product with a second pair of primers, said second pair of primers comprising a fourth primer, said fourth primer comprising at least 10, 15, 20, 25, 30, 35 or 40 consecutive nucleotides of said sequence of one of SEQ ID NO:s 38-1756, and a fifth primer, said fourth and fifth primers being capable of hybridizing to sequences within said first PCR product; and performing a second polymerase chain reaction, thereby generating a second PCR product.

One aspect of the present invention is an isolated or purified cDNA encoding a human secretory protein, said human secretory protein comprising the protein encoded by one of SEQ ID NOs 38-1756, or a fragment thereof oat least 6, 8, 10, 12, 15, 18, 20, 23, 25, 28, 30, 35, 40, or 50 amino acids, said cDNA being obtainable by the method of the preceding paragraph. In one embodiment, the cDNA comprises the full protein coding sequence partially included in one of the sequences of SEQ ID NOs: 38-1756.

Another aspect of the present invention is the method described four paragraphs above in which the second cDNA strand is made by contacting said first cDNA strand with a second primer comprising at least 10, 15, 20, 25, 30, 35 or 40 consecutive nucleotides of the sequences of SEQ ID NOs: 38-1756; hybridizing said second primer to said first strand cDNA; and extending said hybridized second primer to generate said second cDNA strand.

Another aspect of the present invention is an isolated or purified cDNA encoding a human secretory protein, said human secretory protein comprising the protein partially encoded by one of SEQ ID NOs 38-1756 or comprising a fragment thereof of at least 6, 8, 10, 12, 15, 18, 20, 23, 25, 28, 30, 35, 40, or 50 amino acids, said cDNA being obtainable by the method described in the preceding paragraph. In one embodiment, the cDNA comprises the full protein coding sequence partially included in of one of the sequences of SEQ ID NOs: 38-1756.

The present invention also includes isolated or purified "positional segments of polypeptides of SEQ ID NOs: 1757-3475." As used herein, the term "positional segments of polypeptides of SEQ ID NOs: 1757-3475" includes polypeptides comprising amino acid residues 1-25, 26-50, 51-75, 76-100, 101-125, 126-150, 151-175, 176-200, or 201—the C-terminal amino acid of the polypeptides of SEQ ID NOs:

1757-3475, to the extent that such amino acid residues are consistent with the lengths of the particular polypeptides being referred to. The term "positional segments of EST-related polypeptides also includes segments comprising amino acid residues 1-50, 51-100, 101-150, 151-200 or 201—the C-terminal amino acid of the polypeptides of SEQ ID NOs: 1757-3475, to the extent that such amino acid residues are consistent with the lengths of the particular polypeptide being referred to. The term "positional segments of polypeptides of SEQ ID NOs: 1757-3475" also includes segments comprising amino acids 1-100 or 101-200 of the polypeptides polypeptides of SEQ ID NOs: 1757-3475 to the extent that such amino acid residues are consistent with the lengths of particular polypeptides being referred to. In addition, the term "positional segments of polypeptides of SEQ ID NOs: 1757-3475" includes segments comprising amino acid residues 1-200 or 201—the C-terminal amino acid of the polypeptides of SEQ ID NOs: 1757-3475, to the extent that amino acid residues are consistent with the lengths of the particular polypeptide being referred to.

The present invention also includes isolated or purified "fragments of positional segments of the polypeptides of SEQ ID NOs: 1757-3475." The terms "isolated" or "purified" have the meanings provided above. As used herein, the term "fragments of positional segments of the polypeptides of SEQ ID NOs: 1757-3475" means fragments comprising at least 5, 10, 15, 20, 25, 30, 35, 40, 50, 75, 100, or 150 consecutive amino acids of positional segments of the polypeptides of SEQ ID NOs: 1757-3475, to the extent that fragments of these lengths are consistent with the lengths of the particular polypeptides being referred to.

In addition to the "positional segments of polypeptides of SEQ ID NOs: 1757-3475" and "fragments of positional segments of polypeptides of SEQ ID NOs: 1757-3475", for the polypeptides of the present invention, further preferred polypeptides comprise at least 8 amino acids, wherein "at least 8" is defined as any integer between 8 and the integer representing the C-terminal amino acid of the polypeptide of the present invention including the polypeptide sequences of the sequence listing below. Further included are polypeptide fragments at least 8 amino acids in length, as described above, that are further specified in terms of their N-terminal and C-terminal positions. Preferred polypeptide fragments specified by their N-terminal and C-terminal positions include the signal peptides delineated in the sequence listing below. However, included in the present invention as individual species are all polypeptide fragments, at least 5 amino acids in length, as described above, and may be particularly specified by a N-terminal and C-terminal position.

The present invention also provides for the exclusion of any fragments specified by N-terminal and C-terminal positions or by size in amino acid residues as described above. Any number of fragments specified by N-terminal and C-terminal positions or by size in amino acid residues as described above may be excluded as individual species.

The polypeptide fragments of the present invention can be immediately envisaged using the above description and are therefore not individually listed solely for the purpose of not unnecessarily lengthening the specification. The above fragments need not be active since they would be useful, for example, in immunoassays, in epitope mapping, epitope tagging, as vaccines, and as molecular weight markers. The above fragments may also be used to generate antibodies to a particular portion of the polypeptide. These antibodies can then be used in immunoassays well known in the art to distinguish between human and non-human cells and tissues or to determine whether cells or tissues in a biological sample are or are not of the same type which express the polypeptide of the present invention. Further preferred polypeptide fragments of the present invention comprise the signal peptides as delineated in the sequence listing. These signal peptides may be used to facilitate secretion of either the polypeptide of the same gene or a heterologous polypeptide.

Another aspect of the present invention is a method of making a protein comprising one of the sequences of SEQ ID NO: 1757-3475, comprising the steps of obtaining a cDNA encoding the full protein sequence partially included in one of the sequences of sequence of SEQ ID NO: 38-1756; inserting said cDNA in an expression vector such that said cDNA is operably linked to a promoter; introducing said expression vector into a host cell whereby said host cell produces the protein encoded by said cDNA; and isolating said protein.

Another aspect of the present invention is an isolated protein obtainable by the method described in the preceding paragraph.

Another aspect of the present invention is a method of obtaining a promoter DNA comprising the steps of obtaining DNAs located upstream of the nucleic acids of SEQ ID NO: 38-1756 or the sequences complementary thereto; screening said upstream DNAs to identify a promoter capable of directing transcription initiation; and isolating said DNA comprising said identified promoter. In one embodiment, the obtaining step comprises chromosome walking from said nucleic acids of SEQ ID NO: 38-1756 or sequences complementary thereto. In another embodiment, the screening step comprises inserting said upstream sequences into a promoter reporter vector. In another embodiment, the screening step comprises identifying motifs in said upstream DNAs which are transcription factor binding sites or transcription start sites.

Another aspect of the present invention is an isolated promoter obtainable by the method described above.

Another aspect of the present invention is an isolated or purified protein comprising one of the sequences of SEQ ID NO: 1757-3475.

Another aspect of the present invention is the inclusion of at least one of the sequences of SEQ ID NOs: 38-1756, or one of the sequences complementary to the sequences of SEQ ID NOs: 38-1756, or a fragment thereof of at least 8, 10, 12, 15, 20, 23, 25, 28, 30, 35, 40, 50, 75 or 100 consecutive nucleotides in an array of discrete ESTs or fragments thereof. In one embodiment, the array includes at least two of the sequences of SEQ ID NOs: 38-1756, the sequences complementary to the sequences of SEQ ID NOs: 38-1756, or fragments thereof of at least 8, 10, 12, 15, 20, 23, 25, 28, 30, 35, 40, 50, 75, or 100 consecutive nucleotides. In another embodiment, the array includes at least five of the sequences of SEQ ID NOs: 38-1756, the sequences complementary to the sequences of SEQ ID NOs: 38-1756, or fragments thereof of at least 8, 10, 12, 15, 20, 23, 25, 28, 30, 35, 40, 50, 75, or 100 consecutive nucleotides.

The present invention also includes isolated, purified, or enriched "positional segments of the 5' ESTs (or cDNAs or genomic DNAs obtainable therefrom)." The terms "isolated", "purified", or "enriched" have the meanings provided above. As used herein, the term "positional segments of 5' ESTs (or cDNAs or genomic DNAs obtainable therefrom)" includes segments comprising nucleotides 1-25, 26-50, 51-75, 76-100, 101-125, 126-150, 151-175, 176-200, 201-225, 226-250, 251-300, 301-325, 326-350, 351-375, 376-400, 401-425, 426-450, 451-475, 476-500, 501-the terminal nucleotide of the 5' ESTs (or cDNAs or genomic DNAs obtainable therefrom) to the extent that such nucleotide positions are consistent with the lengths of the particular 5' ESTs (or cDNAs or genomic DNAs obtainable therefrom) being referred to, and wherein position "1" is defined as the 5' most position defined in the sequence listing or Tables below. The term "positional segments of 5' ESTs (or cDNAs or genomic DNAs obtainable therefrom)" also includes segments comprising nucleotides 1-50, 51-100, 101-150, 151-200, 201-250, 251-300, 301-350, 351-400, 401-450, 450-500, 501-550, 551-600 or 601—the terminal nucleotide of the 5' ESTs (or cDNAs or genomic DNAs obtainable therefrom) to the extent that such nucleotide positions are consistent with the lengths of the particular 5' ESTs (or cDNAs or genomic DNAs obtainable therefrom) being referred to. The term "positional segments of 5' ESTs (or cDNAs or genomic DNAs obtainable therefrom)" also includes segments comprising nucleotides 1-100, 101-200, 201-300, 301-400, 501-500, 500-600, or 601—the terminal nucleotide of the 5' ESTs (or cDNAs or genomic DNAs obtainable therefrom) to the extent that such nucleotide positions are consistent with the lengths of the particular 5' ESTs (or cDNAs or genomic DNAs obtainable therefrom) being referred to. In addition, the term "positional segments of 5' ESTs (or cDNAs or genomic DNAs obtainable therefrom)" includes segments comprising nucleotides 1-200, 201-400, 400-600, or 601 —the terminal nucleotide of the 5' ESTs (or cDNAs or genomic DNAs obtainable therefrom) to the extent that such nucleotide positions are consistent with the lengths of the particular 5' ESTs (or cDNAs or genomic DNAs obtainable therefrom) being referred to. The present invention also includes the sequences complementary to the positional segments of 5' ESTs (or cDNAs or genomic DNAs obtainable therefrom).

The present invention also includes isolated, purified, or enriched "fragments of positional segments of 5' ESTs (or cDNAs or genomic DNAs obtainable therefrom)." The terms "isolated", "purified", or "enriched" have the meanings provided above. As used herein, the term "fragments of positional segments of 5' ESTs (or cDNAs or genomic DNAs obtainable therefrom)" refers to fragments comprising at least 8, 10, 15, 18, 20, 23, 25, 28, 30, 35, 40, 50, 75, 100, 150, or 200 consecutive nucleotides of the positional segments of 5' ESTs (or cDNAs or genomic DNAs obtainable therefrom). The present invention also includes the sequences complementary to the fragments of positional segments of 5' ESTs (or cDNAs or genomic DNAs obtainable therefrom).

In addition to the "positional segments of 5' ESTs (or cDNAs or genomic DNAs obtainable therefrom)" and "fragments of positional segments of 5' ESTs (or cDNAs or genomic DNAs obtainable therefrom)", for the nucleic acids of SEQ ID NOs.38-1756, further preferred nucleic acids comprise at least 8 nucleotides, wherein "at least 8" is defined as any integer between 8 and the integer representing the 3' most nucleotide position in the sequence listing or Tables below. Further included are nucleic acid fragments at least 8 nucleotides in length, as described above, that are further specified in terms of their 5' and 3' position. The 5' and 3' positions are represented by the position number set forth in the sequence listing below. Therefore, every combination of a 5' and 3' nucleotide position that a fragment at least 8 contiguous nucleotides in length could occupy is included in the invention as an individual species. The polynucleotide fragment specified by 5' and 3' positions can be immediately envisaged and are therefore not individually listed solely for the purpose of not unnecessarily lengthening the specifications. It is noted that the above species of polynucleotides fragments of the present invention may alternatively be described by the formula "a to b"; where "a" equals the 5' nucleotide position and "b" equals 3' nucleotide position of the polynucleotide fragment; and further where "a" equals an integer between 1 and the number of nucleotides of the polynucleotide sequence of the present invention minus 8, and where "b" equals an integer between 9 and the number of nucleotides of the polynucleotide sequence of the present invention; and where "a" is an integer smaller then "b" by at least 8.

The present invention also provides for the exclusion of any polynucleotide fragments specified by 5' and 3' positions or by size in nucleotides as described above. Any number of fragments specified by 5' and 3' positions or by size in nucleotides, as described above, may be excluded.

BRIEF DESCRIPTION OF THE DRAWINGS

FIG. 2 is an analysis of the 43 amino terminal amino acids of all human SwissProt proteins to determine the frequency of false positives and false negatives using the techniques for signal peptide identification described herein.

FIG. 4 shows the distribution of 5' ESTs in each category and the number of 5' ESTs in each category having a given minimnum von Heijne's score.

FIG. 5 shows the tissues from which the mRNAs corresponding to the 5' ESTs in each of the categories described herein were obtained.

FIG. 6 provides a schematic description of the promoters isolated and the way they are assembled with the corresponding 5' tags.

FIG. 7 describes the transcription factor binding sites present in each of these promoters.

DETAILED DESCRIPTION OF THE PREFERRED EMBODIMENT

I. Obtaining 5' ESTs

Figure 1:
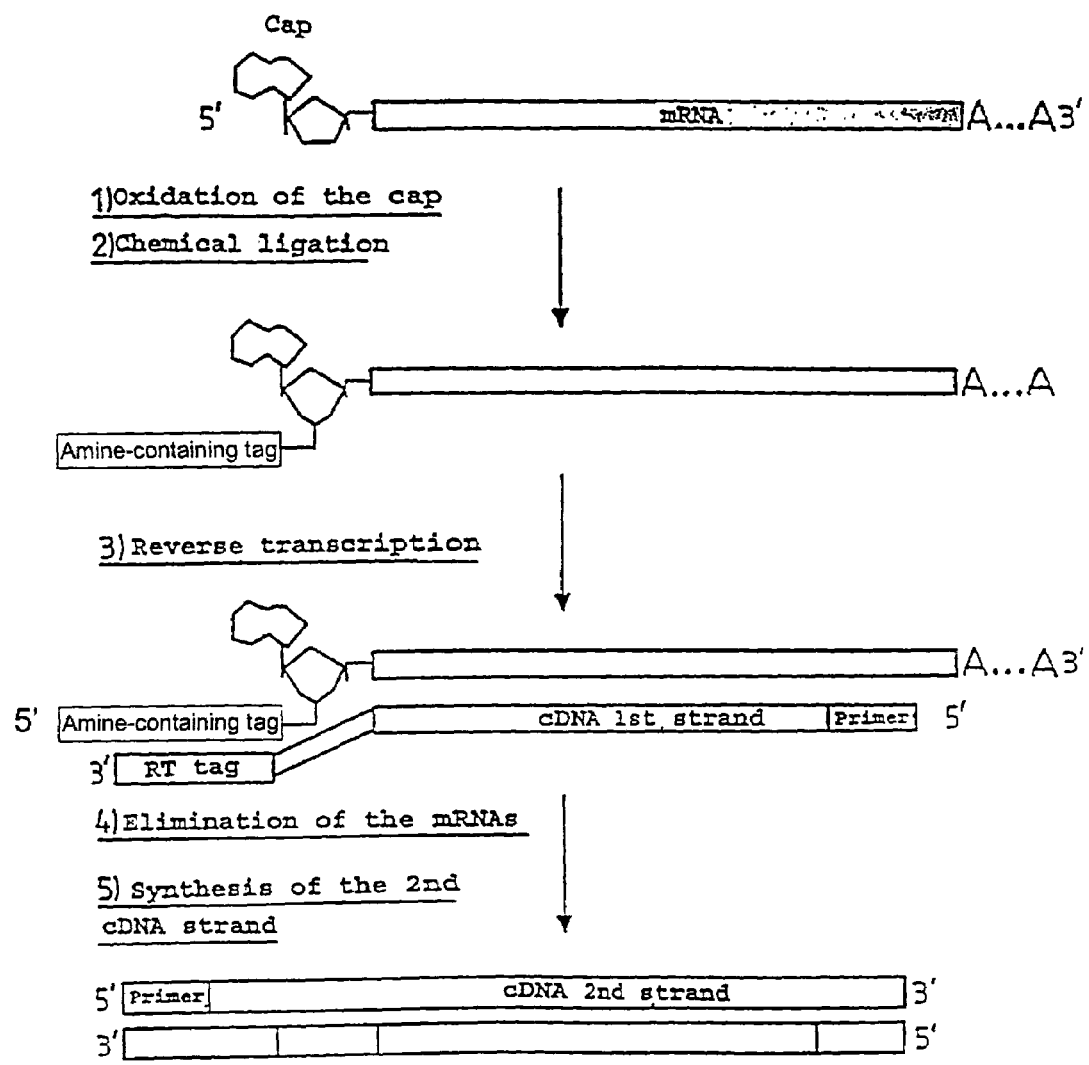
FIG. 1 is a summary of a procedure for obtaining cDNAs which have been selected to include the 5' ends of the mRNAs from which they are derived.

A. Chemical Methods for Obtaining mRNAs having Intact 5' Ends

In order to obtain the 5' ESTs of the present invention, mRNAs having intact 5' ends must be obtained. Currently, there are two approaches for obtaining such mRNAs. One of these approaches is a chemical modification method involving derivatization of the 5' ends of the mRNAs and selection of the derivatized mRNAs. The 5' ends of eucaryotic mRNAs possess a structure referred to as a "cap" which comprises a guanosine methylated at the 7 position. The cap is joined to the first transcribed base of the mRNA by a 5',5'-triphosphate bond. In some instances, the 5' guanosine is methylated in both the 2 and 7 positions. Rarely, the 5' guanosine is trimethylated at the 2, 7 and 7 positions.

In the chemical method for obtaining mRNAs having intact 5' ends, the 5' cap is specifically derivatized and coupled to a reactive group on an immobilizing substrate. This specific derivatization is based on the fact that only the ribose linked to the methylated guanosine at the 5' end of the mRNA and the ribose linked to the base at the 3' terminus of the mRNA, possess 2',3'-cis diols. Optionally, where the 3' terminal ribose has a 2',3'-cis diol, the 2',3'-cis diol at the 3' end may be chemically modified, substituted, converted, or eliminated, leaving only the ribose linked to the methylated guanosine at the 5' end of the mRNA with a 2',3'-cis diol. A variety of techniques are available for eliminating the 2',3'-cis diol on the 3' terminal ribose. For example, controlled alkaline hydrolysis may be used to generate mRNA fragments in which the 3' terminal ribose is a 3'-phosphate, 2'-phosphate or (2',3')-cyclophosphate. Thereafter, the fragment which includes the original 3' ribose may be eliminated from the mixture through chromatography on an oligo-dT column. Alternatively, a base which lacks the 2',3'-cis diol may be added to the 3' end of the mRNA using an RNA ligase such as T4 RNA ligase. Example 1 below describes a method for ligation of pCp to the 3' end of messenger RNA.

EXAMPLE 1

Ligation of the Nucleoside Diphosphate pCp to the 3' End of Messenger RNA

1 µg of RNA was incubated in a final reaction medium of 10 µl in the presence of 5 U of T$_4$ phage RNA ligase in the buffer provided by the manufacturer (Gibco-BRL), 40 U of the RNase inhibitor RNasin (Promega) and, 2 µl of $^{32}$pCp (Amersham #PB 10208).

The incubation was performed at 37° C. for 2 hours or overnight at 7-8° C.

Following modification or elimination of the 2',3'-cis diol at the 3' ribose, the 2',3'-cis diol present at the 5' end of the mRNA may be oxidized using reagents such as NABH$_4$, NaBH$_3$CN, or sodium periodate, thereby converting the 2',3'-cis diol to a dialdehyde. Example 2 describes the oxidation of the 2',3'-cis diol at the 5' end of the mRNA with sodium periodate.

EXAMPLE 2

Oxidation of 2',3'-cis diol at the 5' End of the mRNA 0.1 OD unit of either a capped oligoribonucleotide of 47 nucleotides (including the cap) or an uncapped oligoribonucleotide of 46 nucleotides were treated as follows. The oligoribonucleotides were produced by in vitro transcription using the transcription kit "AmpliScribe T7" (Epicentre Technologies). As indicated below, the DNA template for the RNA transcript contained a single cytosine. To synthesize the uncapped RNA, all four NTPs were included in the in vitro transcription reaction. To obtain the capped RNA, GTP was replaced by an analogue of the cap, m7G(5')ppp(5')G. This compound, recognized by polymerase, was incorporated into the 5' end of the nascent transcript during the step of initiation of transcription but was not capable of incorporation during the extension step. Consequently, the resulting RNA contained a cap at its 5' end. The sequences of the oligoribonucleotides produced by the in vitro transcription reaction were:

+Cap:

(SEQ ID NO:1)
5'm7GpppGCAUCCUACUCCCAUCCAAUUCCACCCUAACUCCUCCCAUCU
CCAC-3'

−Cap:

(SEQ ID NO:2)
5'-pppGCAUCCUACUCCCAUCCAAUUCCACCCUAACUCCUCCCAUCUCC
AC-3'

The oligoribonucleotides were dissolved in 9 µl of acetate buffer (0.1 M sodium acetate, pH 5.2) and 3 µl of freshly prepared 0.1 M sodium periodate solution. The mixture was incubated for 1 hour in the dark at 4° C. or room temperature. Thereafter, the reaction was stopped by adding 4 µl of 10% ethylene glycol. The product was ethanol precipitated, resuspended in 10 µl or more of water or appropriate buffer and dialyzed against water.

The resulting aldehyde groups may then be coupled to molecules having a reactive amine group, such as hydrazine, carbazide, thiocarbazide or semicarbazide groups, in order to facilitate enrichment of the 5' ends of the mRNAs. Molecules having reactive amine groups which are suitable for use in selecting mRNAs having intact 5' ends include avidin, proteins, antibodies, vitamins, ligands capable of specifically binding to receptor molecules, or oligonucleotides. Example 3 below describes the coupling of the resulting dialdehyde to biotin.

EXAMPLE 3

Coupling of the Dialdehyde with Biotin

The oxidation product obtained in Example 2 was dissolved in 50 µl of sodium acetate at a pH of between 5 and 5.2 and 50 µl of freshly prepared 0.02 M solution of biotin hydrazide in a methoxyethanol/water mixture (1:1) of formula:

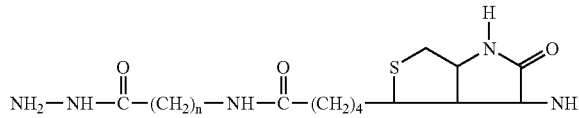

In the compound used in these experiments, n=5. However, it will be appreciated that other commercially available hydrazides may also be used, such as molecules of the formula above in which n varies from 0 to 5.

The mixture was then incubated for 2 hours at 37° C. Following the incubation, the mixture was precipitated with ethanol and dialyzed against distilled water.

Example 4 demonstrates the specificity of the biotinylation reaction.

EXAMPLE 4

Specificity of Biotinylation

The specificity of the biotinylation for capped mRNAs was evaluated by gel electrophoresis of the following samples:

Sample 1. The 46 nucleotide uncapped in vitro transcript prepared as in Example 2 and labeled with $^{32}$pCp as described in Example 1.

Sample 2. The 46 nucleotide uncapped in vitro transcript prepared as in Example 2, labeled with $^{32}$pCp as described in Example 1, treated with the oxidation reaction of Example 2, and subjected to the biotinylation conditions of Example 3.

Sample 3. The 47 nucleotide capped in vitro transcript prepared as in Example 2 and labeled with $^{32}$pCp as described in Example 1.

Sample 4. The 47 nucleotide capped in vitro transcript prepared as in Example 2, labeled with $^{32}$pCp as described in Example 1, treated with the oxidation reaction of Example 2, and subjected to the biotinylation conditions of Example 3.

Samples 1 and 2 had indentical migration rates, demonstrating that the uncapped RNAs were not oxidized and biotinylated. Sample 3 migrated more slowly than Samples 1 and 2, while Sample 4 exhibited the slowest migration. The difference in migration of the RNAs in Samples 3 and 4 demonstrates that the capped RNAs were specifically biotinylated.

In some cases, mRNAs having intact 5' ends may be enriched by binding the molecule containing a reactive amine group to a suitable solid phase substrate such as the inside of the vessel containing the mRNAs, magnetic beads, chromatography matrices, or nylon or nitrocellulose membranes. For example, where the molecule having a reactive amine group is biotin, the solid phase substrate may be coupled to avidin or streptavidin. Alternatively, where the molecule having the reactive amine group is an antibody or receptor ligand, the solid phase substrate may be coupled to the cognate antigen or receptor. Finally, where the molecule having a reactive amine group comprises an oligonucleotide, the solid phase substrate may comprise a complementary oligonucleotide.

The mRNAs having intact 5' ends may be released from the solid phase following the enrichment procedure. For example, where the dialdehyde is coupled to biotin hydrazide and the solid phase comprises streptavidin, the mRNAs may be released from the solid phase by simply heating to 95 degrees Celsius in 2% SDS. In some methods, the molecule having a reactive amine group may also be cleaved from the mRNAs having intact 5' ends following enrichment. Example 5 describes the capture of biotinylated mRNAs with streptavidin coated beads and the release of the biotinylated mRNAs from the beads following enrichment.

EXAMPLE 5

Capture and Release of Biotinylated mRNAs using Streptividin Coated Beads

The streptavidin-coated magnetic beads were prepared according to the manufacturer's instructions (CPG Inc., USA). The biotinylated mRNAs were added to a hybridization buffer (1.5 M NaCl, pH 5-6). After incubating for 30 minutes, the unbound and nonbiotinylated material was removed. The beads were washed several times in water with 1% SDS. The beads obtained were incubated for 15 minutes at 95° C. in water containing 2% SDS.

Example 6 demonstrates the efficiency with which biotinylated mRNAs were recovered from the streptavidin coated beads.

EXAMPLE 6

Efficiency of Recovery of Biotinylated mRNAs

The efficiency of the recovery procedure was evaluated as follows. RNAs were labeled with $^{32}$pCp, oxidized, biotinylated and bound to streptavidin coated beads as described above. Subsequently, the bound RNAs were incubated for 5, 15 or 30 minutes at 95° C. in the presence of 2% SDS.

The products of the reaction were analyzed by electrophoresis on 12% polyacrylamide gels under denaturing conditions (7 M urea). The gels were subjected to autoradiography. During this manipulation, the hydrazone bonds were not reduced.

Increasing amounts of nucleic acids were recovered as incubation times in 2% SDS increased, demonstrating that biotinylated mRNAs were efficiently recovered.

In an alternative method for obtaining mRNAs having intact 5' ends, an oligonucleotide which has been derivatized to contain a reactive amine group is specifically coupled to mRNAs having an intact cap. Preferably, the 3' end of the mRNA is blocked prior to the step in which the aldehyde groups are joined to the derivatized oligonucleotide, as described above, so as to prevent the derivatized oligonucleotide from being joined to the 3' end of the mRNA. For example, pCp may be attached to the 3' end of the mRNA using T4 RNA ligase. However, as discussed above, blocking the 3' end of the mRNA is an optional step. Derivatized oligonucleotides may be prepared as described below in Example 7.

EXAMPLE 7

Derivatization of the Oligonucleotide

An oligonucleotide phosphorylated at its 3' end was converted to a 3' hydrazide in 3' by treatment with an aqueous solution of hydrazine or of dihydrazide of the formula $H_2N(R1)NH_2$ at about 1 to 3 M, and at pH 4.5, in the presence of a carbodiimide type agent soluble in water such as 1-ethyl-3-(3-dimethylaminopropyl)carbodiimide at a final concentration of 0.3 M at a temperature of 8° C. overnight.

The derivatized oligonucleotide was then separated from the other agents and products using a standard technique for isolating oligonucleotides.

As discussed above, the mRNAs to be enriched may be treated to eliminate the 3' OH groups which may be present thereon. This may be accomplished by enzymatic ligation of sequences lacking a 3' OH, such as pCp, as described above in Example 1. Alternatively, the 3' OH groups may be eliminated by alkaline hydrolysis as described in Example 8 below.

EXAMPLE 8

Alkaline Hydrolysis of mRNA

The mRNAs may be treated with alkaline hydrolysis as follows. In a total volume of 100 µl of 0.1N sodium hydroxide, 1.5 µg mRNA is incubated for 40 to 60 minutes at 4° C. The solution is neutralized with acetic acid and precipitated with ethanol.

Following the optional elimination of the 3' OH groups, the diol groups at the 5' ends of the mRNAs are oxidized as described below in Example 9.

EXAMPLE 9

Oxidation of Diols

Up to 1 OD unit of RNA was dissolved in 9 µl of buffer (0.1 M sodium acetate, pH 6-7 or water) and 3 µl of freshly prepared 0.1 M sodium periodate solution. The reaction was incubated for 1 h in the dark at 4° C. or room temperature. Following the incubation, the reaction was stopped by adding 4 µl of 10% ethylene glycol. Thereafter the mixture was incubated at room temperature for 15 minutes. After ethanol precipitation, the product was resuspended in 10 µl or more of water or appropriate buffer and dialyzed against water.

Following oxidation of the diol groups at the 5' ends of the mRNAs, the derivatized oligonucleotide was joined to the resulting aldehydes as described in Example 10.

EXAMPLE 10

Reaction of Aldehydes with Derivatized Oligonucleotides

The oxidized mRNA was dissolved in an acidic medium such as 50 µl of sodium acetate pH 4-6. 50 µl of a solution of the derivatized oligonucleotide was added such that an mRNA:derivatized oligonucleotide ratio of 1:20 was obtained and mixture was reduced with a borohydride. The mixture was allowed to incubate for 2 h at 37° C. or overnight (14 h) at 10° C. The mixture was ethanol precipitated, resuspended in 10 µl or more of water or appropriate buffer and dialyzed against distilled water. If desired, the resulting product may be analyzed using acrylamide gel electrophoresis, HPLC analysis, or other conventional techniques.

Following the attachment of the derivatized oligonucleotide to the mRNAs, a reverse transcription reaction may be performed as described in Example 11 below.

EXAMPLE 11

Reverse Transcription of mRNAs

An oligodeoxyribonucleotide was derivatized as follows. 3 OD units of an oligodeoxyribonucleotide of sequence ATCAAGAATTCGCACGAGACCATTA (SEQ ID NO:3) having 5'-OH and 3'-P ends were dissolved in 70 µl of a 1.5 M hydroxybenzotriazole solution, pH 5.3, prepared in dimethylformamide/water (75:25) containing 2 µg of 1-ethyl-3-(3-dimethylaminopropyl)carbodiimide. The mixture was incubated for 2 h 30 min at 22° C. The mixture was then precipitated twice in LiClO$_4$/acetone. The pellet was resuspended in 200 µl of 0.25 M hydrazine and incubated at 8° C. from 3 to 14 h. Following the hydrazine reaction, the mixture was precipitated twice in LiClO$_4$/acetone.

The messenger RNAs to be reverse transcribed were extracted from blocks of placenta having sides of 2 cm which had been stored at −80° C. The mRNA was extracted using conventional acidic phenol techniques. Oligo-dT chromatography was used to purify the mRNAs. The integrity of the mRNAs was checked by Northern-blotting.

The diol groups on 7 µg of the placental mRNAs were oxidized as described above in Example 9. The derivatized oligonucleotide was joined to the mRNAs as described in Example 10 above except that the precipitation step was replaced by an exclusion chromatography step to remove derivatized oligodeoxyribonucleotides which were not joined to mRNAs. Exclusion chromatography was performed as follows:

10 ml of AcA34 (BioSepra#230151) gel were equilibrated in 50 ml of a solution of 10 mM Tris pH 8.0, 300 mM NaCl, 1 mM EDTA, and 0.05% SDS. The mixture was allowed to sediment. The supernatant was eliminated and the gel was resuspended in 50 ml of buffer. This procedure was repeated 2 or 3 times.

A glass bead (diameter 3 mm) was introduced into a 2 ml disposable pipette (length 25 cm). The pipette was filled with the gel suspension until the height of the gel stabilized at 1 cm from the top of the pipette. The column was then equilibrated with 20 ml of equilibration buffer (10 mM Tris HCl pH 7.4, 20 mM NaCl).

10 µl of the mRNA which had been reacted with the derivatized oligonucleotide were mixed in 39 µl of 10 mM urea and 2 µl of blue-glycerol buffer, which had been prepared by dissolving 5 mg of bromophenol blue in 60% glycerol (v/v), and passing the mixture through a filter with a filter of diameter 0.45 µm.

The column was loaded. As soon as the sample had penetrated, equilibration buffer was added. 100 µl fractions were collected. Derivatized oligonucleotide which had not been attached to mRNA appeared in fraction 16 and later fractions. Fractions 3 to 15 were combined and precipitated with ethanol.

The mRNAs which had been reacted with the derivatized oligonucleotide were spotted on a nylon membrane and hybridized to a radioactive probe using conventional techniques. The radioactive probe used in these hybridizations was an oligodeoxyribonucleotide of sequence TAATGGTCTCGTGCGAATTCTTGAT (SEQ ID NO:4) which was anticomplementary to the derivatized oligonucleotide and was labeled at its 5' end with $^{32}$P. 1/10th of the mRNAs which had been reacted with the derivatized oligonucleotide was spotted in two spots on the membrane and the membrane was visualized by autoradiography after hybridization of the probe. A signal was observed, indicating that the derivatized oligonucleotide had been joined to the mRNA.

The remaining 9/10 of the mRNAs which had been reacted with the derivatized oligonucleotide was reverse transcribed as follows. A reverse transcription reaction was carried out with reverse transcriptase following the manufacturer's instructions. To prime the reaction, 50 pmol of nonamers with random sequence were used.

A portion of the resulting cDNA was spotted on a positively charged nylon membrane using conventional methods. The cDNAs were spotted on the membrane after the cDNA: RNA heteroduplexes had been subjected to an alkaline hydrolysis in order to eliminate the RNAs. An oligonucleotide having a sequence identical to that of the derivatized oligonucleotide was labeled at its 5' end with $^{32}$P and hybridized to the cDNA blots using conventional techniques. Single-stranded cDNAs resulting from the reverse transcription reaction were spotted on the membrane. As controls, the blot contained 1 pmol, 100 fmol, 50 fmol, 10 fmol and 1 fmol respectively of a control oligodeoxyribonucleotide of sequence identical to that of the derivatized oligonucleotide. The signal observed in the spots containing the cDNA indicated that approximately 15 fmol of the derivatized oligonucleotide had been reverse transcribed.

These results demonstrate that the reverse transcription can be performed through the cap and, in particular, that reverse transcriptase crosses the 5'-P-P-P-5' bond of the cap of eukaryotic messenger RNAs.

The single stranded cDNAs obtained after the above first strand synthesis were used as template for PCR reactions. Two types of reactions were carried out. First, specific amplification of the mRNAs for the alpha globin, dehydrogenase, pp15 and elongation factor E4 were carried out using the following pairs of oligodeoxyribonucleotide primers.

alpha-globin (SEQ ID NO:5)
GLO-S:   CCG ACA AGA CCA ACG TCA AGG CCG C

-continued

```
                                      (SEQ ID NO:6)
GLO-As:   TCA CCA GCA GGC AGT GGC TTA GGA G 3'
``` dehydrogenase

```
                                      (SEQ ID NO:7)
3 DH-S:   AGT GAT TCC TGC TAC TTT GGA TGG C (SEQ ID NO:8)
3 DH-As:  GCT TGG TCT TGT TCT GGA GTT TAG A
``` pp15

```
                                      (SEQ ID NO:9)
PP15-S:   TCC AGA ATG GGA GAC AAG CCA ATT T (SEQ ID NO:10)
PP15-As:  AGG GAG GAG GAA ACA GCG TGA GTC C
```

Elongation factor E4

```
                                      (SEQ ID NO:11)
EFA1-S:   ATG GGA AAG GAA AAG ACT CAT ATC A (SEQ ID NO:12)
EF1A-As:  AGC AGC AAC AAT CAG GAC AGC ACA G
```

Non specific amplifications were also carried out with the antisense (_As) oligodeoxyribonucleotides of the pairs described above and a primer chosen from the sequence of the derivatized oligodeoxyribonucleotide

```
                                      (SEQ ID NO:13)
         (ATCAAGAATTCGCACGAGACCATTA).
```

A 1.5% agarose gel containing the following samples corresponding to the PCR products of reverse transcription was stained with ethidium bromide (1/20th of the products of reverse transcription were used for each PCR reaction).

Sample 1: The products of a PCR reaction using the globin primers of SEQ ID NOs 5 and 6 in the presence of cDNA.

Sample 2: The products of a PCR reaction using the globin primers of SEQ ID NOs 5 and 6 in the the absence of added cDNA.

Sample 3: The products of a PCR reaction using the dehydrogenase primers of SEQ ID NOs 7 and 8 in the presence of cDNA.

Sample 4: The products of a PCR reaction using the dehydrogenase primers of SEQ ID NOs 7 and 8 in the absence of added cDNA.

Sample 5: The products of a PCR reaction using the pp15 primers of SEQ ID NOs 9 and 10 in the presence of cDNA.

Sample 6: The products of a PCR reaction using the pp15 primers of SEQ ID NOs 9 and 10 in the the absence of added cDNA.

Sample 7: The products of a PCR reaction using the EIE4 primers of SEQ ID NOs 11 and 12 in the presence of added cDNA.

Sample 8: The products of a PCR reaction using the EIE4 primers of SEQ ID NOs 11 and 12 in the absence of added cDNA.

In Samples 1, 3, 5 and 7, a band of the size expected for the PCR product was observed, indicating the presence of the corresponding sequence in the cDNA population.

PCR reactions were also carried out with the antisense oligonucleotides of the globin and dehydrogenase primers (SEQ ID NOs 6 and 8) and an oligonucleotide whose sequence corresponds to that of the derivatized oligonucleotide. The presence of PCR products of the expected size in the samples corresponding to samples 1 and 3 above indicated that the derivatized oligonucleotide had been incorporated.

The above examples summarize the chemical procedure for enriching mRNAs for those having intact 5' ends. Further detail regarding the chemical approaches for obtaining mRNAs having intact 5' ends are disclosed in International Application No. WO96/34981, published Nov. 7, 1996, which is incorporated herein by reference.

Strategies based on the above chemical modifications to the 5' cap structure may be utilized to generate cDNAs which have been selected to include the 5' ends of the mRNAs from which they are derived. In one version of such procedures, the 5' ends of the mRNAs are modified as described above. Thereafter, a reverse transcription reaction is conducted to extend a primer complementary to the mRNA to the 5' end of the mRNA. Single stranded RNAs are eliminated to obtain a population of cDNA/mRNA heteroduplexes in which the mRNA includes an intact 5' end. The resulting heteroduplexes may be captured on a solid phase coated with a molecule capable of interacting with the molecule used to derivatize the 5' end of the mRNA. Thereafter, the strands of the heteroduplexes are separated to recover single stranded first cDNA strands which include the 5' end of the mRNA. Second strand cDNA synthesis may then proceed using conventional techniques. For example, the procedures disclosed in WO 96/34981 or in Carninci, P. et al. High-Efficiency Full-Length cDNA Cloning by Biotinylated CAP Trapper. Genomics 37:327-336 (1996), the disclosures of which are incorporated herein by reference, may be employed to select cDNAs which include the sequence derived from the 5' end of the coding sequence of the mRNA.

Following ligation of the oligonucleotide tag to the 5' cap of the mRNA, a reverse transcription reaction is conducted to extend a primer complementary to the mRNA to the 5' end of the mRNA. Following elimination of the RNA component of the resulting heteroduplex using standard techniques, second strand cDNA synthesis is conducted with a primer complementary to the oligonucleotide tag.

FIG. 1 summarizes the above procedures for obtaining cDNAs which have been selected to include the 5' ends of the mRNAs from which they are derived.

B. Enzymatic Methods for Obtaining mRNAs having Intact 5' Ends

Other techniques for selecting cDNAs extending to the 5' end of the mRNA from which they are derived are fully enzymatic. Some versions of these techniques are disclosed in Dumas Milne Edwards J. B. (Doctoral Thesis of Paris VI University, Le clonage des ADNc complets: difficultes et perspectives nouvelles. Apports pour l'etude de la regulation de l'expression de la tryptophane hydroxylase de rat, 20 Dec. 1993, EP0 625572 and Kato et al. Construction of a Human Full-Length cDNA Bank. Gene 150:243-250 (1994), the disclosures of which are incorporated herein by reference.

Briefly, in such approaches, isolated mRNA is treated with alkaline phosphatase to remove the phosphate groups present on the 5' ends of uncapped incomplete mRNAs. Following this procedure, the cap present on full length mRNAs is enzymatically removed with a decapping enzyme such as T4 polynucleotide kinase or tobacco acid pyrophosphatase. An oligonucleotide, which may be either a DNA oligonucleotide or a DNA-RNA hybrid oligonucleotide having RNA at its 3' end, is then ligated to the phosphate present at the 5' end of the decapped mRNA using T4 RNA ligase. The oligonucleotide may include a restriction site to facilitate cloning of the cDNAs following their synthesis. Example 12 below describes one enzymatic method based on the doctoral thesis of Dumas.

EXAMPLE 12

Enzymatic Approach for Obtaining 5' ESTs

Twenty micrograms of PolyA+ RNA were dephosphorylated using Calf Intestinal Phosphatase (Biolabs). After a phenol chloroform extraction, the cap structure of mRNA was hydrolysed using the Tobacco Acid Pyrophosphatase (purified as described by Shinshi et al., Biochemistry 15: 2185-2190, 1976 and a hemi 5'DNA/RNA-3' oligonucleotide having an unphosphorylated 5' end, a stretch of adenosine ribophosphate at the 3' end, and an EcoRI site near the 5' end was ligated to the 5'P ends of mRNA using the T4 RNA ligase (Biolabs). Oligonucleotides suitable for use in this procedure are preferably 30-50 bases in length. Oligonucleotides having an unphosphorylated 5' end may be synthesized by adding a fluorochrome at the 5' end. The inclusion of a stretch of adenosine ribophosphates at the 3' end of the oligonucleotide increases ligation efficiency. It will be appreciated that the oligonucleotide may contain cloning sites other than EcoRI.

Following ligation of the oligonucleotide to the phosphate present at the 5' end of the decapped mRNA, first and second strand cDNA synthesis is carried out using conventional methods or those specified in EP0 625,572 and Kato et al. Construction of a Human Full-Length cDNA Bank. Gene 150:243-250 (1994), and Dumas Milne Edwards, supra, the disclosures of which are incorporated herein by reference. The resulting cDNA may then be ligated into vectors such as those disclosed in Kato et al. Construction of a Human Full-Length cDNA Bank. Gene 150:243-250 (1994) or other nucleic acid vectors known to those skilled in the art using techniques such as those described in Sambrook et al., Molecular Cloning: A Laboratory Manual 2d Ed., Cold Spring Harbor Laboratory Press, 1989, the disclosure of which is incorporated herein by reference.

II. Characterization of 5' ESTs

The above chemical and enzymatic approaches for enriching mRNAs having intact 5' ends were employed to obtain 5' ESTs. First, mRNAs were prepared as described in Example 13 below.

EXAMPLE 13

Preparation of mRNA

Total human RNAs or PolyA+ RNAs derived from 29 different tissues were respectively purchased from LABIMO and CLONTECH and used to generate 44 cDNA libraries as described below. The purchased RNA had been isolated from cells or tissues using acid guanidium thiocyanate-phenol-chloroform extraction (Chomczyniski, P and Sacchi, N., Analytical Biochemistry 162:156-159, 1987). PolyA+ RNA was isolated from total RNA (LABIMO) by two passes of oligodT chromatography, as described by Aviv and Leder (Aviv, H. and Leder, P., Proc. Natl. Acad. Sci. USA 69:1408-1412, 1972) in order to eliminate ribosomal RNA.

The quality and the integrity of the poly A+ were checked. Northern blots hybridized with a globin probe were used to confirm that the mRNAs were not degraded. Contamination of the PolyA+ mRNAs by ribosomal sequences was checked using RNAs blots and a probe derived from the sequence of the 28S RNA. Preparations of mRNAs with less than 5% of ribosomal RNAs were used in library construction. To avoid constructing libraries with RNAs contaminated by exogenous sequences (prokaryotic or fingal), the presence of bacterial 16S ribosomal sequences or of two highly expressed mRNAs was examined using PCR.

Following preparation of the mRNAs, the above described chemical and/or the enzymatic procedures for enriching mRNAs having intact 5' ends discussed above were employed to obtain 5' ESTs from various tissues. In both approaches an oligonucleotide tag was attached to the cap at the 5' ends of the mRNAs. The oligonucleotide tag had an EcoRI site therein to facilitate later cloning procedures.

Following attachment of the oligonucleotide tag to the mRNA by either the chemical or enzymatic methods, the integrity of the mRNA was examined by performing a Northern blot with 200-500 ng of mRNA using a probe complementary to the oligonucleotide tag.

EXAMPLE 14 cDNA Synthesis Using mRNA Templates Having Intact 5' Ends

For the mRNAs joined to oligonucleotide tags using both the chemical and enzymatic methods, first strand cDNA synthesis was performed with Superscript II (Gibco BRL) using random nonamers as primers. In order to protect internal EcoRI sites in the cDNA from digestion at later steps in the procedure, methylated dCTP was used for first strand synthesis. After removal of RNA by an alkaline hydrolysis, the first strand of cDNA was precipitated using isopropanol in order to eliminate residual primers.

For both the chemical and the enzymatic methods, synthesis of the second strand of the cDNA was conducted as follows. After removal of RNA by alkaline hydrolysis, the first strand of cDNA was precipitated using isopropanol in order to eliminate residual primers. The second strand of the cDNA was synthesized with Klenow using a primer corresponding to the 5' end of the ligated oligonucleotide described in Example 12. Preferably, the primer is 20-25 bases in length. Methylated dCTP was also used for second strand synthesis in order to protect internal EcoRI sites in the cDNA from digestion during the cloning process.

Following cDNA synthesis, the cDNAs were cloned into pBlueScript as described in Example 15 below.

EXAMPLE 15

Insertion of cDNAs into BlueScrit

Following second strand synthesis, the ends of the cDNA were blunted with T4 DNA polymerase (Biolabs) and the cDNA was digested with EcoRI. Since methylated dCTP was used during cDNA synthesis, the EcoRI site present in the tag was the only site which was hemi-methylated. Consequently, only the EcoRI site in the oligonucleotide tag was susceptible to EcoRI digestion. The cDNA was then size fractionated using exclusion chromatography (AcA, Biosepra). Fractions corresponding to cDNAs of more than 150 bp were pooled and ethanol precipitated. The cDNA was directionally cloned into the SmaI and EcoRI ends of the phagemid pBlueScript vector (Stratagene). The ligation mixture was electroporated into bacteria and propagated under appropriate antibiotic selection.

Clones containing the oligonucleotide tag attached were selected as described in Example 16 below.

EXAMPLE 16

Selection of Clones Having the Oligonucleotide Tag Attached Thereto

The plasmid DNAs containing 5' EST libraries made as described above were purified (Qiagen). A positive selection of the tagged clones was performed using the Gene Trapper kit (Gibco BRL). Briefly, in this selection procedure, the plasmid DNA was converted to single stranded DNA using the geneII product in combination with exonucleaseIII. The resulting single stranded DNA was then hybridized with a biotinylated oligonucleotide having a sequence corresponding to the 3' end of the oligonucleotide described in Example 12. Preferably, the primer has a length of 20-25 bases. Clones including a sequence complementary to the biotinylated oligonucleotide were captured by incubation with streptavidin coated magnetic beads followed by magnetic selection. After capture of the positive clones, the plasmid DNA was released from the magnetic beads and converted into double stranded DNA as recommended by the manufacture. The double stranded DNA was then electroporated into bacteria. The percentage of positive clones having the 5' tag oligonucleotide was estimated using dot blot analysis. Typically the percentage of positive clones was between 90 and 98%.

Following electroporation, the libraries were ordered in 384-microtiter plates (MTP). A copy of the MTP was stored for future needs. Then the libraries were transferred into 96 MTP and sequenced as described below.

EXAMPLE 17

Sequencing of Inserts in Selected Clones

Plasmid inserts were first amplified by PCR on PE 9600 thermocyclers (Perkin-Elmer), using standard SETA-A and SETA-B primers (Genset SA), AmpliTaqGold (Perkin-Elmer), dNTPs (Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers used were either T7 or 21M13 (available from Genset SA) as appropriate. The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data from the 44 cDNA libraries made as described above were transferred to a proprietary database, where quality control and validation steps were performed. A proprietary base-caller ("Trace"), working using a Unix system automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector or ligation oligonucleotides were automatically removed from the EST sequences. However, the resulting EST sequences may contain 1 to 5 bases belonging to the above mentioned sequences at their 5' end. If needed, these can easily be removed on a case by case basis.

Thereafter, the sequences were transferred to the proprietary NETGENE™ Database for further analysis as described below.

Following sequencing as described above, the sequences of the 5' ESTs were entered in a proprietary database called NETGENE™ for storage and manipulation. It will be appreciated by those skilled in the art that the data could be stored and manipulated on any medium which can be read and accessed by a computer. Computer readable media include magnetically readable media, optically readable media, or electronically readable media. For example, the computer readable media may be a hard disc, a floppy disc, a magnetic tape, CD-ROM, RAM, or ROM as well as other types of other media known to those skilled in the art.

In addition, the sequence data may be stored and manipulated in a variety of data processor programs in a variety of formats. For example, the sequence data may be stored as text in a word processing file, such as MicrosoftWORD or WORDPERFECT or as an ASCII file in a variety of database programs familiar to those of skill in the art, such as DB2, SYBASE, or ORACLE.

The computer readable media on which the sequence information is stored may be in a personal computer, a network, a server or other computer systems known to those skilled in the art. The computer or other system preferably includes the storage media described above, and a processor for accessing and manipulating the sequence data.

Once the sequence data has been stored it may be manipulated and searched to locate those stored sequences which contain a desired nucleic acid sequence or which encode a protein having a particular functional domain. For example, the stored sequence information may be compared to other known sequences to identify homologies, motifs implicated in biological function, or structural motifs.

Programs which may be used to search or compare the stored sequences include the MacPattern (EMBL), BLAST, and BLAST2 program series (NCBI), basic local alignment search tool programs for nucleotide (BLASTN) and peptide (BLASTX) comparisons (Altschul et al, J. Mol. Biol. 215: 403 (1990)) and FASTA (Pearson and Lipman, Proc. Natl. Acad. Sci. USA, 85: 2444 (1988)) and the programs listed below in the section relating to computer embodiments. The BLAST programs then extend the alignments on the basis of defined match and mismatch criteria.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Before searching the cDNAs in the NETGENE™ database for sequence motifs of interest, cDNAs derived from mRNAs which were not of interest were identified and eliminated from further consideration as described in Example 18 below.

EXAMPLE 18

Elimination of Undesired Sequences from Further Consideration

5' ESTs in the NETGENE™ database which were derived from undesired sequences such as transfer RNAs, ribosomal RNAs, mitochondrial RNAs, procaryotic RNAs, fungal RNAs, Alu sequences, L1 sequences, or repeat sequences were identified using the FASTA and BLASTN programs with the parameters listed in Table I.

To eliminate 5' ESTs encoding tRNAs from further consideration, the 5' EST sequences were compared to the sequences of 1190 known tRNAs obtained from EMBL release 38, of which 100 were human. The comparison was performed using FASTA on both strands of the 5' ESTs. Sequences having more than 80% homology over more than 60 nucleotides were identified as tRNA. Of the 144,341 sequences screened, 26 were identified as tRNAs and eliminated from further consideration.

To eliminate 5' ESTs encoding rRNAs from further consideration, the 5' EST sequences were compared to the sequences of 2497 known rRNAs obtained from EMBL release 38, of which 73 were human. The comparison was performed using BLASTN on both strands of the 5' ESTs with the parameter S=108. Sequences having more than 80% homology over stretches longer than 40 nucleotides were identified as rRNAs. Of the 144,341 sequences screened, 3,312 were identified as rRNAs and eliminated from further consideration.

To eliminate 5' ESTs encoding mtRNAs from further consideration, the 5' EST sequences were compared to the sequences of the two known mitochondrial genomes for which the entire genomic sequences are available and all sequences transcribed from these mitochondrial genomes including tRNAs, rRNAs, and mRNAs for a total of 38 sequences. The comparison was performed using BLASTN on both strands of the 5' ESTs with the parameter S=108. Sequences having more than 80% homology over stretches longer than 40 nucleotides were identified as mtRNAs. Of the 144,341 sequences screened, 6,110 were identified as mtRNAs and eliminated from further consideration.

Sequences which might have resulted from exogenous contaminants were eliminated from further consideration by comparing the 5' EST sequences to release 46 of the EMBL bacterial and fingal divisions using BLASTN with the parameter S=144. All sequences having more than 90% homology over at least 40 nucleotides were identified as exogenous contaminants. Of the 42 cDNA libraries examined, the average percentages of procaryotic and fungal sequences contained therein were 0.2% and 0.5% respectively. Among these sequences, only one could be identified as a sequence specific to fungi. The others were either fungal or procaryotic sequences having homologies with vertebrate sequences or including repeat sequences which had not been masked during the electronic comparison.

In addition, the 5' ESTs were compared to 6093 Alu sequences and 1115 L1 sequences to mask 5' ESTs containing such repeat sequences from further consideration. 5' ESTs including THE and MER repeats, SSTR sequences or satellite, micro-satellite, or telomeric repeats were also eliminated from further consideration. On average, 11.5% of the sequences in the libraries contained repeat sequences. Of this 11.5%, 7% contained Alu repeats, 3.3% contained L1 repeats and the remaining 1.2% were derived from the other types of repetitive sequences which were screened. These percentages are consistent with those found in cDNA libraries prepared by other groups. For example, the cDNA libraries of Adams et al. contained between 0% and 7.4% Alu repeats depending on the source of the RNA which was used to prepare the cDNA library (Adams et al., Nature 377:174, 1996).

The sequences of those 5' ESTs remaining after the elimination of undesirable sequences were compared with the sequences of known human mRNAs to determine the accuracy of the sequencing procedures described above.

EXAMPLE 19

Measurement of Sequencing Accuracy by Comparison to Known Sequences

To further determine the accuracy of the sequencing procedure described above, the sequences of 5' ESTs derived from known sequences were identified and compared to the known sequences. First, a FASTA analysis with overhangs shorter than 5 bp on both ends was conducted on the 5' ESTs to identify those matching an entry in the public human mRNA database. The 6655 5' ESTs which matched a known human mRNA were then realigned with their cognate mRNA and dynamic programming was used to include substitutions, insertions, and deletions in the list of "errors" which would be recognized. Errors occurring in the last 10 bases of the 5' EST sequences were ignored to avoid the inclusion of spurious cloning sites in the analysis of sequencing accuracy.

This analysis revealed that the sequences incorporated in the NETGENE™ database had an accuracy of more than 99.5%.

To determine the efficiency with which the above selection procedures select cDNAs which include the 5' ends of their corresponding mRNAs, the following analysis was performed.

EXAMPLE 20

Determination of Efficiency of 5' EST Selection

To determine the efficiency at which the above selection procedures isolated cDNAs which included sequences close to the 5' end of the mRNAs from which they were derived, the sequences of the ends of the 5' ESTs which were derived from the elongation factor 1 subunit α and ferritin heavy chain genes were compared to the known cDNA sequences for these genes. Since the transcription start sites for the elongation factor 1 subunit α and ferritin heavy chain are well characterized, they may be used to determine the percentage of 5' ESTs derived from these genes which included the authentic transcription start sites.

For both genes, more than 95% of the cDNAs included sequences close to or upstream of the 5' end of the corresponding mRNAs.

To extend the analysis of the reliability of the procedures for isolating 5' ESTs from cDNAs in the NETGENE™ database, a similar analysis was conducted using a database composed of human mRNA sequences extracted from GenBank database release 97 for comparison. For those 5' ESTs derived from mRNAs included in the GeneBank database, more than 85% had their 5' ends close to the 5' ends of the known sequence. As some of the mRNA sequences available in the GenBank database are deduced from genomic sequences, a 5' end matching with these sequences will be counted as an internal match. Thus, the method used here underestimates the yield of cDNAs including the authentic 5' ends of their corresponding mRNAs.

The cDNA libraries made above included multiple 5' ESTs derived from the same mRNA. The sequences of such 5' ESTs were compared to one another and the longest 5' ESTs for each mRNA were identified. Overlapping cDNAs were assembled into continuous sequences (contigs). The resulting continuous sequences were then compared to public databases to gauge their similarity to known sequences, as described in Example 21 below.

EXAMPLE 21

Clustering of the 5' ESTs and Calculation of Novelty Indices for cDNA Libraries

For each sequenced cDNA library, the sequences were clustered by the 5' end. Each sequence in the library was compared to the others with BLASTN2 (direct strand, parameters S=107). ESTs with High Scoring Segment Pairs (HSPs) at least 25 bp long, having 95% identical bases and beginning closer than 10 bp from each EST 5' end were grouped. The longest sequence found in the cluster was used as representative of the cluster. A global clustering between libraries was then performed leading to the definition of super-contigs.

To assess the yield of new sequences within the cDNA libraries, a novelty rate (NR) was defined as: NR=100×(Number of new unique sequences found in the library/Total number of sequences from the library). Typically, novelty rating range between 10% and 41% depending on the tissue from which the cDNA library was obtained. For most of the libraries, the random sequencing of 5' EST libraries was pursued until the novelty rate reached 20%.

Following characterization as described above, the collection of 5' ESTs in NETGENE™ was screened to identify those 5' ESTs bearing potential signal sequences as described in Example 22 below.

EXAMPLE 22

Identification of Potential Signal Sequences in 5' ESTs

The 5' ESTs in the NETGENETm database (release 21 Jan. 1998) were screened to identify those having an uninterrupted open reading frame (ORF) longer than 45 nucleotides beginning with an ATG codon and extending to the end of the EST. Approximately half of the cDNA sequences in NETGENE™ contained such an ORF. The ORFs of these 5' ESTs were searched to identify potential signal motifs using slight modifications of the procedures disclosed in Von Heijne, G. A New Method for Predicting Signal Sequence Cleavage Sites. Nucleic Acids Res. 14:4683-4690 (1986), the disclosure of which is incorporated herein by reference. Those 5' EST sequences encoding a 15 amino acid long stretch with a score of at least 3.5 in the Von Heijne signal peptide identification matrix were considered to possess a signal sequence. Those 5' ESTs which matched a known human mRNA, EST, or 5' EST sequence were excluded from further analysis. The remaining cDNAs having signal sequences therein were included in a database called SIGNALTAG™.

To confirm the accuracy of the above method for identifying signal sequences, the analysis of Example 23 was performed.

EXAMPLE 23

Confirmation of Accuracy of Identification of Potential Signal Sequences in 5' ESTs The accuracy of the above procedure for identifying signal sequences encoding signal peptides was evaluated by applying the method to the 43 amino terminal amino acids of all human SwissProt proteins. The computed Von Heijne score for each protein was compared with the known characterization of the protein as being a secreted protein or a non-secreted protein. In this manner, the number of non-secreted proteins having a score higher than 3.5 (false positives) and the number of secreted proteins having a score lower than 3.5 (false negatives) could be calculated.

Figure 3:
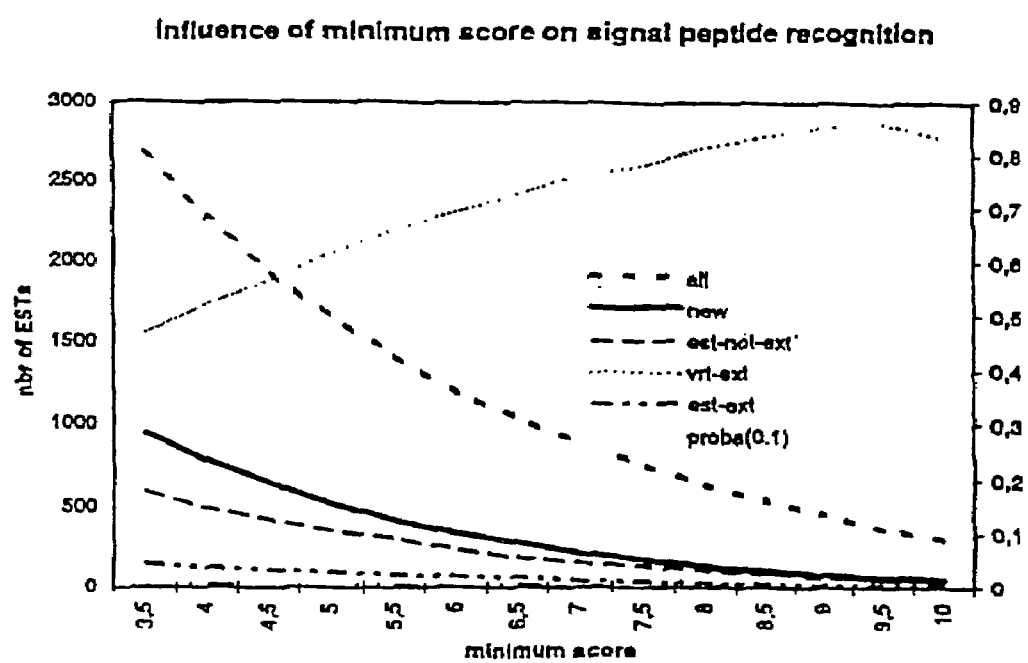
FIG. 3 shows the distribution of von Heijne scores for 5' ESTs in each of the categories described herein and the probability that these 5' ESTs encode a signal peptide.

Using the results of the above analysis, the probability that a peptide encoded by the 5' region of the mRNA is in fact a genuine signal peptide based on its Von Heijne's score was calculated based on either the assumption that 10% of human proteins are secreted or the assumption that 20% of human proteins are secreted. The results of this analysis are shown in FIGS. 2 and 3.

Using the above method of identifying secretory proteins, 5' ESTs for human glucagon, gamma interferon induced monokine precursor, secreted cyclophilin-like protein, human pleiotropin, and human biotinidase precursor all of which are polypeptides which are known to be secreted, were obtained. Thus, the above method successfully identified those 5' ESTs which encode a signal peptide.

To confirm that the signal peptide encoded by the 5' ESTs actually functions as a signal peptide, the signal sequences from the 5' ESTs may be cloned into a vector designed for the identification of signal peptides. Some signal peptide identification vectors are designed to confer the ability to grow in selective medium on host cells which have a signal sequence operably inserted into the vector. For example, to confirm that a 5' EST encodes a genuine signal peptide, the signal sequence of the 5' EST may be inserted upstream and in frame with a non-secreted form of the yeast invertase gene in signal peptide selection vectors such as those described in U.S. Pat. No. 5,536,637, the disclosure of which is incorporated herein by reference. Growth of host cells containing signal sequence selection vectors having the signal sequence from the 5' EST inserted therein confirms that the 5' EST encodes a genuine signal peptide.

Alternatively, the presence of a signal peptide may be confirmed by cloning the extended cDNAs obtained using the ESTs into expression vectors such as pXT1 (as described below), or by constructing promoter-signal sequence-reporter gene vectors which encode fusion proteins between the signal peptide and an assayable reporter protein. After introduction of these vectors into a suitable host cell, such as COS cells or NIH 3T3 cells, the growth medium may be harvested and analyzed for the presence of the secreted protein. The medium from these cells is compared to the medium from cells containing vectors lacking the signal sequence or extended cDNA insert to identify vectors which encode a functional signal peptide or an authentic secreted protein.

Those 5' ESTs which encoded a signal peptide, as determined by the method of Example 22 above, were further grouped into four categories based on their homology to known sequences. The categorization of the 5' ESTs is described in Example 24 below.

EXAMPLE 24

Categorization of 5' ESTs Encoding a Signal Peptide

Those 5' ESTs having a sequence not matching any known vertebrate sequence nor any publicly available EST sequence were designated "new." Of the sequences in the SIGNAL-TAG™ database, 395 of the 5' ESTs having a Von Heijne's score of at least 3.5 fell into this category.

Those 5' ESTs having a sequence not matching any vertebrate sequence but matching a publicly known EST were designated "EST-ext", provided that the known EST sequence was extended by at least 40 nucleotides in the 5' direction. Of the sequences in the SIGNALTAG™ database, 19 of the 5' ESTs having a Von Heijne's score of at least 3.5 fell into this category.

Those ESTs not matching any vertebrate sequence but matching a publicly known EST without extending the known EST by at least 40 nucleotides in the 5' direction were designated "EST-not-ext." Of the sequences in the SIGNAL-TAG™ database, 81 of the 5' ESTs having a Von Heijne's score of at least 3.5 fell into this category.

Those 5' ESTs matching a known vertebrate sequence were designated "vrt." Of the sequences in the SIGNALTAG™ database, 90 of the 5' ESTs having a Von Heijne's score of at least 3.5 fell into this category.

FIG. 4 shows the distribution of 5' ESTs in each category and the number of 5' ESTs in each category having a given minimum von Heijne's score.

Each of the 5' ESTs was categorized based on the tissue from which its corresponding mRNA was obtained, as described below in Example 25.

EXAMPLE 25

Categorization of Expression Patterns

FIG. 5 shows the tissues from which the mRNAs corresponding to the 5' ESTs in each of the above described categories were obtained.

Table II provides the sequence identification numbers of 5' EST sequences, the categories in which these sequences fall, and the von Heijne's score of the signal peptides which they encode. The 5' EST sequences and the amino acid sequences they encode are provided in the appended sequence listings. Table III provides the sequence ID numbers of the 5' ESTs and the sequences of the signal peptides which they encode. The sequences of the 5' ESTs and the polypeptides they encode are provided in the sequence listing appended hereto.

The sequences of DNA SEQ ID NOs: 38-1756 can readily be screened for any errors therein and any sequence ambiguities can be resolved by resequencing a fragment containing such errors or amibiguities on both strands. Such fragments may be obtained from the plasmids stored in the inventors' laboratory or can be isolated using the techniques described herein. Resolution of any such ambiguities or errors may be facilitated by using primers which hybridize to sequences located close to the ambiguous or erroneous sequences. For example, the primers may hybridize to sequences within 50-75 bases of the amibiguity or error. Upon resolution of an error or ambiguity, the corresponding corrections can be made in the protein sequences encoded by the DNA containing the error or ambiguity.

In addition to categorizing the 5' ESTs by the tissue from which the cDNA library in which they were first identified was obtained, the spatial and temporal expression patterns of the mRNAs corresponding to the 5' ESTs, as well as their expression levels, may be determined as described in Example 26 below. Characterization of the spatial and temporal expression patterns and expression levels of these mRNAs is useful for constructing expression vectors capable of producing a desired level of gene product in a desired spatial or temporal manner, as will be discussed in more detail below.

In addition, 5' ESTs whose corresponding mRNAs are associated with disease states may also be identified. For example, a particular disease may result from lack of expression, over expression, or under expression of an mRNA corresponding to a 5' EST. By comparing mRNA expression patterns and quantities in samples taken from healthy individuals with those from individuals suffering from a particular disease, 5' ESTs responsible for the disease may be identified.

EXAMPLE 26

Evaluation of Expression Levels and Patterns of mRNAs Corresponding to 5' ESTs Expression levels and patterns of mRNAs corresponding to 5' ESTs may be analyzed by solution hybridization with long probes as described in International Patent Application No. WO 97/05277, the entire contents of which are hereby incorporated by reference. Briefly, a 5' EST corresponding to a portion of a gene is inserted at a cloning site immediately downstream of a bacteriophage (T3, T7 or SP6) RNA polymerase promoter to produce antisense RNA. Preferably, the 5' EST has 100 or more nucleotides. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

The 5' ESTs may also be tagged with nucleotide sequences for the serial analysis of gene expression (SAGE) as disclosed in UK Patent Application No. 2 305 241 A, the entire contents of which are incorporated by reference. In this method, cDNAs are prepared from a cell, tissue, organism or other source of nucleic acid for which it is desired to determine gene expression patterns. The resulting cDNAs are separated into two pools. The cDNAs in each pool are cleaved with a first restriction endonuclease, called an "anchoring enzyme," having a recognition site which is likely to be present at least once in most cDNAs. The fragments which contain the 5' or 3' most region of the cleaved cDNA are isolated by binding to a capture medium such as streptavidin coated beads. A first oligonucleotide linker having a first sequence for hybridization of an amplification primer and an internal restriction site for a "tagging endonuclease" is ligated to the digested cDNAs in the first pool. Digestion with the second endonuclease produces short "tag" fragments from the cDNAs.

A second oligonucleotide having a second sequence for hybridization of an amplification primer and an internal restriction site is ligated to the digested cDNAs in the second pool. The cDNA fragments in the second pool are also digested with the "tagging endonuclease" to generate short "tag" fragments derived from the cDNAs in the second pool. The "tags" resulting from digestion of the first and second pools with the anchoring enzyme and the tagging endonuclease are ligated to one another to produce "ditags." In some embodiments, the ditags are concatamerized to produce ligation products containing from 2 to 200 ditags. The tag sequences are then determined and compared to the sequences of the 5' ESTs to determine which 5' ESTs are expressed in the cell, tissue, organism, or other source of nucleic acids from which the tags were derived. In this way, the expression pattern of the 5' ESTs in the cell, tissue, organism, or other source of nucleic acids is obtained.

Quantitative analysis of gene expression may also be performed using arrays. As used herein, the term array means a one dimensional, two dimensional, or multidimensional arrangement of full length cDNAs, extended cDNAs, 5' ESTs or fragments thereof of sufficient length to permit specific detection of gene expression. Preferably, the fragments are at least 8, 10, 12, 15, 20, 23, 25, 28, 30, 35, 40, 50, 75, or 100 nucleotides in length.

For example, quantitative analysis of gene expression may be performed with full length cDNAs, extended cDNAs, 5' ESTs, or fragments thereof in a complementary DNA microarray as described by Schena et al. (*Science* 270:467-470, 1995; *Proc. Natl. Acad Sci. U.S.A.* 93:10614-10619, 1996). The full length cDNAs, extended cDNAs, 5' ESTs or fragments thereof are amplified by PCR and arrayed from 96-well microtiter plates onto silylated microscope slides using high-speed robotics. Printed arrays are incubated in a humid chamber to allow rehydration of the array elements and rinsed, once in 0.2% SDS for 1 min. twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the expression of genes may also be performed with full length cDNAs, extended cDNAs, 5' ESTs, or fragments thereof in complementary DNA arrays as described by Pietu et al. (Genome Research 6:492-503, 1996). The full length cDNAs, extended cDNAs, 5' ESTs or fragments thereof are PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis of the 5' ESTs can be done through high density nucleotide arrays as described by Lockhart et al. (Nature Biotechnology 14: 1675-1680, 1996) and Sosnowsky et al. (Proc. Natl. Acad. Sci. 94:1119-1123, 1997). Oligonucleotides of 15-50 nucleotides corresponding to sequences of the 5' ESTs, or cDNAs obtainable therewith, are synthesized directly on the chip (Lockhart et al., supra) or synthesized and then addressed to the chip (Sosnowski et al., supra). Preferably, the oligonucleotides are about 20 nucleotides in length.

cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., Proc. Nail. Acad. Sctl. 94:1119-1123), the dyes or labeling compounds are detected and quantified. Duplicate hybridizations are performed. Comparative analysis of the intensity of the signal originating from cDNA probes on the same target oligonucleotide in different cDNA samples indicates a differential expression of the mRNA corresponding to the 5' EST, or cDNAs obtainable therewith, from which the oligonucleotide sequence has been designed.

III. Use of 5' ESTs to Clone cDNAs Containing the Authentic 5' End of the Corresponding mRNA as well as the Entire Protein Coding Sequence of the Corresponding mRNA and to Clone the Corresponding Genomic DNAs Once 5' ESTs which include the 5' end of the corresponding mRNAs have been selected using the procedures described above, they can be utilized to isolate cDNAs which include the entire coding sequence of the protein encoded by the corresponding mRNA, including the authentic translation start site, hereinafter referred to as "full length cDNAs". Example 27 below describes a general method for obtaining such cDNAs. Example 28 below describes the cloning and sequencing of a cDNA which includes the entire coding sequence and authentic 5' end of the corresponding mRNA for several secreted proteins.

The methods of Examples 27, 28, and 29 can also be used to obtain cDNAs which encode less than the entire coding sequence of the proteins encoded by the 5' ESTs. The cDNAs isolated using these methods encode at least 6, 8, 10, 12, 15, 18, 20, 23, 25, 28, 30, 35, 40, or 50 amino acids of the proteins encoded by the sequences of SEQ ID NOs: 38-1756. In a preferred embodiment, the cDNAs encode a full length protein sequence, which includes the protein coding sequences of SEQ ID NOs: 38-1756.

EXAMPLE 27

General Method for Using 5' ESTs to Clone and Sequence cDNAs which Include the Entire Coding Region and the Authentic 5' End of the Corresponding mRNA The following general method has been used to quickly and efficiently isolate cDNAs having the authentic 5' ends of their corresponding mRNAs as well as the full protein coding sequence. This method may be applied to obtain such cDNAs for any 5' EST in the NETGENE™ database, including those 5' ESTs encoding secreted proteins, as well as to obtain cDNAs which do not include the full coding sequence.

The method takes advantage of the known 5' sequence of the mRNA. An RT-PCR reaction is conducted on purified mRNA using a poly 14dT primer containing a 49 nucleotide sequence at its 5' end which permits the addition of a known sequence at the end of the cDNA which corresponds to the 3' end of the mRNA. For example, the primer may have the following sequence: 5'-ATC GTT GAG ACT CGT ACC AGC AGA GTC ACG AGA GAG ACT ACA CGG TAC TGG TTT TTT TTT TTT TTVN-3' (SEQ ID NO:14). Those skilled in the art will appreciate that other sequences may also be added to the poly dT sequence and used to prime the first strand synthesis. Using this primer and an enzyme having reverse transcriptase activity, such as SuperScriptII (Gibco BRL), a reverse transcript which is anchored at the 3' polyA site of the RNAs is generated.

After removal of the mRNA hybridized to the first cDNA strand by alkaline hydrolysis, the products of the alkaline hydrolysis and the residual poly dT primer are eliminated with an exclusion column such as an Aca34 (Biosepra) matrix, a mix of agarose and acrylamide.

A pair of nested primers on each end is designed based on the known 5' sequence from the 5' EST and the known 3' end resulting from the primer used in the first strand synthesis. Preferably, the nested primers at the 5' end are separated from one another by four to nine bases. The 5' primer sequences may be selected to have melting temperatures and specificities suitable for use in PCR using formulas or software well known to those skilled in the art. If it is desired to obtain cDNAs containing the full length protein coding sequence, including the authentic translation initiation site, primers comprising sequences upstream of the translation initiation site are used. Alternatively, the PCR product is sequenced and the coding region is determined.

Preferably, the nested primers at the 3' end are separated from one another by four to nine bases. For example, the nested 3' primers may have the following sequences: (5'-CCA GCA GAG TCA CGA GAG AGA CTA CAC GG-3' (SEQ ID NO:15), and 5'-CAC GAG AGA GAC TAC ACG GTA CTG G-3' (SEQ ID NO:16). These primers were selected because they have melting temperatures and specificities compatible with their use in PCR. However, those skilled in the art will appreciate that other sequences may also be used as primers.

The first PCR run of 25 cycles is performed using the Clontech Tth Polymerase Mix and the outer primer from each of the nested pairs. 1/2500 of the resulting PCR product is then used in a second 20 cycle PCR using the same enzyme and the liner primer from each of the nested pairs. Thereafter, the primers and nucleotides are removed. Depending on the position of the primer on the EST sequence, the PCR product obtained will or will not comprise the corresponding complete coding region. If a PCR product contains the complete coding sequence, it is cloned into an appropriate vector and sequenced. Alternatively, the full coding sequence can be determined by directly sequencing the PCR product. If needed, the complete coding sequence can be assembled from several partial sequences determined directly from the PCR products. Sequencing is performed using Die Terminator approach using the AmpliTaqFS kit available from Perkin Elmer. If a PCR product does not contain the complete coding sequence, a cDNA product containing the full length protein coding sequence is preferably obtained by determining the coding sequence and performing RT-PCRs with primers spanning the coding region. The PCR product is cloned in an appropriate vector.

For example, the cDNAs can be cloned into pED6dpc2 (DiscoverEase, Genetics Institute, Cambridge, Mass.) as follows. pED6dpc2 vector DNA is prepared with blunt ends by performing an EcoRi digestion followed by a fill in reaction. The blunt ended vector is dephosphorylated. After removal of PCR primers and ethanol precipitation, the PCR product containing the full length protein coding sequence or extended cDNA obtained as described above is phosphorylated with kinase, and the kinase is removed by phenol-Sevag extraction and precipitation. The double stranded cDNA is then ligated to the vector. The resulting expression plasmid is introduced into appropriate host cells.

Since the PCR products obtained as described above are cloned as blunt ended molecules, 4 to 10 clones for each PCR product are ordered in microtiter plates. To determine the orientation of each clone, a PCR reaction is carried out using a first primer located in the vector close to the portion of the cDNA corresponding to the 5' end of the mRNA which has been cloned into the EcoRI site and a second primer located in the portion of the extended cDNA corresponding to the 3' end of the mRNA. Clones in which the start codon of the cDNA is operably linked to the promoter in the vector so as to permit expression of the protein encoded by the extended cDNA are conserved and sequenced. In addition to sequencing the cDNA inserts in the vectors, approximately 50 bp of vector sequence on each side of the cDNA insert is sequenced.

In order to sequence long fragments primer walling is performed using automated computer software such as ASMG (Sutton, G. G. et al. TIGR Assembler: A New Tool for Assembling Large Shotgun Sequencing Projects. Genome Science and Technology 1: 9-19 (1995)) to construct contigs and software such as OSP (Illier, L and Green, P. OSP: A Computer Program for Choosing PCR and DNA sequencing Primers. PCR Methods Appl. 1(2): 124-128 (1991)to choose primers.

Preferably, primer walking is performed until full length cDNAs (i.e. extended cDNAs which include the coding sequence for the signal peptide, the coding sequence for the mature protein, and a stop codon) are obtained. The sequencing of clones is continued until the inserts comprising the full coding sequence have been completely sequenced.

The structural (polyA tail, polyadenyaltion signal) and functional (ORF, signal peptide) features of the sequences are then determined. A polyA tail is defined as an 11 A homopolymeric stretch with at most one alternative base within it. The polyA tail search is restricted to the end of the sequence. The search is limited to stretches of 11 consecutive A's because sequencing reactions are often not readable after such a polyA stretch.

To search for a poly adenylation signal, the polyA tail is first clipped from the full-length sequence. The 50 bp preceding the polyA tail are then searched for consensus polyA signals. First, the 50 bp preceding the polyA tail are searched for the consensus polyA signal AAUAAA. If that consensus site is not detected, the 50 bp preceding the polyA tail are searched for a second alternative polyA signal, AUUAAA. (Sheets, M. D., Ogg, S. C. and Wickens, M. P. (1990) N.A.R. 18, 5799-5805).

When Northern blot data are available, the size of the mRNA detected for a given PCR product is used to finally assess that the sequence is complete. Sequences which do not fulfill the above criteria are discarded and will undergo a new isolation procedure.

The 3 upper strand frames are searched for open reading frames (ORFs). They are defined as the maximum length fragments beginning with an ATG and ending with a stop codon. Only ORFs encoding at least 20 amino acids are considered. Each ORF found is then scanned for the presence of a signal peptide in the first 50 amino-acids or, where appropriate, within shorter regions down to the minimum 20 amino acids in the ORF, using the matrix method of von Heijne, (1986) N.A.R. 4683-4690, the disclosure of which is incorporated herein by reference, as described above. Finally, the conservation of the signal peptide and of the ORF detected from the 5'-tag sequence corresponding to the studied extended cDNA is examined. It should be noted that in some cases, extended cDNA sequences lacking a poly A signal but containing an ORF ending before the poly A tail may also be used to determine the full coding sequence.

Extended cDNAs prepared as described above may be manipulated to obtain nucleic acids which include desired portions of the extended cDNA. Conventional techniques such as subcloning, PCR, or in vitro oligonucleotide synthesis may be employed to obtain nucleic acids containing the desired portions of the extended cDNAs. For example, nucleic acids which include only the full coding sequences (i.e. the sequences encoding the signal peptide and the mature protein remaining after the signal peptide is cleaved off) may be obtained using conventional techniques. Alternatively, conventional techniques may be applied to obtain nucleic acids which contain only the coding sequences for the mature protein remaining after the signal peptide is cleaved off or nucleic acids which contain only the coding sequences for the signal peptides.

Similarly, nucleic acids containing any other desired portion of the coding sequences for the secreted protein may be obtained. For example, the nucleic acid may contain at least 8, 10, 12, 15, 20, 23, 25, 28, 30, 35, 40, 50, 75, 100, 200, 300, 500, or 1000 consecutive bases of an extended cDNA such as one of the extended cDNAs described below.

Once an extended cDNA has been obtained, it can be sequenced to determine the amino acid sequence it encodes. Once the encoded amino acid sequence has been determined, one can create and identify any of the many conceivable cDNAs that will encode that protein by simply using the known genetic code. For example, allelic variants or other homologous nucleic acids can be identified as described below. Alternatively, nucleic acids encoding the desired amino acid sequence can be synthesized in vitro.

In a preferred embodiment, the coding sequence may be selected using the known codon or codon pair preferences for the host organism in which the cDNA is to be expressed.

cDNAs which include the entire coding sequence of secreted proteins may be obtained as described in Example 28 below.

Once a cDNA has been obtained, it can be sequenced to determine the amino acid sequence it encodes. Once the encoded amino acid sequence has been determined, one can create and identify any of the many conceivable cDNAs that will encode that protein by simply using the known genetic code.

In a preferred embodiment, the coding sequence may be selected using the known codon or codon pair preferences for the host organism in which the cDNA is to be expressed.

EXAMPLE 28

Cloning and Sequencing of a Full Length cDNA Encoding a Secreted Protein

The procedure described in Example 27 above was used to obtain full length cDNAs. Using this approach, the full length cDNA of SEQ ID NO:17 (internal identification number 48-19-3-G1-FL1) was obtained. This cDNA falls into the "EST-ext" category described above and encodes the signal peptide MKKVLLLITAILAVAVG (SEQ ID NO: 18) having a von Heijne score of 8.2.

The full length cDNA of SEQ ID NO:19 (internal identification number 58-34-2-E7-FL2) was also obtained using this procedure. This cDNA falls into the "EST-ext" category described above and encodes the signal peptide MWWFQQGLSFLPSALVIWTSA (SEQ ID NO:20) having a von Heijne score of 5.5.

Another full length cDNA obtained using the procedure described above has the sequence of SEQ ID NO:21 (internal identification number 51-27-E8-FL1). This cDNA, falls into the "EST-ext" category described above and encodes the signal peptide MVLTTLPSANSANSPVNMPTTGPNSLSYASSALSPCLT (SEQ ID NO:22) having a von Heijne score of 5.9.

The above procedure was also used to obtain a full length cDNA having the sequence of SEQ ID NO:23 (internal identification number 76-4-1-G5-FL1). This cDNA falls into the "EST-ext" category described above and encodes the signal peptide ILSTVTALTFAXA (SEQ ID NO:24) having a von Heijne score of 5.5.

The full length cDNA of SEQ ID NO:25 (internal identification number 51-3-3-B10-FL3) was also obtained using this procedure. This cDNA falls into the "new" category described above and encodes a signal peptide LVLTLCTLPLAVA (SEQ ID NO:26) having a von Heijne score of 10.1.

The full length cDNA of SEQ ID NO:27 (internal identification number 58-35-2-F10-FL2) was also obtained using this procedure. This cDNA falls into the "new" category described above and encodes a signal peptide LWLLFFLVTAIHA (SEQ ID NO:28) having a von Heijne score of 10.7.

Bacterial clones containing plasmids containing the full length cDNAs described above are presently stored in the inventor's laboratories under the internal identification numbers provided above. The inserts may be recovered from the stored materials by growing an aliquot of the appropriate bacterial clone in the appropriate medium. The plasmid DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the cDNA insertion. The PCR product which corresponds to the cDNA can then be manipulated using standard cloning techniques familiar to those skilled in the art.

In addition to PCR based methods for obtaining cDNAs which include the authentic 5' end of the corresponding mRNA as well as the full protein coding sequence of the corresponding mRNA, traditional hybridization based methods may also be employed. These methods may also be used to obtain the genomic DNAs which encode the mRNAs from which the 5' ESTs were derived. Example 29 below provides an example of such methods.

The polypeptides encoded by the cDNAs obtained as described above may be screened for the presence of known structural or functional motifs or for the presence of signatures, small amino acid sequences which are well conserved amongst the members of a protein family. The conserved regions have been used to derive consensus patterns or matrices included in the PROSITE data bank, in particular in the file prosite.dat (Release 13.0 of November 1995, located at http://expasy.hcuge.ch/sprot/prosite.html. Prosite_convert and prosite_scan programs (http://ulrec3.unil.ch/ftpserveur/prosite_scan) may be used to find signatures on the cDNAs.

For each pattern obtained with the prosite_convert program from the prosite.dat file, the accuracy of the detection on a new protein sequence may be tested by evaluating the frequency of irrelevant hits on the population of human secreted proteins included in the data bank SWISSPROT. The ratio between the number of hits on shuffled proteins (with a window size of 20 amino acids) and the number of hits on native (unshuffled) proteins may be used as an index. Every pattern for which the ratio is greater than 20% (one hit on shuffled proteins for 5 hits on native proteins) may be skipped during the search with prosite_scan. A program which may be used to shuffle protein sequences (db_shuffled) and a program which may be used to determine the statistics for each pattern in the protein data banks (prosite_statistics) are available on the ftp site http://ulrec3. unil.ch/ftpserveur/prosite_scan.

The cDNAs may be further categorized based on the homology to known sequences. Genbank release #104, division ESTs, and Geneseq release #28 may be used to scan the cDNAs using Blast. For each cDNA, the covering rate of the sequence by another sequence maybe determined as follows. The length in nucleotides of the matching segment is calculated (even when gaps are present) and divided by the length in nucleotides of the cDNA sequence. When more than one covering rate is obtained for a given cDNA, the higher covering rate may be used to classify the extended cDNA.

EXAMPLE 29

Methods for Obtaining cDNAs which Include the Entire Coding Region and the Authentic 5' End of the Corresponding mRNA A full length cDNA library can be made using the strategies described in Examples 13, 14, 15, and 16 above by replacing the random nonamer used in Example 14 with an oligo-dT primer. For instance, the oligonucleotide sequence of SEQ ID NO:14 may be used.

Alternatively, a cDNA library or genomic DNA library may be obtained from a commercial source or made using techniques familiar to those skilled in the art. The cDNA library or genomic DNA library is hybridized to a detectable probe comprising at least 8, 10, 12, 15, 20, 23, 25, 28, 30, 35, 40, 50, 75, 100, 200, 300, or 500 consecutive nucleotides from the 5' EST using conventional techniques. In some embodiments, the probe comprises more than 40 nucleotides from the 5' EST.

Techniques for identifying cDNA clones in a cDNA library which hybridize to a given probe sequence are disclosed in Sambrook et al., Molecular Cloning: A Laboratory Manual 2d Ed., Cold Spring Harbor Laboratory Press, 1989, the disclosure of which is incorporated herein by reference. The same techniques may be used to isolate genomic DNAs.

Briefly, cDNA or genomic DNA clones which hybridize to the detectable probe are identified and isolated for further manipulation as follows. A probe comprising at least 8, 10, 12, 15, 20, 23, 25, 28, 30, 35, 40, 50, 75, 100, 200, 300, 500, or more than 500 consecutive nucleotides from the 5' EST is labeled with a detectable label such as a radioisotope or a fluorescent molecule.

Techniques for labeling the probe are well known and include phosphorylation with polynucleotide kinase, nick translation, in vitro transcription, and non-radioactive techniques. The cDNAs or genomic DNAs in the library are transferred to a nitrocellulose or nylon filter and denatured. After incubation of the filter with a blocking solution, the filter is contacted with the labeled probe and incubated for a sufficient amount of time for the probe to hybridize to cDNAs or genomic DNAs containing a sequence capable of hybridizing to the probe.

By varying the stringency of the hybridization conditions used to identify cDNAs or genomic DNAs which hybridize to the detectable probe, cDNAS having different levels of homology to the probe can be identified and isolated. To identify cDNAs or genomic DNAs having a high degree of homology to the probe sequence, the melting temperature of the probe may be calculated using the following formulas:

For probes between 14 and 70 nucleotides in length the melting temperature (Tm) is calculated using the formula: Tm=81.5+16.6(log [Na+])+0.41 (fraction G+C)−(600/N) where N is the length of the probe.

If the hybridization is carried out in a solution containing formamide, the melting temperature may be calculated using the equation Tm=81.5+16.6(log [Na+])+0.41 (fraction G+C)−(0.63% formamide)−(600/N) where N is the length of the probe.

Prehybridization may be carried out in 6×SSC, 5× Denhardt's reagent, 0.5% SDS, 100 µg denatured fragmented salmon sperm DNA or 6×SSC, 5× Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprised double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 15-25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under "stringent" conditions.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

cDNAs or genomic DNAs which have hybridized to the probe are identified by autoradiography or other conventional techniques.

The above procedure may be modified to identify cDNAs or genomic DNAs having decreasing levels of homology to the probe sequence. For example, to obtain cDNAs or genomic DNAs of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide.

cDNAs or genomic DNAs which have hybridized to the probe are identified by autoradiography.

In some embodiments, the methods above are used to identify and isolate inserts in genomic DNA libraries which contain sequences encoding a secreted polypeptide or a portion thereof. For example, the library may comprise genomic fragments generated by the U.S. Human Genome Projects or other public and private genome sequencing projects. Clones in the library which hybridize to detectable probes comprising the polynucleotides of the present invention are identified and their inserts, or portions thereof, are isolated using conventional methods such as restriction digestion or amplification reactions. The genomic inserts or portions thereof, are then cloned into a desired vector, such as an expression vector.

Alternatively, cDNAs may be prepared by obtaining mRNA from the tissue, cell, or organism of interest using mRNA preparation procedures utilizing poly A selection procedures or other techniques known to those skilled in the art. A first primer capable of hybridizing to the poly A tail of the mRNA is hybridized to the mRNA and a reverse transcription reaction is performed to generate a first cDNA strand.

The first cDNA strand is hybridized to a second primer containing at least 10, 15, 20, 25, 30, 35 or 40 consecutive nucleotides of the sequences of SEQ ID NOs 38-1756. In some embodiments, the primer comprises more than 40 nucleotides from the sequences of SEQ ID NOs 38-1756. If it is desired to obtain cDNAs containing the full protein coding sequence, including the authentic translation initiation site, the second primer used contains sequences located upstream of the translation initiation site. The second primer is extended to generate a second cDNA strand complementary to the first cDNA strand. Alternatively, RTPCR may be performed as described above using primers from both ends of the cDNA to be obtained.

cDNAs containing 5' fragments of the mRNA may be prepared by contacting an mRNA comprising the sequences of SEQ ID NOs: 38-1756 with a primer comprising at least 10, 15, 20, 25, 30, 35 or 40 consecutive nucleotides of the sequences complementary to SEQ ID NOs: 38-1756, hybridizing the primer to the mRNAs, and reverse transcribing the hybridized primer to make a first cDNA strand from the mRNAs.

Thereafter, a second cDNA strand complementary to the first cDNA strand is synthesized. The second cDNA strand may be made by hybridizing a primer complementary to sequences in the first cDNA strand to the first cDNA strand and extending the primer to generate the second cDNA strand.

The double stranded cDNAs made using the methods above are isolated and cloned. The cDNAs may be cloned into vectors such as plasmids or viral vectors capable of replicating in an appropriate host cell. For example, the host cell may be a bacterial, mammalian, avian, or insect cell.

Techniques for isolating mRNA, reverse transcribing a primer hybridized to mRNA to generate a first cDNA strand, extending a primer to make a second cDNA strand complementary to the first cDNA strand, isolating the double stranded cDNA and cloning the double stranded cDNA are well known to those skilled in the art and are described in Current Protocols in Molecular Biology, John Wiley 503 Sons, Inc. 1997 and Sambrook et al. Molecular Cloning: A Laboratory Manual, Second Edition, Cold Spring Harbor Laboratory Press, 1989, the entire disclosures of which are incorporated herein by reference.

Alternatively, kits for obtaining full length cDNAs, such as the GeneTrapper (Cat. No. 10356-020, Gibco, BRL), may be used for obtaining full length cDNAs. In this approach, cDNA inserts are cloned into double stranded phagemids. The cDNA library in the double stranded phagemids is then rendered single stranded by treatment with an endonuclease, such as the Gene II product of the phage F1, and Exonuclease III as described in the manual accompanying the GeneTrapper kit, which is incorporated herein by reference. A biotinylated oligonucleotide comprising the sequence of a 5' EST, or a fragment containing at least 10, 15, 20, 25, 30, 35 or 40 nucleotides thereof, is hybridized to the single stranded phagemids. In some procedures, the fragment may comprise more than 40 consecutive nucleotides from the 5' EST.

Hybrids between the biotinylated oligonucleotide and phagemids having inserts containing the 5' EST sequence are isolated by incubating the hybrids with streptavidin coated paramagnetic beads and retrieving the beads with a magnet. Thereafter, the resulting phagemids containing the 5' EST sequence are released from the beads and converted into double stranded DNA using a primer specific for the 5' EST sequence. The resulting double stranded DNA is transformed into bacteria. cDNAs containing the 5' EST sequence are identified by colony PCR or colony hybridization.

A plurality of cDNAs containing full length protein coding sequences, or sequences encoding only the mature protein remaining after the signal peptide is cleaved, may be provided as selected cDNA libraries for subsequent evaluation of the encoded proteins or use in diagnostic assays as described below.

IV. Expression of Proteins Encoded by cDNAs Isolated Using 5' ESTs cDNAs containing the full protein coding sequences of their corresponding mRNAs, or portions thereof, such as cDNAs encoding the mature protein remaining after the signal peptide is cleaved, may be used to express the secreted proteins, or portions thereof, which they encode as described in Example 30 below. If desired, the cDNAs may contain the sequences encoding the signal peptide to facilitate secretion of the expressed protein. It will be appreciated that a plurality of cDNAs containing the full protein coding sequences may be simultaneously cloned into expression vectors to create an expression library for analysis of the encoded proteins as described below.

EXAMPLE 30

Expression of the Proteins Encoded by the Genes Corresponding to the 5' ESTs

To express the proteins encoded by the genes corresponding to 5' ESTs (or portions thereof), full length cDNAs containing the entire protein coding region or extended cDNAs containing sequences adjacent to the 5' ESTs (or portions thereof) are obtained as described in Examples 27-29. If desired, the cDNAs may contain the sequences encoding the signal peptide to facilitate secretion of the expressed protein. The cDNAs may also contain sequences upstream of the sequences encoding the signal peptide, such as sequences which regulate expression levels or sequences which confer tissue specific expression.

The cDNA is operably linked to a promoter in an expression vector using conventional cloning technology. The expression vector may be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism in which the expression vector is introduced, as explained by Hatfield, et al., U.S. Pat. No. 5,082,767, incorporated herein by this reference.

The cDNA cloned into the expression vector may encode the entire protein (i.e. the signal peptide and the mature protein), the mature protein (i.e. the protein created by cleaving the signal peptide off), only the signal peptide or any other portion thereof.

The following is provided as one exemplary method to express the proteins encoded by the cDNAs corresponding to the 5' ESTs. First, the methionine initiation codon for the gene and the poly A signal of the gene are identified. If the nucleic acid encoding the polypeptide to be expressed lacks a methionine to serve as the intitiation site, an intiating methionine can be introduced next to the first codon of the nucleic acid using conventional techniques. Similarly, if the cDNA lacks a poly A signal, this sequence can be added to the construct by, for example, splicing out the Poly A sequence from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The cDNA or portion thereof encoding the polpypeptide to be expressed is obtained by PCR from the bacterial vector using oligonucleotide primers complementary to the cDNA or portion thereof and containing restriction endonuclease sequences for Pst I incorporated into the 5' primer and BglII at the 5' end of the corresponding cDNA 3' primer, taking care to ensure that the cDNA is positioned in frame with the poly A signal. The purified fragment obtained from the resulting PCR reaction is digested with PstI, blunt ended with an exonuclease, digested with BglII, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). Preferably the expressed protein is released into the culture medium, thereby facilitating purification.

Alternatively, the extended cDNAs may be cloned into pED6dpc2 as described above. The resulting pED6dpc2 constructs may be transfected into a suitable host cell, such as COS 1 cells. Methotrexate resistant cells are selected and expanded. Preferably, the protein expressed from the extended cDNA is released into the culture medium thereby facilitating purification.

Proteins in the culture medium are separated by gel electrophoresis. If desired, the proteins may be ammonium sulfate precipitated or separated based on size or charge prior to electrophoresis.

As a control, the expression vector lacking a cDNA insert is introduced into host cells or organisms and the proteins in the medium are harvested. The secreted proteins present in the medium are detected using techniques such as Coomassie or silver staining or using antibodies against the protein encoded by the cDNA. Coomassie and silver staining techniques are familiar to those skilled in the art.

Antibodies capable of specifically recognizing the protein of interest may be generated using synthetic 15-mer peptides having a sequence encoded by the appropriate 5' EST, full length cDNA, extended cDNA or portion thereof. The synthetic peptides are injected into mice to generate antibody to the polypeptide encoded by the cDNA.

Secreted proteins from the host cells or organisms containing an expression vector which contains the cDNA derived from a 5' EST or a portion thereof are compared to those from the control cells or organism. The presence of a band in the medium from the cells containing the expression vector which is absent in the medium from the control cells indicates that the cDNA encodes a secreted protein. Generally, the band corresponding to the protein encoded by the cDNA will have a mobility near that expected based on the number of amino acids in the open reading frame of the cDNA. However, the band may have a mobility different than that expected as a result of modifications such as glycosylation, ubiquitination, or enzymatic cleavage.

Alternatively, if the protein expressed from the above expression vectors does not contain sequences directing its secretion, the proteins expressed from host cells containing an expression vector containing an insert encoding a secreted protein or portion thereof can be compared to the proteins expressed in host cells containing the expression vector without an insert. The presence of a band in samples from cells containing the expression vector with an insert which is absent in samples from cells containing the expression vector without an insert indicates that the desired protein or portion thereof is being expressed. Generally, the band will have the mobility expected for the secreted protein or portion thereof. However, the band may have a mobility different than that expected as a result of modifications such as glycosylation, ubiquitination, or enzymatic cleavage.

The protein encoded by the cDNA may be purified using standard immunochromatography techniques. In such procedures, a solution containing the secreted protein, such as the culture medium or a cell extract, is applied to a column having antibodies against the secreted protein attached to the chromatography matrix. The secreted protein is allowed to bind the immunochromatography column. Thereafter, the column is washed to remove non-specifically bound proteins. The specifically bound secreted protein is then released from the column and recovered using standard techniques.

If antibody production is not possible, the cDNA sequence or a portion thereof may be incorporated into expression vectors designed for use in purification schemes employing chimeric polypeptides. In such strategies the coding sequence of the cDNA is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites may be engineered between the β-globin gene or the nickel binding polypeptide and the cDNA or portion thereof. Thus, the two polypeptides of the chimera may be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (Basic Methods in Molecular Biology, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems such as the In vitro Express™ Translation Kit (Stratagene).

Following expression and purification of the secreted proteins encoded by the 5' ESTs, cDNAs, or portions thereof, the purified proteins may be tested for the ability to bind to the surface of various cell types as described in Example 31 below. It will be appreciated that a plurality of proteins expressed from these cDNAs may be included in a panel of proteins to be simultaneously evaluated for the activities specifically described below, as well as other biological roles for which assays for determining activity are available.

EXAMPLE 31

Analysis of Secreted Proteins to Determine Whether they Bind to the Cell Surface The proteins encoded by the 5' ESTs, cDNAs, or portions thereof are cloned into expression vectors such as those described in Example 30. The proteins are purified by size, charge, immunochromatography or other techniques familiar to those skilled in the art. Following purification, the proteins are labeled using techniques known to those skilled in the art. The labeled proteins are incubated with cells or cell lines derived from a variety of organs or tissues to allow the proteins to bind to any receptor present on the cell surface. Following the incubation, the cells are washed to remove non-specifically bound protein. The labeled proteins are detected by autoradiography. Alternatively, unlabeled proteins may be incubated with the cells and detected with antibodies having a detectable label, such as a fluorescent molecule, attached thereto.

Specificity of cell surface binding may be analyzed by conducting a competition analysis in which various amounts of unlabeled protein are incubated along with the labeled protein. The amount of labeled protein bound to the cell surface decreases as the amount of competitive unlabeled protein increases. As a control, various amounts of an unlabeled protein unrelated to the labeled protein is included in some binding reactions. The amount of labeled protein bound to the cell surface does not decrease in binding reactions containing increasing amounts of unrelated unlabeled protein, indicating that the protein encoded by the cDNA binds specifically to the cell surface.

As discussed above, secreted proteins have been shown to have a number of important physiological effects and, consequently, represent a valuable therapeutic resource. The secreted proteins encoded by the cDNAs or portions thereof made according to Examples 27-29 may be evaluated to determine their physiological activities as described below.

EXAMPLE 32

Assaying the Proteins Expressed from cDNAs for Cytokine, Cell Proliferation or Cell Differentiation Activity As discussed above, secreted proteins may act as cytokines or may affect cellular proliferation or differentiation. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7c and CMK. The proteins encoded by the above cDNAs may be evaluated for their ability to regulate T cell or thymocyte proliferation in assays such as those described above or in the following references, which are incorporated herein by reference: Current Protocols in Immunology, Ed. by J. E. Coligan et al., Greene Publishing Associates and Wiley-Interscience; Takai et al. J. Immunol. 137:3494-3500, 1986. Bertagnolli et al. J. Immunol. 145:1706-1712, 1990. Bertagnolli et al., Cellular Immunology 133:327-341, 1991. Bertagnolli, et al. J. Immunol. 149:3778-3783, 1992; Bowman et al., J. Immunol. 152: 1756-1761, 1994.

In addition, numerous assays for cytokine production and/or the proliferation of spleen cells, lymph node cells and thymocytes are known. These include the techniques disclosed in Current Protocols in Immunology. J. E. Coligan et al. Eds., Vol 1 pp. 3.12.1-3.12.14 John Wiley and Sons, Toronto. 1994; and Schreiber, R. D. In Current Protocols in Immunology., supra Vol 1 pp. 6.8.1-6.8.8, John Wiley and Sons, Toronto. 1994.

The proteins encoded by the cDNAs may also be assayed for the ability to regulate the proliferation and differentiation of hematopoietic or lymphopoietic cells. Many assays for such activity are familiar to those skilled in the art, including the assays in the following references, which are incorporated herein by reference: Bottomly, K., Davis, L. S. and Lipsky, P. E., Measurement of Human and Murine Interleukin 2 and Interleukin 4, In Current Protocols in Immunology., J. E. Coligan et al. Eds. Vol 1 pp. 6.3.1-6.3.12, John Wiley and Sons, Toronto. 1991; deVries et al., J. Exp. Med. 173:1205-1211, 1991; Moreau et al., Nature 36:690-692, 1988; Greenberger et al., Proc. Natl. Acad. Sci. U.S.A. 80:2931-2938, 1983; Nordan, R., Measurement of Mouse and Human Interleukin 6 In Current Protocols in Immunology. J. E. Coligan et al. Eds. Vol 1 pp. 6.6.1-6.6.5, John Wiley and Sons, Toronto. 1991; Smith et al., Proc. Natl. Acad. Sci. U.S.A. 83:1857-1861, 1986; Bennett, F., Giannotti, J., Clark, S. C. and Turner, K. J., Measurement of Human Interleukin 11 in Current Protocols in Immunology. J. E. Coligan et al. Eds. Vol 1 pp. 6.15.1 John Wiley and Sons, Toronto. 1991; Ciarletta, A., Giannotti, J., Clark, S. C. and Turner, K. J., Measurement of Mouse and Human Interleukin 9 In Current Protocols in Immunology. J. E. Coligan et al., Eds. Vol 1 pp. 6.13.1, John Wiley and Sons, Toronto. 1991.

The proteins encoded by the cDNAs may also be assayed for their ability to regulate T-cell responses to antigens. Many assays for such activity are familiar to those skilled in the art, including the assays described in the following references, which are incorporated herein by reference: Chapter 3 (In Vitro Assays for Mouse Lymphocyte Function), Chapter 6 (Cytokines and Their Cellular Receptors) and Chapter 7, (Immunologic Studies in Humans) in Current Protocols in Immunology, J. E. Coligan et al. Eds. Greene Publishing Associates and Wiley-Interscience; Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

Those proteins which exhibit cytokine, cell proliferation, or cell differentiation activity may then be formulated as pharmaceuticals and used to treat clinical conditions in which induction of cell proliferation or differentiation is beneficial. Alternatively, as described in more detail below, genes encoding these proteins or nucleic acids regulating the expression of these proteins may be introduced into appropriate host cells to increase or decrease the expression of the proteins as desired.

EXAMPLE 33

Assaying the Proteins Expressed from cDNAs or Portions thereof for Activity as Immune System Regulators The proteins encoded by the cDNAs or portions thereof may also be evaluated for their effects as immune regulators. For example, the proteins may be evaluated for their activity to influence thymocyte or splenocyte cytotoxicity. Numerous assays for such activity are familiar to those skilled in the art including the assays described in the following references, which are incorporated herein by reference: Chapter 3 (In Vitro Assays for Mouse Lymphocyte Function 3.1-3.19) and Chapter 7 (Immunologic studies in Humans) in Current Protocols in Immunology, J. E. Coligan et al. Eds, Greene Publishing Associates and Wiley-Interscience; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137: 3494-3500, 1986; Takai et al., J. Immunol. 140:508-512, 1988; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Bowman et al., J. Virology 61:1992-1998; Takai et al., J. Immunol. 140:508-512, 1988; Bertagnolli et al., Cellular Immunology 133:327-341, 1991; Brown et al., J. Immunol. 153:3079-3092, 1994.

The proteins encoded by the cDNAs or portions thereof may also be evaluated for their effects on T-cell dependent immunoglobulin responses and isotype switching. Numerous assays for such activity are familiar to those skilled in the art, including the assays disclosed in the following references, which are incorporated herein by reference: Maliszewski, J. Immunol. 144:3028-3033, 1990; Mond, J. J. and Brunswick, M Assays for B Cell Function: In vitro Antibody Production, Vol 1 pp. 3.8.1-3.8.16 in Current Protocols in Immunology. J. E. Coligan et al Eds., John Wiley and Sons, Toronto. 1994.

The proteins encoded by the cDNAs or portions thereof may also be evaluated for their effect on immune effector cells, including their effect on Th1 cells and cytotoxic lymphocytes. Numerous assays for such activity are familiar to those skilled in the art, including the assays disclosed in the following references, which are incorporated herein by reference: Chapter 3 (In Vitro Assays for Mouse Lymphocyte Function 3.1-3.19) and Chapter 7 (Immunologic Studies in Humans) in Current Protocols in Immunology, J. E. Coligan et al. Eds., Greene Publishing Associates and Wiley-Interscience; Takai et al., J. Immunol. 137:3494-3500, 1986; Takai et al.; J. Immunol. 140:508-512, 1988; Bertagnolli et al., J. Immunol. 149:3778-3783, 1992.

The proteins encoded by the cDNAs or portions thereof may also be evaluated for their effect on dendritic cell mediated activation of naive T-cells. Numerous assays for such activity are familiar to those skilled in the art, including the assays disclosed in the following references, which are incorporated herein by reference: Guery et al., J. Immunol. 134: 536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169:1255-1264, 1989; Bhardwaj et al., Journal of Clinical Investigation 94:797-807, 1994; and Inaba et al., Journal of Experimental Medicine 172:631-640, 1990.

The proteins encoded by the cDNAs or portions thereof may also be evaluated for their influence on the lifetime of lymphocytes. Numerous assays for such activity are familiar to those skilled in the art, including the assays disclosed in the following references, which are incorporated herein by reference: Darzynkiewicz et al., Cytometry 13:795-808, 1992; Gorczyca et al., Leukemia 7:659-670, 1993; Gorczyca et al., Cancer Research 53:1945-1951, 1993; Itoh etal., Cell 66:233-243, 1991; Zacharchuk, Journal of Immunology 145: 4037-4045, 1990; Zamai et al., Cytometry 14:891-897, 1993; Gorczyca et al., International Journal of Oncology 1:639-648, 1992.

Assays for proteins that influence early steps of T-cell commitment and development include, without limitation, those described in: Antica et al., Blood 84:111-117, 1994; Fine et al., Cellular immunology 155:111-122, 1994; Galy et al., Blood 85:2770-2778, 1995; Toki et al., Proc. Nat. Acad Sci. USA 88:7548-7551, 1991.

Those proteins which exhibit activity as immune system regulators activity may then be formulated as pharmaceuticals and used to treat clinical conditions in which regulation of immune activity is beneficial.

For example, the protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infection may be treatable using a protein of the present invention, including infections by HIV, hepatitis viruses, herpesviruses, mycobacteria, *Leishmania* spp., *malaria* spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses, in a number of ways. Down regulation may be in the form of inhibiting or blocking an immune response already in progress or may involve preventing the induction of an immune response. The functions of activated T-cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allergenic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci USA, 89:11102-11105 (1992). In addition, murine models of GVHD (see Paul ed., Fundamental Immunology, Raven Press, New York, 1989, pp. 846-847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/pr/pr mice or NZB hybrid mice, murine autoimmuno collagen arthritis, diabetes mellitus in OD mice and BB rats, and murine experimental myasthenia gravis (see Paul ed., Fundamental Immunology, Raven Press, New York, 1989, pp. 840-856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory form of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. The infected cells would now be capable of delivering a costimulatory signal to T cells in vivo, thereby activating the T cells.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acids encoding all or a portion of (e.g., a cytoplasmic-domain truncated portion) of an MHC class I $\alpha$ chain protein and $\beta_2$ macroglobulin protein or an MHC class II $\alpha$ chain protein and an MHC class II $\alpha$ chain protein to thereby express MHC class I or MHC class II proteins on the cell surface. Expression of the appropriate class II or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

Alternatively, as described in more detail below, genes encoding these proteins or nucleic acids regulating the expression of these proteins may be introduced into appropriate host cells to increase or decrease the expression of the proteins as desired.

EXAMPLE 34

Assaying the Proteins Expressed from cDNAs or Portions thereof for Hematopoiesis Regulating Activity The proteins encoded by the cDNAs or portions thereof may also be evaluated for their hematopoiesis regulating activity. For example, the effect of the proteins on embryonic stem cell differentiation may be evaluated. Numerous assays for such activity are familiar to those skilled in the art, including the assays disclosed in the following references, which are incorporated herein by reference: Johansson et al. Cellular Biology 15:141-151, 1995; Keller et al., Molecular and Cellular Biology 13:473-486, 1993; McClanahan et al., Blood 81:2903-2915, 1993.

The proteins encoded by the cDNAs or portions thereof may also be evaluated for their influence on the lifetime of stem cells and stem cell differentiation. Numerous assays for such activity are familiar to those skilled in the art, including the assays disclosed in the following references, which are incorporated herein by reference: Freshney, M. G. Methylcellulose Colony Forming Assays, in Culture of Hematopoietic Cells. R. I. Freshney, et al. Eds. pp. 265-268, Wiley-Liss, Inc., New York, N.Y. 1994; Hirayama et al., Proc. Natl. Acad. Sci. USA 89:5907-5911, 1992; McNiece, I. K. and Briddell, R. A. Primitive Hematopoietic Colony Forming Cells with High Proliferative Potential, in Culture of Hematopoietic Cells. R. I. Freshney, et al. eds. Vol pp. 23-39, Wiley-Liss, Inc., New York, N.Y. 1994; Neben et al., Experimental Hematology 22:353-359, 1994; Ploemacher, R. E. Cobblestone Area Forming Cell Assay, In Culture of Hematopoietic Cells. R. I. Freshney, et al. Eds. pp. 1-21, Wiley-Liss, Inc., New York, N.Y. 1994; Spooncer, E., Dexter, M. and Allen, T. Long Term Bone Marrow Cultures in the Presence of Stromal Cells, in Culture of Hematopoietic Cells. R. I. Freshney, et al. Eds. pp. 163-179, Wiley-Liss, Inc., New York, N.Y. 1994; Sutherland, H. J. Long Term Culture Initiating Cell Assay, in Culture of Hematopoietic Cells. R. I. Freshney, et al. Eds. pp. 139-162, Wiley-Liss, Inc., New York, N.Y. 1994.

Those proteins which exhibit hematopoiesis regulatory activity may then be formulated as pharmaceuticals and used to treat clinical conditions in which regulation of hematopoiesis is beneficial.

For example, a protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically anipulated for gene therapy. Alternatively, as described in more detail below, genes encoding these proteins or nucleic acids regulating the expression of these proteins may be introduced into appropriate host cells to increase or decrease the expression of the proteins as desired.

EXAMPLE 35

Assaying the Proteins Expressed from Extended cDNAs or Portions thereof for Regulation of Tissue Growth The proteins encoded by the extended cDNAs or portions thereof may also be evaluated for their effect on tissue growth. Numerous assays for such activity are familiar to those skilled in the art, including the assays disclosed in International Patent Publication No. WO95/16035, International Patent Publication No. WO95/05846 and International Patent Publication No. WO91/07491, which are incorporated herein by reference.

Assays for wound healing activity include, without limitation, those described in: Winter, *Epidermal Wound Healing*, pps. 71-112 (Maibach, Hl and Rovee, D T, eds.), Year Book Medical Publishers, Inc., Chicago, as modified by Eaglstein and Mertz, J. Invest. Dermatol 71:382-84 (1978) which are incorporated herein by reference.

Those proteins which are involved in the regulation of tissue growth may then be formulated as pharmaceuticals and used to treat clinical conditions in which regulation of tissue growth is beneficial. For example, a protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e., for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium) muscle (smooth, skeletal or cardiac) and vascular (including vascular endotheliun) tissue, or for promoting the growth of cells comprising such tissues. Part of the desired effects may be by inhibition or modulation of fibrotic scarring to allow normal tissue to generate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokinc damage.

A protein of the present invention may also be useful for promoting or inhibiting differentiation of tissues described above from precursor tissues or cells; or for inhibiting the growth of tissues described above.

Alternatively, as described in more detail below, genes encoding these proteins or nucleic acids regulating the expression of these proteins may be introduced into appropriate host cells to increase or decrease the expression of the proteins as desired.

EXAMPLE 36

Assaying the Proteins Expressed from cDNAs or Portions thereof for Regulation of Reproductive Hormones or Cell Movement The proteins encoded by the cDNAs or portions thereof may also be evaluated for their ability to regulate reproductive hormones, such as follicle stimulating hormone. Numerous assays for such activity are familiar to those skilled in the art, including the assays disclosed in the following references, which are incorporated herein by reference: Vale et al., Endocrinology 91:562-572, 1972; Ling et al., Nature 321:779-782, 1986; Vale et al., Nature 321:776-779, 1986; Mason et al., Nature 318:659-663, 1985; Forage et al., Proc. Natl. Acad. Sci. USA 83:3091-3095, 1986. Chapter 6.12 (Measurement of Alpha and Beta Chemokines) Current Protocols in Immunology, J. E. Coligan et al. Eds. Greene Publishing Associates and Wiley-Intersciece; Taub et al. J. Clin. Invest. 95:1370-1376, 1995; Lind et al. APMIS 103:140-146, 1995; Muller et al. Eur. J. Immunol. 25:1744-1748; Gruber et al. J. of Immunol. 152:5860-5867, 1994; Johnston et al. J. of Immunol. 153:1762-1768, 1994.

Those proteins which exhibit activity as reproductive hormones or regulators of cell movement may then be formulated as pharmaceuticals and used to treat clinical conditions in which regulation of reproductive hormones or cell movement are beneficial.

For example, a protein of the present invention may also exhibit activin- or inhibin-related activities. inhibins are characterized by their ability to inhibit the release of follicle stimulating hormone (FSH), while activins are characterized by their ability to stimulate the release of folic stimulating horme (FSH). Thus, a protein of the present invention, alone or in heterodimers with a member of the Inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-B group, may be useful as a fertility inducing therapeutic, based upon the ability of activin molecules in stimulating FSH release from cells of the anterior pituitary. See, for example, U.S. Pat. No. 4,798,885, the disclosure of which is incorporated herein by reference. A protein of the invention may also be useful for advancement of the onset of fertility in sexually immature mammals, so as to increase the lifetime reproductive performance of domestic animals such as cows, sheep and pigs.

Alternatively, as described in more detail below, genes encoding these proteins or nucleic acids regulating the expression of these proteins may be introduced into appropriate host cells to increase or decrease the expression of the proteins as desired.

EXAMPLE 36A

Assaying the Proteins Expressed from cDNAs or Portions thereof for Chemotactic/Chemokinetic Activity The proteins encoded by the cDNAs or portions thereof may also be evaluated for chemotacti/chemokinetic activity. For example, a protein of the present invention may have chemotactic or chemokinetic activity (e.g., act as a chemokine) for mammalian cells, including, for example, monocytes, fibroblasts, neutrophils, T-cells, mast cells, cosinophils, epithelial and/or endothelial cells. Chemotactic and chmokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokincs 6.12.1-6.12.28; Taub et al. J. Clin. Invest. 95:1370-1376, 1995; Lind et al. APMIS 103:140-146, 1995; Mueller et al Eur. J. Immunol. 25:1744-1748; Gruber et al. J. of Immunol. 152:5860-5867, 1994; Johnston et al. J. of Immunol, 153:1762-1768, 1994.

EXAMPLE 37

Assaying the Proteins Expressed from cDNAs or Portions thereof for Regulation of Blood Clotting The proteins encoded by the cDNAs or portions thereof may also be evaluated for their effects on blood clotting. Numerous assays for such activity are familiar to those skilled in the art, including the assays disclosed in the following references, which are incorporated herein by reference: Linet et al., J. Clin. Pharmacol. 26:131-140, 1986; Burdick et al., Thrombosis Res. 45:413-419, 1987; Humphrey et al., Fibrinolysis 5:71-79 (1991); Schaub, Prostaglandins 35:467-474, 1988.

Those proteins which are involved in the regulation of blood clotting may then be formulated as pharmaceuticals and used to treat clinical conditions in which regulation of blood clotting is beneficial.

For example, a protein of the invention may also exhibit hemostatic or thrombolytic activity. As a result, such a protein is expected to be useful in treatment of various coagulations disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as,for example, infarction of cardiac and central nervous system vessels (e.g., stroke).

Alternatively, as described in more detail below, genes encoding these proteins or nucleic acids regulating the expression of these proteins may be introduced into appropriate host cells to increase or decrease the expression of the proteins as desired.

EXAMPLE 38

Assaying the Proteins Expressed from cDNAs or Portions thereof for Involvement in Receptor/Ligand Interactions The proteins encoded by the cDNAs or portions thereof may also be evaluated for their involvement in receptor/ligand interactions. Numerous assays for such involvement are familiar to those skilled in the art, including the assays disclosed in the following references, which are incorporated herein by reference: Chapter 7.28 (Measurement of Cellular Adhesion under Static Conditions 7.28.1-7.28.22) in Current Protocols in Immunology, J. E. Coligan et al. Eds. Greene Publishing Associates and Wiley-Interscience; Takai et al., Proc. Natl. Acad. Sci. USA 84:6864-6868, 1987; Bierer et al., J. Exp. Med. 168:1145-1156, 1988; Rosenstein et al., J. Exp. Med. 169:149-160, 1989; Stoltenborg et al., J. Immunol. Methods 175:59-68, 1994; Stitt et al., Cell 80:661-670, 1995; Gyuris et al., Cell 75:791-803, 1993.

For example, the proteins of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as sclectins, integrins and their ligands) and receptor/ligand pairs involved in antigen presentation, antigen recognition and development of cellular and humoral immune respones). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

EXAMPLE 38A

Assaying the Proteins Expressed from cDNAs or Portions thereof for Anti-Inflammatory Activity The proteins encoded by the cDNAs or portions thereof may also be evaluated for anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemic-reperfusioninury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

EXAMPLE 38B

Assaying the Proteins Expressed from cDNAs or Portions thereof for Tumor Inhibition Activity The proteins encoded by the cDNAs or portions thereof may also be evaluated for tumor inhibition activity. In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

EXAMPLE 39

Identification of Proteins which Interact with Polypeptides Encoded by 5' ESTs

Proteins which interact with the polypeptides encoded by cDNAs derived from the 5' ESTs or fragments thereof, such as receptor proteins, may be identified using two hybrid systems such as the Matchmaker Two Hybrid System 2 (Catalog No. K1604-1, Clontech). As described in the manual accompanying the Matchmaker Two Hybrid System 2 (Catalog No. K1604-1, Clontech), which is incorporated herein by reference, the cDNAs derived from 5' ESTs, or fragments thereof, are inserted into an expression vector such that they are in frame with DNA encoding the DNA binding domain of the yeast transcriptional activator GAL4. cDNAs in a cDNA library which encode proteins which might interact with the polypeptides encoded by cDNAs derived from the 5' ESTs or fragments thereof are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins which interact with the polypeptide encoded by the cDNAs derived from the 5' ESTs or fragments thereof.

Alternatively, the system described in Lustig et al., Methods in Enzymology 283: 83-99 (1997), the disclosure of which is incorporated herein by reference, may be used for identifying molecules which interact with the polypeptides encoded by extended cDNAs. In such systems, in vitro transcription reactions are performed on a pool of vectors containing extended cDNA inserts cloned downstream of a promoter which drives in vitro transcription. The resulting pools of mRNAs are introduced into *Xenopus laevis* oocytes. The oocytes are then assayed for a desired acitivity.

Alternatively, the pooled in vitro transcription products produced as described above may be translated in vitro. The pooled in vitro translation products can be assayed for a desired activity or for interaction with a known polypeptide.

Proteins or other molecules interacting with polypeptides encoded by extended cDNAs can be found by a variety of additional techniques. In one method, affinity columns containing the polypeptide encoded by the extended cDNA or a portion thereof can be constructed. In some versions, of this method the affinity column contains chimeric proteins in which the protein encoded by the extended cDNA or a portion thereof is fused to glutathione S-transferase. A mixture of cellular proteins or pool of expressed proteins as described above and is applied to the affinity column. Proteins interacting with the polypeptide attached to the column can then be isolated and analyzed on 2-D electrophoresis gel as described in Ramunsen et al. Electrophoresis, 18, 588-598 (1997), the disclosure of which is incorporated herein by reference. Alternatively, the proteins retained on the affinity column can be purified by electrophoresis based methods and sequenced. The same method can be used to isolate antibodies, to screen phage display products, or to screen phage display human antibodies.

Proteins interacting with polypeptides encoded by extended cDNAs or portions thereof can also be screened by using an Optical Biosensor as described in Edwards et Leatherbarrow, Analytical Biochemistry, 246, 1-6 (1997), the disclosure of which is incorporated herein by reference. The main advantage of the method is that it allows the determination of the association rate between the protein and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred manometers from the sensor surface). In these screening assays, the target molecule can be one of the polypeptides encoded by extended cDNAs or a portion thereof and the test sample can be a collection of proteins extracted from tissues or cells, a pool of expressed proteins, combinatorial peptide and/or chemical libraries,or phage displayed peptides. The tissues or cells from which the test proteins are extracted can originate from any species.

In other methods, a target protein is immobilized and the test population is a collection of unique polypeptides encoded by the extended cDNAs or portions thereof.

To study the interaction of the proteins encoded by the extended cDNAs or portions thereof with drugs, the microdialysis coupled to HPLC method described by Wang et al., Chromatographia, 44, 205-208 (1997) or the affinity capillary electrophoresis method described by Busch et al., J. Chromatogr. 777:311-328 (1997), the disclosures of which are incorporated herein by reference can be used. The system described in U.S. Pat. No. 5,654,150, the disclosure of which is incorporated herein by reference, may also be used to identify molecules which interact with the polypeptides encoded by the extended cDNAs. In this system, pools of extended cDNAs are transcribed and translated in vitro and the reaction products are assayed for interaction with a known polypeptide or antibody.

It will be appreciated by those skilled in the art that the proteins expressed from the cDNAs or portions thereof may be assayed for numerous activities in addition to those specifically enumerated above. For example, the expressed proteins may be evaluated for applications involving control and regulation of inflammation, tumor proliferation or metastasis, infection, or other clinical conditions. In addition, the proteins expressed from the cDNAs or portions thereof may be useful as nutritional agents or cosmetic agents.

Epitopes and Antibody Fusions

A preferred embodiment of the present invention is directed to epitope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes. See, e.g., Geysen, et al. (1983) Proc. Natl. Acad. Sci. USA 81:39984002. It is particularly noted that although a particular epitope may not be immunogenic, it is nonetheless useful since antibodies can be made in vitro to any epitope.

An epitope can comprise as few as 3 amino acids in a spatial conformation which is unique to the epitope. Generally an epitope consists of at least 6 such amino acids, and more often at least 8-10 such amino acids. In preferred embodiment, antigenic epitopes comprise a number of amino acids that is any integer between 3 and 50. Fragments which function as epitopes may be produced by any conventional means. See, e.g., Houghten, R. A., Proc. Natl. Acad. Sci. USA 82:5131-5135 (1985), further described in U.S. Pat. No. 4,631,211. Methods for determining the amino acids which make up an epitope include x-ray crystallography, 2-dimensional nuclear magnetic resonance, and epitope mapping, e.g., the Pepscan method described by H. Mario Geysen et al. (1984);. Proc. Natl. Acad. Sci. U.S.A. 81:3998-4002; PCT Publication No. WO 84/03564; and PCT Publication No. WO 84/03506. Another example is the algorithm of Jameson and Wolf, Comp. Appl. Biosci. 4:181-186 (1988) (said references incorporated by reference in their entireties). The Jameson-Wolf antigenic analysis, for example, may be performed using the computer program PROTEAN, using default parameters (Version 3.11 for the Power MacIntosh, DNASTAR, Inc., 1228 South Park Street Madison, Wis.

Antigenic epitopes are useful, for example, to raise antibodies, including monoclonal antibodies, that specifically bind the epitope. (See, for instance, Wilson et al., Cell 37:767-778 (1984); Sutcliffe, J. G. et al., Science 219:660-666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

Epitope-bearing polypeptides of the present invention are used to induce antibodies according to methods well known in the art including, but not limited to, in vivo immunization, in vitro immunization, and phage display methods. See, e.g., Sutcliffe, et al., supra; Wilson, et al., supra, and Bittle, et al. (1985) J. Gen. Virol. 66:2347-2354. If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al. (1988) Nature 331:84-86. Fusion proteins that have a disulfide-linked dimeric structure due to the IgG portion can also be more efficient in binding and neutralizing other molecules than monomeric polypeptides or fragments thereof alone. See, e.g., Fountoulakis et al. (1995) J. Biochem. 270:3958-3964. Nucleic acids encoding the above epitopes can also be recombined with a gene of interest as an epitope tag to aid in detection and purification of the expressed polypeptide.

Additonal fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos.: 5,605,793; 5,811,238; 5,834,252; 5,837,458; and Patten, P. A., et al., Curr. Opinion Biotechnol. 8:724-733 (1997); Harayama, S., Trends Biotechnol. 16(2):76-82 (1998); Hansson, L. O., et al. J. Mol. Biol. 287:265-276 (1999); and Lorenzo, M. M. and Blasco, R., Biotechniques 24(2):308-313 (1998) (each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991) J. Immunol. 147:60-69; U.S. Pat. Nos. 5,573,920, 4,474,893, 5,601,819, 4,714,681, 4,925,648; Kostelny, S. A. et al. (1992) J. Immunol. 148:1547-1553.

In some embodiments, the antibodies may be capable of specifically binding to a protein or polypeptide encoded by 5' ESTs (or cDNAs or genomic DNAs obtainable therefrom), fragments of 5' ESTs (or cDNAs or genomic DNAs obtainable therefrom), positional segments of 5' ESTs (or cDNAs or genomic DNAs obtainable therefrom) or fragments of positional segments of 5' ESTs (or cDNAs or genomic DNAs obtainable therefrom). For example, the antibody may be capable of specifically binding to a polypeptide of one of SEQ ID NOs: 1757-3475, a fragment of a polypeptide of one of SEQ ID NOs: 1757-3475, a positional segment of a polypeptide of one of SEQ ID NOs.: 1757-3475, or a fragment of a positional segment of a polypeptide of one of SEQ ID NOs.: 1757-3475. In some embodiments, the antibody may be capable of binding an antigenic determinant or an epitope in a protein or polypeptide encoded by 5' ESTs (or cDNAs or genomic DNAs obtainable therefrom), fragments of 5' ESTs (or cDNAs or genomic DNAs obtainable therefrom), positional segments of 5' ESTs (or cDNAs or genomic DNAs obtainable therefrom) or fragments of positional segments of 5' ESTs (or cDNAs or genomic DNAs obtainable therefrom) nucleic acids. For example, the antibody may be capable of binding to an antigenic determinant or an epitope in a polypeptide of one of SEQ ID NOs: 1757-3475, a fragment of a polypeptide of one of SEQ ID NOs: 1757-3475, a positional segment of a polypeptide of one of SEQ ID NOs.: 1757-3475, or a fragment of a positional segment of a polypeptide of one of SEQ ID NOs.: 1757-3475.

Antibodies of the present invention may be described or specified in terms of the epitope(s) or portion(s) of a polypeptide of the present invention which are recognized or specifically bound by the antibody.

In the case of secreted proteins, the antibodies may specifically bind a full-length protein encoded by a nucleic acid of the present invention, a mature protein (i.e. the protein generated by cleavage of the signal peptide) encoded by a nucleic acid of the present invention, or a signal peptide encoded by a nucleic acid of the present invention. Moreover, the epitope(s) or polypeptide portion(s) may be specified as described herein, e.g., by N-terminal and C-terminal positions, by size in contiguous amino acid residues, or listed in the Tables and sequence listing. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *ANTIBODIES: A LABORATORY MANUAL*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563-681 (Elsevier, N.Y., 1981) (said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41-50; Ames, R. S. et al. (1995) J. Immunol. Methods 184:177-186; Kettleborough, C. A. et al. (1994) Eur. J. Immunol. 24:952-958; Persic, L. et al. (1997) Gene 187 9-18; Burton, D. R. et al. (1994) Advances in Immunology 57:191-280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992) BioTechniques 12(6):864-869; and Sawai, H. et al. (1995) AJRI 34:26-34; and Better, M. et al. (1988) Science 240:1041-1043 (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46-88; Shu, L. et al. (1993) PNAS 90:7995-7999; and Skerra, A. et al. (1988) Science 240:1038-1040. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) J. Immunol. Methods 125:191-202; and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., (1991) Molecular Immunology 28(4/5):489-498; Studnicka G. M. et al. (1994) Protein Engineering 7(6):805-814; Roguska M. A. et al. (1994) PNAS 91:969-973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91-99; U.S. Pat. No. 5,474,981; Gillies, S. O. et al. (1992) PNAS 89:1428-1432; Fell, H. P. et al. (1991) J. Immunol. 146:2446-2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535-10539; Zheng, X. X. et al. (1995) J. Immunol. 154:5590-5600; and Vil, H. et al. (1992) PNAS 89:11337-11341 (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998) Blood 92(6):1981-1988; Chen, Z. et al. (1998) Cancer Res. 58(16):3668-3678; Harrop, J. A. et al. (1998) J. Immunol. 161(4):1786-1794; Zhu, Z. et al. (1998) Cancer Res. 58(15):3209-3214; Yoon, D. Y. et al. (1998) J. Immunol. 160(7):3170-3179; Prat, M. et al. (1998) J. Cell. Sci. 111 (Pt2):237-247; Pitard, V. et al. (1997) J. Immunol. Methods 205(2):177-190; Liautard, J. et al. (1997) Cytokinde 9(4): 233-241; Carlson, N. G. et al. (1997) J. Biol. Chem. 272(17): 11295-11301; Taryman, R. E. et al. (1995) Neuron 14(4):755-762; Muller, Y. A. et al. (1998) Structure 6(9):1153-1167; Bartunek, P. et al. (1996) Cytokine 8(1):14-20 (said references incorporated by reference in their entireties).

As discussed above, antibodies of the polypeptides of the invention can, in turn, be utilized to generate anti-idiotypic antibodies that "mimic" polypeptides of the invention using techniques well known to those skilled in the art. See, e.g. Greenspan and Bona, FASEB J. 7(5):437-444 (1989); Nissinoff, J. Immunol. 147(8):2429-2438 (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and therby block its biological activity,

EXAMPLE 40

Production of an Antibody to a Human Protein

Substantially pure protein or polypeptide is isolated from the transfected or transformed cells as described in Example 30. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes of any of the peptides identified and isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

B. Polyclonal Antibody Production by Immunization

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

V. Use of 5' ESTs or Sequences Obtainable therefrom as Reagents

The 5' ESTs of the present invention (or cDNAs or genomic DNAs obtainable therefrom) therefrom may be used as reagents in isolation procedures, diagnostic assays, and forensic procedures. For example, sequences from the 5' ESTs (or cDNAs or genomic DNAs obtainable therefrom), may be detectably labeled and used as probes to isolate other sequences capable of hybridizing to them. In addition, sequences from the 5' ESTs (or cDNAs or genomic DNAs obtainable therefrom), may be used to design PCR primers to be used in isolation, diagnostic, or forensic procedures.

EXAMPLE 41

Preparation of PCR Primers and Amplification of DNA

The 5' EST sequences (or cDNAs or genomic DNAs obtainable therefrom) may be used to prepare PCR primers for a variety of applications, including isolation procedures for cloning nucleic acids capable of hybridizing to such sequences, diagnostic techniques and forensic techniques. In some embodiments, the PCR primers may be used to amplify a sequence encoding all or a portion of a secreted polypeptide from a genomic library, such as genomic libraries generated by the U.S. Human Genome Project or other public and private genome sequencing projects.

The PCR primers may be at least 10, 15, 20, 25, 30, 35, or 40 bases in length. In some embodiments, the PCR primers may be more than 40 bases in length. It is preferred that the primer pairs have approximately the same G/C ratio, so that melting temperatures are approximately the same. A variety of PCR techniques are familiar to those skilled in the art. For a review of PCR technology, see Molecular Cloning to Genetic Engineering White, B. A. Ed. in Methods in Molecular Biology 67: Humana Press, Totowa 1997. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

EXAMPLE 42

Use of 5' ESTs or Nucleic Acids Obtainable therefrom as Probes

Probes derived from 5' ESTs (or cDNAs or genomic DNAs obtainable therefrom), including full length cDNAs or genomic sequences, may be labeled with detectable labels familiar to those skilled in the art, including radioisotopes and non-radioactive labels, to provide a detectable probe. The detectable probe may be single stranded or double stranded and may be made using techniques known in the art, including in vitro transcription, nick translation, or kinase reactions.

A nucleic acid sample containing a sequence capable of hybridizing to the labeled probe is contacted with the labeled probe. If the nucleic acid in the sample is double stranded, it may be denatured prior to contacting the probe. In some applications, the nucleic acid sample may be immobilized on a surface such as a nitrocellulose or nylon membrane. The nucleic acid sample may comprise nucleic acids obtained from a variety of sources, including genomic DNA, cDNA libraries, RNA, or tissue samples.

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described above.

In some embodiments, the detectable probes may be used to identify clones in a genomic DNA library which include sequences encoding all or part of a secreted protein. For example, the genomic library may be a genomic library generated by the U.S. Human Genome Project or other public and private genome sequencing projects.

PCR primers made as described in Example 41 above may be used in forensic analyses, such as the DNA fingerprinting techniques described in Examples 43-47 below. Such analyses may utilize detectable probes or primers based on the sequences of the 5' ESTs or of cDNAs or genomic DNAs isolated using the 5' ESTs.

EXAMPLE 43

Forensic Matching by DNA Sequencing

In one exemplary method, DNA samples are isolated from forensic specimens of, for example, hair, semen, blood or skin cells by conventional methods. A panel of PCR primers based on a number of the 5' ESTs, or cDNAs or genomic DNAs isolated therefrom as described above, is then utilized in accordance with Example 41 to amplify DNA of approximately 100-200 bases in length from the forensic specimen. Corresponding sequences are obtained from a test subject. Each of these identification DNAs is then sequenced using standard techniques, and a simple database comparison determines the differences, if any, between the sequences from the subject and those from the sample. Statistically significant differences between the suspect's DNA sequences and those from the sample conclusively prove a lack of identity. This lack of identity can be proven, for example, with only one sequence. Identity, on the other hand, should be demonstrated with a large number of sequences, all matching. Preferably, a minimum of 50 statistically identical sequences of 100 bases in length are used to prove identity between the suspect and the sample.

EXAMPLE 44

Positive Identification by DNA Sequencing

The technique outlined in the previous example may also be used on a larger scale to provide a unique fingerprint-type identification of any individual. In this technique, primers are prepared from a large number of sequences from Example 25, or cDNA or genomic DNA sequences obtainable therefrom. Preferably, 20 to 50 different primers are used. These primers are used to obtain a corresponding number of PCR-generated DNA segments from the individual in question in accordance with Example 41. Each of these DNA segments is sequenced, using the methods set forth in Example 43. The database of sequences generated through this procedure uniquely identifies the individual from whom the sequences were obtained. The same panel of primers may then be used at any later time to absolutely correlate tissue or other biological specimen with that individual.

EXAMPLE 45

Southern Blot Forensic Identification

The procedure of Example 44 is repeated to obtain a panel of at least 10 amplified sequences from an individual and a specimen. Preferably, the panel contains at least 50 amplified sequences. More preferably, the panel contains 100 amplified sequences. In some embodiments, the panel contains 200 amplified sequences. This PCR-generated DNA is then digested with one or a combination of, preferably, four base specific restriction enzymes. Such enzymes are commercially available and known to those of skill in the art. After digestion, the resultant gene fragments are size separated in multiple duplicate wells on an agarose gel and transferred to nitrocellulose using Southern blotting techniques well known to those with skill in the art. For a review of Southern blotting see Davis et al. (*Basic Methods in Molecular Biology,* 1986, Elsevier Press. pp 62-65).

A panel of probes based on the sequences of the 5' ESTs (or cDNAs or genomic DNAs obtainable therefrom), or fragments thereof of at least 8, 10, 12, 15, 20, 23, 25, 28, 30, 35, 40, 50, 75, 100, 200, 300, 500, or 1000 bases, are radioactively or colorimetrically labeled using methods known in the art, such as nick translation or end labeling, and hybridized to the Southern blot using techniques known in the art (Davis et al., supra).

Preferably, at least 5 to 10 of these labeled probes are used, and more preferably at least about 20 or 30 are used to provide a unique pattern. The resultant bands appearing from the hybridization of a large sample of 5' ESTs (or cDNAs or genomic DNAs obtainable therefrom) will be a unique identifier. Since the restriction enzyme cleavage will be different for every individual, the band pattern on the Southern blot will also be unique. Increasing the number of probes derived from 5' ESTs (or cDNAs or genomic DNAs obtainable therefrom) will provide a statistically higher level of confidence in the identification since there will be an increased number of sets of bands used for identification.

EXAMPLE 46

Dot Blot Identification Procedure

Another technique for identifying individuals using the 5' EST sequences disclosed herein utilizes a dot blot hybridization technique.

Genomic DNA is isolated from nuclei of subject to be identified. Oligonucleotide probes of approximately 30 bp in length are synthesized that correspond to at least 10, preferably 50 sequences from the 5' ESTs or cDNAs or genomic DNAs obtainable therefrom. The probes are used to hybridize to the genomic DNA through conditions known to those in the art. The oligonucleotides are end labeled with $P^{32}$ using polynucleotide kinase (Pharmacia). Dot Blots are created by spotting the genomic DNA onto nitrocellulose or the like using a vacuum dot blot manifold (BioRad, Richmond Calif.). The nitrocellulose filter containing the genomic sequences is baked or UV linked to the filter, prehybridized and hybridized with labeled probe using techniques known in the art (Davis et al. supra). The $^{32}P$ labeled DNA fragments are sequentially hybridized with successively stringent conditions to detect minimal differences between the 30 bp sequence and the DNA. Tetramethylammonium chloride is useful for identifying clones containing small numbers of nucleotide mismatches (Wood et al., Proc. Natl. Acad. Sci. USA 82(6):1585-1588 (1985)) which is hereby incorporated by reference. A unique pattern of dots distinguishes one individual from another individual.

5' EST sequences (or cDNAs or genomic DNAs obtainable therefrom) or oligonucleotides containing at least 10, 15, 20, 25, 30, 35, or 40 consecutive bases from these sequences can be used as probes in the following alternative fingerprinting technique.

Preferably, a plurality of probes having sequences from different genes are used in the alternative fingerprinting technique. Example 47 below provides a representative alternative fingerprinting procedure in which the probes are derived from 5' ESTs. However, those skilled in the art will appreciate that the procedure of Example 47 may readily be implemented with probes containing sequences from cDNAs or genomic sequences obtainable from the 5' ESTs.

EXAMPLE 47

Alternative "Fingerprint" Identification Technique 20-mer oligonucleotides are prepared from a large number, e.g. 50, 100, or 200, 5' EST sequences using commercially available oligonucleotide services such as Genset, Paris, France. Cell samples from the test subject are processed for DNA using techniques well known to those with skill in the art. The nucleic acid is digested with restriction enzymes such as EcoRI and XbaI. Following digestion, samples are applied to wells for electrophoresis. The procedure, as known in the art, may be modified to accommodate polyacrylamide electrophoresis, however in this example, samples containing 5 ug of DNA are loaded into wells and separated on 0.8% agarose gels. The gels are transferred onto nitrocellulose using standard Southern blotting techniques.

10 ng of each of the oligonucleotides are pooled and end-labeled with $P^{32}$. The nitrocellulose is prehybridized with blocking solution and hybridized with the labeled probes. Following hybridization and washing, the nitrocellulose filter is exposed to X-Omat AR X-ray film. The resulting hybridization pattern will be unique for each individual.

It is additionally contemplated within this example that the number of probe sequences used can be varied for additional accuracy or clarity.

The antibodies generated in Examples 30 and 40 above may be used to identify the tissue type or cell species from which a sample is derived as described above.

EXAMPLE 48

Identification of Tissue Types or Cell Species by Means of Labeled Tissue Specific Antibodies Identification of specific tissues is accomplished by the visualization of tissue specific antigens by means of antibody preparations according to Examples 30 and 40 which are conjugated, directly or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

Antisera for these procedures must have a potency exceeding that of the native preparation, and for that reason, antibodies are concentrated to a mg/ml level by isolation of the gamma globulin fraction, for example, by ion-exchange chromatography or by ammonium sulfate fractionation. Also, to provide the most specific antisera, unwanted antibodies, for example to common proteins, must be removed from the gamma globulin fraction, for example by means of insoluble immunoabsorbents, before the antibodies are labeled with the marker. Either monoclonal or heterologous antisera is suitable for either procedure.

A. Immunohistochemical Techniques

Purified, high-titer antibodies, prepared as described above, are conjugated to a detectable marker, as described, for example, by Fudenberg, H., Chap. 26 in: Basic 503 Clinical Immunology, 3rd Ed. Lange, Los Altos, Calif. (1980) or Rose, N. et al., Chap. 12 in: Methods in Immunodiagnosis, 2d Ed. John Wiley 503 Sons, New York (1980).

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific antitissue antibodies can be labeled with ferritin or other electron dense particles, and localization of the ferritin coupled antigen-antibody complexes achieved by means of an electron microscope. In yet another approach, the antibodies are radiolabeled, with, for example $^{125}I$, and detected by overlaying the antibody treated preparation with photographic emulsion.

Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required.

Tissue sections and cell suspensions are prepared for immunohistochemical examination according to common histological techniques. Multiple cryostat sections (about 4 μm, unfixed) of the unknown tissue and known control, are mounted and each slide covered with different dilutions of the antibody preparation. Sections of known and unknown tissues should also be treated with preparations to provide a positive control, a negative control, for example, pre-immune sera, and a control for non-specific staining, for example, buffer.

Treated sections are incubated in a humid chamber for 30 min at room temperature, rinsed, then washed in buffer for 30-45 min. Excess fluid is blotted away, and the marker developed.

If the tissue specific antibody was not labeled in the first incubation, it can be labeled at this time in a second antibody-antibody reaction, for example, by adding antiserum-producing species, for example, fluorescein labeled antibody to mouse IgG. Such labeled sera are commercially available.

The antigen found in the tissues by the above procedure can be quantified by measuring the intensity of color or fluorescence on the tissue section, and calibrating that signal using appropriate standards.

B. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection.

A tissue sample is homogenized using a Virtis apparatus; cell suspensions are disrupted by Dounce homogenization or osmotic lysis, using detergents in either case as required to disrupt cell membranes, as is the practice in the art. Insoluble cell components such as nuclei, microsomes, and membrane fragments are removed by ultracentrifugation, and the soluble protein-containing fraction concentrated if necessary and reserved for analysis.

A sample of the soluble protein solution is resolved into individual protein species by conventional SDS polyacrylamide electrophoresis as described, for example, by Davis, L. et al., Section 19-2 in: Basic Methods in Molecular Biology (P. Leder, ed), Elsevier, New York (1986), using a range of amounts of polyacrylamide in a set of gels to resolve the entire molecular weight range of proteins to be detected in the sample. A size marker is run in parallel for purposes of estimating molecular weights of the constituent proteins. Sample size for analysis is a convenient volume of from 5 to 55 μl, and containing from about 1 to 100 μg protein. An aliquot of each of the resolved proteins is transferred by blotting to a nitrocellulose filter paper, a process that maintains the pattern of resolution. Multiple copies are prepared. The procedure, known as Western Blot Analysis, is well described in Davis, L. et al., (above) Section 19-3. One set of nitrocellulose blots is stained with Coomassie Blue dye to visualize the entire set of proteins for comparison with the antibody bound proteins. The remaining nitrocellulose filters are then incubated with a solution of one or more specific antisera to tissue specific proteins prepared as described in Examples 30 and 40. In this procedure, as in procedure A above, appropriate positive and negative sample and reagent controls are run.

In either procedure A or B, a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody.

The visualization of tissue specific antigen binding at levels above those seen in control tissues to one or more tissue specific antibodies, prepared from the gene sequences identified from EST sequences, can identify tissues of unknown origin, for example, forensic samples, or differentiated tumor tissue that has metastasized to foreign bodily sites.

In addition to their applications in forensics and identification, 5' ESTs (or cDNAs or genomic DNAs obtainable therefrom) may be mapped to their chromosomal locations. Example 49 below describes radiation hybrid (RH) mapping of human chromosomal regions using 5' ESTs. Example 50 below describes a representative procedure for mapping a 5' EST to its location on a human chromosome. Example 51 below describes mapping of 5' ESTs on metaphase chromosomes by Fluorescence In Situ Hybridization (FISH). Those skilled in the art will appreciate that the method of Examples 49-51 may also be used to map cDNAs or genomic DNAs obtainable from the 5' ESTs to their chromosomal locations.

EXAMPLE 49

Radiation Hybrid Mapping of 5' ESTs to the Human Genome

Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends on the radiation dose. These fragments are rescued by fusion with cultured rodent cells, yielding subclones containing different portions of the human genome. This technique is described by Benham et al. (*Genomics* 4:509-517, 1989) and Cox et al., (*Science* 250:245-250, 1990), the entire contents of which are hereby incorporated by reference. The random and independent nature of the subclones permits efficient mapping of any human genome marker. Human DNA isolated from a panel of 80-100 cell lines provides a mapping reagent for ordering 5' ESTs. In this approach, the frequency of breakage between markers is used to measure distance, allowing construction of fine resolution maps as has been done using conventional ESTs (Schuler et al., *Science* 274:540-546, 1996, hereby incorporated by reference).

RH mapping has been used to generate a high-resolution whole genome radiation hybrid map of human chromosome 17q22-q25.3 across the genes for growth hormone (GH) and thymidine kinase (TK) (Foster et al., *Genomics* 33:185-192, 1996), the region surrounding the Gorlin syndrome gene (Obermayr et al., *Eur. J Hum. Genet.* 4:242-245, 1996), 60 loci covering the entire short arm of chromosome 12 (Raeymaekers et al., *Genomics* 29:170-178, 1995), the region of human chromosome 22 containing the neurofibromatosis type 2 locus (Frazer et al., *Genomics* 14:574-584, 1992) and 13 loci on the long arm of chromosome 5 (Warrington et al., *Genomics* 11:701-708, 1991).

EXAMPLE 50

Mapping of 5' ESTs to Human Chromosomes Using PCR Techniques

5' ESTs (or cDNAs or genomic DNAs obtainable therefrom) may be assigned to human chromosomes using PCR based methodologies. In such approaches, oligonucleotide primer pairs are designed from sequences in the 5' ESTs (or cDNAs or genomic DNAs obtainable therefrom) to minimize the chance of amplifying through an intron. Preferably, the oligonucleotide primers are 18-23 bp in length and are designed for PCR amplification. The creation of PCR primers from known sequences is well known to those with skill in the art. For a review of PCR technology see Erlich, H. A., *PCR Technology; Principles and Applications for DNA Amplification.* 1992. W.H. Freeman and Co., New York.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 μCu of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the distance between the ends of the primer sequences in the 5' ESTs (or cDNAs or genomic DNAs obtainable therefrom) from which the primers are derived, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given 5' EST (or cDNA or genomic DNA obtainable therefrom). DNA is isolated from the somatic hybrids and used as starting templates for PCR reactions using the primer pairs from the 5' ESTs (or cDNAs or genomic DNAs obtainable therefrom). Only those somatic cell hybrids with chromosomes containing the human gene corresponding to the 5' EST (or cDNA or genomic DNA obtainable therefrom) will yield an amplified fragment. The 5' ESTs are assigned to a chromosome by analysis of the segregation pattern of PCR products from the somatic hybrid DNA templates. The single human chromosome present in all cell hybrids that give rise to an amplified fragment is the chromosome containing that 5' EST (or cDNA or genomic DNA obtainable therefrom). For a review of techniques and analysis of results from somatic cell gene mapping experiments. (See Ledbetter et al., Genomics 6:475-481 (1990).)

Alternatively, the 5' ESTs (or cDNAs or genomic DNAs obtainable therefrom) may be mapped to individual chromosomes using FISH as described in Example 51 below.

EXAMPLE 51

Mapping of 5' ESTs to Chromosomes using Fluorescence In Situ Hybridization

Fluorescence in situ hybridization allows the 5' EST (or cDNAs or genomic DNAs obtainable therefrom) to be mapped to a particular location on a given chromosome. The chromosomes to be used for fluorescence in situ hybridization techniques may be obtained from a variety of sources including cell cultures, tissues, or whole blood.

In a preferred embodiment, chromosomal localization of a 5' EST (or cDNA or genomic DNAs obtained therefrom) are obtained by FISH as described by Cherif et al. (*Proc. Natl. Acad Sci. U.S.A.*, 87:6639-6643, 1990). Metaphase chromosomes are prepared from phytohemagglutinin (PHA)-stimulated blood cell donors. PHA-stimulated lymphocytes from healthy males are cultured for 72 h in RPMI-1640 medium. For synchronization, methotrexate (10 µM) is added for 17 h, followed by addition of 5-bromodeoxyuridine (5-BudR, 0.1 mM) for 6 h. Colcemid (1 µg/ml) is added for the last 15 min before harvesting the cells. Cells are collected, washed in RPMI, incubated with a hypotonic solution of KCl (75 mM) at 37° C. for 15 min and fixed in three changes of methanol: acetic acid (3:1). The cell suspension is dropped onto a glass slide and air dried. The 5' EST (or cDNA or genomic DNA obtainable therefrom) is labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5-10 min.

Slides kept at −20° C. are treated for 1 h at 37° C. with RNase A (100 µg/ml), rinsed three times in 2×SSC and dehydrated in an ethanol series. Chromosome preparations are denatured in 70% formamide, 2×SSC for 2 min at 70° C., then dehydrated at 4° C. The slides are treated with proteinase K (10 µg/100 ml in 20 mM Tris-HCl, 2 mM $CaCl_2$) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al., supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular 5' EST (or cDNA or genomic DNA obtainable therefrom) may be localized to a particular cytogenetic R-band on a given chromosome.

Once the 5' ESTs (or cDNAs or genomic DNAs obtainable therefrom) have been assigned to particular chromosomes using the techniques described in Examples 49-51 above, they may be utilized to construct a high resolution map of the chromosomes on which they are located or to identify the chromosomes in a sample.

EXAMPLE 52

Use of 5' ESTs to Construct or Expand Chromosome Maps

Chromosome mapping involves assigning a given unique sequence to a particular chromosome as described above. Once the unique sequence has been mapped to a given chromosome, it is ordered relative to other unique sequences located on the same chromosome. One approach to chromosome mapping utilizes a series of yeast artificial chromosomes (YACs) bearing several thousand long inserts derived from the chromosomes of the organism from which the 5' ESTs (or cDNAs or genomic DNAs obtainable therefrom) are obtained. This approach is described in Ranaiah Nagaraja et al. Genome Research 7:210-222, March 1997. Briefly, in this approach each chromosome is broken into overlapping pieces which are inserted into the YAC vector. The YAC inserts are screened using PCR or other methods to determine whether they include the 5' EST (or cDNA or genomic DNA obtainable therefrom) whose position is to be determined. Once an insert has been found which includes the 5' EST (or cDNA or genomic DNA obtainable therefrom), the insert can be analyzed by PCR or other methods to determine whether the insert also contains other sequences known to be on the chromosome or in the region from which the 5' EST (or cDNA or genomic DNA obtainable therefrom) was derived. This process can be repeated for each insert in the YAC library to determine the location of each of the 5' ESTs (or cDNAs or genomic DNAs obtainable therefrom) relative to one another and to other known chromosomal markers. In this way, a high resolution map of the distribution of numerous unique markers along each of the organisms chromosomes may be obtained.

As described in Example 53 below 5' ESTs (or cDNAs or genomic DNAs obtainable therefrom) may also be used to identify genes associated with a particular phenotype, such as hereditary disease or drug response.

EXAMPLE 53

Identification of Genes Associated with Hereditary Diseases or Drug Response This example illustrates an approach useful for the association of 5' EST sequences (or cDNAs or genomic DNAs obtainable therefrom) with particular phenotypic characteristics. In this example, a particular 5' EST (or cDNAs or genomic DNAs obtainable therefrom) is used as a test probe to associate that 5' EST (or cDNAs or genomic DNAs obtainable therefrom) with a particular phenotypic characteristic.

5' ESTs (or cDNAs or genomic DNAs obtainable therefrom) are mapped to a particular location on a human chromosome using techniques such as those described in Examples 49 and 50 or other techniques known in the art. A search of Mendelian Inheritance in Man (V. McKusick, Mendelian Inheritance in Man (available on line through Johns Hopkins University Welch Medical Library) reveals the region of the human chromosome which contains the 5' EST (or cDNAs or genomic DNAs obtainable therefrom) to be a very gene rich region containing several known genes and several diseases or phenotypes for which genes have not been identified. The gene corresponding to this 5' EST (or cDNAs or genomic DNAs obtainable therefrom) thus becomes an immediate candidate for each of these genetic diseases.

Cells from patients with these diseases or phenotypes are isolated and expanded in culture. PCR primers from the 5'

EST sequences (or cDNAs or genomic DNAs obtainable therefrom) are used to screen genomic DNA, mRNA or cDNA obtained from the patients. 5' ESTs (or cDNAs or genomic DNAs obtainable therefrom) that are not amplified in the patients can be positively associated with a particular disease by further analysis. Alternatively, the PCR analysis may yield fragments of different lengths when the samples are derived from an individual having the phenotype associated with the disease than when the sample is derived from a healthy individual, indicating that the gene containing the 5' EST may be responsible for the genetic disease.

VI. Use of 5' ESTs (or cDNAs or Genomic DNAs Obtainable therefrom) to Construct Vectors The present 5' ESTs (or cDNAs or genomic DNAs obtainable therefrom) may also be used to construct secretion vectors capable of directing the secretion of the proteins encoded by genes inserted in the vectors. Such secretion vectors may facilitate the purification or enrichment of the proteins encoded by genes inserted therein by reducing the number of background proteins from which the desired protein must be purified or enriched. Exemplary secretion vectors are described in Example 54 below.

EXAMPLE 54

Construction of Secretion Vectors

The secretion vectors of the present invention include a promoter capable of directing gene expression in the host cell, tissue, or organism of interest. Such promoters include the Rous Sarcoma Virus promoter, the SV40 promoter, the human cytomegalovirus promoter, and other promoters familiar to those skilled in the art.

A signal sequence from a 5' EST (or cDNAs or genomic DNAs obtainable therefrom) is operably linked to the promoter such that the mRNA transcribed from the promoter will direct the translation of the signal peptide. The host cell, tissue, or organism may be any cell, tissue, or organism which recognizes the signal peptide encoded by the signal sequence in the 5' EST (or cDNAs or genomic DNAs obtainable therefrom). Suitable hosts include mammalian cells, tissues or organisms, avian cells, tissues, or organisms, insect cells, tissues or organisms, or yeast.

In addition, the secretion vector contains cloning sites for inserting genes encoding the proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

The secretion vector may be DNA or RNA and may integrate into the chromosome of the host, be stably maintained as an extrachromosomal replicon in the host, be an artificial chromosome, or be transiently present in the host. Many nucleic acid backbones suitable for use as secretion vectors are known to those skilled in the art, including retroviral vectors, SV40 vectors, Bovine Papilloma Virus vectors, yeast integrating plasmids, yeast episomal plasmids, yeast artificial chromosomes, human artificial chromosomes, P element vectors, baculovirus vectors, or bacterial plasmids capable of being transiently introduced into the host.

The secretion vector may also contain a polyA signal such that the polyA signal is located downstream of the gene inserted into the secretion vector.

After the gene encoding the protein for which secretion is desired is inserted into the secretion vector, the secretion vector is introduced into the host cell, tissue, or organism using calcium phosphate precipitation, DEAE-Dextran, electroporation, liposome-mediated transfection, viral particles or as naked DNA. The protein encoded by the inserted gene is then purified or enriched from the supernatant using conventional techniques such as ammonium sulfate precipitation, immunoprecipitation, immunochromatography, size exclusion chromatography, ion exchange chromatography, and hplc. Alternatively, the secreted protein may be in a sufficiently enriched or pure state in the supernatant or growth media of the host to permit it to be used for its intended purpose without further enrichment.

The signal sequences may also be inserted into vectors designed for gene therapy. In such vectors, the signal sequence is operably linked to a promoter such that mRNA transcribed from the promoter encodes the signal peptide. A cloning site is located downstream of the signal sequence such that a gene encoding a protein whose secretion is desired may readily be inserted into the vector and filsed to the signal sequence. The vector is introduced into an appropriate host cell. The protein expressed from the promoter is secreted extracellularly, thereby producing a therapeutic effect.

EXAMPLE 55

Fusion Vectors

The 5' ESTs (or cDNAs or genomic DNAs obtainable therefrom) may be used to construct fusion vectors for the expression of chimeric polypeptides. The chimeric polypeptides comprise a first polypeptide portion and a second polypeptide portion. In the fusion vectors of the present invention, nucleic acids encoding the first polypeptide portion and the second polypeptide portion are joined in frame with one another so as to generate a nucleic acid encoding the chimeric polypeptide. The nucleic acid encoding the chimeric polypeptide is operably linked to a promoter which directs the expression of an mRNA encoding the chimeric polypeptide. The promoter may be in any of the expression vectors described herein including those described in Examples 30 and 54.

Preferably, the fusion vector is maintained in multiple copies in each host cell. In some embodiments, the multiple copies are maintained extrachromosomally. In other embodiments, the multiple copies result from amplification of a chromosomal sequence.

The first polypeptide portion may comprise any of the polypeptides encoded by the 5' ESTs (or cDNAs or genomic DNAs obtainable therefrom) or fragments thereof. For example, the fragments may comprise at least 6, 8, 10, 12, 15, 18, 20, 23, 25, 28, 30, 35, 40, 50 or more than 50 consecutive amino acids of the polypeptides encoded by the 5' ESTs (or cDNAs or genomic DNAs obtainable therefrom).

The second polypeptide portion may comprise any polypeptide of interest. In some embodiments, the second polypeptide portion may comprise a polypeptide having a detectable enzymatic activity such as green fluorescent protein or β galactosidase. Chimeric polypeptides in which the second polypeptide portion comprises a detectable polypeptide may be used to determine the intracellular localization of the first polypeptide portion. In such procedures, the fusion vector encoding the chimeric polypeptide is introduced into a host cell under conditions which facilitate the expression of the chimeric polypeptide. Where appropriate, the cells are treated with a detection reagent which is visible under the microscope following a catalytic reaction with the detectable polypeptide and the cellular location of the detection reagent is determined. For example, if the polypeptide having a detectable enzymatic activity is β galactosidase, the cells may be treated with Xgal. Alternatively, where the detectable polypeptide is directly detectable without the addition of a detection reagent, the intracellular location of the chimeric polypeptide is determined by performing microscopy under conditions in which the dectable polypeptide is visible. For example, if the detectable polypeptide is green fluorescent protein or a modified version thereof, microscopy is performed by exposing the host cells to light having an appropriate wavelength to cause the green fluorescent protein or modified version thereof to fluoresce.

Alternatively, the second polypeptide portion may comprise a polypeptide whose isolation, purification, or enrichment is desired. In such embodiments, the isolation, purification, or enrichment of the second polypeptide portion may be achieved by performing the immunoaffinity chromatography procedures described below using an immunoaffinity column having an antibody directed against the first polypeptide portion coupled thereto.

The proteins encoded by the 5' ESTs (or cDNAs or genomic DNAs obtainable therefrom) or fragments thereof may also be used to generate antibodies as described herein in order to identify the tissue type or cell species from which a sample is derived.

EXAMPLE 56

Identification of Tissue Types or Cell Species by Means of Labeled Tissue Specific Antibodies Identification of specific tissues is accomplished by the visualization of tissue specific antigens by means of antibody preparations according to Examples 30 and 40 which are conjugated, directly or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

Antisera for these procedures must have a potency exceeding that of the native preparation, and for that reason, antibodies are concentrated to a mg/ml level by isolation of the gamma globulin fraction, for example, by ion-exchange chromatography or by ammonium sulfate fractionation. Also, to provide the most specific antisera, unwanted antibodies, for example to common proteins, must be removed from the gamma globulin fraction, for example by means of insoluble immunoabsorbents, before the antibodies are labeled with the marker. Either monoclonal or heterologous antisera is suitable for either procedure.

1. Immunohistochemical Techniques

Purified, high-titer antibodies, prepared as described above, are conjugated to a detectable marker, as described, for example, by Fudenberg, H., Chap. 26 in: *Basic 503 Clinical Immunology*, 3$^{rd}$ Ed. Lange, Los Altos, Calif. (1980) or Rose, et al., Chap. 12 in: *Methods in ImmunodiagNOsis*, 2d Ed. John Wiley and Sons, New York (1980), the disclosures of which are incorporated herein by reference.

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific antitissue antibodies can be labeled with ferritin or other electron dense particles, and localization of the ferritin coupled antigen-antibody complexes achieved by means of an electron microscope. In yet another approach, the antibodies are radiolabeled, with, for example $^{125}$I, and detected by overlaying the antibody treated preparation with photographic emulsion.

Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required.

Tissue sections and cell suspensions are prepared for immunohistochemical examination according to common histological techniques. Multiple cryostat sections (about 4 µm, unfixed) of the unknown tissue and known control, are mounted and each slide covered with different dilutions of the antibody preparation. Sections of known and unknown tissues should also be treated with preparations to provide a positive control, a negative control, for example, pre-immune sera, and a control for non-specific staining, for example, buffer.

Treated sections are incubated in a humid chamber for 30 min at room temperature, rinsed, then washed in buffer for 30-45 min. Excess fluid is blotted away, and the marker developed.

If the tissue specific antibody was not labeled in the first incubation, it can be labeled at this time in a second antibody-antibody reaction, for example, by adding fluorescein- or enzyme-conjugated antibody against the immunoglobulin class of the antiserum-producing species, for example, fluorescein labeled antibody to mouse IgG. Such labeled sera are commercially available.

The antigen found in the tissues by the above procedure can be quantified by measuring the intensity of color or fluorescence on the tissue section, and calibrating that signal using appropriate standards.

2. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection.

A tissue sample is homogenized using a Virtis apparatus; cell suspensions are disrupted by Dounce homogenization or osmotic lysis, using detergents in either case as required to disrupt cell membranes, as is the practice in the art. Insoluble cell components such as nuclei, microsomes, and membrane fragments are removed by ultracentrifugation, and the soluble protein-containing fraction concentrated if necessary and reserved for analysis.

A sample of the soluble protein solution is resolved into individual protein species by conventional SDS polyacrylamide electrophoresis as described, for example, by Davis, L. et al., Section 19-2 in: *Basic Methods in Molecular Biology* (P. Leder, ed), Elsevier, New York (1986), the disclosure of which is incorporated herein by reference, using a range of amounts of polyacrylamide in a set of gels to resolve the entire molecular weight range of proteins to be detected in the sample. A size marker is run in parallel for purposes of estimating molecular weights of the constituent proteins. Sample size for analysis is a convenient volume of from 5 to 55 µl, and containing from about 1 to 100 µg protein. An aliquot of each of the resolved proteins is transferred by blotting to a nitrocellulose filter paper, a process that maintains the pattern of resolution. Multiple copies are prepared. The procedure, known as Western Blot Analysis, is well described in Davis, L. et al., supra Section 19-3. One set of nitrocellulose blots is stained with Coomassie Blue dye to visualize the entire set of proteins for comparison with the antibody bound proteins. The remaining nitrocellulose filters are then incubated with a solution of one or more specific antisera to tissue specific proteins prepared as described in Examples 30 and 40. In this procedure, as in procedure A above, appropriate positive and negative sample and reagent controls are run.

In either procedure described above a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody.

EXAMPLE 57

Immunohistochemical Localization of Polypeptides

The antibodies prepared as described in Examples 30 and 40 above may be utilized to determine the cellular location of a polypeptide. The polypeptide may be any of the polypeptides encoded by the 5' ESTs (or cDNAs or genomic DNAs obtainable therefrom) or fragments thereof. For example, the fragments may comprise at least 6, 8, 10, 12, 15, 18, 20, 23, 25, 28, 30, 35, 40, 50 or more than 50 consecutive amino acids of the polypeptides encoded by the 5' ESTs (or cDNAs or genomic DNAs obtainable therefrom). In some embodiments, the polypeptide may be a chimeric polypeptide such as those encoded by the fusion vectors described above.

Cells expressing the polypeptide to be localized are applied to a microscope slide and fixed using any of the procedures typically employed in immunohistochemical localization techniques, including the methods described in Current Protocols in Molecular Biology, John Wiley and Sons, Inc. 1997. Following a washing step, the cells are contacted with the antibody. In some embodiments, the antibody is conjugated to a detectable marker as described above to facilitate detection. Alternatively, in some embodiments, after the cells have been contacted with an antibody to the polypeptide to be localized, a secondary antibody which has been conjugated to a detectable marker is placed in contact with the antibody against the polypeptide to be localized.

Thereafter, microscopy is performed under conditions suitable for visualizing the cellular location of the polypeptide.

The visualization of tissue specific antigen binding at levels above those seen in control tissues to one or more tissue specific antibodies, directed against the polypeptides encoded by 5' ESTs (or cDNAs or genomic DNAs obtainable therefrom) or fragments thereof, can identify tissues of unknown origin, for example, forensic samples, or differentiated tumor tissue that has metastasized to foreign bodily sites.

The antibodies of Example 30 and 40 may also be used in the immunoaffinity chromatography techniques described below to isolate, purify or enrich the polypeptides encoded by the 5' ESTs (or cDNAs or genomic DNAs obtainable therefrom) or fragments thereof. The immunoaffinity chromatography techniques described below may also be used to isolate, purify or enrich polypeptides which have been linked to the polypeptides encoded by the 5' ESTs (or cDNAs or genomic DNAs obtainable therefrom) or fragments thereof.

EXAMPLE 58

Immunoaffinity Chromatography

Antibodies prepared as described above are coupled to a support. Preferably, the antibodies are monoclonal antibodies, but polyclonal antibodies may also be used. The support may be any of those typically employed in immunoaffinity chromatography, including Sepharose CL-4B (Pharmacia, Piscataway, N.J.), Sepharose CL-2B (Pharmacia, Piscataway, N.J.), Affi-gel 10 (Biorad, Richmond, Calif.), or glass beads.

The antibodies may be coupled to the support using any of the coupling reagents typically used in immunoaffinity chromatography, including cyanogen bromide. After coupling the antibody to the support, the support is contacted with a sample which contains a target polypeptide whose isolation, purification or enrichment is desired. The target polypeptide may be a polypeptide encoded by the 5' ESTs (or cDNAs or genomic DNAs obtainable therefrom) or fragments thereof. The target polypeptides may also be polypeptides which have been linked to the polypeptides encoded by the 5' ESTs (or cDNAs or genomic DNAs obtainable therefrom) or fragments thereof using the fusion vectors described above.

Preferably, the sample is placed in contact with the support for a sufficient amount of time and under appropriate conditions to allow at least 50% of the target polypeptide to specifically bind to the antibody coupled to the support.

Thereafter, the support is washed with an appropriate wash solution to remove polypeptides which have non-specifically adhered to the support. The wash solution may be any of those typically employed in immunoaffinity chromatography, including PBS, Tris-lithium chloride buffer (0.1M lysine base and 0.5M lithium chloride, pH 8.0), Tris-hydrochloride buffer (0.05M Tris-hydrochloride, pH 8.0), or Tris/Triton/NaCl buffer (50 mM Tris.cl, pH 8.0 or 9.0, 0.1% Triton X-100, and 0.5M NaCl).

After washing, the specifically bound target polypeptide is eluted from the support using the high pH or low pH elution solutions typically employed in immunoaffinity chromatography. In particular, the elution solutions may contain an eluant such as triethanolamine, diethylamine, calcium chloride, sodium thiocyanate, potasssium bromide, acetic acid, or glycine. In some embodiments, the elution solution may also contain a detergent such as Triton X-100 or octyl-β-D-glucoside.

The 5' ESTs (or cDNAs or genomic DNAs obtainable therefrom) may also be used to clone sequences located upstream of the 5' ESTs which are capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative fashion. Example 59 describes a method for cloning sequences upstream of the 5' ESTs (or cDNAs or genomic DNAs obtainable therefrom).

The 5' ESTs (or cDNAs or genomic DNAs obtainable therefrom) may also be used to clone sequences located upstream of the 5' ESTs (or cDNAs or genomic DNAs obtainable therefrom) which are capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative fashion as described below.

EXAMPLE 59

Use of 5' ESTs to Clone Upstream Sequences from Genomic DNA

Sequences derived from 5' ESTs may be used to isolate the promoters of the corresponding genes using chromosome walking techniques. In one chromosome walking technique, which utilizes the GenomeWalker™ kit available from Clontech, five complete genomic DNA samples are each digested with a different restriction enzyme which has a 6 base recognition site and leaves a blunt end. Following digestion, oligonucleotide adapters are ligated to each end of the resulting genomic DNA fragments.

For each of the five genomic DNA libraries, a first PCR reaction is performed according to the manufacturer's instructions (which are incorporated herein by reference) using an outer adaptor primer provided in the kit and an outer gene specific primer. The gene specific primer should be selected to be specific for the 5' EST of interest and should have a melting temperature, length, and location in the 5' EST which is consistent with its use in PCR reactions. Each first PCR reaction contains 5 ng of genomic DNA, 5 µl of 10× Tth reaction buffer, 0.2 mM of each dNTP, 0.2 µM each of outer adaptor primer and outer gene specific primer, 1.1 mM of Mg(OAc)$_2$, and 1 µl of the Tth polymerase 50× mix in a total volume of 50 µl. The reaction cycle for the first PCR reaction is as follows: 1 min—94° C./2 sec—94° C., 3 min—72° C. (7 cycles)/2 sec—94° C., 3 min—67° C. (32 cycles)/5 min—67° C.

The product of the first PCR reaction is diluted and used as a template for a second PCR reaction according to the manufacturer's instructions using a pair of nested primers which are located internally on the amplicon resulting from the first PCR reaction. For example, 5 µl of the reaction product of the first PCR reaction mixture may be diluted 180 times. Reactions are made in a 50 µl volume having a composition identical to that of the first PCR reaction except the nested primers are used. The first nested primer is specific for the adaptor, and is provided with the GenomeWalker™ kit. The second nested primer is specific for the particular 5' EST for which the promoter is to be cloned and should have a melting temperature, length, and location in the 5' EST which is consistent with its use in PCR reactions. The reaction parameters of the second PCR reaction are as follows: 1 min—94° C./2 sec—94° C., 3 min—72° C. (6 cycles)/2 sec—94° C., 3 min—67° C. (25 cycles)/5 min—67° C.

The product of the second PCR reaction is purified, cloned, and sequenced using standard techniques. Alternatively, tow or more human genomic DNA libraries can be constructed by using two or more restriction enzymes. The digested genomic DNA is cloned into vectors which can be converted into single stranded, circular, or linear DNA. A biotinylated oligonucleotide comprising at least 15 nucleotides from the 5' EST sequence is hybridized to the single stranded DNA. Hybrids between the biotinylated oligonucleotide and the single stranded DNA containing the EST sequence are isolated as described in Example 29 above. Thereafter, the single stranded DNA containing the EST sequence is released from the beads and converted into double stranded DNA using a primer specific for the 5' EST sequence or a primer corresponding to a sequence included in the cloning vector. The resulting double stranded DNA is transformed into bacteria. cDNAS containing the 5' sequence are identified by colony PCR or colony hybridization.

Once the upstream genomic sequences have been cloned and sequenced as described above, prospective promoters and transcription start sites within the upstream sequences may be identified by comparing the sequences upstream of the 5 ESTs with databases containing known transcription start sites, transcription factor binding sites, or promoter sequences.

In addition, promoters in the upstream sequences may be identified using promoter reporter vectors as described in Example 60.

EXAMPLE 60

Identification of Promoters in Cloned Upstream Sequences

The genomic sequences upstream of the 5' ESTs are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the 5' ESTs are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Appropriate host cells for the promoter reporter vectors may be chosen based on the results of the above described determination of expression patterns of the ESTs. For example, if the expression pattern analysis indicates that the mRNA corresponding to a particular 5' EST is expressed in fibroblasts, the promoter reporter vector may be introduced into a human fibroblast cell line.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into the cloning sites in the promoter reporter vectors.

EXAMPLE 61

Cloning and Identification of Promoters

Using the method described in Example 59 above, sequences upstream of several genes were obtained. Using the primer pairs GGG AAG ATG GAG ATA GTA TTG CCT G (SEQ ID NO:29) and CTG CCA TGT ACA TGA TAG AGA GAT TC (SEQ ID NO:30), the promoter having the internal designation P13H2 (SEQ ID NO:31) was obtained.

Using the primer pairs GTA CCA GGGG ACT GTG ACC ATT GC (SEQ ID NO:32) and CTG TGA CCA TTG CTC CCA AGA GAG (SEQ ID NO:33), the promoter having the internal designation P15B4 (SEQ ID NO:34) was obtained.

Using the primer pairs CTG GGA TGG AAG GCA CGG TA (SEQ ID NO:35) and GAG ACC ACA CAG CTA GAC AA (SEQ ID NO:36), the promoter having the internal designation P29B6 (SEQ ID NO:37) was obtained.

FIG. 6 provides a schematic description of the promoters isolated and the way they are assembled with the corresponding 5' tags. The upstream sequences were screened for the presence of motifs resembling transcription factor binding sites or known transcription start sites using the computer program MatInspector release 2.0, August 1996.

FIG. 7 describes the transcription factor binding sites present in each of these promoters. The columns labeled matrice provides the name of the MatInspector matrix used. The column labeled position provides the 5' postion of the promoter site. Numeration of the sequence starts from the transcription site as determined by matching the genomic sequence with the 5' EST sequence. The column labeled "orientation" indicates the DNA strand on which the site is found, with the +strand bding the coding strand as determined by matching the genomic sequence with the sequence of the 5' EST. The column labeled "score" provides the MatInspector score found for this site. The column labeled "length" provides the length of the site in nucleotides. The column labeled "sequence" provides the sequence of the site found.

Bacterial clones containing plasmids containing the promoter sequences described above described above are presently stored in the inventor's laboratories under the internal identification numbers provided above. The inserts may be recovered from these stored materials by growing an aliquot of the appropriate bacterial clone in the appropriate medium. The plasmid DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the EST insertion. The PCR product which corresponds to the 5' EST can then be manipulated using standard cloning techniques familiar to those skilled in the art.

The promoters and other regulatory sequences located upstream of the 5' ESTs may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described in Example 26 above. For example, if a promoter which confers a high level of expression in muscle is desired, the promoter sequence upstream of a 5' EST derived from an mRNA which is expressed at a high level in muscle, as determined by the method of Example 26, may be used in the expression vector.

Preferably, the desired promoter is placed near multiple restriction sites to facilitate the cloning of the desired insert downstream of the promoter, such that the promoter is able to drive expression of the inserted gene. The promoter may be inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA signal downstream of the multiple restriction sites for directing the polyadenylation of mRNA transcribed from the gene inserted into the expression vector.

Following the identification of promoter sequences using the procedures of Examples 59-61, proteins which interact with the promoter may be identified as described in Example 62 below.

EXAMPLE 62

Identification of Proteins which Interact with Promoter Sequences, Upstream Regulatory Sequences, or mRNA Sequences within the promoter region which are likely to bind transcription factors may be identified by homology to known transcription factor binding sites or through conventional mutagenesis or deletion analyses of reporter plasmids containing the promoter sequence. For example, deletions may be made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels may be further localized using site directed mutagenesis, linker scanning analysis, or other techniques familiar to those skilled in the art.

Nucleic acids encoding proteins which interact with sequences in the promoter may be identified using one-hybrid systems such as those described in the manual accompanying the Matchmaker One-Hybrid System kit avalilabe from Clontech (Catalog No. K1603-1), the disclosure of which is incorporated herein by reference. Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem.

A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts may be inserted into expression vectors or in vitro transcription vectors. Binding of the polypeptides encoded by the inserts to the promoter DNA may be confirmed by techniques familiar to those skilled in the art, such as gel shift analysis or DNAse protection analysis.

VII. Use of 5' ESTs (or cDNAs or Genomic DNAs Obtainable therefrom) in Gene Therapy The present invention also comprises the use of 5' ESTs (or cDNAs or genomic DNAs obtainable therefrom) in gene therapy strategies, including antisense and triple helix strategies as described in Examples 63 and 64 below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

EXAMPLE 63

Preparation and Use of Antisense Oligonucleotides

The antisense nucleic acid molecules to be used in gene therapy may be either DNA or RNA sequences. They may comprise a sequence complementary to the sequence of the 5' EST or cDNAs or genomic DNAs obtainable therefrom. The antisense nucleic acids should have a length and melting temperature sufficient to permit formation of an intracellular duplex having sufficient stability to inhibit the expression of the mRNA in the duplex. Strategies for designing antisense nucleic acids suitable for use in gene therapy are disclosed in Green et al., Ann. Rev. Biochem. 55:569-597 (1986) and Izant and Weintraub, Cell 36:1007-1015 (1984), which are hereby incorporated by reference.

In some strategies, antisense molecules are obtained from a nucleotide sequence encoding a protein by reversing the orientation of the coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of the antisense nucleic acids in vivo by operably linking DNA containing the antisense sequence to a promoter in an expression vector.

Alternatively, oligonucleotides which are complementary to the strand normally transcribed in the cell may be synthesized in vitro. Thus, the antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies are described by Rossi et al., Pharmacol. Ther. 50(2):245-254, (1991).

Various types of antisense oligonucleotides complementary to the sequence of the 5' EST or cDNAs or genomic DNAs obtainable therefrom may be used. In one preferred embodiment, stable and semi-stable antisense oligonucleotides described in International Application No. PCT WO94/23026, hereby incorporated by reference, are used. In these moleucles, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, hereby incorporated by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The antisense molecules are introduced onto cell samples at a number of different concentrations preferably between $1 \times 10^{-10}$M to $1 \times 10^{-4}$M. Once the minimum concentration that can adequately control gene expression is identified, the optimized dose is translated into a dosage suitable for use in vivo. For example, an inhibiting concentration in culture of $1 \times 10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

It is further contemplated that the antisense oligonucleotide sequence is incorporated into a ribozyme sequence to enable the antisense to specifically bind and cleave its target mRNA. For technical applications of ribozyme and antisense oligonucleotides see Rossi et al., supra.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

The 5' ESTs of the present invention (or cDNAs or genomic DNAs obtainable therefrom) may also be used in gene therapy approaches based on intracellular triple helix formation. Triple helix oligonucleotides are used to inhibit transcription from a genome. They are particularly useful for studying alterations in cell activity as it is associated with a particular gene. The 5' EST sequences (or cDNAs or genomic DNAs obtainable therefrom) of the present invention or, more preferably, a portion of those sequences, can be used to inhibit gene expression in individuals having diseases associated with expression of a particular gene. Similarly, a portion of the 5' EST (or cDNAs or genomic DNAs obtainable therefrom) can be used to study the effect of inhibiting transcription of a particular gene within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from either the 5' EST or from the gene corresponding to the 5' EST are contemplated within the scope of this invention.

EXAMPLE 64

Preparation and Use of Triple Helix Probes

The sequences of the 5' ESTs (or cDNAs or genomic DNAs obtainable therefrom) are scanned to identify 10-mer to 20-mer homopyrimidine or homopurine stretches which could be used in triple-helix based strategies for inhibiting gene expression. Following identification of candidate homopyrimidine or homopurine stretches, their efficiency in inhibiting gene expression is assessed by introducing varying amounts of oligonucleotides containing the candidate sequences into tissue culture cells which normally express the target gene. The oligonucleotides may be prepared on an oligonucleotide synthesizer or they may be purchased commercially from a company specializing in custom oligonucleotide synthesis, such as GENSET, Paris, France.

The oligonucleotides may be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced gene expression using techniques such as Northern blotting, RNase protection assays, or PCR based strategies to monitor the transcription levels of the target gene in cells which have been treated with the oligonucleotide. The cell functions to be monitored are predicted based upon the homologies of the target gene corresponding to the 5' EST from which the oligonucleotide was derived with known gene sequences that have been associated with a particular function. The cell functions can also be predicted based on the presence of abnormal physiologies within cells derived from individuals with a particular inherited disease, particularly when the 5' EST is associated with the disease using techniques described in Example 53.

The oligonucleotides which are effective in inhibiting gene expression in tissue culture cells may then be introduced in vivo using the techniques described above and in Example 69 at a dosage calculated based on the in vitro results, as described in Example 69.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (Science 245:967-971 (1989), which is hereby incorporated by this reference).

EXAMPLE 65

Use of cDNAs Obtained Using the 5' ESTs to Express an Encoded Protein in a Host Organism The cDNAs obtained as described above using the 5' ESTs of the present invention may also be used to express an encoded protein in a host organism to produce a beneficial effect. In such procedures, the encoded protein may be transiently expressed in the host organism or stably expressed in the host organism. The encoded protein may have any of the activities described above. The encoded protein may be a protein which the host organism lacks or, alternatively, the encoded protein may augment the existing levels of the protein in the host organism.

A full length cDNA encoding the signal peptide and the mature protein, or an extended cDNA encoding only the mature protein is introduced into the host organism. The cDNA may be introduced into the host organism using a variety of techniques known to those of skill in the art. For example, the cDNA may be injected into the host organism as naked DNA such that the encoded protein is expressed in the host organism, thereby producing a beneficial effect.

Alternatively, the cDNA may be cloned into an expression vector downstream of a promoter which is active in the host organism. The expression vector may be any of the expression vectors designed for use in gene therapy, including viral or retroviral vectors.

The expression vector may be directly introduced into the host organism such that the encoded protein is expressed in the host organism to produce a beneficial effect. In another approach, the expression vector may be introduced into cells in vitro. Cells containing the expression vector are thereafter selected and introduced into the host organism, where they express the encoded protein to produce a beneficial effect.

As discussed above, the cDNAs or portions thereof obtained using the 5' ESTs of the present invention can be used for various purposes. The cDNAs can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; for selecting and making oligomers for attachment to a "gene chip" or other support, including for examination for expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791-803 (1993)) to identify polynucleotides encoding the other protein with which binding occurs or to identify inhibitors of the binding interaction.

The proteins or polypeptides encoded by the cDNAs can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning; A Laboratory Manual", 2d ed., Cole Spring Harbor Laboratory Press, Sambrook, J., E. F. Fritsch and T. Maniatis eds., 1989, and "Methods in Enzymology; Guide to Molecular Cloning Techniques", Academic Press, Berger, S. L. and A. R. Kimmel eds., 1987.

Polynucleotides and proteins obtained using the 5' ESTs of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

EXAMPLE 66

Use of Signal Peptides to Import Proteins into Cells

The short core hydrophobic region (h) of signal peptides encoded by the sequences of SEQ ID NOs. 38-1756 may also be used as a carrier to import a peptide or a protein of interest, so-called cargo, into tissue culture cells (Lin et al., J. Biol. Chem., 270: 14225-14258 (1995); Du et al., J. Peptide Res., 51: 235-243 (1998); Rojas et al., Nature Biotech., 16: 370-375 (1998)).

When cell permeable peptides of limited size (approximately up to 25 amino acids) are to be translocated across cell membrane, chemical synthesis may be used in order to add the h region to either the C-terminus or the N-terminus to the cargo peptide of interest. Alternatively, when longer peptides or proteins are to be imported into cells, nucleic acids can be genetically engineered, using techniques familiar to those skilled in the art, in order to link the extended cDNA sequence encoding the h region to the 5' or the 3' end of a DNA sequence coding for a cargo polypeptide. Such genetically engineered nucleic acids are then translated either in vitro or in vivo after transfection into appropriate cells, using conventional techniques to produce the resulting cell permeable polypeptide. Suitable hosts cells are then simply incubated with the cell permeable polypeptide which is then translocated across the membrane.

This method may be applied to study diverse intracellular functions and cellular processes. For instance, it has been used to probe functionally relevant domains of intracellular proteins and to examine protein-protein interactions involved in signal transduction pathways (Lin et al., supra; Lin et al., J. Biol. Chem., 271:5305-5308 (1996); Rojas et al., J. Biol. Chem., 271: 27456-27461 (1996); Liu et al., Proc. Natl. Acad. Sci. USA, 93: 11819-11824 (1996); Rojas et al., Bioch. Biophys. Res. Commun., 234: 675-680 (1997)).

Such techniques may be used in cellular therapy to import proteins producing therapeutic effects. For instance, cells isolated from a patient may be treated with imported therapeutic proteins and then re-introduced into the host organism.

Alternatively, the h region of signal peptides of the present invention could be used in combination with a nuclear localization signal to deliver nucleic acids into cell nucleus. Such oligonucleotides may be antisense oligonucleotides or oligonucleotides designed to form triple helixes, as described-above, in order to inhibit processing and maturation of a target cellular RNA.

EXAMPLE 67

Computer Embodiments

As used herein the term "cDNA codes of SEQ ID NOs. 38-1756" encompasses the nucleotide sequences of SEQ ID NOs. 38-1756, fragments of SEQ ID NOs. 38-1756, nucleotide sequences homologous to SEQ ID NOs. 38-1756 or homologous to fragments of SEQ ID NOs. 38-1756, positional segments of the nucleotide sequences of SEQ ID NOs: 38-1756, fragments of positional segments of the nucleotide sequences of SEQ ID NOs: 38-1756, and sequences complementary to all of the preceding sequences. The fragments include fragments of SEQ ID NOs. 38-1756 comprising at least 8, 10, 12, 15, 18, 20, 25, 28, 30, 35, 40, 50, 75, 100, 150, 200, 300, 400, 500, or more than 500 consecutive nucleotides of SEQ ID NOs. 38-1756 to the extent that fragments of such lengths are consistent with the lengths of specific sequences. Positional segments of the nucleotide sequences of SEQ ID NOs: 38-1756 and fragments of positional segments of the nucleotide sequences of SEQ ID NOs: 38-1756 are as defmed above. Homologous sequences and fragments of SEQ ID NOs. 38-1756 refer to a sequence having at least 99%, 98%, 97%, 96%, 95%, 90%, 85%, 80%, or 75% homology to these sequences using any of the algorithms and parameters described herein, including BLAST2N with the default parameters or with any modified parameters. Homologous sequences also include RNA sequences in which uridines replace the thymines in the cDNA codes of SEQ ID NOs. 38-1756. The homologous sequences may be obtained using any of the procedures described herein or may result from the correction of a sequencing error as described above. It will be appreciated that the cDNA codes of SEQ ID NOs. 38-1756 can be represented in the traditional single character format (See the inside back cover of Styer, Lubert. *Biochemistry*, $3^{rd}$ edition. W. H Freeman & Co., New York.) or in any other format which records the identity of the nucleotides in a sequence.

As used herein the term "polypeptide codes of SEQ ID NOS. 1757-3475" encompasses the polypeptide sequence of SEQ ID NOs. 1757-3475 which are encoded by the cDNAs of SEQ ID NOs. 1757-3475, polypeptide sequences homologous to the polypeptides of SEQ ID NOS. 1757-3475, fragments of any of the preceding sequences, positional segments of the polypeptides of SEQ ID NOs: 1757-3475, polypeptides homologous to positional segments of the polypeptides of SEQ ID NOs: 1757-3475, fragments of positional segments of the polypeptides the polypeptides of SEQ ID NOs: 1757-3475, and polypeptides homologous to fragments of positional segments of the polypeptides of SEQ ID NOs: 1757-3475. Homologous polypeptide sequences refer to a polypeptide sequence having at least 99%, 98%, 97%, 96%, 95%, 90%, 85%, 80%, 75% homology to one of the polypeptide sequences of SEQ ID NOS. 1757-3475, positional segments of the polypeptides of SEQ ID NOs: 1757-3475, or fragments of positional segments of the polypeptides of SEQ ID NOs: 1757-3475. Homology may be determined using any of the computer programs and parameters described herein, including FASTA with the default parameters or with any modified parameters. The homologous sequences may be obtained using any of the procedures described herein or may result from the correction of a sequencing error as described above. The polypeptide fragments comprise at least 5, 8, 10, 12, 15, 20, 25, 30, 35, 40, 50, 60, 75, 100, 150 or 200 consecutive amino acids of the polypeptides of SEQ ID NOS. 1757-3475. Positional segments of the polypeptides of SEQ ID NOs: 1757-3475 and fragments of positional segments of the polypeptides of SEQ ID NOs: 1757-3475 have the meanings provided above. It will be appreciated that the polypeptide codes of the SEQ ID NOS. 1757-3475 can be represented in the traditional single character format or three letter format (See the inside back cover of Starrier, Lubert. *Biochemistry*, $3^{rd}$ edition. W. H Freeman & Co., New York.) or in any other format which relates the identity of the polypeptides in a sequence.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad Sci. USA* 85(8): 2444-2448; Altschul et al., 1990, *J. Mol. Biol.* 215(3):403-410; Thompson et al., 1994, *Nucleic Acids Res.* 22(2):4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272).

In some embodiments, protein and nucleic acid sequence homologies are evaluated using the Basic Local Alignment Search Tool ("BLAST") which is well known in the art (see, e.g., Karlin and Altschul, 1990, *Proc. Natl. Acad. Sci. USA* 87:2267-2268; Altschul et al., 1990, *J. Mol. Biol.* 215:403-410; Altschul et al., 1993, *Nature Genetics* 3:266-272; Altschul et al., 1997, *Nuc. Acids Res.* 25:3389-3402). In particular, five specific BLAST programs are used to perform the following tasks:
(1) BLASTP and BLAST3 compares an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, *Science* 256:1443-1445; Henikoff and Henikoff, 1993, *Proteins* 17:49-61). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation)

The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, *Proc. Natl. Acad. Sci. USA* 87:2267-2268).

The parameters used with the above algorithms may be adapted depending on the sequence length and degree of homology studied. In some embodiments, the parameters may be the default parameters used by the algorithms in the absence of instructions from the user.

In some embodiments, the level of homology may be determiined using the FASTDB algorithm described in Brutlag et al. *Comp. App. Biosci.* 6:237-245, 1990. In such analyses the parameters may be selected as follows: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the sequence which hybridizes to the probe, whichever is shorter. Because the FASTDB program does not consider 5' or 3' truncations when calculating homology levels, if the sequence homologous to the 5' EST (or cDNA or genomic DNA obtainable therefrom) is truncated relative to the sequence of the 5' EST (or cDNA or genomic DNA obtainable therefrom) the homology level is manually adjusted by calculating the number of nucleotides of the 5' EST (or cDNA or genomic DNA obtainable therefrom) which are not matched or aligned with the sequence, determining the percentage of total nucleotides of the homologous sequence which the non-matched or non-aligned nucleotides represent, and subtracting this percentage from the homology level. For example, if the homologous sequence is 700 nucleotides in length and the 5' EST (or cDNA or genomic DNA obtainable therefrom) sequence is 1000 nucleotides in length wherein the first 300 bases at the 5' end of the 5' EST (or cDNA or genomic DNA obtainable therefrom) are absent from the hybridizing sequence, and wherein the overlapping 700 nucleotides are identical, the homology level would be adjusted as follows. The non-matched, non-aligned 300 bases represent 30% of the length of the 5' EST (or cDNA or genomic DNA obtainable therefrom). If the overlapping 700 nucleotides are 100% identical, the adjusted homology level would be 100−30=70% homology. It should be noted that the preceding adjustments are only made when the non-matched or non-aligned nucleotides are at the 5' or 3' ends. No adjustments are made if the non-matched or non-aligned sequences are internal or under any other conditions.

Using the above algorithms with parameters depending on the sequence length and degree of homology studied, for example the default parameters used by the algorithms in the absence of instructions from the user, one can identify nucleic acids encoding proteins having at least 99%, at least 98%, at least 97%, at least 96%, at least 95%, at least 90%, at least 85%, at least 80% or at least 75% homology to the protein encoded by the 5' EST (or cDNA or genomic DNA obtainable therefrom). In some embodiments, the homology levels can be determined using the "default" opening penalty and the "default" gap penalty, and a scoring matrix such as PAM 250 (a standard scoring matrix; see Dayhoff et al., in: Atlas of Protein Sequence and Structure, Vol. 5, Supp. 3 (1978)).

Alternatively, the level of polypeptide homology may be determined using the FASTDB algorithm described by Brutlag et al. Comp. App. Biosci. 6:237-245, 1990. In such analyses the parameters may be selected as follows: Matrix=PAM 0, k-tuple=2, Mismatch Penalty=1, Joining Penalty=20, Randomization Group Length=0, Cutoff Score=1, Window Size=Sequence Length, Gap Penalty=5, Gap Size Penalty=0.05, Window Size=500 or the length of the homologous sequence, whichever is shorter. If the homologous amino acid sequence is shorter than the amino acid sequence encoded by the 5' EST (or cDNA or genomic DNA obtainable therefrom) as a result of an N terminal and/or C terminal deletion the results may be manually corrected as follows. First, the number of amino acid residues of the amino acid sequence encoded by the 5' EST (or cDNA or genomic DNA obtainable therefrom) which are not matched or aligned with the homologous sequence is determined. Then, the percentage of the length of the sequence encoded by the 5' EST (or cDNA or genomic DNA obtainable therefrom) which the non-matched or non-aligned amino acids represent is calculated. This percentage is subtracted from the homology level. For example wherein the amino acid sequence encoded by the 5' EST (or cDNA or genomic DNA obtainable therefrom) is 100 amino acids in length and the length of the homologous sequence is 80 amino acids and wherein the amino acid sequence encoded by the 5' EST (or cDNA or genomic DNA obtainable therefrom) is truncated at the N terminal end with respect to the homologous sequence, the homology level is calculated as follows. In the preceding scenario there are 20 non-matched, non-aligned amino acids in the sequence encoded by the 5' EST (or cDNA or genomic DNA obtainable therefrom). This represents 20% of the length of the amino acid sequence encoded by the 5' EST (or cDNA or genomic DNA obtainable therefrom). If the remaining amino acids are 1005 identical between the two sequences, the homology level would be 100%−20%=80% homology. No adjustments are made if the non-matched or non-aligned sequences are internal or under any other conditions.

It will be appreciated by those skilled in the art that the cDNA codes of SEQ ID NOs. 38-1756 and polypeptide codes of SEQ ID NOS. 1757-3475 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the cDNA codes of SEQ ID NOs. 38-1756, one or more of the polypeptide codes of SEQ ID NOS. 1757-3475. Another aspect of the present invention is a computer readable medium having recorded thereon at least 2, 5, 10, 15, 20, 25, 30, or 50 cDNA codes of SEQ ID NOs. 38-1756. Another aspect of the present invention is a computer readable medium having recorded thereon at least 2, 5, 10, 15, 20, 25, 30, or 50 polypeptide codes of SEQ ID NOS. 1757-3475.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 8:
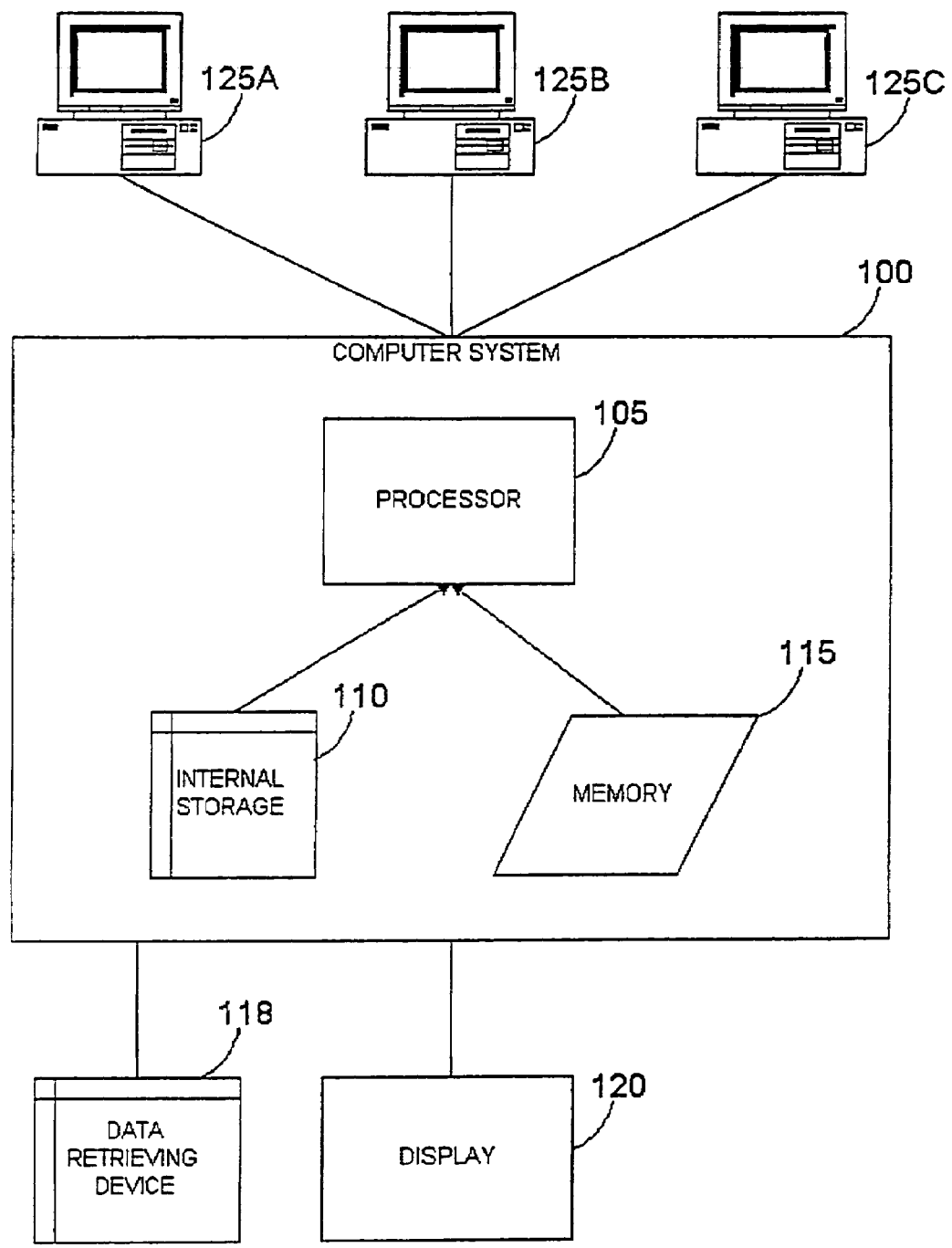
FIG. 8 is a block diagram of an exemplary computer system.

Embodiments of the present invention include systems, particularly computer systems which store and manipulate the sequence information described herein. One example of a computer system 100 is illustrated in block diagram form in FIG. 8. As used herein, "a computer system" refers to the hardware components, software components, and data storage components used to analyze the nucleotide sequences of the cDNA codes of SEQ ID NOs. 38-1756, or the amino acid sequences of the polypeptide codes of SEQ ID NOS. 1757-3475. In one embodiment, the computer system 100 is a Sun Enterprise 1000 server (Sun Microsystems, Palo Alto, Calif.). The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125 A-C in a network or wide area network to provide centralized access to the computer system 100.

Software for accessing and processing the nucleotide sequences of the cDNA codes of SEQ ID NOs. 38-1756, or the amino acid sequences of the polypeptide codes of SEQ ID NOS. 1757-3475 (such as search tools, compare tools, and modeling tools etc.) may reside in main memory 115 during execution.

In some embodiments, the computer system 100 may further comprise a sequence comparer for comparing the above-described cDNA codes of SEQ ID NOs. 38-1756 or polypeptide codes of SEQ ID NOS. 1757-3475 stored on a computer readable medium to reference nucleotide or polypeptide sequences stored on a computer readable medium. A "sequence comparer" refers to one or more programs which are implemented on the computer system 100 to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of the cDNA codes of SEQ ID NOs. 38-1756, or the amino acid sequences of the polypeptide codes of SEQ ID NOS. 1757-3475 stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

Figure 9:
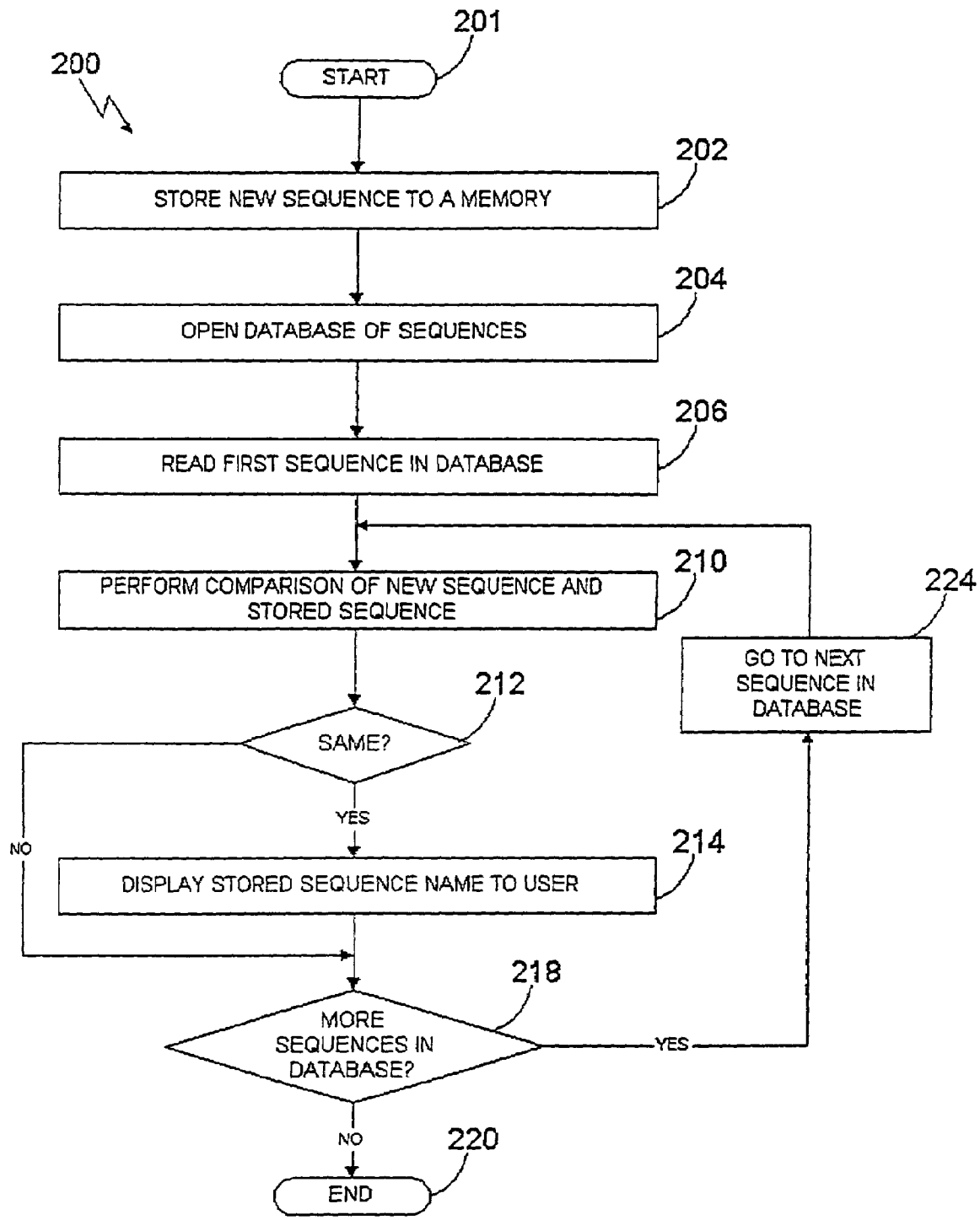
FIG. 9 is a flow diagram illustrating one embodiment of a process 200 for comparing a new nucleotide or protein sequence with a database of sequences in order to determine the homology levels between the new sequence and the sequences in the database.

FIG. 9 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK, PIR or SWISSPROT that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of SEQ ID NOs. 38-1756 or a polypeptide code of SEQ ID NOS. 1757-3475, a data storage device having retrievably stored thereon reference nucleotide sequences or polypeptide sequences to be compared to the nucleic acid code of SEQ ID NOs. 38-1756 or polypeptide code of SEQ ID NOS. 1757-3475 and a sequence comparer for conducting the comparison. The sequence comparer may indicate a homology level between the sequences compared or identify structural motifs in the above described nucleic acid code of SEQ ID NOs. 38-1756 and polypeptide codes of SEQ ID NOS. 1757-3475 or it may identify structural motifs in sequences which are compared to these cDNA codes and polypeptide codes. In some embodiments, the data storage device may have stored thereon the sequences of at least 2, 5, 10, 15, 20, 25, 30, or 50 of the cDNA codes of SEQ ID NOs. 38-1756 or polypeptide codes of SEQ ID NOS. 1757-3475.

Another aspect of the present invention is a method for determining the level of homology between a nucleic acid code of SEQ ID NOs. 38-1756 and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described cDNA codes of SEQ ID NOs. 38-1756 through use of the computer program and determining homology between the cDNA codes and reference nucleotide sequences.

Figure 10:
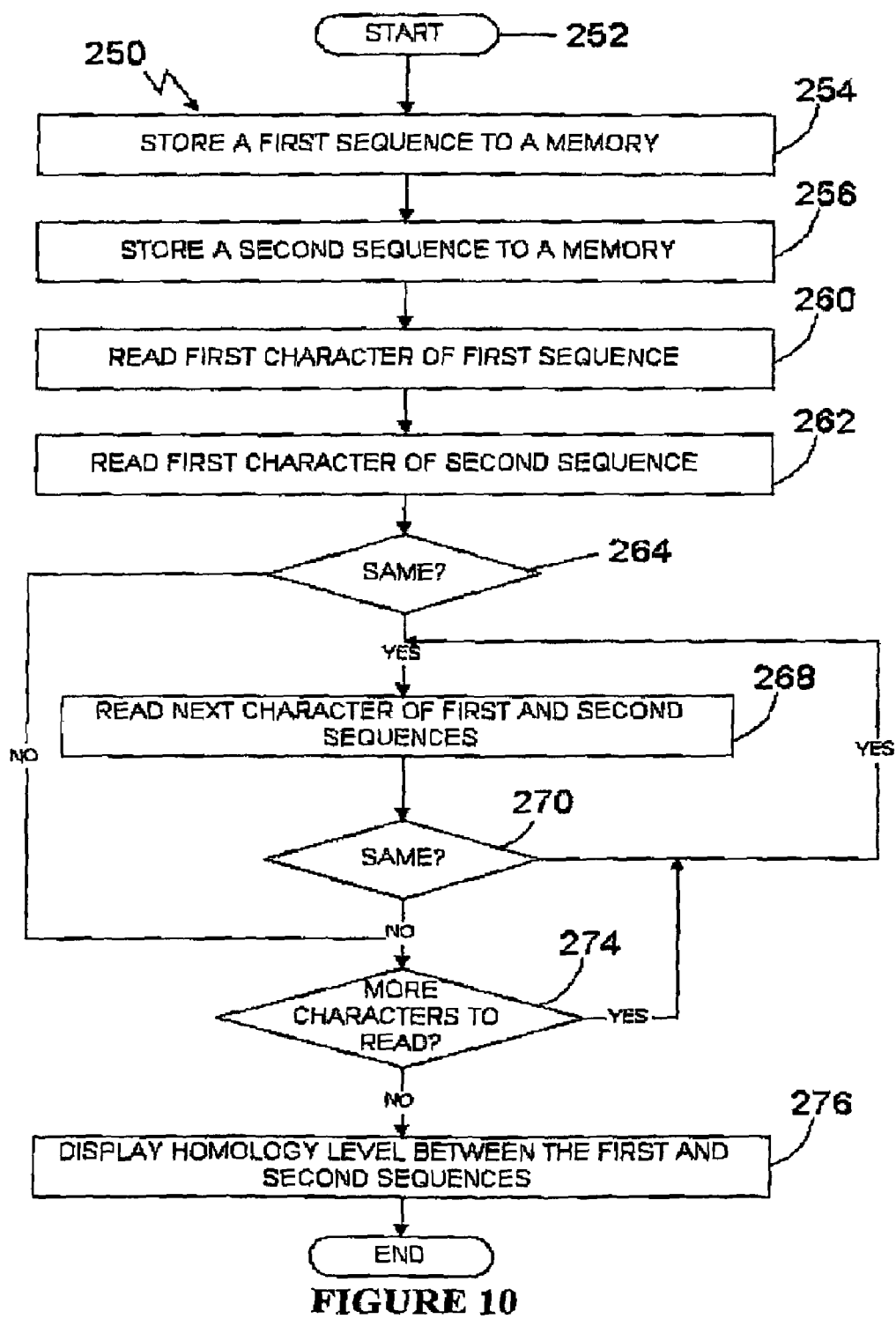
FIG. 10 is a flow diagram illustrating one embodiment of a process 250 in a computer for determining whether two sequences are homologous.

FIG. 10 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made at a decision state 270 whether the next characters are the same. If they are, then the process 250 continues this loop until two characters are not the same. If a determination is made that the next two characters are not the same, the process 250 moves to a decision state 274 to determine whether there are any more characters in either sequence to read.

If there aren't any more characters to read, then the process 250 moves to a state 276 wherein the level of homology between the first and second sequences is displayed to the user. The level of homology is determined by calculating the profragment of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of the cDNA codes of the present invention, to reference nucleotide sequences in order to determine whether the nucleic acid code of SEQ ID NOs. 38-1756 differs from a reference nucleic acid sequence at one or more positions. Optionally such a program records the length and identity of inserted, deleted or substituted nucleotides with respect to the sequence of either the reference polynucleotide or the nucleic acid code of SEQ ID NOs. 38-1756. In one embodiment, the computer program may be a program which determines whether the nucleotide sequences of the cDNA codes of SEQ ID NOs. 38-1756 contain a biallelic marker or single nucleotide polymorphism (SNP) with respect to a reference nucleotide sequence. This single nucleotide polymorphism may comprise a single base substitution, insertion, or deletion, while this biallelic marker may comprise about one to ten consecutive bases substituted, inserted or deleted.

Another aspect of the present invention is a method for determining the level of homology between a polypeptide code of SEQ ID NOS. 1757-3475 and a reference polypeptide sequence, comprising the steps of reading the polypeptide code of SEQ ID NOS. 1757-3475 and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of SEQ ID NOs. 38-1756 differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 10. The method may also be performed by reading at least 2, 5, 10, 15, 20, 25, 30, or 50 of the cDNA codes of SEQ ID NOs. 38-1756 and the reference nucleotide sequences through the use of the computer program and identifying differences between the cDNA codes and the reference nucleotide sequences with the computer program.

In other embodiments the computer based system may further comprise an identifier for identifying features within the nucleotide sequences of the cDNA codes of SEQ ID NOs. 38-1756 or the amino acid sequences of the polypeptide codes of SEQ ID NOS. 1757-3475.

An "identifier" refers to one or more programs which identifies certain features within the above-described nucleotide sequences of the cDNA codes of SEQ ID NOs. 38-1756 or the amino acid sequences of the polypeptide codes of SEQ ID NOS. 1757-3475. In one embodiment, the identifier may comprise a program which identifies an open reading frame in the cDNAs codes of SEQ ID NOs. 38-1756.

Figure 11:
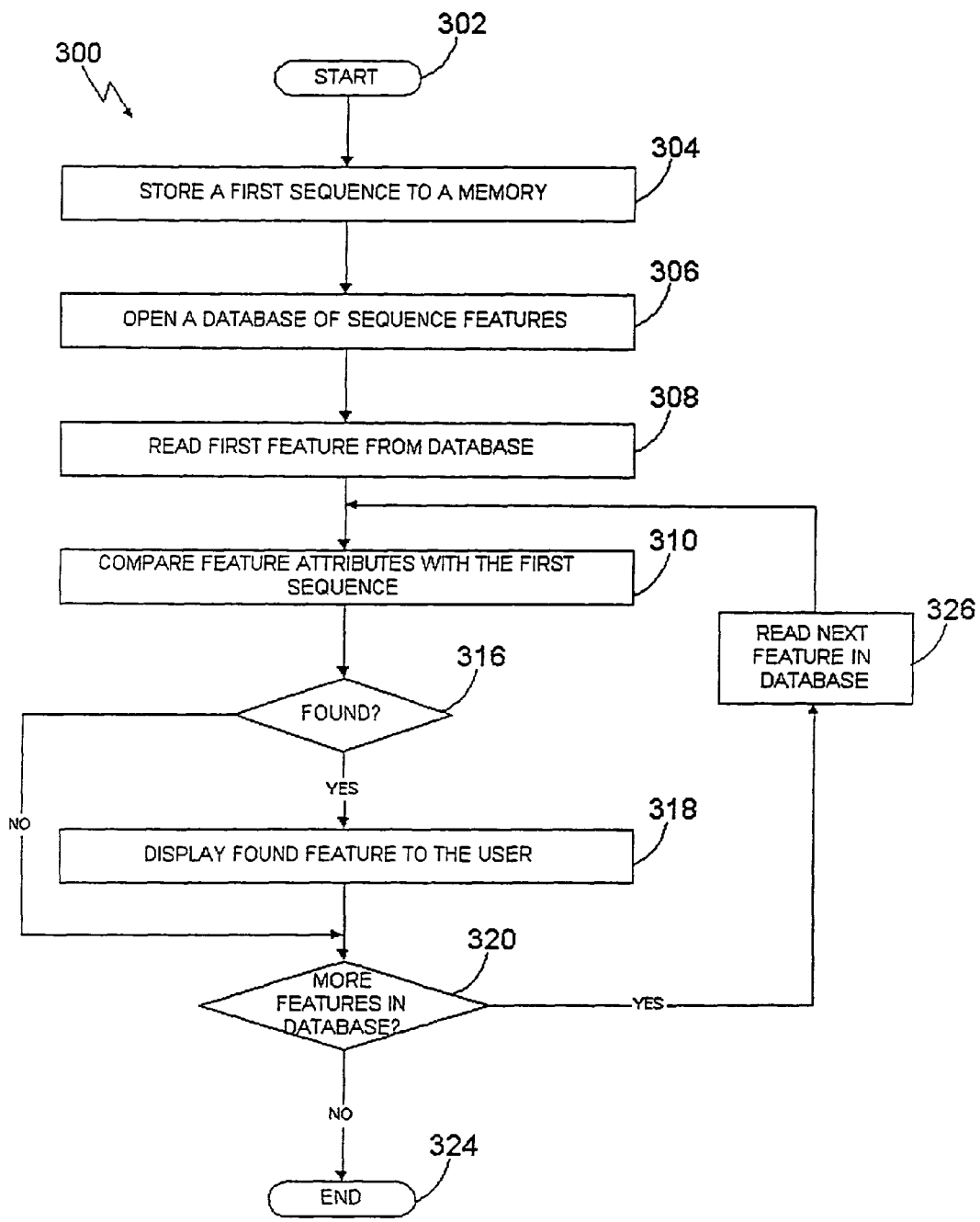
FIG. 11 is a flow diagram illustrating one embodiment of an identifier process 300 for detecting the presence of a feature in a sequence.

FIG. 11 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com).

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

In another embodiment, the identifier may comprise a molecular modeling program which determines the 3-dimensional structure of the polypeptides codes of SEQ ID NOS. 1757-3475. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of the polypeptide codes of SEQ ID NOS. 1757-3475. (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into inter-residue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins:Structure, Function, and Genetics, Supplement 1:38-42 (1997)).

The results of the molecular modeling analysis may then be used in rational drug design techniques to identify agents which modulate the activity of the polypeptide codes of SEQ ID NOS. 1757-3475.

Accordingly, another aspect of the present invention is a method of identifying a feature within the cDNA codes of SEQ ID NOs. 38-1756 or the polypeptide codes of SEQ ID NOS. 1757-3475 comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program identifies structural motifs in a polypeptide sequence. In another embodiment, the computer program comprises a molecular modeling program. The method may be performed by reading a single sequence or at least 2, 5, 10, 15, 20, 25, 30, or 50 of the cDNA codes of SEQ ID NOs. 38-1756 or the polypeptide codes of SEQ ID NOS. 1757-3475 through the use of the computer program and identifying features within the cDNA codes or polypeptide codes with the computer program.

The cDNA codes of SEQ ID NOs. 38-1756 or the polypeptide codes of SEQ ID NOS. 1757-3475 may be stored and manipulated in a variety of data processor programs in a variety of formats. For example, the cDNA codes of SEQ ID NOs. 38-1756 or the polypeptide codes of SEQ ID NOS. 1757-3475 may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the cDNA codes of SEQ ID NOs. 38-1756 or the polypeptide codes of SEQ ID NOS. 1757-3475. The following list is intended not to limit the invention but to provide guidance to programs and databases which are useful with the cDNA codes of SEQ ID NOs. 38-1756 or the polypeptide codes of SEQ ID NOS. 1757-3475. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), FASTDB (Brutlag et al. Comp. App. Biosci. 6:237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/ Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

EXAMPLE 68

Methods of Making Nucleic Acids

The present invention also comprises methods of making the 5' ESTs (or cDNAs or genomic DNAs obtainable therefrom) of the present invention or fragments thereof. The methods comprise sequentially linking together nucleotides to produce the nucleic acids having the preceding sequences. A variety of methods of synthesizing nucleic acids are known to those skilled in the art.

In many of these methods, synthesis is conducted on a solid support. These included the 3' phosphoramidite methods in which the 3' terminal base of the desired oligonucleotide is immobilized on an insoluble carrier. The nucleotide base to be added is blocked at the 5' hydroxyl and activated at the 3' hydroxyl so as to cause coupling with the immobilized nucleotide base. Deblocking of the new immobilized nucleotide compound and repetition of the cycle will produce the desired polynucleotide. Alternatively, polynucleotides may be prepared as described in U.S. Pat. No. 5,049,656, the disclosure of which is incorporated herein by reference. In some embodiments, several polynucleotides prepared as described above are ligated together to generate longer polynucleotides having a desired sequence.

EXAMPLE 69

Methods of Making Polypeptides

The present invention also comprises methods of making the polynucleotides encoded by the 5' ESTs (or cDNAs or genomic DNAs obtainable therefrom) or fragments thereof. The methods comprise sequentially linking together amino acids to produce the nucleic polypeptides having the preceding sequences. In some embodiments, the polypeptides made by these methods are 150 amino acid or less in length. In other embodiments, the polypeptides made by these methods are 120 amino acids or less in length.

A variety of methods of making polypeptides are known to those skilled in the art, including methods in which the carboxyl terminal amino acid is bound to polyvinyl benzene or another suitable resin. The amino acid to be added possesses blocking groups on its amino moiety and any side chain reactive groups so that only its carboxyl moiety can react. The carboxyl group is activated with carbodiimide or another activating agent and allowed to couple to the immobilized amino acid. After removal of the blocking group, the cycle is repeated to generate a polypeptide having the desired sequence. Alternatively, the methods described in U.S. Pat. No. 5,049,656, the disclosure of which is incorporated herein by reference, may be used.

As discussed above, the 5' ESTs (or cDNAs or genomic DNAs obtainable therefrom) or fragments thereof can be used for various purposes. The polynucleotides can be used to express recombinant protein for analysis, characterization or therapeutic use; production of secreted polypeptides or chimeric polypeptides, antibody production, as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; for selecting and making oligomers for attachment to a "gene chip" or other support, including for examination for expression patterns; to raise anti-protein antibodies using DNA immunization techniques; and as an antigen to raise anti-DNA antibodies or elicit another immune response. Where the polynucleotide encodes a protein or polypeptide which binds or potentially binds to another protein or polypeptide (such as, for example, in a receptor-ligand interaction), the polynucleotide can also be used in interaction trap assays (such as, for example, that described in Gyuris et al., *Cell* 75:791-803 (1993), the disclosure of which is hereby incorporated by reference) to identify polynucleotides encoding the other protein or polypeptide with which binding occurs or to identify inhibitors of the binding interaction.

The proteins or polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively detennine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein or polypeptide binds or potentially binds to another protein or polypeptide (such as, for example, in a receptor-ligand interaction), the protein can be used to identify the other protein with which binding occurs or to identify inhibitors of the binding interaction. Proteins or polypeptides involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning; A Laboratory Manual", 2d ed., Cold Spring Harbor Laboratory Press, Sambrook, J., E. F. Fritsch and T. Maniatis eds., 1989, and "Methods in Enzymology; Guide to Molecular Cloning Techniques", Academic Press, Berger, S. L. and A. R. Kimmel eds., 1987.

Polynucleotides and proteins or polypeptides of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

TABLE I

Parameters used for each step of EST analysis

| Step | Search Characteristics | | | Selection Characteristics | |
|---|---|---|---|---|---|
| | Program | Strand | Parameters | Identity (%) | Length (bp) |
| Miscellaneous | blastn | both | S = 61 X = 16 | 90 | 17 |
| tRNA | fasta | both | — | 80 | 60 |
| rRNA | blastn | both | S = 108 | 80 | 40 |
| mtRNA | blastn | both | S = 108 | 80 | 40 |
| Procaryotic | blastn | both | S = 144 | 90 | 40 |
| Fungal | blastn | both | S = 144 | 90 | 40 |
| Alu | fasta* | both | — | 70 | 40 |

TABLE I-continued

Parameters used for each step of EST analysis

| Step | Search Characteristics | | | Selection Characteristics | |
|---|---|---|---|---|---|
| | Program | Strand | Parameters | Identity (%) | Length (bp) |
| L1 | blastn | both | S = 72 | 70 | 40 |
| Repeats | blastn | both | S = 72 | 70 | 40 |
| Promoters | blastn | top | S = 54 X = 16 | 90 | 15⊥ |
| Vertebrate | fasta* | both | S = 108 | 90 | 30 |
| ESTs | blatsn | both | S = 108 X = 16 | 90 | 30 |
| Proteins | blastxη | top | E = 0.001 | — | — |

*use "Quick Fast" Database Scanner
⊥alignment further constrained to begin closer than 10 bp to EST\5' end
ηusing BLOSUM62 substitution matrix

TABLE II

| SEQ. ID NO. | CATEGORY | VON HEIJNE SCORE | TISSUE SOURCE | INTERNAL DESIGNATION |
|---|---|---|---|---|
| ID38 | new | 10.8 | Brain | 33-19-2-H2-PU |
| ID39 | new | 10.8 | Brain | 33-56-1-E8-PU |
| ID40 | new | 10 | Brain | 33-79-3-D12-PU |
| ID41 | new | 9.6 | Brain | 33-72-2-B2-PU |
| ID42 | new | 9.5 | Brain | 33-13-2-B9-PU |
| ID43 | new | 9.1 | Brain | 33-113-1-E9-PU |
| ID44 | new | 9 | Brain | 33-28-4-E8-PU |
| ID45 | new | 8.8 | Brain | 33-12-3-F2-PU |
| ID46 | new | 8.8 | Brain | 33-70-1-C11-PU |
| ID47 | new | 8.5 | Brain | 33-74-1-B2-PU |
| ID48 | new | 8.5 | Brain | 33-29-3-F1-PU |
| ID49 | new | 8.4 | Brain | 33-8-2-A1-PU |
| ID50 | new | 8.3 | Brain | 17-17-3-A9-PU |
| ID51 | new | 8.3 | Brain | 33-106-2-A8-PU |
| ID52 | new | 8.3 | Brain | 33-112-4-E7-PU |
| ID53 | new | 8.2 | Brain | 33-98-1-E6-PU |
| ID54 | new | 8.2 | Brain | 33-76-1-B6-PU |
| ID55 | new | 8 | Brain | 33-35-4-G8-PU |
| ID56 | new | 7.9 | Brain | 33-17-3-E4-PU |
| ID57 | new | 7.9 | Brain | 33-110-4-B5-PU |
| ID58 | new | 7.8 | Brain | 33-40-1-A11-PU |
| ID59 | new | 7.7 | Brain | 33-71-1-A8-PU |
| ID60 | new | 7.7 | Brain | 33-96-3-G7-PU |
| ID61 | new | 7.6 | Brain | 33-112-3-D12-PU |
| ID62 | new | 7.6 | Brain | 33-62-2-B3-PU |
| ID63 | new | 7.6 | Brain | 33-6-4-G6-PU |
| ID64 | new | 7.5 | Brain | 33-82-4-E2-PU |
| ID65 | new | 7.4 | Brain | 23-81-3-H11-PU |
| ID66 | new | 7.3 | Brain | 33-64-1-B4-PU |
| ID67 | new | 7.2 | Brain | 33-31-1-B12-PU |
| ID68 | new | 7 | Brain | 33-24-4-F9-PU |
| ID69 | new | 7 | Brain | 33-110-3-E9-PU |
| ID70 | new | 7 | Brain | 33-4-2-G5-PU |
| ID71 | new | 6.9 | Brain | 33-74-2-A4-PU |
| ID72 | new | 6.9 | Brain | 33-52-4-F9-PU |
| ID73 | new | 6.9 | Brain | 33-74-1-B11-PU |
| ID74 | new | 6.8 | Brain | 33-10-4-D9-PU |
| ID75 | new | 6.8 | Brain | 33-15-2-H3-PU |
| ID76 | new | 6.7 | Brain | 33-38-2-D5-PU |
| ID77 | new | 6.7 | Brain | 33-78-3-D2-PU |
| ID78 | new | 6.7 | Brain | 33-96-3-D3-PU |
| ID79 | new | 6.6 | Brain | 33-76-4-B11-PU |
| ID80 | new | 6.3 | Brain | 33-39-1-C6-PU |
| ID81 | new | 6.1 | Brain | 33-106-3-B12-PU |
| ID82 | new | 6 | Brain | 33-4-2-B7-PU |
| ID83 | new | 5.9 | Brain | 33-99-2-E4-PU |
| ID84 | new | 5.9 | Brain | 33-34-1-B1-PU |
| ID85 | new | 5.8 | Brain | 33-67-4-E9-PU |
| ID86 | new | 5.7 | Brain | 33-11-3-H11-PU |
| ID87 | new | 5.6 | Brain | 33-13-2-A8-PU |

TABLE II-continued

| SEQ. ID NO. | CATEGORY | VON HEIJNE SCORE | TISSUE SOURCE | INTERNAL DESIGNATION |
|---|---|---|---|---|
| ID88 | new | 5.6 | Brain | 33-83-4-B6-PU |
| ID89 | new | 5.6 | Brain | 33-70-1-E4-PU |
| ID90 | new | 5.6 | Brain | 33-5-3-H11-PU |
| ID91 | new | 5.6 | Brain | 33-10-3-G5-PU |
| ID92 | new | 5.5 | Brain | 33-97-4-G4-PU |
| ID93 | new | 5.5 | Brain | 33-46-4-F4-PU |
| ID94 | new | 5.4 | Brain | 33-4-1-G11-PU |
| ID95 | new | 5.3 | Brain | 33-105-1-H5-PU |
| ID96 | new | 5.3 | Brain | 33-74-2-B10-PU |
| ID97 | new | 5.3 | Brain | 33-49-3-E5-PU |
| ID98 | new | 5.3 | Brain | 33-114-2-A1-PU |
| ID99 | new | 5.2 | Brain | 33-71-1-G12-PU |
| ID100 | new | 5.2 | Brain | 33-47-3-E6-PU |
| ID101 | new | 5.2 | Brain | 33-1-2-E8-PU |
| ID102 | new | 5.2 | Brain | 33-93-4-E12-PU |
| ID103 | new | 5.1 | Brain | 33-1-2-H1-PU |
| ID104 | new | 5.1 | Brain | 17-10-1-H8-PU |
| ID105 | new | 5 | Brain | 33-110-2-B8-PU |
| ID106 | new | 5 | Brain | 33-104-3-D9-PU |
| ID107 | new | 5 | Brain | 33-72-2-H11-PU |
| ID108 | new | 4.9 | Brain | 33-7-4-D6-PU |
| ID109 | new | 4.9 | Brain | 33-31-4-G2-PU |
| ID110 | new | 4.9 | Brain | 33-109-1-E8-PU |
| ID111 | new | 4.8 | Brain | 17-1-2-B11-PU |
| ID112 | new | 4.8 | Brain | 33-19-4-H3-PU |
| ID113 | new | 4.8 | Brain | 33-14-4-E1-PU |
| ID114 | new | 4.8 | Brain | 33-70-3-H1-PU |
| ID115 | new | 4.7 | Brain | 33-86-4-H10-PU |
| ID116 | new | 4.7 | Brain | 33-107-3-D5-PU |
| ID117 | new | 4.7 | Brain | 33-23-4-B9-PU |
| ID118 | new | 4.7 | Brain | 33-82-4-H5-PU |
| ID119 | new | 4.6 | Brain | 33-16-3-F4-PU |
| ID120 | new | 4.6 | Brain | 33-97-4-C5-PU |
| ID121 | new | 4.6 | Brain | 33-100-3-B10-PU |
| ID122 | new | 4.6 | Brain | 33-59-3-E3-PU |
| ID123 | new | 4.5 | Brain | 33-25-1-G2-PU |
| ID124 | new | 4.5 | Brain | 17-16-3-B2-PU |
| ID125 | new | 4.4 | Brain | 33-52-4-E7-PU |
| ID126 | new | 4.4 | Brain | 33-91-1-D1-PU |
| ID127 | new | 4.4 | Brain | 33-26-1-B9-PU |
| ID128 | new | 4.4 | Brain | 33-97-3-H6-PU |
| ID129 | new | 4.4 | Brain | 33-109-2-E8-PU |
| ID130 | new | 4.3 | Brain | 33-59-2-B7-PU |
| ID131 | new | 4.3 | Brain | 33-28-4-D1-PU |
| ID132 | new | 4.3 | Brain | 33-29-4-E2-PU |
| ID133 | new | 4.1 | Brain | 33-70-1-H6-PU |
| ID134 | new | 4.1 | Brain | 33-7-1-B2-PU |
| ID135 | new | 4.1 | Brain | 33-52-4-F8-PU |
| ID136 | new | 4.1 | Brain | 33-23-2-A6-PU |
| ID137 | new | 4.1 | Brain | 33-39-3-E5-PU |
| ID138 | new | 4.1 | Brain | 33-81-4-H6-PU |
| ID139 | new | 4.1 | Brain | 33-105-3-F5-PU |
| ID140 | new | 4 | Brain | 33-35-2-H11-PU |
| ID141 | new | 4 | Brain | 33-50-3-E12-PU |
| ID142 | new | 4 | Brain | 33-16-3-H7-PU |
| ID143 | new | 4 | Brain | 33-79-2-H4-PU |
| ID144 | new | 3.9 | Brain | 33-32-4-B12-PU |
| ID145 | new | 3.9 | Brain | 33-110-4-A5-PU |
| ID146 | new | 3.9 | Brain | 33-109-2-H1-PU |
| ID147 | new | 3.9 | Brain | 33-100-1-E6-PU |
| ID148 | new | 3.9 | Brain | 33-78-2-E7-PU |
| ID149 | new | 3.9 | Brain | 33-82-4-G3-PU |
| ID150 | new | 3.9 | Brain | 17-1-1-A9-PU |
| ID151 | new | 3.9 | Brain | 33-89-4-E1-PU |
| ID152 | new | 3.9 | Brain | 33-89-1-B4-PU |
| ID153 | new | 3.9 | Brain | 33-96-3-A3-PU |
| ID154 | new | 3.8 | Brain | 33-92-3-D1-PU |
| ID155 | new | 3.8 | Brain | 33-104-4-H4-PU |
| ID156 | new | 3.8 | Brain | 33-106-1-B8-PU |
| ID157 | new | 3.6 | Brain | 33-1-3-D1-PU |
| ID158 | new | 3.6 | Brain | 33-40-2-F5-PU |
| ID159 | new | 3.6 | Brain | 33-4-1-E8-PU |
| ID160 | new | 3.6 | Brain | 33-36-3-E2-PU |
| ID161 | new | 3.6 | Brain | 17-18-3-A6-PU |
| ID162 | new | 3.6 | Brain | 33-12-1-B1-PU |
| ID163 | new | 3.6 | Brain | 33-29-1-H1-PU |

TABLE II-continued

| SEQ. ID NO. | CATEGORY | VON HEIJNE SCORE | TISSUE SOURCE | INTERNAL DESIGNATION |
|---|---|---|---|---|
| ID164 | new | 3.6 | Brain | 33-103-1-E1-PU |
| ID165 | new | 3.5 | Brain | 33-10-4-H2-PU |
| ID166 | new | 3.5 | Brain | 33-25-1-H2-PU |
| ID167 | new | 3.5 | Brain | 33-10-4-G2-PU |
| ID168 | new | 3.5 | Brain | 33-67-1-F4-PU |
| ID169 | ext-est-not-vrt | 12.5 | Brain | 33-77-4-E2-PU |
| ID170 | ext-est-not-vrt | 10.1 | Brain | 33-31-3-C11-PU |
| ID171 | ext-est-not-vrt | 9.8 | Brain | 33-28-2-H7-PU |
| ID172 | ext-est-not-vrt | 9.2 | Brain | 33-112-3-C8-PU |
| ID173 | ext-est-not-vrt | 7.9 | Brain | 33-23-3-A11-PU |
| ID174 | ext-est-not-vrt | 7.9 | Brain | 33-29-2-E11-PU |
| ID175 | ext-est-not-vrt | 7.9 | Brain | 33-66-4-C7-PU |
| ID176 | ext-est-not-vrt | 7.1 | Brain | 33-78-1-D7-PU |
| ID177 | ext-est-not-vrt | 6.6 | Brain | 33-31-3-D7-PU |
| ID178 | ext-est-not-vrt | 6.3 | Brain | 33-19-1-C11-PU |
| ID179 | ext-est-not-vrt | 6 | Brain | 33-67-1-A5-PU |
| ID180 | ext-est-not-vrt | 5.9 | Brain | 33-58-3-C8-PU |
| ID181 | ext-est-not-vrt | 4.9 | Brain | 33-107-4-C3-PU |
| ID182 | ext-est-not-vrt | 4.9 | Brain | 33-7-2-G12-PU |
| ID183 | ext-est-not-vrt | 4.8 | Brain | 33-11-1-G5-PU |
| ID184 | ext-est-not-vrt | 4.7 | Brain | 33-31-4-D9-PU |
| ID185 | ext-est-not-vrt | 4.6 | Brain | 33-26-4-E10-PU |
| ID186 | ext-est-not-vrt | 4.5 | Brain | 33-70-4-F7-PU |
| ID187 | ext-est-not-vrt | 4.5 | Brain | 33-19-2-D1-PU |
| ID188 | ext-est-not-vrt | 4.4 | Brain | 33-48-4-F8-PU |
| ID189 | ext-est-not-vrt | 4.3 | Brain | 33-109-3-B10-PU |
| ID190 | ext-est-not-vrt | 4.1 | Brain | 33-30-2-A6-PU |
| ID191 | ext-est-not-vrt | 3.8 | Brain | 33-75-3-D7-PU |
| ID192 | ext-est-not-vrt | 3.7 | Brain | 33-109-4-C1-PU |
| ID193 | est-not-ext | 10.5 | Brain | 33-97-3-D4-PU |
| ID194 | est-not-ext | 10.1 | Brain | 33-61-2-F6-PU |
| ID195 | est-not-ext | 9.5 | Brain | 33-54-1-B9-PU |
| ID196 | est-not-ext | 9.3 | Brain | 33-39-4-D1-PU |
| ID197 | est-not-ext | 9.1 | Brain | 33-57-4-H5-PU |
| ID198 | est-not-ext | 9 | Brain | 33-60-2-B3-PU |
| ID199 | est-not-ext | 8.6 | Brain | 33-52-1-A1-PU |
| ID200 | est-not-ext | 8.4 | Brain | 33-82-2-H10-PU |
| ID201 | est-not-ext | 7.5 | Brain | 33-79-4-B11-PU |
| ID202 | est-not-ext | 7.5 | Brain | 33-18-3-H3-PU |
| ID203 | est-not-ext | 7.5 | Brain | 33-21-1-D6-PU |
| ID204 | est-not-ext | 7.4 | Brain | 33-17-3-F9-PU |
| ID205 | est-not-ext | 7.4 | Brain | 33-70-2-G3-PU |
| ID206 | est-not-ext | 7.4 | Brain | 33-89-3-H4-PU |
| ID207 | est-not-ext | 7.4 | Brain | 33-46-3-E10-PU |
| ID208 | est-not-ext | 7 | Brain | 33-36-2-F9-PU |
| ID209 | est-not-ext | 6.8 | Brain | 33-39-1-C4-PU |
| ID210 | est-not-ext | 6.8 | Brain | 33-65-4-C6-PU |
| ID211 | est-not-ext | 6.4 | Brain | 33-18-2-G6-PU |
| ID212 | est-not-ext | 6.4 | Brain | 33-36-3-C6-PU |
| ID213 | est-not-ext | 6 | Brain | 33-79-2-B6-PU |
| ID214 | est-not-ext | 5.9 | Brain | 33-71-4-D11-PU |
| ID215 | est-not-ext | 5.9 | Brain | 17-12-2-A3-PU |
| ID216 | est-not-ext | 5.9 | Brain | 33-95-1-A12-PU |
| ID217 | est-not-ext | 5.8 | Brain | 33-5-3-E3-PU |
| ID218 | est-not-ext | 5.8 | Brain | 33-74-2-D3-PU |
| ID219 | est-not-ext | 5.7 | Brain | 33-50-3-H8-PU |
| ID220 | est-not-ext | 5.6 | Brain | 33-19-1-A2-PU |
| ID221 | est-not-ext | 5.5 | Brain | 33-22-1-D3-PU |
| ID222 | est-not-ext | 5.5 | Brain | 33-97-1-G4-PU |
| ID223 | est-not-ext | 5.4 | Brain | 33-65-4-D10-PU |
| ID224 | est-not-ext | 5.4 | Brain | 33-79-4-C4-PU |
| ID225 | est-not-ext | 5.3 | Brain | 33-20-2-C5-PU |
| ID226 | est-not-ext | 5.2 | Brain | 33-34-4-A5-PU |
| ID227 | est-not-ext | 5.2 | Brain | 33-6-2-F11-PU |
| ID228 | est-not-ext | 5.2 | Brain | 33-2-2-G5-PU |
| ID229 | est-not-ext | 5.1 | Brain | 33-98-1-G7-PU |
| ID230 | est-not-ext | 5.1 | Brain | 33-20-3-B10-PU |
| ID231 | est-not-ext | 5 | Brain | 33-106-2-D9-PU |
| ID232 | est-not-ext | 4.9 | Brain | 33-72-2-A9-PU |
| ID233 | est-not-ext | 4.9 | Brain | 33-83-3-G8-PU |
| ID234 | est-not-ext | 4.8 | Brain | 33-31-3-E6-PU |
| ID235 | est-not-ext | 4.7 | Brain | 33-28-4-E2-PU |
| ID236 | est-not-ext | 4.6 | Brain | 33-101-3-F4-PU |
| ID237 | est-not-ext | 4.6 | Brain | 33-98-4-C1-PU |
| ID238 | est-not-ext | 4.5 | Brain | 33-31-2-E11-PU |
| ID239 | est-not-ext | 4.5 | Brain | 33-26-2-B6-PU |

TABLE II-continued

| SEQ. ID NO. | CATEGORY | VON HEIJNE SCORE | TISSUE SOURCE | INTERNAL DESIGNATION |
|---|---|---|---|---|
| ID240 | est-not-ext | 4.4 | Brain | 33-75-4-H7-PU |
| ID241 | est-not-ext | 4.3 | Brain | 33-13-1-C6-PU |
| ID242 | est-not-ext | 4.3 | Brain | 33-35-4-G1-PU |
| ID243 | est-not-ext | 4.3 | Brain | 33-76-3-G11-PU |
| ID244 | est-not-ext | 4.2 | Brain | 33-72-1-A3-PU |
| ID245 | est-not-ext | 4.2 | Brain | 33-71-2-A2-PU |
| ID246 | est-not-ext | 4.2 | Brain | 33-23-3-H10-PU |
| ID247 | est-not-ext | 4.2 | Brain | 33-13-1-C1-PU |
| ID248 | est-not-ext | 4.2 | Brain | 33-43-2-G12-PU |
| ID249 | est-not-ext | 4.2 | Brain | 33-91-4-E10-PU |
| ID250 | est-not-ext | 4.1 | Brain | 33-113-2-B8-PU |
| ID251 | est-not-ext | 4 | Brain | 33-104-3-G9-PU |
| ID252 | est-not-ext | 3.9 | Brain | 33-66-2-B10-PU |
| ID253 | est-not-ext | 3.9 | Brain | 33-1-2-E9-PU |
| ID254 | est-not-ext | 3.9 | Brain | 33-51-1-G7-PU |
| ID255 | est-not-ext | 3.9 | Brain | 33-32-3-D11-PU |
| ID256 | est-not-ext | 3.8 | Brain | 33-43-2-H10-PU |
| ID257 | est-not-ext | 3.8 | Brain | 33-48-4-H11-PU |
| ID258 | est-not-ext | 3.8 | Brain | 33-8-4-C5-PU |
| ID259 | est-not-ext | 3.8 | Brain | 33-24-1-F5-PU |
| ID260 | est-not-ext | 3.8 | Brain | 33-70-1-A9-PU |
| ID261 | est-not-ext | 3.8 | Brain | 33-30-4-C4-PU |
| ID262 | est-not-ext | 3.8 | Brain | 33-10-2-G7-PU |
| ID263 | est-not-ext | 3.6 | Brain | 33-18-4-E12-PU |
| ID264 | est-not-ext | 3.6 | Brain | 33-52-1-G7-PU |
| ID265 | est-not-ext | 3.6 | Brain | 33-57-1-H10-PU |
| ID266 | est-not-ext | 3.5 | Brain | 33-80-3-E2-PU |
| ID267 | est-not-ext | 3.5 | Brain | 33-36-1-D3-PU |
| ID268 | ext-vrt-not-genomic | 11.3 | Brain | 33-101-1-A2-PU |
| ID269 | ext-vrt-not-genomic | 6.6 | Brain | 33-55-2-E8-PU |
| ID270 | ext-vrt-not-genomic | 4.8 | Brain | 33-14-2-H3-PU |
| ID271 | new | 15 | Liver<br>Fetal liver | 22-6-1-A10-PU |
| ID272 | new | 13.2 | Ovary<br>Hypertrophic prostate<br>Brain | 77-16-3-B7-PU |
| ID273 | new | 13.1 | Fetal brain<br>Substantia nigra | 47-47-1-F2-PU |
| ID274 | new | 11.6 | Fetal kidney<br>Cancerous prostate | 58-12-2-E11-PU |
| ID275 | new | 10.7 | Liver<br>Kidney | 21-4-2-D1-PU |
| ID276 | new | 9.6 | Hypertrophic prostate<br>Cancerous prostate<br>Large intestine | 77-38-4-B2-PU |
| ID277 | new | 9.4 | Fetal kidney<br>Cancerous prostate | 76-10-2-B7-PU |
| ID278 | new | 9.4 | Prostate<br>Brain | 33-99-2-G8-PU |
| ID279 | new | 9.1 | Hypertrophic prostate<br>Normal prostate<br>Brain | 78-32-2-C2-PU |
| ID280 | new | 9.1 | Ovary<br>Brain | 26-40-3-D6-PU |
| ID281 | new | 8 | Fetal kidney<br>Brain | 33-106-2-F10-PU |
| ID282 | new | 7.8 | Fetal kidney<br>Lung (cells) | 58-38-1-A2-PU |
| ID283 | new | 7.4 | Lymph ganglia<br>Surrenals | 62-10-3-A11-PU |
| ID284 | new | 7.4 | Hypertrophic prostate<br>Cancerous prostate | 76-45-1-F5-PU |
| ID285 | new | 7.1 | Fetal kidney<br>Lung (cells)<br>Umbilical cord<br>Hypertrophic prostate<br>Cancerous prostate<br>Substantia nigra | 37-10-3-D7-PU |
| ID286 | new | 6.9 | Hypertrophic prostate<br>Normal prostate<br>Lymph ganglia<br>Spleen | 78-16-2-B12-PU |
| ID287 | new | 6.8 | Fetal brain<br>Brain | 33-38-2-A4-PU |

TABLE II-continued

| SEQ. ID NO. | CATEGORY | VON HEIJNE SCORE | TISSUE SOURCE | INTERNAL DESIGNATION |
|---|---|---|---|---|
| ID288 | new | 6.7 | Heart<br>Spleen<br>Substantia nigra | 47-25-4-A2-PU |
| ID289 | new | 6.3 | Fetal brain<br>Spleen | 20-10-3-D9-PU |
| ID290 | new | 6.3 | Hypertrophic prostate<br>Thyroid | 84-5-1-C9-PU |
| ID291 | new | 6.3 | Prostate<br>Hypertrophic prostate<br>Normal prostate<br>Cancerous prostate | 76-40-1-A8-PU |
| ID292 | new | 6.3 | Fetal kidney<br>Normal prostate<br>Hypertrophic prostate<br>Cancerous prostate | 76-5-1-F4-PU |
| ID293 | new | 6.3 | Fetal kidney<br>Hypertrophic prostate<br>Kidney | 77-25-3-H5-PU |
| ID294 | new | 5.7 | Prostate<br>Lymph ganglia<br>Lung | 42-1-4-H1-PU |
| ID295 | new | 5.6 | Brain<br>Lymph ganglia<br>Pancreas | 33-80-4-E4-PU |
| ID296 | new | 5.6 | Fetal kidney<br>Normal prostate | 58-47-2-E11-PU |
| ID297 | new | 5.6 | Muscle<br>Brain | 33-56-4-F4-PU |
| ID298 | new | 5.5 | Placenta<br>Lung (cells)<br>Colon<br>Cancerous prostate | 23-1-4-F6-PU |
| ID299 | new | 5.3 | Normal prostate<br>Cancerous prostate | 76-44-2-F7-PU |
| ID300 | new | 5.2 | Hypertrophic prostate<br>Cancerous prostate | 76-19-1-E9-PU |
| ID301 | new | 5.1 | Colon<br>Normal prostate<br>Kidney | 78-31-1-D12-PU |
| ID302 | new | 4.9 | Prostate<br>Spleen | 20-1-4-H6-PU |
| ID303 | new | 4.9 | Lymphocytes<br>Cancerous prostate | 24-3-4-C4-PU |
| ID304 | new | 4.7 | Kidney<br>Brain | 33-102-2-C9-PU |
| ID305 | new | 4.7 | Colon<br>Lymph ganglia | 48-47-3-A5-PU |
| ID306 | new | 4.6 | Placenta<br>Hypertrophic prostate | 77-2-3-D1-PU |
| ID307 | new | 4.6 | Normal prostate<br>Thyroid<br>Cancerous prostate<br>Substantia nigra | 76-3-3-C7-PU |
| ID308 | new | 4.5 | Fetal kidney<br>Large intestine | 83-1-3-H6-PU |
| ID309 | new | 4.4 | Fetal brain<br>Brain | 33-7-2-D11-PU |
| ID310 | new | 4 | Normal prostate<br>Substantia nigra | 78-28-2-G12-PU |
| ID311 | new | 3.9 | Normal prostate<br>Cancerous prostate | 76-23-3-D8-PU |
| ID312 | new | 3.9 | Heart<br>Lymph ganglia | 48-3-3-H9-PU |
| ID313 | new | 3.8 | Brain<br>Lung | 42-2-4-B8-PU |
| ID314 | new | 3.8 | Normal prostate<br>Hypertrophic prostate | 77-37-2-H1-PU |
| ID315 | new | 3.8 | Lung (cells)<br>Testis<br>Lung | 51-37-4-B1-PU |
| ID316 | new | 3.7 | Ovary<br>Lung (cells)<br>Colon<br>Normal prostate | 23-9-4-G9-PU |

TABLE II-continued

| SEQ. ID NO. | CATEGORY | VON HEIJNE SCORE | TISSUE SOURCE | INTERNAL DESIGNATION |
|---|---|---|---|---|
| ID317 | new | 3.5 | Ovary<br>Muscle<br>Hypertrophic prostate | 27-3-2-B6-PU |
| ID318 | new | 3.5 | Normal prostate<br>Hypertrophic prostate<br>Cancerous prostate | 76-30-3-B7-PU |
| ID319 | ext-est-not-vrt | 13.4 | Ovary<br>Prostate<br>Cancerous prostate | 76-9-4-G9-PU |
| ID320 | ext-est-not-vrt | 12.6 | Normal prostate<br>Hypertrophic prostate | 78-25-4-H1-PU |
| ID321 | ext-est-not-vrt | 11.8 | Fetal kidney<br>Hypertrophic prostate | 77-1-4-D10-PU |
| ID322 | ext-est-not-vrt | 11.2 | Lung (cells)<br>Normal prostate<br>Cancerous prostate | 78-37-1-A12-PU |
| ID323 | ext-est-not-vrt | 10.3 | Umbilical cord<br>Hypertrophic prostate | 37-10-2-C10-PU |
| ID324 | ext-est-not-vrt | 10.1 | Brain<br>Cancerous prostate | 76-16-1-H5-PU |
| ID325 | ext-est-not-vrt | 9.8 | Lymphocytes<br>Lung (cells)<br>Umbilical cord<br>Normal prostate | 24-1-4-G11-PU |
| ID326 | ext-est-not-vrt | 9.3 | Thyroid<br>Heart<br>Lymph ganglia<br>Lung | 48-51-2-C10-PU |
| ID327 | ext-est-not-vrt | 8.4 | | 33-97-4-G8-PU |
| ID328 | ext-est-not-vrt | 7.8 | Fetal brain<br>Brain | 33-22-1-F9-PU |
| ID329 | ext-est-not-vrt | 7.4 | Ovary<br>Liver<br>Umbilical cord<br>Kidney<br>Surrenals | 37-7-4-E7-PU |
| ID330 | ext-est-not-vrt | 7.2 | Muscle<br>Liver<br>Dystrophic muscle<br>Normal prostate<br>Testis<br>Cancerous prostate<br>Lymph ganglia<br>Large intestine | 27-12-3-H8-PU |
| ID331 | ext-est-not-vrt | 7.1 | Fetal kidney<br>Ovary | 58-23-4-G9-PU |
| ID332 | ext-est-not-vrt | 6.9 | Placenta<br>Fetal kidney | 58-34-2-H8-PU |
| ID333 | ext-est-not-vrt | 6.7 | Fetal kidney<br>Fetal brain<br>Umbilical cord<br>Heart<br>Fetal liver | 37-9-1-D4-PU |
| ID334 | ext-est-not-vrt | 6.6 | Fetal kidney<br>Liver<br>Thyroid<br>Kidney<br>Cancerous prostate<br>Lung (cells)<br>Normal prostate<br>Lymph ganglia | 58-5-3-A8-PU |
| ID335 | ext-est-not-vrt | 6.6 | Cancerous prostate<br>Normal prostate | 76-35-1-A11-PU |
| ID336 | ext-est-not-vrt | 5.4 | Hypertrophic prostate<br>Lung (cells) | 77-35-2-E10-PU |
| ID337 | ext-est-not-vrt | 5.4 | Fetal kidney<br>Fetal brain<br>Normal prostate | 58-52-4-D8-PU |
| ID338 | ext-est-not-vrt | 5.3 | Cancerous prostate<br>Substantia nigra | 47-26-3-D2-PU |
| ID339 | ext-est-not-vrt | 5.1 | Cancerous prostate<br>Fetal brain<br>Lung (cells)<br>Brain | 30-9-1-G8-PU |
| ID340 | ext-est-not-vrt | 4.9 | Lung<br>Brain | 33-98-1-C6-PU |

TABLE II-continued

| SEQ. ID NO. | CATEGORY | VON HEIJNE SCORE | TISSUE SOURCE | INTERNAL DESIGNATION |
|---|---|---|---|---|
| ID341 | ext-est-not-vrt | 4.5 | Ovary<br>Prostate<br>Normal prostate<br>Brain | 78-26-1-B12-PU |
| ID342 | ext-est-not-vrt | 4.2 | Fetal kidney<br>Cancerous prostate<br>Normal prostate | 58-7-2-F8-PU |
| ID343 | ext-est-not-vrt | 3.7 | Fetal kidney<br>Ovary<br>Prostate<br>Normal prostate | 58-33-1-F9-PU |
| ID344 | ext-est-not-vrt | 3.6 | Brain<br>Lymph ganglia | 33-19-1-F1-PU |
| ID345 | ext-est-not-vrt | 3.5 | Fetal kidney<br>Liver<br>Kidney<br>Brain | 58-14-2-D3-PU |
| ID346 | ext-est-not-vrt | 3.5 | Ovary<br>Hypertrophic prostate | 26-40-2-B2-PU |
| ID347 | est-not-ext | 13.9 | Fetal kidney<br>Cancerous prostate<br>Normal prostate | 58-52-4-F10-PU |
| ID348 | est-not-ext | 13.9 | Fetal kidney<br>Lung (cells) | 58-15-1-H6-PU |
| ID349 | est-not-ext | 11.6 | Ovary<br>Dystrophic muscle<br>Cancerous prostate<br>Uterus<br>Testis<br>Lymph ganglia<br>Surrenals | 51-29-2-B2-PU |
| ID350 | est-not-ext | 11.6 | Lymph ganglia<br>Large intestine | 48-7-1-F2-PU |
| ID351 | est-not-ext | 11.6 | Umbilical cord<br>Pancreas | 37-6-1-E12-PU |
| ID352 | est-not-ext | 11.4 | Heart<br>Brain | 67-3-4-G7-PU |
| ID353 | est-not-ext | 11.2 | Dystrophic muscle<br>Brain | 33-35-4-F4-PU |
| ID354 | est-not-ext | 11 | Ovary<br>Heart<br>Kidney<br>Cancerous prostate<br>Lymph ganglia | 48-14-1-A11-PU |
| ID355 | est-not-ext | 10.5 | Lung<br>Umbilical cord<br>Normal prostate | 37-11-1-G2-PU |
| ID356 | est-not-ext | 10 | Fetal kidney<br>Cancerous prostate<br>Normal prostate<br>Brain | 58-3-4-G2-PU |
| ID357 | est-not-ext | 9.5 | Fetal kidney<br>Cancerous prostate<br>Umbilical cord<br>Normal prostate | 76-18-1-F6-PU |
| ID358 | est-not-ext | 9.5 | Placenta<br>Muscle<br>Substantia nigra | 47-24-2-C1-PU |
| ID359 | est-not-ext | 9.3 | Ovary<br>Cancerous prostate<br>Umbilical cord<br>Colon<br>Normal prostate<br>Testis | 37-11-4-H11-PU |
| ID360 | est-not-ext | 9.3 | Cancerous prostate<br>Normal prostate<br>Substantia nigra | 47-37-2-E3-PU |
| ID361 | est-not-ext | 9.3 | Spleen<br>Muscle | 27-16-1-E4-PU |
| ID362 | est-not-ext | 9.3 | Colon<br>Substantia nigra | 47-5-1-G3-PU |
| ID363 | est-not-ext | 9.2 | Ovary<br>Hypertrophic prostate<br>Fetal brain | 57-2-4-E11-PU |
| ID364 | est-not-ext | 9 | Cancerous prostate<br>Normal prostate | 76-32-1-G12-PU |

TABLE II-continued

| SEQ. ID NO. | CATEGORY | VON HEIJNE SCORE | TISSUE SOURCE | INTERNAL DESIGNATION |
|---|---|---|---|---|
| ID365 | est-not-ext | 8.9 | Fetal kidney<br>Hypertrophic prostate<br>Placenta<br>Normal prostate<br>Brain | 77-25-1-C6-PU |
| ID366 | est-not-ext | 8.8 | Dystrophic muscle<br>Umbilical cord<br>Brain | 37-7-2-B11-PU |
| ID367 | est-not-ext | 8.8 | Fetal kidney<br>Dystrophic muscle<br>Hypertrophic prostate<br>Thyroid<br>Cancerous prostate<br>Fetal brain<br>Muscle<br>Lung (cells)<br>Normal prostate<br>Brain<br>Lymph ganglia<br>Large intestine | 77-7-3-C8-PU |
| ID368 | est-not-ext | 8.7 | Fetal kidney<br>Prostate<br>Hypertrophic prostate<br>Spleen<br>Lung (cells)<br>Umbilical cord<br>Testis<br>Brain<br>Lymph ganglia | 48-7-3-G5-PU |
| ID369 | est-not-ext | 8.6 | Fetal kidney<br>Normal prostate | 78-17-2-E5-PU |
| ID370 | est-not-ext | 8.6 | Placenta<br>Brain | 33-10-4-E2-PU |
| ID371 | est-not-ext | 8.5 | Umbilical cord<br>Normal prostate | 37-11-1-C7-PU |
| ID372 | est-not-ext | 8.5 | Fetal kidney<br>Lymphocytes<br>Ovary<br>Hypertrophic prostate | 26-48-1-H10-PU |
| ID373 | est-not-ext | 8.3 | Prostate<br>Cancerous prostate<br>Spleen<br>Normal prostate<br>Brain<br>Lymph ganglia<br>Large intestine | 60-13-3-F6-PU |
| ID374 | est-not-ext | 8.3 | Cancerous prostate<br>Normal prostate | 78-22-4-A12-PU |
| ID375 | est-not-ext | 8.1 | Fetal kidney<br>Ovary<br>Dystrophic muscle<br>Hypertrophic prostate<br>Cancerous prostate<br>Lung<br>Spleen<br>Placenta<br>Fetal brain<br>Normal prostate<br>Colon<br>Brain<br>Substantia nigra | 57-28-4-B11-PU |
| ID376 | est-not-ext | 8 | Cancerous prostate<br>Uterus<br>Lung (cells)<br>Colon<br>Brain<br>Substantia nigra | 33-106-3-D8-PU |
| ID377 | est-not-ext | 7.9 | Normal prostate<br>Colon | 23-8-3-F5-PU |
| ID378 | est-not-ext | 7.8 | Placenta<br>Brain | 17-1-3-H5 |
| ID379 | est-not-ext | 7.6 | Lung<br>Normal prostate<br>Brain<br>Substantia nigra | 33-37-2-G9-PU |

TABLE II-continued

| SEQ. ID NO. | CATEGORY | VON HEIJNE SCORE | TISSUE SOURCE | INTERNAL DESIGNATION |
|---|---|---|---|---|
| ID380 | est-not-ext | 7.6 | Brain<br>Testis | 51-16-4-H4-PU |
| ID381 | est-not-ext | 7.6 | Hypertrophic prostate<br>Cancerous prostate<br>Fetal brain<br>Muscle<br>Brain<br>Lymph ganglia<br>Large intestine<br>Surrenals | 33-32-3-G1-PU |
| ID382 | est-not-ext | 7.6 | Fetal kidney<br>Hypertrophic prostate<br>Cancerous prostate<br>Lung (cells)<br>Umbilical cord<br>Normal prostate<br>Brain<br>Surrenals<br>Substantia nigra | 47-10-4-F3-PU |
| ID383 | est-not-ext | 7.4 | Heart<br>Cancerous prostate<br>Testis | 51-1-3-G10-PU |
| ID384 | est-not-ext | 7.4 | Umbilical cord<br>Brain<br>Lymph ganglia | 33-39-4-B2-PU |
| ID385 | est-not-ext | 7.4 | Normal prostate<br>Brain<br>Substantia nigra | 47-14-3-A3-PU |
| ID386 | est-not-ext | 7.4 | Liver<br>Lymph ganglia | 48-53-3-H11-PU |
| ID387 | est-not-ext | 7.4 | Cerebellum<br>Dystrophic muscle<br>Hypertrophic prostate<br>Heart<br>Uterus<br>Umbilical cord<br>Brain | 33-63-1-C3-PU |
| ID388 | est-not-ext | 7.3 | Fetal kidney<br>Ovary<br>Hypertrophic prostate<br>Spleen<br>Lung (cells)<br>Umbilical cord<br>Normal prostate<br>Brain<br>Substantia nigra | 53-3-4-F11-PU |
| ID389 | est-not-ext | 7.2 | Fetal kidney<br>Fetal brain<br>Uterus<br>Muscle<br>Umbilical cord<br>Lung (cells)<br>Colon<br>Normal prostate<br>Brain<br>Lymph ganglia<br>Fetal liver<br>Substantia nigra<br>Surrenals | 48-5-4-E8-PU |
| ID390 | est-not-ext | 7.1 | Cancerous prostate<br>Lymph ganglia<br>Large intestine<br>Surrenals | 48-54-3-D2-PU |
| ID391 | est-not-ext | 7.1 | Prostate<br>Hypertrophic prostate<br>Cancerous prostate<br>Normal prostate | 78-18-3-C8-PU |
| ID392 | est-not-ext | 7.1 | Normal prostate<br>Testis | 51-4-2-E10-PU |
| ID393 | est-not-ext | 7 | Fetal kidney<br>Lymphocytes<br>Umbilical cord | 24-11-1-E4-PU |
| ID394 | est-not-ext | 7 | Cancerous prostate<br>Brain | 76-1-2-B8-PU |

TABLE II-continued

| SEQ. ID NO. | CATEGORY | VON HEIJNE SCORE | TISSUE SOURCE | INTERNAL DESIGNATION |
|---|---|---|---|---|
| ID395 | est-not-ext | 6.7 | Ovary<br>Thyroid<br>Cancerous prostate<br>Uterus<br>Muscle<br>Normal prostate<br>Testis<br>Lymph ganglia | 51-11-3-G9-PU |
| ID396 | est-not-ext | 6.7 | Hypertrophic prostate<br>Lung<br>Brain<br>Surrenals | 77-16-4-G3-PU |
| ID397 | est-not-ext | 6.6 | Fetal kidney<br>Hypertrophic prostate | 77-38-2-D5-PU |
| ID398 | est-not-ext | 6.6 | Fetal kidney<br>Cancerous prostate<br>Brain | 58-3-3-C8-PU |
| ID399 | est-not-ext | 6.5 | Brain<br>Testis | 51-1-4-C1-PU |
| ID400 | est-not-ext | 6.5 | Fetal kidney<br>Brain<br>Lymph ganglia | 58-9-2-A6-PU |
| ID401 | est-not-ext | 6.3 | Fetal kidney<br>Cancerous prostate<br>Lung (cells) | 30-4-1-E7-PU |
| ID402 | est-not-ext | 6.3 | Normal prostate<br>Brain | 33-51-3-H4-PU |
| ID403 | est-not-ext | 6.3 | Cancerous prostate<br>Fetal brain | 57-27-3-A11-PU |
| ID404 | est-not-ext | 6.3 | Hypertrophic prostate<br>Fetal brain<br>Normal prostate<br>Brain | 57-5-4-G1-PU |
| ID405 | est-not-ext | 6.2 | Fetal kidney<br>Normal prostate<br>Testis | 58-6-1-H4-PU |
| ID406 | est-not-ext | 6.2 | Fetal kidney<br>Liver<br>Cancerous prostate<br>Umbilical cord | 37-12-1-D7-PU |
| ID407 | est-not-ext | 6.2 | Cancerous prostate<br>Normal prostate<br>Large intestine | 78-13-1-H1-PU |
| ID408 | est-not-ext | 6.2 | Brain<br>Substantia nigra | 33-18-3-G10-PU |
| ID409 | est-not-ext | 6.2 | Normal prostate<br>Substantia nigra | 78-39-4-B9-PU |
| ID410 | est-not-ext | 6.2 | Brain<br>Substantia nigra | 33-18-2-B1-PU |
| ID411 | est-not-ext | 6.1 | Fetal kidney<br>Umbilical cord<br>Normal prostate | 37-4-3-D5-PU |
| ID412 | est-not-ext | 6.1 | Cerebellum<br>Muscle<br>Brain<br>Substantia nigra<br>Fetal kidney<br>Prostate<br>Hypertrophic prostate<br>Cancerous prostate<br>Lung<br>Lung (cells)<br>Umbilical cord<br>Normal prostate<br>Testis<br>Lymph ganglia<br>Large intestine<br>Surrenals | 58-35-3-D12-PU |
| ID413 | est-not-ext | 6.1 | Fetal liver<br>Testis | 51-38-3-D10-PU |
| ID414 | est-not-ext | 6.1 | Uterus<br>Fetal liver<br>Substantia nigra<br>Ovary<br>Cancerous prostate<br>Fetal brain | 76-14-3-G2-PU |

TABLE II-continued

| SEQ. ID NO. | CATEGORY | VON HEIJNE SCORE | TISSUE SOURCE | INTERNAL DESIGNATION |
|---|---|---|---|---|
| | | | Normal prostate | |
| | | | Lymph ganglia | |
| ID415 | est-not-ext | 6.1 | Cancerous prostate | 76-30-1-F7-PU |
| | | | Normal prostate | |
| ID416 | est-not-ext | 6 | Brain | 76-43-3-E11-PU |
| | | | Cancerous prostate | |
| ID417 | est-not-ext | 6 | Thyroid | 78-41-2-H7-PU |
| | | | Pancreas | |
| | | | Fetal kidney | |
| | | | Normal prostate | |
| ID418 | est-not-ext | 5.9 | Liver | 59-8-1-B7-PU |
| | | | Lung | |
| ID419 | est-not-ext | 5.8 | Brain | 78-37-4-E6-PU |
| | | | Lung | |
| | | | Normal prostate | |
| ID420 | est-not-ext | 5.8 | Kidney | 59-1-2-E4-PU |
| | | | Cancerous prostate | |
| | | | Lung | |
| ID421 | est-not-ext | 5.7 | Umbilical cord | 78-38-4-G2-PU |
| | | | Normal prostate | |
| ID422 | est-not-ext | 5.7 | Lymphocytes | 20-1-3-G5-PU |
| | | | Spleen | |
| | | | Uterus | |
| | | | Substantia nigra | |
| | | | Fetal kidney | |
| | | | Hypertrophic prostate | |
| | | | Cancerous prostate | |
| | | | Normal prostate | |
| | | | Testis | |
| ID423 | est-not-ext | 5.7 | Brain | 58-37-3-E3-PU |
| | | | Fetal kidney | |
| ID424 | est-not-ext | 5.7 | Brain | 33-15-1-H3-PU |
| | | | Fetal brain | |
| ID425 | est-not-ext | 5.6 | Lymphocytes | 37-1-1-C2-PU |
| | | | Thyroid | |
| | | | Spleen | |
| | | | Uterus | |
| | | | Substantia nigra | |
| | | | Hypertrophic prostate | |
| | | | Umbilical cord | |
| | | | Normal prostate | |
| | | | Surrenals | |
| ID426 | est-not-ext | 5.6 | Fetal kidney | 48-10-1-A8-PU |
| | | | Umbilical cord | |
| | | | Lymph ganglia | |
| ID427 | est-not-ext | 5.6 | Surrenals | 62-1-2-D2-PU |
| ID428 | est-not-ext | 5.6 | Brain | 33-12-4-A7-PU |
| | | | Hypertrophic prostate | |
| ID429 | est-not-ext | 5.6 | Brain | 78-30-4-H3-PU |
| | | | Normal prostate | |
| ID430 | est-not-ext | 5.6 | Cerebellum | 47-8-4-C11-PU |
| | | | Brain | |
| | | | Substantia nigra | |
| | | | Fetal kidney | |
| | | | Hypertrophic prostate | |
| | | | Lung | |
| | | | Fetal brain | |
| | | | Normal prostate | |
| | | | Lymph ganglia | |
| ID431 | est-not-ext | 5.6 | Thyroid | 84-4-2-C1-PU |
| | | | Brain | |
| ID432 | est-not-ext | 5.6 | Brain | 30-12-4-C2-PU |
| | | | Dystrophic muscle | |
| | | | Lung (cells) | |
| | | | Normal prostate | |
| | | | Testis | |
| ID433 | est-not-ext | 5.6 | Placenta | 1-32-0-D10 |
| | | | Lung | |
| ID434 | est-not-ext | 5.5 | Ovary | 30-1-2-E3-PU |
| | | | Lung (cells) | |
| ID435 | est-not-ext | 5.5 | Ovary | 60-11-1-F1-PU |
| | | | Prostate | |
| | | | Lymph ganglia | |
| ID436 | est-not-ext | 5.5 | Spleen | 33-105-2-C3-PU |
| | | | Brain | |
| | | | Fetal kidney | |

TABLE II-continued

| SEQ. ID NO. | CATEGORY | VON HEIJNE SCORE | TISSUE SOURCE | INTERNAL DESIGNATION |
|---|---|---|---|---|
| | | | Prostate | |
| | | | Hypertrophic prostate | |
| | | | Lung (cells) | |
| | | | Umbilical cord | |
| | | | Testis | |
| | | | Lymph ganglia | |
| ID437 | est-not-ext | 5.5 | Cancerous prostate | 76-31-4-H1-PU |
| | | | Normal prostate | |
| ID438 | est-not-ext | 5.5 | Fetal kidney | 30-10-3-B10-PU |
| | | | Ovary | |
| | | | Cancerous prostate | |
| | | | Umbilical cord | |
| | | | Lung (cells) | |
| ID439 | est-not-ext | 5.4 | Muscle | 27-3-2-E11-PU |
| | | | Fetal kidney | |
| | | | Cancerous prostate | |
| | | | Lung | |
| | | | Lymph ganglia | |
| ID440 | est-not-ext | 5.3 | Placenta | 31-9-2-F9-PU |
| | | | Muscle | |
| | | | Brain | |
| | | | Substantia nigra | |
| | | | Cancerous prostate | |
| | | | Umbilical cord | |
| ID441 | est-not-ext | 5.3 | Brain | 47-40-3-D2-PU |
| | | | Substantia nigra | |
| | | | Fetal kidney | |
| ID442 | est-not-ext | 5.3 | Brain | 33-77-1-F10-PU |
| | | | Substantia nigra | |
| | | | Lung | |
| ID443 | est-not-ext | 5.2 | Cerebellum | 51-19-3-D6-PU |
| | | | Ovary | |
| | | | Umbilical cord | |
| | | | Testis | |
| ID444 | est-not-ext | 5.2 | Brain | 51-6-2-F10-PU |
| | | | Hypertrophic prostate | |
| | | | Colon | |
| | | | Testis | |
| ID445 | est-not-ext | 5.2 | Brain | 33-72-4-C5-PU |
| | | | Fetal kidney | |
| | | | Fetal brain | |
| | | | Umbilical cord | |
| | | | Normal prostate | |
| ID446 | est-not-ext | 5 | Brain | 33-18-3-E6-PU |
| | | | Normal prostate | |
| ID447 | est-not-ext | 5 | Brain | 33-5-2-E1-PU |
| | | | Substantia nigra | |
| | | | Fetal kidney | |
| | | | Umbilical cord | |
| | | | Lymph ganglia | |
| ID448 | est-not-ext | 5 | Liver | 76-22-3-E4-PU |
| | | | Uterus | |
| | | | Muscle | |
| | | | Heart | |
| | | | Cancerous prostate | |
| ID449 | est-not-ext | 5 | Fetal kidney | 51-15-2-H5-PU |
| | | | Testis | |
| ID450 | est-not-ext | 4.9 | Colon | 78-33-3-A9-PU |
| | | | Normal prostate | |
| ID451 | est-not-ext | 4.9 | Brain | 58-42-2-H11-PU |
| | | | Substantia nigra | |
| | | | Fetal kidney | |
| | | | Dystrophic muscle | |
| | | | Cancerous prostate | |
| | | | Lung | |
| | | | Lymph ganglia | |
| ID452 | est-not-ext | 4.9 | Brain | 33-111-3-F7-PU |
| | | | Substantia nigra | |
| ID453 | est-not-ext | 4.9 | Substantia nigra | 76-44-3-C5-PU |
| | | | Fetal kidney | |
| | | | Hypertrophic prostate | |
| | | | Cancerous prostate | |
| ID454 | est-not-ext | 4.9 | Substantia nigra | 78-40-4-B10-PU |
| | | | Normal prostate | |
| | | | Testis | |
| | | | Surrenals | |

TABLE II-continued

| SEQ. ID NO. | CATEGORY | VON HEIJNE SCORE | TISSUE SOURCE | INTERNAL DESIGNATION |
|---|---|---|---|---|
| ID455 | est-not-ext | 4.9 | Fetal kidney<br>Normal prostate | 78-6-3-F5-PU |
| ID456 | est-not-ext | 4.9 | Thyroid<br>Brain<br>Fetal kidney | 58-48-4-E2-PU |
| ID457 | est-not-ext | 4.8 | Placenta<br>Hypertrophic prostate<br>Normal prostate | 77-38-1-F10-PU |
| ID458 | est-not-ext | 4.8 | Lung (cells)<br>Normal prostate | 30-7-4-D6-PU |
| ID459 | est-not-ext | 4.8 | Cancerous prostate<br>Lymph ganglia | 48-4-2-H3-PU |
| ID460 | est-not-ext | 4.8 | Brain<br>Dystrophic muscle<br>Normal prostate | 33-77-4-E8-PU |
| ID461 | est-not-ext | 4.8 | Brain<br>Substantia nigra | 33-111-2-B4-PU |
| ID462 | est-not-ext | 4.7 | Normal prostate<br>Surrenals | 62-8-1-A5-PU |
| ID463 | est-not-ext | 4.7 | Brain<br>Fetal kidney | 33-6-1-G11-PU |
| ID464 | est-not-ext | 4.7 | Fetal liver<br>Substantia nigra<br>Fetal kidney<br>Heart<br>Cancerous prostate<br>Umbilical cord<br>Normal prostate | 58-13-1-H2-PU |
| ID465 | est-not-ext | 4.7 | Liver<br>Brain<br>Substantia nigra<br>Fetal kidney<br>Lung (cells)<br>Testis<br>Large intestine | 58-40-2-H6-PU |
| ID466 | est-not-ext | 4.7 | Brain<br>Fetal brain | 33-50-3-C3-PU |
| ID467 | est-not-ext | 4.7 | Thyroid<br>Spleen<br>Placenta<br>Muscle<br>Brain<br>Substantia nigra<br>Fetal kidney<br>Ovary<br>Heart<br>Cancerous prostate<br>Lung<br>Fetal brain<br>Umbilical cord<br>Normal prostate<br>Colon<br>Testis<br>Lymph ganglia<br>Surrenals | 62-10-4-C5-PU |
| ID468 | est-not-ext | 4.6 | Prostate<br>Lung (cells) | 60-16-2-F2-PU |
| ID469 | est-not-ext | 4.6 | Muscle<br>Brain<br>Substantia nigra<br>Fetal brain<br>Testis | 33-87-2-D2-PU |
| ID470 | est-not-ext | 4.6 | Liver<br>Brain | 33-80-3-B8-PU |
| ID471 | est-not-ext | 4.5 | Liver<br>Cancerous prostate<br>Normal prostate | 22-12-3-D4-PU |
| ID472 | est-not-ext | 4.5 | Lymphocytes<br>Spleen<br>Uterus<br>Placenta<br>Muscle<br>Brain<br>Substantia nigra<br>Fetal kidney<br>Ovary | 48-51-4-C11-PU |

TABLE II-continued

| SEQ. ID NO. | CATEGORY | VON HEIJNE SCORE | TISSUE SOURCE | INTERNAL DESIGNATION |
|---|---|---|---|---|
| | | | Prostate | |
| | | | Dystrophic muscle | |
| | | | Hypertrophic prostate | |
| | | | Heart | |
| | | | Cancerous prostate | |
| | | | Lung | |
| | | | Fetal brain | |
| | | | Lung (cells) | |
| | | | Umbilical cord | |
| | | | Normal prostate | |
| | | | Colon | |
| | | | Testis | |
| | | | Lymph ganglia | |
| | | | Surrenals | |
| ID473 | est-not-ext | 4.5 | Cerebellum | 47-15-1-H8-PU |
| | | | Substantia nigra | |
| | | | Normal prostate | |
| ID474 | est-not-ext | 4.4 | Hypertrophic prostate | 30-12-3-G5-PU |
| | | | Lung (cells) | |
| ID475 | est-not-ext | 4.4 | Brain | 58-4-4-D4-PU |
| | | | Fetal kidney | |
| | | | Cancerous prostate | |
| | | | Umbilical cord | |
| | | | Normal prostate | |
| ID476 | est-not-ext | 4.4 | Spleen | 53-3-2-D4-PU |
| ID477 | est-not-ext | 4.4 | Pancreas | 58-54-2-H8-PU |
| | | | Fetal kidney | |
| ID478 | est-not-ext | 4.4 | Thyroid | 27-17-2-C12-PU |
| | | | Kidney | |
| | | | Muscle | |
| | | | Brain | |
| | | | Ovary | |
| | | | Cancerous prostate | |
| | | | Umbilical cord | |
| | | | Normal prostate | |
| ID479 | est-not-ext | 4.4 | Liver | 48-5-3-A1-PU |
| | | | Placenta | |
| | | | Heart | |
| | | | Normal prostate | |
| | | | Lymph ganglia | |
| ID480 | est-not-ext | 4.4 | Placenta | 33-21-3-D12-PU |
| | | | Brain | |
| ID481 | est-not-ext | 4.4 | Substantia nigra | 47-2-3-B3-PU |
| | | | Fetal kidney | |
| | | | Umbilical cord | |
| ID482 | est-not-ext | 4.3 | Muscle | 58-15-2-D7-PU |
| | | | Fetal kidney | |
| | | | Cancerous prostate | |
| | | | Lung (cells) | |
| ID483 | est-not-ext | 4.3 | Substantia nigra | 58-41-1-G7-PU |
| | | | Fetal kidney | |
| | | | Fetal brain | |
| ID484 | est-not-ext | 4.2 | Brain | 77-5-3-F3-PU |
| | | | Fetal kidney | |
| | | | Hypertrophic prostate | |
| | | | Normal prostate | |
| ID485 | est-not-ext | 4.2 | Brain | 33-106-2-B3-PU |
| | | | Fetal kidney | |
| ID486 | est-not-ext | 4.2 | | 58-3-3-B2-PU |
| ID487 | est-not-ext | 4.2 | Normal prostate | 48-46-2-G12-PU |
| | | | Lymph ganglia | |
| ID488 | est-not-ext | 4.1 | Brain | 58-44-2-B3-PU |
| | | | Substantia nigra | |
| | | | Fetal kidney | |
| | | | Hypertrophic prostate | |
| | | | Lung (cells) | |
| | | | Testis | |
| ID489 | est-not-ext | 4.1 | Cerebellum | 47-18-4-E3-PU |
| | | | Substantia nigra | |
| ID490 | est-not-ext | 4.1 | Muscle | 78-21-3-F8-PU |
| | | | Substantia nigra | |
| | | | Normal prostate | |
| ID491 | est-not-ext | 4.1 | Brain | 33-49-1-H4-PU |
| | | | Surrenals | |
| ID492 | est-not-ext | 4.1 | Brain | 23-11-1-E11-PU |
| | | | Fetal kidney | |

TABLE II-continued

| SEQ. ID NO. | CATEGORY | VON HEIJNE SCORE | TISSUE SOURCE | INTERNAL DESIGNATION |
|---|---|---|---|---|
| ID493 | est-not-ext | 4 | Fetal brain<br>Normal prostate<br>Colon<br>Cerebellum<br>Brain<br>Heart | 33-5-2-H4-PU |
| ID494 | est-not-ext | 4 | Fetal brain<br>Normal prostate<br>Brain | 78-12-4-D9-PU |
| ID495 | est-not-ext | 4 | Normal prostate<br>Spleen | 33-103-1-D10-PU |
| ID496 | est-not-ext | 4 | Brain<br>Hypertrophic prostate<br>Normal prostate<br>Placenta | 33-100-4-B7-PU |
| ID497 | est-not-ext | 3.9 | Brain<br>Substantia nigra<br>Hypertrophic prostate<br>Dystrophic muscle<br>Umbilical cord | 29-11-2-D6-PU |
| ID498 | est-not-ext | 3.9 | Normal prostate | 78-27-3-D1-PU |
| ID499 | est-not-ext | 3.9 | Brain<br>Hypertrophic prostate<br>Cancerous prostate | 76-30-1-H7-PU |
| ID500 | est-not-ext | 3.9 | Uterus<br>Substantia nigra<br>Hypertrophic prostate | 74-10-3-C9-PU |
| ID501 | est-not-ext | 3.9 | Cancerous prostate | 76-19-1-A9-PU |
| ID502 | est-not-ext | 3.9 | Liver<br>Muscle<br>Brain<br>Cancerous prostate<br>Normal prostate | 76-44-4-A6-PU |
| ID503 | est-not-ext | 3.8 | Uterus<br>Brain<br>Substantia nigra | 74-2-1-H4-PU |
| ID504 | est-not-ext | 3.8 | Muscle<br>Lung (cells) | 27-21-1-H3-PU |
| ID505 | est-not-ext | 3.8 | Placenta<br>Brain | 33-13-3-E8-PU |
| ID506 | est-not-ext | 3.8 | Thyroid<br>Brain<br>Heart<br>Cancerous prostate<br>Fetal brain<br>Lung (cells)<br>Normal prostate<br>Testis<br>Lymph ganglia | 84-3-1-G10-PU |
| ID507 | est-not-ext | 3.7 | Uterus<br>Brain<br>Fetal kidney<br>Cancerous prostate | 33-8-1-A3-PU |
| ID508 | est-not-ext | 3.7 | Dystrophic muscle<br>Cancerous prostate | 76-43-4-H1-PU |
| ID509 | est-not-ext | 3.7 | Thyroid<br>Placenta | 84-5-4-H7-PU |
| ID510 | est-not-ext | 3.7 | Brain<br>Lung (cells)<br>Umbilical cord<br>Testis<br>Lymph ganglia | 37-4-1-B2-PU |
| ID511 | est-not-ext | 3.7 | Kidney<br>Placenta<br>Uterus<br>Hypertrophic prostate<br>Normal prostate<br>Lymph ganglia<br>Surrenals | 74-11-4-A9-PU |
| ID512 | est-not-ext | 3.7 | Substantia nigra<br>Hypertrophic prostate<br>Cancerous prostate | 77-2-2-B9-PU |
| ID513 | est-not-ext | 3.7 | Fetal kidney<br>Cancerous prostate<br>Lymph ganglia | 58-8-1-F2-PU |

TABLE II-continued

| SEQ. ID NO. | CATEGORY | VON HEIJNE SCORE | TISSUE SOURCE | INTERNAL DESIGNATION |
|---|---|---|---|---|
| ID514 | est-not-ext | 3.7 | Uterus<br>Prostate<br>Normal prostate<br>Lymph ganglia | 74-7-2-F2-PU |
| ID515 | est-not-ext | 3.6 | Fetal kidney<br>Umbilical cord<br>Testis<br>Large intestine | 37-2-1-H11-PU |
| ID516 | est-not-ext | 3.5 | Lymphocytes<br>Brain<br>Fetal kidney<br>Normal prostate | 58-6-1-F3-PU |
| ID517 | est-not-ext | 3.5 | Muscle<br>Brain<br>Hypertrophic prostate | 33-54-3-G1-PU |
| ID518 | est-not-ext | 3.5 | Fetal liver<br>Substantia nigra | 47-39-2-H6-PU |
| ID519 | est-not-ext | 3.5 | Brain<br>Cancerous prostate<br>Surrenals | 76-17-1-F5-PU |
| ID520 | est-not-ext | 3.5 | Placenta<br>Muscle<br>Heart<br>Cancerous prostate<br>Lung (cells)<br>Umbilical cord<br>Colon | 27-7-3-D1-PU |
| ID521 | est-not-ext | 3.5 | Liver<br>Uterus<br>Muscle<br>Brain<br>Ovary<br>Dystrophic muscle<br>Cancerous prostate<br>Normal prostate<br>Colon<br>Large intestine | 74-5-1-E4-PU |
| ID522 | est-not-ext | 3.5 | Brain<br>Cancerous prostate<br>Fetal brain<br>Umbilical cord<br>Surrenals | 57-20-1-F6-PU |
| ID523 | ext-vrt-not-genomic | 7.4 | Spleen<br>Hypertrophic prostate<br>Lymph ganglia | 48-25-3-A3-PU |
| ID524 | ext-vrt-not-genomic | 7 | Brain<br>Pancreas<br>Hypertrophic prostate<br>Normal prostate | 46-1-3-F4-PU |
| ID525 | new | 11.8 | Umbilical cord | 37-4-1-A12-PU |
| ID526 | new | 10 | Lymph ganglia | 48-50-1-G11-PU |
| ID527 | new | 10 | Lymph ganglia | 48-16-2-C11-PU |
| ID528 | new | 10 | Placenta | 14-8-1-C10-PU |
| ID529 | new | 9.9 | Lymph ganglia | 48-48-3-E11-PU |
| ID530 | new | 9.6 | Lymph ganglia | 48-26-2-B9-PU |
| ID531 | new | 9.2 | Lymph ganglia | 48-25-4-D9-PU |
| ID532 | new | 8.9 | Lymph ganglia | 48-67-2-F5-PU |
| ID533 | new | 8.9 | Lymph ganglia | 48-47-4-H7-PU |
| ID534 | new | 8.6 | Lymph ganglia | 48-52-1-E10-PU |
| ID535 | new | 8.5 | Placenta | 14-8-4-G8-PU |
| ID536 | new | 8.4 | Lymph ganglia | 48-4-2-G5-PU |
| ID537 | new | 8.2 | Lymph ganglia | 48-27-2-D7-PU |
| ID538 | new | 7 | Lymph ganglia | 48-61-3-F5-PU |
| ID539 | new | 6.9 | Placenta | 14-7-4-G8 |
| ID540 | new | 6.9 | Lymph ganglia | 48-5-4-B6-PU |
| ID541 | new | 6.8 | Lymph ganglia | 48-46-3-C8-PU |
| ID542 | new | 6.7 | Lymph ganglia | 48-20-3-A6-PU |
| ID543 | new | 6.6 | Lymph ganglia | 48-18-2-F6-PU |
| ID544 | new | 6.5 | Lymph ganglia | 48-2-2-A10-PU |
| ID545 | new | 6.5 | Lymph ganglia | 48-25-4-C11-PU |
| ID546 | new | 6.3 | Lymph ganglia | 48-26-1-C4-PU |
| ID547 | new | 6.3 | Lymph ganglia | 48-31-2-G8-PU |
| ID548 | new | 6.3 | Lymph ganglia | 48-24-1-D8-PU |
| ID549 | new | 6.3 | Umbilical cord | 37-11-2-D10-PU |
| ID550 | new | 6.3 | Lymph ganglia | 48-8-2-C2-PU |
| ID551 | new | 6.2 | Lymph ganglia | 48-20-4-A8-PU |

TABLE II-continued

| SEQ. ID NO. | CATEGORY | VON HEIJNE SCORE | TISSUE SOURCE | INTERNAL DESIGNATION |
|---|---|---|---|---|
| ID552 | new | 6.1 | Lymph ganglia | 48-2-1-B9-PU |
| ID553 | new | 6.1 | Lymph ganglia | 48-54-1-G9-PU |
| ID554 | new | 6.1 | Lymph ganglia | 48-47-4-B7-PU |
| ID555 | new | 6.1 | Lymph ganglia | 48-8-1-D8-PU |
| ID556 | new | 5.9 | Lymph ganglia | 48-12-3-G8-PU |
| ID557 | new | 5.9 | Umbilical cord | 37-39-4-A5-PU |
| ID558 | new | 5.9 | Lymph ganglia | 48-25-1-B6-PU |
| ID559 | new | 5.7 | Lymph ganglia | 48-15-1-D2-PU |
| ID560 | new | 5.5 | Umbilical cord | 37-3-4-D1-PU |
| ID561 | new | 5.4 | Lymph ganglia | 48-13-1-G4-PU |
| ID562 | new | 5.4 | Lymph ganglia | 48-10-1-E4-PU |
| ID563 | new | 5.2 | Lymph ganglia | 48-8-1-A3-PU |
| ID564 | new | 5.2 | Umbilical cord | 37-7-4-F2-PU |
| ID565 | new | 5.2 | Lymph ganglia | 48-50-3-F1-PU |
| ID566 | new | 5.2 | Lymph ganglia | 48-8-2-B5-PU |
| ID567 | new | 5 | Placenta | 11-4-0-B11-RP |
| ID568 | new | 5 | Lymph ganglia | 48-48-4-H11-PU |
| ID569 | new | 4.9 | Umbilical cord | 37-2-1-B4-PU |
| ID570 | new | 4.8 | Lymph ganglia | 48-47-2-B2-PU |
| ID571 | new | 4.8 | Lymph ganglia | 48-3-4-C11-PU |
| ID572 | new | 4.8 | Lymphocytes | 24-6-1-C8-PU |
| ID573 | new | 4.8 | Placenta | 31-10-3-D2-PU |
| ID574 | new | 4.7 | Lymph ganglia | 48-54-3-F9-PU |
| ID575 | new | 4.7 | Lymph ganglia | 48-47-1-C9-PU |
| ID576 | new | 4.7 | Lymph ganglia | 48-4-2-C9-PU |
| ID577 | new | 4.6 | Umbilical cord | 37-33-2-E2-PU |
| ID578 | new | 4.5 | Umbilical cord | 37-2-1-B7-PU |
| ID579 | new | 4.5 | Lymph ganglia | 48-51-2-C3-PU |
| ID580 | new | 4.5 | Lymph ganglia | 48-23-4-D4-PU |
| ID581 | new | 4.4 | Umbilical cord | 37-4-1-A6-PU |
| ID582 | new | 4.4 | Lymph ganglia | 48-11-4-C10-PU |
| ID583 | new | 4.4 | Umbilical cord | 37-1-4-F3-PU |
| ID584 | new | 4.3 | Lymphocytes | 24-2-2-G10-PU |
| ID585 | new | 4.3 | Lymph ganglia | 48-26-3-G3-PU |
| ID586 | new | 4.1 | Lymph ganglia | 48-20-3-H2-PU |
| ID587 | new | 4.1 | Lymph ganglia | 48-31-3-F7-PU |
| ID588 | new | 4.1 | Lymph ganglia | 48-29-1-H9-PU |
| ID589 | new | 4.1 | Umbilical cord | 37-1-3-G4-PU |
| ID590 | new | 4.1 | Umbilical cord | 37-8-3-G12-PU |
| ID591 | new | 4.1 | Lymph ganglia | 48-26-4-G1-PU |
| ID592 | new | 4 | Lymph ganglia | 48-27-1-B12-PU |
| ID593 | new | 4 | Lymph ganglia | 48-22-1-H7-PU |
| ID594 | new | 4 | Lymphocytes | 24-1-4-F9-PU |
| ID595 | new | 4 | Lymph ganglia | 48-6-2-A1-PU |
| ID596 | new | 4 | Umbilical cord | 37-3-3-B3-PU |
| ID597 | new | 3.8 | Umbilical cord | 37-7-2-F6-PU |
| ID598 | new | 3.8 | Lymph ganglia | 48-52-1-A6-PU |
| ID599 | new | 3.8 | Lymph ganglia | 48-7-2-F5-PU |
| ID600 | new | 3.8 | Umbilical cord | 37-12-2-D12-PU |
| ID601 | new | 3.8 | Umbilical cord | 37-11-3-D2-PU |
| ID602 | new | 3.8 | Lymph ganglia | 48-1-1-H7-PU |
| ID603 | new | 3.7 | Lymph ganglia | 48-21-3-E1-PU |
| ID604 | new | 3.6 | Lymph ganglia | 48-26-3-B8-PU |
| ID605 | new | 3.6 | Umbilical cord | 37-9-2-D9-PU |
| ID606 | new | 3.6 | Lymph ganglia | 48-3-3-A3-PU |
| ID607 | new | 3.6 | Lymphocytes | 24-1-3-G11-PU |
| ID608 | new | 3.6 | Lymphocytes | 24-4-1-A4-PU |
| ID609 | new | 3.5 | Lymph ganglia | 48-23-2-B12-PU |
| ID610 | new | 3.5 | Lymph ganglia | 48-47-3-F2-PU |
| ID611 | new | 3.5 | Lymphocytes | 24-4-4-H11-PU |
| ID612 | new | 3.5 | Lymph ganglia | 48-7-3-B8-PU |
| ID613 | ext-est-not-vrt | 12.8 | Lymph ganglia | 48-12-4-E3-PU |
| ID614 | ext-est-not-vrt | 9.3 | Umbilical cord | 37-12-3-G9-PU |
| ID615 | ext-est-not-vrt | 9.3 | Lymph ganglia | 48-67-4-A6-PU |
| ID616 | ext-est-not-vrt | 8.1 | Lymph ganglia | 48-28-3-A9-PU |
| ID617 | ext-est-not-vrt | 7.7 | Lymphocytes | 24-3-3-C6-PU |
| ID618 | ext-est-not-vrt | 6.6 | Lymph ganglia | 48-28-4-C2-PU |
| ID619 | ext-est-not-vrt | 6.2 | Lymph ganglia | 48-25-2-A1-PU |
| ID620 | ext-est-not-vrt | 5.8 | Lymph ganglia | 48-24-4-B7-PU |
| ID621 | ext-est-not-vrt | 5.3 | Lymph ganglia | 48-6-1-C9-PU |
| ID622 | ext-est-not-vrt | 5.1 | Lymph ganglia | 48-7-4-H2-PU |
| ID623 | ext-est-not-vrt | 4.6 | Lymph ganglia | 48-28-3-B6-PU |
| ID624 | ext-est-not-vrt | 4.4 | Lymph ganglia | 48-3-1-H9-PU |
| ID625 | ext-est-not-vrt | 4.4 | Umbilical cord | 37-6-4-B11-PU |
| ID626 | ext-est-not-vrt | 3.9 | Lymph ganglia | 48-26-1-G10-PU |
| ID627 | ext-est-not-vrt | 3.8 | Umbilical cord | 37-9-4-H9-PU |

TABLE II-continued

| SEQ. ID NO. | CATEGORY | VON HEIJNE SCORE | TISSUE SOURCE | INTERNAL DESIGNATION |
|---|---|---|---|---|
| ID628 | ext-est-not-vrt | 3.7 | Lymphocytes | 24-1-4-F8-PU |
| ID629 | ext-est-not-vrt | 3.5 | Lymph ganglia | 48-21-3-H7-PU |
| ID630 | est-not-ext | 11.7 | Lymph ganglia | 48-6-4-G3-PU |
| ID631 | est-not-ext | 10.9 | Umbilical cord | 37-5-1-A12-PU |
| ID632 | est-not-ext | 10.9 | Lymph ganglia | 48-22-4-A8-PU |
| ID633 | est-not-ext | 9.6 | Lymph ganglia | 48-27-1-B8-PU |
| ID634 | est-not-ext | 9.6 | Umbilical cord | 37-4-1-G3-PU |
| ID635 | est-not-ext | 9.3 | Lymph ganglia | 48-11-4-E3-PU |
| ID636 | est-not-ext | 8.2 | Lymph ganglia | 48-25-4-D8-PU |
| ID637 | est-not-ext | 8.2 | Lymph ganglia | 48-19-3-G1-PU |
| ID638 | est-not-ext | 8.1 | Placenta | 31-11-4-B2-PU |
| ID639 | est-not-ext | 7.9 | Lymph ganglia | 48-7-4-H10-PU |
| ID640 | est-not-ext | 7.7 | Lymph ganglia | 48-11-4-F7-PU |
| ID641 | est-not-ext | 7.2 | Lymph ganglia | 48-10-3-B5-PU |
| ID642 | est-not-ext | 6.9 | Umbilical cord | 37-8-4-D3-PU |
| ID643 | est-not-ext | 6.4 | Umbilical cord | 37-6-2-D10-PU |
| ID644 | est-not-ext | 6.3 | Lymph ganglia | 48-17-1-D11-PU |
| ID645 | est-not-ext | 6.1 | Lymphocytes | 24-8-3-G1-PU |
| ID646 | est-not-ext | 6.1 | Umbilical cord | 37-12-2-D1-PU |
| ID647 | est-not-ext | 6.1 | Umbilical cord | 37-6-2-A10-PU |
| ID648 | est-not-ext | 6 | Lymph ganglia | 48-26-1-A11-PU |
| ID649 | est-not-ext | 5.9 | Lymph ganglia | 48-60-4-H5-PU |
| ID650 | est-not-ext | 5.8 | Umbilical cord | 37-29-2-G3-PU |
| ID651 | est-not-ext | 5.7 | Umbilical cord | 37-28-2-D3-PU |
| ID652 | est-not-ext | 5.6 | Lymph ganglia | 48-49-1-F5-PU |
| ID653 | est-not-ext | 5.5 | Umbilical cord | 37-2-2-D12-PU |
| ID654 | est-not-ext | 5.5 | Umbilical cord | 37-7-4-B3-PU |
| ID655 | est-not-ext | 5.3 | Lymph ganglia | 48-24-1-D2-PU |
| ID656 | est-not-ext | 5 | Lymph ganglia | 48-21-4-H4-PU |
| ID657 | est-not-ext | 4.9 | Umbilical cord | 37-41-4-B9-PU |
| ID658 | est-not-ext | 4.9 | Lymph ganglia | 48-12-3-E2-PU |
| ID659 | est-not-ext | 4.6 | Lymph ganglia | 48-5-4-C5-PU |
| ID660 | est-not-ext | 4.3 | Lymphocytes | 24-5-1-E2-PU |
| ID661 | est-not-ext | 4.1 | Lymph ganglia | 48-18-3-F9-PU |
| ID662 | est-not-ext | 4.1 | Lymphocytes | 24-5-1-H2-PU |
| ID663 | est-not-ext | 3.8 | Lymph ganglia | 48-6-2-G1-PU |
| ID664 | est-not-ext | 3.8 | Umbilical cord | 37-9-2-G10-PU |
| ID665 | est-not-ext | 3.7 | Lymph ganglia | 48-19-3-A7-PU |
| ID666 | est-not-ext | 3.5 | Lymph ganglia | 48-13-3-E3-PU |
| ID667 | est-not-ext | 3.5 | Lymph ganglia | 48-20-4-G6-PU |
| ID668 | est-not-ext | 3.5 | Lymphocytes | 24-4-1-G11-PU |
| ID669 | est-not-ext | 3.5 | Lymph ganglia | 48-4-2-E4-PU |
| ID670 | ext-vrt-not-genomic | 8.4 | Lymph ganglia | 48-24-1-B3-PU |
| ID671 | ext-vrt-not-genomic | 7.4 | Lymph ganglia | 48-30-2-B2-PU |
| ID672 | ext-vrt-not-genomic | 6.5 | Umbilical cord | 37-30-2-B3-PU |
| ID673 | new | 11.4 | Cancerous prostate | 76-36-2-G4-PU |
| ID674 | new | 11.3 | Normal prostate | 78-26-1-A7-PU |
| ID675 | new | 11 | Normal prostate | 78-4-3-G8-PU |
| ID676 | new | 10.7 | Hypertrophic prostate | 77-16-3-D7-PU |
| ID677 | new | 10.7 | Hypertrophic prostate | 77-7-1-H9-PU |
| ID678 | new | 10.6 | Hypertrophic prostate | 77-42-1-D10-PU |
| ID679 | new | 10.6 | Cancerous prostate | 76-34-4-C6-PU |
| ID680 | new | 10.4 | Normal prostate | 78-31-3-B8-PU |
| ID681 | new | 10.2 | Normal prostate | 78-38-1-C10-PU |
| ID682 | new | 10.2 | Cancerous prostate | 76-16-4-D5-PU |
| ID683 | new | 9 | Hypertrophic prostate | 77-38-2-B9-PU |
| ID684 | new | 8.8 | Normal prostate | 78-30-1-G12-PU |
| ID685 | new | 8.6 | Prostate | 60-17-1-F1-PU |
| ID686 | new | 8.5 | Prostate | 60-17-3-G8-PU |
| ID687 | new | 8.3 | Normal prostate | 78-8-2-H8-PU |
| ID688 | new | 8.3 | Normal prostate | 78-26-2-A1-PU |
| ID689 | new | 8.3 | Cancerous prostate | 76-23-2-B10-PU |
| ID690 | new | 8.2 | Cancerous prostate | 76-23-4-H9-PU |
| ID691 | new | 8.1 | Normal prostate | 78-44-2-C3-PU |
| ID692 | new | 8 | Hypertrophic prostate | 77-37-1-H3-PU |
| ID693 | new | 8 | Normal prostate | 78-35-2-G12-PU |
| ID694 | new | 7.8 | Normal prostate | 78-17-4-G2-PU |
| ID695 | new | 7.7 | Normal prostate | 78-5-4-F7-PU |
| ID696 | new | 7.6 | Normal prostate | 78-16-3-E2-PU |
| ID697 | new | 7.6 | Hypertrophic prostate | 77-5-1-B6-PU |
| ID698 | new | 7.6 | Normal prostate | 78-26-1-B5-PU |
| ID699 | new | 7.5 | Cancerous prostate | 76-12-1-B1-PU |
| ID700 | new | 7.5 | Normal prostate | 78-4-4-E7-PU |
| ID701 | new | 7.2 | Hypertrophic prostate | 77-11-1-A3-PU |
| ID702 | new | 7.2 | Hypertrophic prostate | 77-5-4-G9-PU |
| ID703 | new | 7.2 | Normal prostate | 78-23-4-H11-PU |

TABLE II-continued

| SEQ. ID NO. | CATEGORY | VON HEIJNE SCORE | TISSUE SOURCE | INTERNAL DESIGNATION |
|---|---|---|---|---|
| ID704 | new | 7.2 | Hypertrophic prostate | 77-39-3-H7-PU |
| ID705 | new | 7.2 | Cancerous prostate | 76-23-4-H2-PU |
| ID706 | new | 7.2 | Cancerous prostate | 76-24-1-F8-PU |
| ID707 | new | 7 | Normal prostate | 78-39-4-D2-PU |
| ID708 | new | 7 | Normal prostate | 78-28-3-D2-PU |
| ID709 | new | 7 | Normal prostate | 78-29-3-H11-PU |
| ID710 | new | 7 | Normal prostate | 78-40-3-G2-PU |
| ID711 | new | 7 | Cancerous prostate | 76-1-2-F8-PU |
| ID712 | new | 7 | Normal prostate | 78-13-4-B10-PU |
| ID713 | new | 6.9 | Cancerous prostate | 76-12-1-A9-PU |
| ID714 | new | 6.9 | Normal prostate | 78-20-3-C11-PU |
| ID715 | new | 6.9 | Cancerous prostate | 76-9-2-D10-PU |
| ID716 | new | 6.8 | Normal prostate | 78-6-2-D12-PU |
| ID717 | new | 6.7 | Hypertrophic prostate | 77-10-1-C8-PU |
| ID718 | new | 6.7 | Cancerous prostate | 76-13-2-F11-PU |
| ID719 | new | 6.7 | Cancerous prostate | 76-4-1-G5-PU |
| ID720 | new | 6.5 | Normal prostate | 78-3-4-B8-PU |
| ID721 | new | 6.4 | Prostate | 60-11-3-G2-PU |
| ID722 | new | 6.3 | Normal prostate | 78-25-1-G5-PU |
| ID723 | new | 6.3 | Normal prostate | 78-2-2-G5-PU |
| ID724 | new | 6.3 | Cancerous prostate | 76-7-3-A1-PU |
| ID725 | new | 6.3 | Hypertrophic prostate | 77-5-1-C2-PU |
| ID726 | new | 6.2 | Normal prostate | 78-49-2-A11-PU |
| ID727 | new | 6.1 | Normal prostate | 78-7-1-B9-PU |
| ID728 | new | 6 | Normal prostate | 78-39-4-G3-PU |
| ID729 | new | 6 | Normal prostate | 78-32-2-H6-PU |
| ID730 | new | 5.9 | Cancerous prostate | 76-30-3-H2-PU |
| ID731 | new | 5.9 | Normal prostate | 78-24-3-H4-PU |
| ID732 | new | 5.9 | Cancerous prostate | 76-43-3-B6-PU |
| ID733 | new | 5.8 | Prostate | 60-16-3-A3-PU |
| ID734 | new | 5.8 | Cancerous prostate | 76-20-4-C11-PU |
| ID735 | new | 5.7 | Cancerous prostate | 76-11-1-C5-PU |
| ID736 | new | 5.7 | Hypertrophic prostate | 77-37-3-C1-PU |
| ID737 | new | 5.7 | Prostate | 60-13-2-B5-PU |
| ID738 | new | 5.7 | Normal prostate | 78-49-4-E4-PU |
| ID739 | new | 5.6 | Normal prostate | 78-37-4-C11-PU |
| ID740 | new | 5.6 | Prostate | 60-17-1-D8-PU |
| ID741 | new | 5.5 | Normal prostate | 78-36-3-D7-PU |
| ID742 | new | 5.5 | Cancerous prostate | 76-24-3-E11-PU |
| ID743 | new | 5.5 | Prostate | 60-14-2-A7-PU |
| ID744 | new | 5.4 | Hypertrophic prostate | 77-10-4-F9-PU |
| ID745 | new | 5.3 | Cancerous prostate | 76-23-3-G5-PU |
| ID746 | new | 5.3 | Normal prostate | 78-42-3-D3-PU |
| ID747 | new | 5.3 | Prostate | 60-12-1-H1-PU |
| ID748 | new | 5.3 | Hypertrophic prostate | 77-5-2-A3-PU |
| ID749 | new | 5.2 | Normal prostate | 78-37-2-G12-PU |
| ID750 | new | 5.2 | Cancerous prostate | 76-39-2-H1-PU |
| ID751 | new | 5.1 | Prostate | 60-12-3-C2-PU |
| ID752 | new | 5.1 | Normal prostate | 78-25-1-F11-PU |
| ID753 | new | 5.1 | Normal prostate | 78-36-2-C10-PU |
| ID754 | new | 5.1 | Hypertrophic prostate | 77-13-1-B7-PU |
| ID755 | new | 5.1 | Hypertrophic prostate | 77-4-4-H7-PU |
| ID756 | new | 5 | Normal prostate | 78-33-4-F9-PU |
| ID757 | new | 5 | Cancerous prostate | 76-21-1-D5-PU |
| ID758 | new | 4.8 | Normal prostate | 78-3-4-B3-PU |
| ID759 | new | 4.8 | Cancerous prostate | 76-29-4-B3-PU |
| ID760 | new | 4.8 | Normal prostate | 78-46-3-C6-PU |
| ID761 | new | 4.8 | Hypertrophic prostate | 77-13-3-F8-PU |
| ID762 | new | 4.7 | Cancerous prostate | 76-12-4-C3-PU |
| ID763 | new | 4.7 | Cancerous prostate | 76-34-4-C1-PU |
| ID764 | new | 4.7 | Normal prostate | 78-42-4-D2-PU |
| ID765 | new | 4.7 | Cancerous prostate | 76-38-2-H9-PU |
| ID766 | new | 4.6 | Normal prostate | 78-49-4-B5-PU |
| ID767 | new | 4.6 | Cancerous prostate | 76-1-1-E3-PU |
| ID768 | new | 4.6 | Normal prostate | 78-46-3-C4-PU |
| ID769 | new | 4.5 | Cancerous prostate | 76-22-2-D2-PU |
| ID770 | new | 4.5 | Prostate | 60-11-4-F6-PU |
| ID771 | new | 4.5 | Normal prostate | 78-32-2-G1-PU |
| ID772 | new | 4.4 | Prostate | 60-14-3-C7-PU |
| ID773 | new | 4.4 | Hypertrophic prostate | 77-3-4-H3-PU |
| ID774 | new | 4.4 | Normal prostate | 78-36-4-E12-PU |
| ID775 | new | 4.3 | Hypertrophic prostate | 77-42-1-A9-PU |
| ID776 | new | 4.3 | Normal prostate | 78-23-2-H3-PU |
| ID777 | new | 4.2 | Cancerous prostate | 76-39-3-C11-PU |
| ID778 | new | 4.2 | Normal prostate | 78-23-3-D10-PU |
| ID779 | new | 4.2 | Cancerous prostate | 76-32-2-B7-PU |

TABLE II-continued

| SEQ. ID NO. | CATEGORY | VON HEIJNE SCORE | TISSUE SOURCE | INTERNAL DESIGNATION |
|---|---|---|---|---|
| ID780 | new | 4.2 | Normal prostate | 78-40-1-G9-PU |
| ID781 | new | 4.2 | Prostate | 60-12-1-E11-PU |
| ID782 | new | 4.1 | Cancerous prostate | 76-27-3-A6-PU |
| ID783 | new | 4 | Cancerous prostate | 76-43-3-B2-PU |
| ID784 | new | 4 | Normal prostate | 78-18-3-B4-PU |
| ID785 | new | 4 | Normal prostate | 78-41-2-D11-PU |
| ID786 | new | 4 | Normal prostate | 78-34-2-G9-PU |
| ID787 | new | 4 | Normal prostate | 78-4-3-G2-PU |
| ID788 | new | 4 | Hypertrophic prostate | 77-22-2-G2-PU |
| ID789 | new | 3.9 | Cancerous prostate | 76-4-4-F6-PU |
| ID790 | new | 3.9 | Hypertrophic prostate | 77-40-3-E10-PU |
| ID791 | new | 3.9 | Normal prostate | 78-10-1-H5-PU |
| ID792 | new | 3.9 | Normal prostate | 78-6-2-E3-PU |
| ID793 | new | 3.9 | Hypertrophic prostate | 77-20-3-E5-PU |
| ID794 | new | 3.9 | Normal prostate | 78-38-2-B5-PU |
| ID795 | new | 3.8 | Prostate | 60-11-2-G12-PU |
| ID796 | new | 3.8 | Cancerous prostate | 76-44-3-E8-PU |
| ID797 | new | 3.8 | Normal prostate | 78-41-3-A2-PU |
| ID798 | new | 3.7 | Cancerous prostate | 76-20-4-E7-PU |
| ID799 | new | 3.7 | Cancerous prostate | 76-17-1-E4-PU |
| ID800 | new | 3.7 | Normal prostate | 78-5-2-D2-PU |
| ID801 | new | 3.7 | Prostate | 60-11-3-B11-PU |
| ID802 | new | 3.7 | Hypertrophic prostate | 77-21-2-F1-PU |
| ID803 | new | 3.6 | Prostate | 60-12-1-A5-PU |
| ID804 | new | 3.6 | Cancerous prostate | 76-18-2-G12-PU |
| ID805 | new | 3.6 | Normal prostate | 78-7-1-G5-PU |
| ID806 | new | 3.6 | Cancerous prostate | 76-37-4-A5-PU |
| ID807 | new | 3.5 | Normal prostate | 78-50-4-A2-PU |
| ID808 | new | 3.5 | Normal prostate | 78-43-2-H10-PU |
| ID809 | new | 3.5 | Normal prostate | 78-44-3-B6-PU |
| ID810 | new | 3.5 | Cancerous prostate | 76-10-1-D6-PU |
| ID811 | new | 3.5 | Prostate | 60-11-4-F2-PU |
| ID812 | new | 3.5 | Cancerous prostate | 76-45-2-B12-PU |
| ID813 | ext-est-not-vrt | 14.8 | Normal prostate | 78-34-3-D9-PU |
| ID814 | ext-est-not-vrt | 13.6 | Normal prostate | 78-46-4-F4-PU |
| ID815 | ext-est-not-vrt | 12.7 | Normal prostate | 78-8-3-D9-PU |
| ID816 | ext-est-not-vrt | 8.8 | Prostate | 60-15-4-F6-PU |
| ID817 | ext-est-not-vrt | 8.5 | Normal prostate | 78-8-3-E6-PU |
| ID818 | ext-est-not-vrt | 7.3 | Normal prostate | 78-7-3-A4-PU |
| ID819 | ext-est-not-vrt | 7.1 | Cancerous prostate | 76-33-2-F5-PU |
| ID820 | ext-est-not-vrt | 6.6 | Cancerous prostate | 76-34-4-G12-PU |
| ID821 | ext-est-not-vrt | 6.3 | Normal prostate | 78-13-1-H7-PU |
| ID822 | ext-est-not-vrt | 5.9 | Normal prostate | 78-49-3-B11-PU |
| ID823 | ext-est-not-vrt | 5.9 | Normal prostate | 78-42-2-A10-PU |
| ID824 | ext-est-not-vrt | 5.5 | Cancerous prostate | 76-7-4-D9-PU |
| ID825 | ext-est-not-vrt | 5.2 | Normal prostate | 78-40-3-B12-PU |
| ID826 | ext-est-not-vrt | 5 | Hypertrophic prostate | 77-36-1-G2-PU |
| ID827 | ext-est-not-vrt | 4.8 | Prostate | 60-17-3-H11-PU |
| ID828 | ext-est-not-vrt | 4.4 | Normal prostate | 78-28-3-E4-PU |
| ID829 | ext-est-not-vrt | 4.1 | Cancerous prostate | 76-28-2-H5-PU |
| ID830 | ext-est-not-vrt | 4.1 | Normal prostate | 78-27-1-D11-PU |
| ID831 | ext-est-not-vrt | 3.9 | Cancerous prostate | 76-42-2-B5-PU |
| ID832 | ext-est-not-vrt | 3.9 | Hypertrophic prostate | 77-39-3-F8-PU |
| ID833 | ext-est-not-vrt | 3.7 | Cancerous prostate | 76-43-1-G9-PU |
| ID834 | est-not-ext | 13.8 | Normal prostate | 78-40-1-B10-PU |
| ID835 | est-not-ext | 13.4 | Cancerous prostate | 76-15-1-F4-PU |
| ID836 | est-not-ext | 13 | Cancerous prostate | 76-45-4-E7-PU |
| ID837 | est-not-ext | 11.6 | Normal prostate | 78-26-2-H7-PU |
| ID838 | est-not-ext | 11.2 | Normal prostate | 78-21-1-B7-PU |
| ID839 | est-not-ext | 11.2 | Cancerous prostate | 76-40-2-F5-PU |
| ID840 | est-not-ext | 10.6 | Cancerous prostate | 76-29-2-G8-PU |
| ID841 | est-not-ext | 10.5 | Hypertrophic prostate | 77-23-4-H11-PU |
| ID842 | est-not-ext | 20.3 | Normal prostate | 78-48-1-F10-PU |
| ID843 | est-not-ext | 9.5 | Cancerous prostate | 76-41-4-G9-PU |
| ID844 | est-not-ext | 9.3 | Hypertrophic prostate | 77-3-3-C10-PU |
| ID845 | est-not-ext | 9.1 | Cancerous prostate | 76-45-4-C8-PU |
| ID846 | est-not-ext | 8.8 | Normal prostate | 78-50-4-C10-PU |
| ID847 | est-not-ext | 8.8 | Normal prostate | 78-38-4-F7-PU |
| ID848 | est-not-ext | 8.6 | Cancerous prostate | 76-16-4-C9-PU |
| ID849 | est-not-ext | 8.6 | Normal prostate | 78-49-2-D10-PU |
| ID850 | est-not-ext | 8.4 | Cancerous prostate | 76-1-1-H7-PU |
| ID851 | est-not-ext | 7.9 | Normal prostate | 78-4-2-F10-PU |
| ID852 | est-not-ext | 7.9 | Normal prostate | 78-46-3-B6-PU |
| ID853 | est-not-ext | 7.7 | Normal prostate | 78-7-1-F2-PU |
| ID854 | est-not-ext | 7.6 | Normal prostate | 78-35-2-D3-PU |
| ID855 | est-not-ext | 7.6 | Cancerous prostate | 76-20-2-G7-PU |

TABLE II-continued

| SEQ. ID NO. | CATEGORY | VON HEIJNE SCORE | TISSUE SOURCE | INTERNAL DESIGNATION |
|---|---|---|---|---|
| ID856 | est-not-ext | 7.6 | Normal prostate | 78-39-1-E11-PU |
| ID857 | est-not-ext | 7.5 | Cancerous prostate | 76-4-4-C2-PU |
| ID858 | est-not-ext | 7.1 | Normal prostate | 78-48-2-F6-PU |
| ID859 | est-not-ext | 7 | Cancerous prostate | 76-32-4-A10-PU |
| ID860 | est-not-ext | 6.8 | Cancerous prostate | 76-39-1-E7-PU |
| ID861 | est-not-ext | 6.7 | Cancerous prostate | 76-29-4-E1-PU |
| ID862 | est-not-ext | 6.7 | Normal prostate | 78-28-4-B9-PU |
| ID863 | est-not-ext | 6.7 | Normal prostate | 78-37-4-B2-PU |
| ID864 | est-not-ext | 6.7 | Normal prostate | 78-50-2-E12-PU |
| ID865 | est-not-ext | 6.7 | Hypertrophic prostate | 77-21-2-F8-PU |
| ID866 | est-not-ext | 6.6 | Normal prostate | 78-27-4-E2-PU |
| ID867 | est-not-ext | 6.5 | Normal prostate | 78-45-4-G12-PU |
| ID868 | est-not-ext | 6.3 | Cancerous prostate | 76-7-4-H8-PU |
| ID869 | est-not-ext | 6.3 | Normal prostate | 78-23-1-D10-PU |
| ID870 | est-not-ext | 6.3 | Cancerous prostate | 76-34-1-C2-PU |
| ID871 | est-not-ext | 6.2 | Hypertrophic prostate | 77-8-1-F11-PU |
| ID872 | est-not-ext | 6.2 | Cancerous prostate | 76-41-1-F3-PU |
| ID873 | est-not-ext | 6.1 | Cancerous prostate | 76-22-3-G4-PU |
| ID874 | est-not-ext | 6.1 | Normal prostate | 78-40-1-A6-PU |
| ID875 | est-not-ext | 6 | Normal prostate | 78-41-2-H11-PU |
| ID876 | est-not-ext | 6 | Normal prostate | 78-6-3-A12-PU |
| ID877 | est-not-ext | 6 | Hypertrophic prostate | 77-25-1-A6-PU |
| ID878 | est-not-ext | 5.9 | Hypertrophic prostate | 77-35-2-E4-PU |
| ID879 | est-not-ext | 5.9 | Hypertrophic prostate | 77-36-1-G4-PU |
| ID880 | est-not-ext | 5.8 | Hypertrophic prostate | 77-40-3-D6-PU |
| ID881 | est-not-ext | 5.8 | Normal prostate | 78-17-3-A3-PU |
| ID882 | est-not-ext | 5.7 | Normal prostate | 78-33-3-D7-PU |
| ID883 | est-not-ext | 5.7 | Hypertrophic prostate | 77-23-4-E10-PU |
| ID884 | est-not-ext | 5.7 | Cancerous prostate | 76-25-4-F11-PU |
| ID885 | est-not-ext | 5.7 | Cancerous prostate | 76-33-2-F8-PU |
| ID886 | est-not-ext | 5.7 | Normal prostate | 78-47-4-D6-PU |
| ID887 | est-not-ext | 5.7 | Normal prostate | 78-34-4-G6-PU |
| ID888 | est-not-ext | 5.6 | Cancerous prostate | 76-23-3-G8-PU |
| ID889 | est-not-ext | 5.6 | Normal prostate | 78-41-1-A6-PU |
| ID890 | est-not-ext | 5.6 | Cancerous prostate | 76-38-1-E4-PU |
| ID891 | est-not-ext | 5.5 | Normal prostate | 78-2-4-F11-PU |
| ID892 | est-not-ext | 5.4 | Cancerous prostate | 76-13-3-A9-PU |
| ID893 | est-not-ext | 5.4 | Normal prostate | 78-7-3-D9-PU |
| ID894 | est-not-ext | 5.2 | Cancerous prostate | 76-6-2-G5-PU |
| ID895 | est-not-ext | 5.1 | Hypertrophic prostate | 77-39-4-H4-PU |
| ID896 | est-not-ext | 5 | Hypertrophic prostate | 77-13-3-F1-PU |
| ID897 | est-not-ext | 5 | Normal prostate | 78-24-4-A4-PU |
| ID898 | est-not-ext | 4.9 | Hypertrophic prostate | 77-1-2-B4-PU |
| ID899 | est-not-ext | 4.9 | Cancerous prostate | 76-42-2-F3-PU |
| ID900 | est-not-ext | 4.9 | Cancerous prostate | 76-40-3-G6-PU |
| ID901 | est-not-ext | 4.8 | Cancerous prostate | 76-44-1-E3-PU |
| ID902 | est-not-ext | 4.8 | Hypertrophic prostate | 77-3-4-H1-PU |
| ID903 | est-not-ext | 4.8 | Cancerous prostate | 76-45-2-C4-PU |
| ID904 | est-not-ext | 4.8 | Prostate | 60-12-1-D7-PU |
| ID905 | est-not-ext | 4.8 | Normal prostate | 78-46-2-B4-PU |
| ID906 | est-not-ext | 4.7 | Prostate | 60-12-3-A7-PU |
| ID907 | est-not-ext | 4.7 | Normal prostate | 78-24-3-A8-PU |
| ID908 | est-not-ext | 4.6 | Hypertrophic prostate | 77-17-3-A7-PU |
| ID909 | est-not-ext | 4.6 | Hypertrophic prostate | 77-10-1-F6-PU |
| ID910 | est-not-ext | 4.5 | Prostate | 60-13-1-E11-PU |
| ID911 | est-not-ext | 4.4 | Normal prostate | 78-24-3-C6-PU |
| ID912 | est-not-ext | 4.4 | Cancerous prostate | 76-23-1-B4-PU |
| ID913 | est-not-ext | 4.3 | Hypertrophic prostate | 77-9-1-E2-PU |
| ID914 | est-not-ext | 4.2 | Normal prostate | 78-4-4-B10-PU |
| ID915 | est-not-ext | 4.2 | Normal prostate | 78-30-2-C1-PU |
| ID916 | est-not-ext | 4.2 | Normal prostate | 78-38-2-E9-PU |
| ID917 | est-not-ext | 4.2 | Normal prostate | 78-8-2-F2-PU |
| ID918 | est-not-ext | 4.1 | Cancerous prostate | 76-20-3-H1-PU |
| ID919 | est-not-ext | 4.1 | Cancerous prostate | 76-14-1-B3-PU |
| ID920 | est-not-ext | 4.1 | Normal prostate | 78-18-4-D6-PU |
| ID921 | est-not-ext | 4 | Hypertrophic prostate | 77-11-4-B3-PU |
| ID922 | est-not-ext | 4 | Normal prostate | 78-16-2-C2-PU |
| ID923 | est-not-ext | 4 | Hypertrophic prostate | 77-38-2-G5-PU |
| ID924 | est-not-ext | 3.9 | Normal prostate | 78-25-1-H11-PU |
| ID925 | est-not-ext | 3.9 | Hypertrophic prostate | 77-12-3-H7-PU |
| ID926 | est-not-ext | 3.8 | Cancerous prostate | 76-21-4-A3-PU |
| ID927 | est-not-ext | 3.8 | Normal prostate | 78-41-1-C6-PU |
| ID928 | est-not-ext | 3.7 | Cancerous prostate | 76-5-2-H11-PU |
| ID929 | est-not-ext | 3.7 | Cancerous prostate | 76-8-4-D9-PU |
| ID930 | est-not-ext | 3.7 | Cancerous prostate | 76-18-2-D4-PU |
| ID931 | est-not-ext | 3.7 | Prostate | 60-12-3-G4-PU |

TABLE II-continued

| SEQ. ID NO. | CATEGORY | VON HEIJNE SCORE | TISSUE SOURCE | INTERNAL DESIGNATION |
|---|---|---|---|---|
| ID932 | est-not-ext | 3.7 | Hypertrophic prostate | 77-20-2-E11-PU |
| ID933 | est-not-ext | 3.6 | Cancerous prostate | 76-1-2-G6-PU |
| ID934 | est-not-ext | 3.6 | Normal prostate | 78-8-3-F2-PU |
| ID935 | est-not-ext | 3.6 | Normal prostate | 78-12-4-E9-PU |
| ID936 | est-not-ext | 3.6 | Hypertrophic prostate | 77-15-2-E2-PU |
| ID937 | est-not-ext | 3.5 | Cancerous prostate | 76-7-3-A12-PU |
| ID938 | est-not-ext | 3.5 | Normal prostate | 78-22-3-E10-PU |
| ID939 | est-not-ext | 3.5 | Hypertrophic prostate | 77-2-3-E11-PU |
| ID940 | est-not-ext | 3.5 | Normal prostate | 78-29-1-B2-PU |
| ID941 | ext-vrt-not-genomic | 12 | Normal prostate | 78-47-2-C1-PU |
| ID942 | ext-vrt-not-genomic | 12 | Normal prostate | 78-43-4-G12-PU |
| ID943 | ext-vrt-not-genomic | 12 | Hypertrophic prostate | 77-38-1-A8-PU |
| ID944 | ext-vrt-not-genomic | 8.9 | Normal prostate | 78-45-4-F12-PU |
| ID945 | ext-vrt-not-genomic | 8.1 | Normal prostate | 78-35-3-D1-PU |
| ID946 | ext-vrt-not-genomic | 7.7 | Normal prostate | 78-10-1-H8-PU |
| ID947 | ext-vrt-not-genomic | 6.9 | Cancerous prostate | 76-43-1-E3-PU |
| ID948 | ext-vrt-not-genomic | 5.9 | Normal prostate | 78-29-2-C10-PU |
| ID949 | ext-vrt-not-genomic | 5.3 | Hypertrophic prostate | 77-38-3-B11-PU |
| ID950 | ext-vrt-not-genomic | 5.1 | Normal prostate | 78-36-4-A8-PU |
| ID951 | new | 13.2 | Testis | 51-39-3-H2-PU |
| ID952 | new | 12 | Testis | 51-34-3-F8-PU |
| ID953 | new | 11 | Testis | 51-43-2-C5-PU |
| ID954 | new | 10.6 | Testis | 51-2-4-C4-PU |
| ID955 | new | 10.4 | Ovary | 26-49-1-A5-PU |
| ID956 | new | 10.1 | Testis | 51-3-3-B10-PU |
| ID957 | new | 9.8 | Testis | 51-15-4-A12-PU |
| ID958 | new | 9.8 | Testis | 51-14-1-G6-PU |
| ID959 | new | 9.5 | Spleen | 53-1-4-A1-PU |
| ID960 | new | 9.4 | Ovary | 26-40-1-A11-PU |
| ID961 | new | 9.4 | Testis | 51-19-4-A10-PU |
| ID962 | new | 9.2 | Ovary | 26-25-2-D2-PU |
| ID963 | new | 9.2 | Testis | 51-17-2-C6-PU |
| ID964 | new | 9.2 | Ovary | 26-40-3-A6-PU |
| ID965 | new | 9.1 | Ovary | 26-49-1-A9-PU |
| ID966 | new | 9.1 | Spleen | 20-7-2-D6-PU |
| ID967 | new | 9.1 | Testis | 51-2-1-A11-PU |
| ID968 | new | 9 | Testis | 51-43-3-G3-PU |
| ID969 | new | 8.9 | Ovary | 26-47-2-B1-PU |
| ID970 | new | 8.8 | Ovary | 26-11-1-G8-PU |
| ID971 | new | 8.8 | Testis | 51-37-4-E11-PU |
| ID972 | new | 8.7 | Ovary | 26-25-2-G1-PU |
| ID973 | new | 8.5 | Testis | 51-13-1-F7-PU |
| ID974 | new | 8.4 | Spleen | 20-2-1-D7-PU |
| ID975 | new | 8.1 | Ovary | 26-12-2-B5-PU |
| ID976 | new | 8 | Testis | 51-1-1-G12-PU |
| ID977 | new | 7.6 | Spleen | 20-8-2-F3-PU |
| ID978 | new | 7.5 | Spleen | 20-10-3-D4-PU |
| ID979 | new | 7.5 | Spleen | 20-3-3-G4-PU |
| ID980 | new | 7.5 | Testis | 51-10-3-B6-PU |
| ID981 | new | 7.5 | Ovary | 26-27-3-E8-PU |
| ID982 | new | 7.4 | Testis | 51-44-4-A6-PU |
| ID983 | new | 7.3 | Testis | 51-7-2-A6-PU |
| ID984 | new | 7.3 | Ovary | 26-31-1-D11-PU |
| ID985 | new | 7.1 | Testis | 51-28-2-G1-PU |
| ID986 | new | 6.9 | Spleen | 20-10-1-B12-PU |
| ID987 | new | 6.9 | Testis | 51-39-1-A5-PU |
| ID988 | new | 6.9 | Ovary | 26-23-2-A11-PU |
| ID989 | new | 6.9 | Testis | 51-1-4-C5-PU |
| ID990 | new | 6.8 | Spleen | 53-2-4-D8-PU |
| ID991 | new | 6.8 | Spleen | 20-3-2-C11-PU |
| ID992 | new | 6.8 | Testis | 51-29-4-B4-PU |
| ID993 | new | 6.8 | Ovary | 26-27-3-E11-PU |
| ID994 | new | 6.6 | Ovary | 26-10-1-H8-PU |
| ID995 | new | 6.5 | Testis | 51-18-2-G10-PU |
| ID996 | new | 6.5 | Spleen | 20-2-1-H12-PU |
| ID997 | new | 6.4 | Testis | 51-10-3-G3-PU |
| ID998 | new | 6.4 | Uterus | 74-9-4-H2-PU |
| ID999 | new | 6.4 | Ovary | 26-23-3-G2-PU |
| ID1000 | new | 6.4 | Testis | 51-2-4-F5-PU |
| ID1001 | new | 6.4 | Uterus | 74-4-3-C4-PU |
| ID1002 | new | 6.3 | Testis | 51-31-3-D1-PU |
| ID1003 | new | 6.3 | Spleen | 20-5-1-H1-PU |
| ID1004 | new | 6.2 | Ovary | 26-41-1-G3-PU |
| ID1005 | new | 6.2 | Uterus | 74-11-4-G3-PU |
| ID1006 | new | 6.1 | Ovary | 26-4-4-E9-PU |
| ID1007 | new | 6.1 | Spleen | 20-2-3-C2-PU |

TABLE II-continued

| SEQ. ID NO. | CATEGORY | VON HEIJNE SCORE | TISSUE SOURCE | INTERNAL DESIGNATION |
|---|---|---|---|---|
| ID1008 | new | 6.1 | Ovary | 26-48-1-A9-PU |
| ID1009 | new | 6 | Spleen | 20-1-2-C7-PU |
| ID1010 | new | 6 | Ovary | 26-28-4-H1-PU |
| ID1011 | new | 6 | Uterus | 74-8-4-C11-PU |
| ID1012 | new | 6 | Ovary | 26-6-3-B9-PU |
| ID1013 | new | 5.9 | Testis | 51-16-4-B10-PU |
| ID1014 | new | 5.9 | Testis | 51-47-3-F9-PU |
| ID1015 | new | 5.9 | Testis | 51-4-2-D10-PU |
| ID1016 | new | 5.9 | Ovary | 26-10-4-D9-PU |
| ID1017 | new | 5.8 | Testis | 51-18-1-C3-PU |
| ID1018 | new | 5.8 | Ovary | 26-45-2-C4-PU |
| ID1019 | new | 5.7 | Ovary | 26-26-3-D7-PU |
| ID1020 | new | 5.7 | Ovary | 26-5-3-A8-PU |
| ID1021 | new | 5.7 | Ovary | 26-47-1-C6-PU |
| ID1022 | new | 5.6 | Testis | 51-19-1-F10-PU |
| ID1023 | new | 5.6 | Testis | 51-11-4-G10-PU |
| ID1024 | new | 5.5 | Testis | 51-39-3-F7-PU |
| ID1025 | new | 5.5 | Testis | 51-2-1-E10-PU |
| ID1026 | new | 5.4 | Testis | 51-26-2-F5-PU |
| ID1027 | new | 5.4 | Ovary | 26-2-2-G10-PU |
| ID1028 | new | 5.4 | Testis | 51-35-4-G9-PU |
| ID1029 | new | 5.4 | Ovary | 26-39-1-A6-PU |
| ID1030 | new | 5.3 | Ovary | 26-47-1-E2-PU |
| ID1031 | new | 5.3 | Testis | 51-26-2-C7-PU |
| ID1032 | new | 5.2 | Uterus | 74-11-3-F8-PU |
| ID1033 | new | 5.2 | Spleen | 53-3-1-E2-PU |
| ID1034 | new | 5.2 | Testis | 51-31-3-G12-PU |
| ID1035 | new | 5.1 | Spleen | 20-6-4-G5-PU |
| ID1036 | new | 5.1 | Uterus | 74-6-3-F1-PU |
| ID1037 | new | 5.1 | Uterus | 74-11-1-F8-PU |
| ID1038 | new | 5.1 | Ovary | 26-7-4-B3-PU |
| ID1039 | new | 5 | Ovary | 26-5-3-F10-PU |
| ID1040 | new | 5 | Ovary | 26-49-3-C2-PU |
| ID1041 | new | 5 | Testis | 51-29-3-E1-PU |
| ID1042 | new | 5 | Ovary | 26-26-3-D2-PU |
| ID1043 | new | 5 | Uterus | 74-9-4-B4-PU |
| ID1044 | new | 5 | Testis | 51-1-3-E9-PU |
| ID1045 | new | 4.9 | Ovary | 26-5-1-C6-PU |
| ID1046 | new | 4.9 | Ovary | 26-3-1-H5-PU |
| ID1047 | new | 4.9 | Ovary | 26-51-4-D9-PU |
| ID1048 | new | 4.9 | Ovary | 26-27-3-D7-PU |
| ID1049 | new | 4.8 | Uterus | 74-3-4-D8-PU |
| ID1050 | new | 4.8 | Ovary | 26-29-1-E1-PU |
| ID1051 | new | 4.8 | Spleen | 20-3-1-H3-PU |
| ID1052 | new | 4.8 | Testis | 51-3-3-D8-PU |
| ID1053 | new | 4.8 | Spleen | 20-5-3-D9-PU |
| ID1054 | new | 4.7 | Testis | 51-44-4-HA-PU |
| ID1055 | new | 4.7 | Testis | 51-5-4-G12-PU |
| ID1056 | new | 4.7 | Spleen | 20-9-2-F7-PU |
| ID1057 | new | 4.7 | Spleen | 53-3-2-A10-PU |
| ID1058 | new | 4.6 | Ovary | 26-30-4-C1-PU |
| ID1059 | new | 4.6 | Testis | 51-29-3-H6-PU |
| ID1060 | new | 4.6 | Testis | 51-5-3-G2-PU |
| ID1061 | new | 4.6 | Testis | 51-11-3-D5-PU |
| ID1062 | new | 4.6 | Testis | 51-7-1-E7-PU |
| ID1063 | new | 4.6 | Testis | 51-27-1-G12-PU |
| ID1064 | new | 4.6 | Uterus | 74-4-1-F5-PU |
| ID1065 | new | 4.5 | Ovary | 26-24-1-F8-PU |
| ID1066 | new | 4.5 | Spleen | 20-7-3-F6-PU |
| ID1067 | new | 4.5 | Ovary | 26-1-2-A8-PU |
| ID1068 | new | 4.4 | Testis | 51-1-3-H9-PU |
| ID1069 | new | 4.4 | Testis | 51-27-1-E8-PU |
| ID1070 | new | 4.3 | Testis | 51-44-4-B2-PU |
| ID1071 | new | 4.3 | Ovary | 26-44-1-C3-PU |
| ID1072 | new | 4.3 | Spleen | 20-4-2-E2-PU |
| ID1073 | new | 4.3 | Testis | 51-19-4-F5-PU |
| ID1074 | new | 4.3 | Spleen | 20-8-4-D7-PU |
| ID1075 | new | 4.3 | Testis | 51-24-1-B11-PU |
| ID1076 | new | 4.3 | Spleen | 20-6-2-G10-PU |
| ID1077 | new | 4.2 | Testis | 51-6-4-F8-PU |
| ID1078 | new | 4.2 | Testis | 51-36-2-A9-PU |
| ID1079 | new | 4.2 | Ovary | 26-7-3-H10-PU |
| ID1080 | new | 4.2 | Testis | 51-1-3-D9-PU |
| ID1081 | new | 4.2 | Spleen | 20-2-1-B11-PU |
| ID1082 | new | 4.2 | Uterus | 74-6-4-A5-PU |
| ID1083 | new | 4.2 | Testis | 51-14-3-F3-PU |

TABLE II-continued

| SEQ. ID NO. | CATEGORY | VON HEIJNE SCORE | TISSUE SOURCE | INTERNAL DESIGNATION |
|---|---|---|---|---|
| ID1084 | new | 4.1 | Ovary | 26-33-3-E2-PU |
| ID1085 | new | 4 | Testis | 51-26-4-C7-PU |
| ID1086 | new | 4 | Testis | 51-25-3-F3-PU |
| ID1087 | new | 4 | Ovary | 26-8-3-D5-PU |
| ID1088 | new | 4 | Testis | 51-42-3-F9-PU |
| ID1089 | new | 4 | Ovary | 26-27-1-C5-PU |
| ID1090 | new | 4 | Ovary | 26-1-1-G2-PU |
| ID1091 | new | 3.9 | Ovary | 26-8-3-H3-PU |
| ID1092 | new | 3.9 | Ovary | 26-40-2-A9-PU |
| ID1093 | new | 3.9 | Ovary | 26-24-4-A5-PU |
| ID1094 | new | 3.9 | Uterus | 74-5-3-B12-PU |
| ID1095 | new | 3.8 | Testis | 51-37-2-G12-PU |
| ID1096 | new | 3.8 | Spleen | 20-8-2-E7-PU |
| ID1097 | new | 3.8 | Testis | 51-2-1-H9-PU |
| ID1098 | new | 3.8 | Ovary | 26-46-4-D12-PU |
| ID1099 | new | 3.8 | Ovary | 26-40-1-A12-PU |
| ID1100 | new | 3.7 | Testis | 51-3-4-E2-PU |
| ID1101 | new | 3.7 | Ovary | 26-47-3-G12-PU |
| ID1102 | new | 3.7 | Ovary | 26-2-4-E12-PU |
| ID1103 | new | 3.7 | Uterus | 74-4-4-D6-PU |
| ID1104 | new | 3.7 | Testis | 51-36-4-A3-PU |
| ID1105 | new | 3.7 | Uterus | 74-11-1-B8-PU |
| ID1106 | new | 3.7 | Spleen | 20-10-2-G2-PU |
| ID1107 | new | 3.7 | Testis | 51-37-4-D6-PU |
| ID1108 | new | 3.6 | Ovary | 26-27-4-G9-PU |
| ID1109 | new | 3.6 | Testis | 51-2-3-A6-PU |
| ID1110 | new | 3.6 | Ovary | 26-24-2-A3-PU |
| ID1111 | new | 3.6 | Uterus | 74-3-3-F6-PU |
| ID1112 | new | 3.5 | Spleen | 20-10-2-B2-PU |
| ID1113 | new | 3.5 | Testis | 51-13-2-G2-PU |
| ID1114 | new | 3.5 | Testis | 51-17-4-A4-PU |
| ID1115 | new | 3.5 | Spleen | 20-10-3-E5-PU |
| ID1116 | new | 3.5 | Testis | 51-30-1-B6-PU |
| ID1117 | new | 3.5 | Ovary | 26-40-2-G12-PU |
| ID1118 | new | 3.5 | Ovary | 26-9-3-G4-PU |
| ID1119 | ext-est-not-vrt | 12.7 | Testis | 51-18-4-A4-PU |
| ID1120 | ext-est-not-vrt | 7.4 | Ovary | 26-44-1-B5-PU |
| ID1121 | ext-est-not-vrt | 7.3 | Testis | 51-20-1-A2-PU |
| ID1122 | ext-est-not-vrt | 7.1 | Ovary | 26-2-1-A12-PU |
| ID1123 | ext-est-not-vrt | 6.7 | Testis | 51-2-1-A7-PU |
| ID1124 | ext-est-not-vrt | 5.6 | Spleen | 53-1-1-C10-PU |
| ID1125 | ext-est-not-vrt | 5.6 | Uterus | 74-10-1-B10-PU |
| ID1126 | ext-est-not-vrt | 5.3 | Testis | 51-31-4-A1-PU |
| ID1127 | ext-est-not-vrt | 4.4 | Testis | 51-25-1-A2-PU |
| ID1128 | ext-est-not-vrt | 4.1 | Testis | 51-35-2-F8-PU |
| ID1129 | ext-est-not-vrt | 3.9 | Testis | 51-8-3-E7-PU |
| ID1130 | ext-est-not-vrt | 3.9 | Testis | 51-34-2-H6-PU |
| ID1131 | ext-est-not-vrt | 3.5 | Uterus | 74-7-2-F11-PU |
| ID1132 | est-not-ext | 10.5 | Testis | 51-18-1-G7-PU |
| ID1133 | est-not-ext | 9.5 | Testis | 51-23-1-G1-PU |
| ID1134 | est-not-ext | 8.3 | Ovary | 26-8-1-B12-PU |
| ID1135 | est-not-ext | 8.3 | Testis | 51-41-1-F10-PU |
| ID1136 | est-not-ext | 8.2 | Ovary | 26-12-1-A2-PU |
| ID1137 | est-not-ext | 8.1 | Spleen | 53-3-3-B8-PU |
| ID1138 | est-not-ext | 8 | Testis | 51-4-4-A12-PU |
| ID1139 | est-not-ext | 7.8 | Testis | 51-18-1-H7-PU |
| ID1140 | est-not-ext | 7.6 | Spleen | 20-6-4-G3-PU |
| ID1141 | est-not-ext | 7.5 | Testis | 51-2-3-F10-PU |
| ID1142 | est-not-ext | 7.1 | Testis | 51-7-2-C2-PU |
| ID1143 | est-not-ext | 7.1 | Testis | 51-6-4-F9-PU |
| ID1144 | est-not-ext | 6.5 | Spleen | 20-6-1-D11-PU |
| ID1145 | est-not-ext | 6.4 | Ovary | 26-26-1-A11-PU |
| ID1146 | est-not-ext | 6.4 | Testis | 51-9-3-A12-PU |
| ID1147 | est-not-ext | 6.2 | Ovary | 26-8-3-F5-PU |
| ID1148 | est-not-ext | 6.1 | Ovary | 26-27-2-A12-PU |
| ID1149 | est-not-ext | 6 | Uterus | 74-11-3-H4-PU |
| ID1150 | est-not-ext | 5.8 | Ovary | 26-51-2-G10-PU |
| ID1151 | est-not-ext | 5.8 | Testis | 51-23-1-G2-PU |
| ID1152 | est-not-ext | 5.7 | Uterus | 74-1-2-H1-PU |
| ID1153 | est-not-ext | 5.7 | Testis | 51-9-1-E7-PU |
| ID1154 | est-not-ext | 5.3 | Testis | 51-1-4-E9-PU |
| ID1155 | est-not-ext | 4.8 | Testis | 51-6-4-G2-PU |
| ID1156 | est-not-ext | 4.8 | Spleen | 20-2-1-C5-PU |
| ID1157 | est-not-ext | 4.7 | Testis | 51-23-1-H2-PU |
| ID1158 | est-not-ext | 4.6 | Testis | 51-19-3-H6-PU |
| ID1159 | est-not-ext | 4.6 | Testis | 51-10-3-D11-PU |

TABLE II-continued

| SEQ. ID NO. | CATEGORY | VON HEIJNE SCORE | TISSUE SOURCE | INTERNAL DESIGNATION |
|---|---|---|---|---|
| ID1160 | est-not-ext | 4.6 | Testis | 51-20-2-G7-PU |
| ID1161 | est-not-ext | 4.6 | Ovary | 26-38-4-C2-PU |
| ID1162 | est-not-ext | 4.5 | Ovary | 26-44-3-C5-PU |
| ID1163 | est-not-ext | 4.4 | Ovary | 26-47-4-H1-PU |
| ID1164 | est-not-ext | 4.4 | Spleen | 20-5-2-C3-PU |
| ID1165 | est-not-ext | 4.3 | Testis | 51-21-3-B10-PU |
| ID1166 | est-not-ext | 4.3 | Spleen | 20-4-4-B3-PU |
| ID1167 | est-not-ext | 4.2 | Ovary | 26-5-1-F8-PU |
| ID1168 | est-not-ext | 4.1 | Testis | 51-22-3-B10-PU |
| ID1169 | est-not-ext | 4.1 | Testis | 51-18-1-G1-PU |
| ID1170 | est-not-ext | 4.1 | Testis | 51-12-2-H4-PU |
| ID1171 | est-not-ext | 3.9 | Testis | 51-25-1-A12-PU |
| ID1172 | est-not-ext | 3.8 | Spleen | 20-2-1-B4-PU |
| ID1173 | est-not-ext | 3.8 | Spleen | 20-7-2-A6-PU |
| ID1174 | est-not-ext | 3.8 | Ovary | 26-27-4-D3-PU |
| ID1175 | est-not-ext | 3.8 | Ovary | 26-5-4-F9-PU |
| ID1176 | est-not-ext | 3.8 | Uterus | 74-3-1-B9-PU |
| ID1177 | est-not-ext | 3.7 | Spleen | 20-8-4-A11-PU |
| ID1178 | est-not-ext | 3.6 | Testis | 51-15-4-G10-PU |
| ID1179 | est-not-ext | 3.6 | Testis | 51-2-1-A10-PU |
| ID1180 | est-not-ext | 3.5 | Spleen | 53-1-1-A10-PU |
| ID1181 | est-not-ext | 3.5 | Testis | 51-15-4-H10-PU |
| ID1182 | ext-vrt-not-genomic | 8.1 | Ovary | 26-36-1-D11-PU |
| ID1183 | ext-vrt-not-genomic | 4 | Testis | 51-39-2-D9-PU |
| ID1184 | new | 15.8 | Fetal liver | 65-5-1-C9-PU |
| ID1185 | new | 11.4 | Lung (cells) | 30-4-2-A11-PU |
| ID1186 | new | 11.1 | Large intestine | 83-3-2-H8-PU |
| ID1187 | new | 10.4 | Pancreas | 19-8-1-F2 |
| ID1188 | new | 10 | Liver | 22-11-2-H9-PU |
| ID1189 | new | 9.4 | Lung (cells) | 30-12-1-H1-PU |
| ID1190 | new | 9.2 | Lung | 59-1-3-E7-PU |
| ID1191 | new | 9.1 | Large intestine | 83-2-2-D9-PU |
| ID1192 | new | 9 | Lung (cells) | 30-2-1-G4-PU |
| ID1193 | new | 8.9 | Colon | 23-11-3-C4-PU |
| ID1194 | new | 8.9 | Large intestine | 83-2-1-C3-PU |
| ID1195 | new | 8.6 | Lung (cells) | 30-3-2-H6-PU |
| ID1196 | new | 8.6 | Lung (cells) | 30-13-1-D9-PU |
| ID1197 | new | 8.6 | Colon | 23-1-4-E6-PU |
| ID1198 | new | 8.2 | Liver | 22-3-3-C4-PU |
| ID1199 | new | 8 | Pancreas | 19-4-4-H9 |
| ID1200 | new | 7.7 | Lung (cells) | 30-8-1-F2-PU |
| ID1201 | new | 7.5 | Lung (cells) | 30-6-1-B1-PU |
| ID1202 | new | 7.5 | Lung (cells) | 30-6-3-H1-PU |
| ID1203 | new | 7.5 | Colon | 23-10-3-F10-PU |
| ID1204 | new | 7.4 | Lung | 42-1-1-E3-PU |
| ID1205 | new | 7.3 | Lung | 42-3-3-B1-PU |
| ID1206 | new | 7.3 | Lung | 42-3-4-B1-PU |
| ID1207 | new | 7.2 | Lung | 59-9-2-E6-PU |
| ID1208 | new | 7 | Thyroid | 84-4-2-D2-PU |
| ID1209 | new | 7 | Lung (cells) | 30-8-3-E3-PU |
| ID1210 | new | 7 | Lung | 59-9-4-A10-PU |
| ID1211 | new | 7 | Lung (cells) | 30-10-2-A2-PU |
| ID1212 | new | 6.9 | Lung | 59-9-1-B9-PU |
| ID1213 | new | 6.5 | Fetal liver | 65-4-4-A3-PU |
| ID1214 | new | 6.5 | Lung (cells) | 30-2-1-C8-PU |
| ID1215 | new | 6.4 | Colon | 23-9-4-F2-PU |
| ID1216 | new | 6.4 | Lung (cells) | 30-9-3-A2-PU |
| ID1217 | new | 6.3 | Liver | 22-11-2-A9-PU |
| ID1218 | new | 6.3 | Liver | 22-13-4-G8-PU |
| ID1219 | new | 6.2 | Liver | 22-1-2-A11-PU |
| ID1220 | new | 6.1 | Lung (cells) | 30-6-1-D11-PU |
| ID1221 | new | 5.9 | Thyroid | 84-4-3-A5-PU |
| ID1222 | new | 5.8 | Lung (cells) | 30-5-4-C1-PU |
| ID1223 | new | 5.7 | Liver | 22-5-2-A4-PU |
| ID1224 | new | 5.7 | Lung (cells) | 30-2-4-B7-PU |
| ID1225 | new | 5.6 | Pancreas | 46-3-4-G2-PU |
| ID1226 | new | 5.6 | Thyroid | 84-4-3-E9-PU |
| ID1227 | new | 5.5 | Lung (cells) | 30-7-2-C7-PU |
| ID1228 | new | 5.5 | Lung (cells) | 30-6-3-H11-PU |
| ID1229 | new | 5.5 | Large intestine | 83-5-3-C5-PU |
| ID1230 | new | 5.4 | Pancreas | 19-1-4-D10 |
| ID1231 | new | 5.3 | Lung | 59-5-3-A7-PU |
| ID1232 | new | 5.2 | Lung (cells) | 30-13-1-G11-PU |
| ID1233 | new | 5.2 | Lung (cells) | 30-7-3-E3-PU |
| ID1234 | new | 5.2 | Lung (cells) | 30-9-1-B10-PU |
| ID1235 | new | 5.1 | Lung (cells) | 30-8-1-G2-PU |

TABLE II-continued

| SEQ. ID NO. | CATEGORY | VON HEIJNE SCORE | TISSUE SOURCE | INTERNAL DESIGNATION |
|---|---|---|---|---|
| ID1236 | new | 5.1 | Lung (cells) | 30-13-2-E9-PU |
| ID1237 | new | 5.1 | Thyroid | 84-3-3-B4-PU |
| ID1238 | new | 5 | Lung (cells) | 30-4-4-D2-PU |
| ID1239 | new | 4.9 | Colon | 23-2-4-D1-PU |
| ID1240 | new | 4.9 | Colon | 23-9-1-A7-PU |
| ID1241 | new | 4.9 | Lung (cells) | 30-11-3-E2-PU |
| ID1242 | new | 4.9 | Fetal liver | 65-4-4-C8-PU |
| ID1243 | new | 4.9 | Large intestine | 83-2-4-H6-PU |
| ID1244 | new | 4.8 | Lung (cells) | 30-5-2-G2-PU |
| ID1245 | new | 4.8 | Liver | 22-9-4-B1-PU |
| ID1246 | new | 4.8 | Lung | 42-2-2-F2-PU |
| ID1247 | new | 4.8 | Lung (cells) | 30-1-1-D5-PU |
| ID1248 | new | 4.8 | Thyroid | 84-2-2-G8-PU |
| ID1249 | new | 4.7 | Colon | 23-10-4-H5-PU |
| ID1250 | new | 4.7 | Colon | 23-8-3-B1-PU |
| ID1251 | new | 4.7 | Lung (cells) | 30-8-3-A7-PU |
| ID1252 | new | 4.6 | Lung (cells) | 30-11-2-D9-PU |
| ID1253 | new | 4.5 | Lung (cells) | 30-6-4-E3-PU |
| ID1254 | new | 4.5 | Large intestine | 83-3-2-D3-PU |
| ID1255 | new | 4.5 | Pancreas | 19-2-2-E7 |
| ID1256 | new | 4.4 | Pancreas | 46-1-2-H7-PU |
| ID1257 | new | 4.4 | Colon | 23-1-3-C5-PU |
| ID1258 | new | 4.3 | Lung (cells) | 30-11-2-E12-PU |
| ID1259 | new | 4.3 | Fetal liver | 65-2-3-E3-PU |
| ID1260 | new | 4.3 | Colon | 23-11-1-G5-PU |
| ID1261 | new | 4.2 | Pancreas | 19-2-2-B4 |
| ID1262 | new | 4.2 | Lung (cells) | 30-4-4-H10-PU |
| ID1263 | new | 4.2 | Lung | 42-3-2-F6-PU |
| ID1264 | new | 4.1 | Lung (cells) | 30-1-4-G3-PU |
| ID1265 | new | 4.1 | Pancreas | 19-4-2-F6 |
| ID1266 | new | 4 | Lung | 42-3-3-F2-PU |
| ID1267 | new | 4 | Large intestine | 83-1-3-H10-PU |
| ID1268 | new | 4 | Lung (cells) | 30-11-1-D4-PU |
| ID1269 | new | 4 | Fetal liver | 65-5-1-E9-PU |
| ID1270 | new | 4 | Lung (cells) | 30-2-3-D4-PU |
| ID1271 | new | 4 | Colon | 23-8-4-G8-PU |
| ID1272 | new | 3.9 | Pancreas | 19-1-2-D9 |
| ID1273 | new | 3.9 | Lung (cells) | 30-7-2-D3-PU |
| ID1274 | new | 3.8 | Pancreas | 19-3-3-H4 |
| ID1275 | new | 3.7 | Fetal liver | 65-4-2-F9-PU |
| ID1276 | new | 3.6 | Lung (cells) | 30-3-3-G4-PU |
| ID1277 | new | 3.6 | Fetal liver | 65-5-2-C3-PU |
| ID1278 | new | 3.6 | Liver | 52-3-2-B1-PU |
| ID1279 | new | 3.6 | Large intestine | 83-2-2-B12-PU |
| ID1280 | new | 3.6 | Liver | 22-10-4-C1-PU |
| ID1281 | new | 3.6 | Thyroid | 84-4-1-H8-PU |
| ID1282 | new | 3.6 | Lung (cells) | 30-13-4-B11-PU |
| ID1283 | new | 3.6 | Lung (cells) | 30-13-1-G12-PU |
| ID1284 | new | 3.5 | Pancreas | 46-1-4-E11-PU |
| ID1285 | new | 3.5 | Thyroid | 84-1-3-C10-PU |
| ID1286 | new | 3.5 | Thyroid | 84-4-4-H11-PU |
| ID1287 | new | 3.5 | Lung | 59-8-3-A1-PU |
| ID1288 | ext-est-not-vrt | 7.6 | Large intestine | 83-4-2-H4-PU |
| ID1289 | ext-est-not-vrt | 6.6 | Lung (cells) | 30-2-2-C3-PU |
| ID1290 | ext-est-not-vrt | 6.6 | Thyroid | 84-4-1-F7-PU |
| ID1291 | ext-est-not-vrt | 5.4 | Pancreas | 19-10-1-C2 |
| ID1292 | ext-est-not-vrt | 5.2 | Thyroid | 84-5-1-F9-PU |
| ID1293 | ext-est-not-vrt | 5 | Lung | 59-9-3-A5-PU |
| ID1294 | ext-est-not-vrt | 4.7 | Lung (cells) | 30-7-3-H4-PU |
| ID1295 | ext-est-not-vrt | 4.5 | Lung (cells) | 30-11-3-F3-PU |
| ID1296 | ext-est-not-vrt | 4.4 | Lung (cells) | 30-12-1-D12-PU |
| ID1297 | est-not-ext | 16.4 | Liver | 22-5-3-G5-PU |
| ID1298 | est-not-ext | 14.4 | Large intestine | 83-3-2-E8-PU |
| ID1299 | est-not-ext | 10.3 | Liver | 52-3-1-B1-PU |
| ID1300 | est-not-ext | 9.5 | Pancreas | 19-9-1-C4 |
| ID1301 | est-not-ext | 9.5 | Pancreas | 19-8-4-F5-PU |
| ID1302 | est-not-ext | 8.8 | Colon | 23-2-1-D11-PU |
| ID1303 | est-not-ext | 8.7 | Large intestine | 83-4-4-B11-PU |
| ID1304 | est-not-ext | 8.5 | Liver | 22-13-3-F7-PU |
| ID1305 | est-not-ext | 8.1 | Lung | 42-2-3-A4-PU |
| ID1306 | est-not-ext | 7.6 | Liver | 22-10-3-C3-PU |
| ID1307 | est-not-ext | 7.5 | Lung (cells) | 30-5-1-B12-PU |
| ID1308 | est-not-ext | 7.5 | Liver | 52-1-2-B3-PU |
| ID1309 | est-not-ext | 6.8 | Pancreas | 19-8-3-B2 |
| ID1310 | est-not-ext | 6.8 | Lung | 59-1-3-A4-PU |
| ID1311 | est-not-ext | 6.8 | Thyroid | 84-3-1-F10-PU |

TABLE II-continued

| SEQ. ID NO. | CATEGORY | VON HEIJNE SCORE | TISSUE SOURCE | INTERNAL DESIGNATION |
|---|---|---|---|---|
| ID1312 | est-not-ext | 6.1 | Lung (cells) | 30-12-4-B11-PU |
| ID1313 | est-not-ext | 5.9 | Lung (cells) | 30-2-4-B6-PU |
| ID1314 | est-not-ext | 5.7 | Thyroid | 84-4-2-D5-PU |
| ID1315 | est-not-ext | 5.7 | Fetal liver | 65-2-1-E6-PU |
| ID1316 | est-not-ext | 5.6 | Large intestine | 83-5-4-E3-PU |
| ID1317 | est-not-ext | 5.3 | Lung (cells) | 30-9-3-E12-PU |
| ID1318 | est-not-ext | 5 | Colon | 23-10-3-G8-PU |
| ID1319 | est-not-ext | 4.9 | Lung (cells) | 30-10-3-H3-PU |
| ID1320 | est-not-ext | 4.7 | Pancreas | 19-3-4-F4 |
| ID1321 | est-not-ext | 4.5 | Colon | 23-8-3-H9-PU |
| ID1322 | est-not-ext | 4.3 | Large intestine | 83-5-4-A4-PU |
| ID1323 | est-not-ext | 3.8 | Pancreas | 19-1-3-E11 |
| ID1324 | est-not-ext | 3.8 | Lung | 59-5-4-A8-PU |
| ID1325 | est-not-ext | 3.7 | Fetal liver | 65-4-4-H3-PU |
| ID1326 | est-not-ext | 3.7 | Lung | 42-2-1-A1-PU |
| ID1327 | est-not-ext | 3.6 | Liver | 22-6-2-C1-PU |
| ID1328 | est-not-ext | 3.5 | Pancreas | 46-1-2-B2-PU |
| ID1329 | est-not-ext | 3.5 | Colon | 23-12-2-G6-PU |
| ID1330 | est-not-ext | 3.5 | Lung (cells) | 30-11-2-H2-PU |
| ID1331 | new | 15.8 | Heart | 25-13-1-H10-PU |
| ID1332 | new | 14 | Fetal kidney | 58-47-2-B11-PU |
| ID1333 | new | 12.3 | Dystrophic muscle | 29-3-3-H8-PU |
| ID1334 | new | 12.2 | Fetal kidney | 58-4-2-A3-PU |
| ID1335 | new | 11.9 | Kidney | 21-10-4-G1-PU |
| ID1336 | new | 11.3 | Fetal kidney | 58-27-3-B10-PU |
| ID1337 | new | 10.7 | Fetal kidney | 58-35-2-F10-PU |
| ID1338 | new | 10.7 | Fetal kidney | 58-37-2-G10-PU |
| ID1339 | new | 10.6 | Dystrophic muscle | 29-11-1-C11-PU |
| ID1340 | new | 10 | Fetal kidney | 58-20-4-G7-PU |
| ID1341 | new | 10 | Fetal kidney | 58-2-4-E9-PU |
| ID1342 | new | 9.6 | Fetal kidney | 58-37-3-D8-PU |
| ID1343 | new | 9.5 | Fetal kidney | 58-46-1-F1-PU |
| ID1344 | new | 9.2 | Dystrophic muscle | 29-9-4-D8-PU |
| ID1345 | new | 9.2 | Muscle | 27-10-4-C6-PU |
| ID1346 | new | 8.3 | Heart | 67-5-4-H9-PU |
| ID1347 | new | 8.1 | Fetal kidney | 58-4-3-H4-PU |
| ID1348 | new | 8 | Muscle | 27-16-3-D12-PU |
| ID1349 | new | 7.9 | Fetal kidney | 58-54-2-C2-PU |
| ID1350 | new | 7.9 | Heart | 25-9-3-A3-PU |
| ID1351 | new | 7.9 | Dystrophic muscle | 29-11-3-F1-PU |
| ID1352 | new | 7.9 | Fetal kidney | 58-32-3-G6-PU |
| ID1353 | new | 7.8 | Fetal kidney | 58-22-2-H8-PU |
| ID1354 | new | 7.8 | Fetal kidney | 58-2-4-H4-PU |
| ID1355 | new | 7.8 | Heart | 67-4-3-G3-PU |
| ID1356 | new | 7.8 | Fetal kidney | 58-24-1-G11-PU |
| ID1357 | new | 7.7 | Fetal kidney | 58-19-3-H1-PU |
| ID1358 | new | 7.5 | Fetal kidney | 58-45-4-B11-PU |
| ID1359 | new | 7.3 | Fetal kidney | 58-44-2-D3-PU |
| ID1360 | new | 7.2 | Dystrophic muscle | 29-3-3-E7-PU |
| ID1361 | new | 7.1 | Dystrophic muscle | 29-12-3-A3-PU |
| ID1362 | new | 7.1 | Fetal kidney | 58-14-2-B3-PU |
| ID1363 | new | 7.1 | Fetal kidney | 58-10-3-D12-PU |
| ID1364 | new | 7 | Fetal kidney | 58-6-2-E5-PU |
| ID1365 | new | 7 | Dystrophic muscle | 29-7-1-C1-PU |
| ID1366 | new | 6.9 | Fetal kidney | 58-26-4-A12-PU |
| ID1367 | new | 6.9 | Fetal kidney | 58-7-2-H9-PU |
| ID1368 | new | 6.9 | Fetal kidney | 58-14-2-D5-PU |
| ID1369 | new | 6.7 | Fetal kidney | 58-3-4-E1-PU |
| ID1370 | new | 6.7 | Fetal kidney | 58-43-4-G3-PU |
| ID1371 | new | 6.7 | Fetal kidney | 58-11-1-G10-PU |
| ID1372 | new | 6.6 | Fetal kidney | 58-4-4-G2-PU |
| ID1373 | new | 6.6 | Fetal kidney | 58-41-3-D6-PU |
| ID1374 | new | 6.6 | Heart | 25-8-2-H10-PU |
| ID1375 | new | 6.5 | Muscle | 27-18-4-E5-PU |
| ID1376 | new | 6.4 | Dystrophic muscle | 29-4-1-G6-PU |
| ID1377 | new | 6.4 | Muscle | 27-10-2-B1-PU |
| ID1378 | new | 6.4 | Fetal kidney | 58-38-1-E5-PU |
| ID1379 | new | 6.3 | Muscle | 27-4-3-D9-PU |
| ID1380 | new | 6.3 | Fetal kidney | 58-53-1-G1-PU |
| ID1381 | new | 6.3 | Fetal kidney | 58-7-3-F6-PU |
| ID1382 | new | 6.3 | Heart | 25-7-2-B12-PU |
| ID1383 | new | 6.1 | Fetal kidney | 58-16-3-E11-PU |
| ID1384 | new | 6 | Fetal kidney | 58-15-4-C2-PU |
| ID1385 | new | 6 | Fetal kidney | 58-34-3-A9-PU |
| ID1386 | new | 5.9 | Fetal kidney | 58-16-1-E1-PU |
| ID1387 | new | 5.9 | Fetal kidney | 58-4-3-E6-PU |

TABLE II-continued

| SEQ. ID NO. | CATEGORY | VON HEIJNE SCORE | TISSUE SOURCE | INTERNAL DESIGNATION |
|---|---|---|---|---|
| ID1388 | new | 5.9 | Fetal kidney | 58-37-3-B11-PU |
| ID1389 | new | 5.9 | Fetal kidney | 58-35-3-C6-PU |
| ID1390 | new | 5.8 | Fetal kidney | 58-35-1-D9-PU |
| ID1391 | new | 5.8 | Fetal kidney | 58-26-3-B2-PU |
| ID1392 | new | 5.7 | Fetal kidney | 58-48-1-F8-PU |
| ID1393 | new | 5.7 | Fetal kidney | 58-27-4-A6-PU |
| ID1394 | new | 5.7 | Fetal kidney | 58-26-3-D1-PU |
| ID1395 | new | 5.7 | Muscle | 27-19-4-B4-PU |
| ID1396 | new | 5.6 | Fetal kidney | 58-23-3-B2-PU |
| ID1397 | new | 5.5 | Heart | 25-1-2-C1-PU |
| ID1398 | new | 5.5 | Fetal kidney | 58-14-3-F10-PU |
| ID1399 | new | 5.5 | Fetal kidney | 58-25-1-E11-PU |
| ID1400 | new | 5.5 | Muscle | 27-9-4-A10-PU |
| ID1401 | new | 5.5 | Heart | 25-4-2-D8-PU |
| ID1402 | new | 5.4 | Fetal kidney | 58-29-3-G8-PU |
| ID1403 | new | 5.4 | Fetal kidney | 58-4-4-E5-PU |
| ID1404 | new | 5.4 | Fetal kidney | 58-24-2-H2-PU |
| ID1405 | new | 5.4 | Muscle | 27-11-2-C8-PU |
| ID1406 | new | 5.4 | Fetal kidney | 58-41-2-E3-PU |
| ID1407 | new | 5.3 | Muscle | 27-22-1-G8-PU |
| ID1408 | new | 5.3 | Dystrophic muscle | 29-1-1-C9-PU |
| ID1409 | new | 5.3 | Fetal kidney | 58-22-2-A3-PU |
| ID1410 | new | 5.2 | Fetal kidney | 58-42-2-G1-PU |
| ID1411 | new | 5.2 | Fetal kidney | 58-52-2-E5-PU |
| ID1412 | new | 5.2 | Fetal kidney | 58-24-2-G2-PU |
| ID1413 | new | 5.2 | Fetal kidney | 58-29-1-A3-PU |
| ID1414 | new | 5.1 | Fetal kidney | 58-26-1-G8-PU |
| ID1415 | new | 5.1 | Fetal kidney | 58-29-4-G12-PU |
| ID1416 | new | 5.1 | Dystrophic muscle | 29-8-3-E8-PU |
| ID1417 | new | 5.1 | Dystrophic muscle | 29-3-4-C1-PU |
| ID1418 | new | 5 | Fetal kidney | 58-17-2-H1-PU |
| ID1419 | new | 5 | Fetal kidney | 58-9-3-E3-PU |
| ID1420 | new | 5 | Muscle | 27-19-3-G7-PU |
| ID1421 | new | 5 | Fetal kidney | 58-41-3-B4-PU |
| ID1422 | new | 5 | Dystrophic muscle | 29-7-4-G7-PU |
| ID1423 | new | 5 | Muscle | 27-9-3-D4-PU |
| ID1424 | new | 4.9 | Kidney | 21-3-4-C5-PU |
| ID1425 | new | 4.9 | Heart | 25-11-2-D6-PU |
| ID1426 | new | 4.9 | Heart | 67-7-2-F3-PU |
| ID1427 | new | 4.8 | Fetal kidney | 58-4-3-D3-PU |
| ID1428 | new | 4.8 | Fetal kidney | 58-49-3-B5-PU |
| ID1429 | new | 4.8 | Fetal kidney | 58-28-3-G12-PU |
| ID1430 | new | 4.7 | Fetal kidney | 58-53-1-A5-PU |
| ID1431 | new | 4.7 | Fetal kidney | 58-3-3-E10-PU |
| ID1432 | new | 4.7 | Fetal kidney | 58-8-1-G7-PU |
| ID1433 | new | 4.6 | Fetal kidney | 58-23-1-G9-PU |
| ID1434 | new | 4.6 | Fetal kidney | 58-21-1-H8-PU |
| ID1435 | new | 4.6 | Fetal kidney | 58-54-2-E10-PU |
| ID1436 | new | 4.6 | Fetal kidney | 58-46-3-E4-PU |
| ID1437 | new | 4.6 | Fetal kidney | 58-6-3-G3-PU |
| ID1438 | new | 4.6 | Fetal kidney | 58-41-2-B5-PU |
| ID1439 | new | 4.6 | Dystrophic muscle | 29-7-3-F2-PU |
| ID1440 | new | 4.5 | Fetal kidney | 58-2-4-G12-PU |
| ID1441 | new | 4.5 | Fetal kidney | 58-11-2-G8-PU |
| ID1442 | new | 4.4 | Fetal kidney | 58-17-1-C4-PU |
| ID1443 | new | 4.4 | Fetal kidney | 58-46-1-G7-PU |
| ID1444 | new | 4.4 | Heart | 67-3-2-F4-PU |
| ID1445 | new | 4.4 | Fetal kidney | 58-8-4-E12-PU |
| ID1446 | new | 4.4 | Fetal kidney | 58-4-2-D9-PU |
| ID1447 | new | 4.4 | Fetal kidney | 58-25-1-B5-PU |
| ID1448 | new | 4.4 | Fetal kidney | 58-15-1-C10-PU |
| ID1449 | new | 4.3 | Dystrophic muscle | 29-4-4-A10-PU |
| ID1450 | new | 4.3 | Fetal kidney | 58-32-3-H7-PU |
| ID1451 | new | 4.3 | Kidney | 21-4-4-D12-PU |
| ID1452 | new | 4.3 | Fetal kidney | 58-45-4-G9-PU |
| ID1453 | new | 4.3 | Fetal kidney | 58-1-2-E2-PU |
| ID1454 | new | 4.2 | Fetal kidney | 58-25-4-E6-PU |
| ID1455 | new | 4.2 | Fetal kidney | 58-36-4-C6-PU |
| ID1456 | new | 4.2 | Dystrophic muscle | 29-9-3-D5-PU |
| ID1457 | new | 4.2 | Fetal kidney | 58-3-3-B8-PU |
| ID1458 | new | 4.2 | Heart | 25-4-4-B4-PU |
| ID1459 | new | 4.2 | Kidney | 21-10-3-A3-PU |
| ID1460 | new | 4.2 | Muscle | 27-19-4-B5-PU |
| ID1461 | new | 4.2 | Fetal kidney | 58-23-3-D10-PU |
| ID1462 | new | 4.1 | Fetal kidney | 58-41-1-F8-PU |
| ID1463 | new | 4.1 | Heart | 25-7-2-B1-PU |

TABLE II-continued

| SEQ. ID NO. | CATEGORY | VON HEIJNE SCORE | TISSUE SOURCE | INTERNAL DESIGNATION |
|---|---|---|---|---|
| ID1464 | new | 4.1 | Fetal kidney | 58-53-3-G4-PU |
| ID1465 | new | 4.1 | Fetal kidney | 58-52-2-C2-PU |
| ID1466 | new | 4 | Muscle | 27-21-4-E12-PU |
| ID1467 | new | 4 | Fetal kidney | 58-22-2-B8-PU |
| ID1468 | new | 4 | Fetal kidney | 58-9-3-A8-PU |
| ID1469 | new | 4 | Muscle | 27-5-4-C10-PU |
| ID1470 | new | 4 | Fetal kidney | 58-38-1-G5-PU |
| ID1471 | new | 4 | Fetal kidney | 58-34-4-F6-PU |
| ID1472 | new | 4 | Heart | 25-1-4-D2-PU |
| ID1473 | new | 4 | Fetal kidney | 58-48-2-D6-PU |
| ID1474 | new | 3.9 | Fetal kidney | 58-9-3-C10-PU |
| ID1475 | new | 3.9 | Fetal kidney | 58-9-4-F2-PU |
| ID1476 | new | 3.9 | Fetal kidney | 58-32-3-G3-PU |
| ID1477 | new | 3.9 | Fetal kidney | 58-52-1-F6-PU |
| ID1478 | new | 3.9 | Fetal kidney | 58-29-1-E1-PU |
| ID1479 | new | 3.9 | Muscle | 27-3-4-A3-PU |
| ID1480 | new | 3.9 | Muscle | 27-16-3-H2-PU |
| ID1481 | new | 3.9 | Fetal kidney | 58-1-3-E1-PU |
| ID1482 | new | 3.8 | Kidney | 21-5-4-F10-PU |
| ID1483 | new | 3.8 | Kidney | 21-1-3-C9-PU |
| ID1484 | new | 3.8 | Fetal kidney | 58-1-2-C7-PU |
| ID1485 | new | 3.8 | Fetal kidney | 58-10-3-B6-PU |
| ID1486 | new | 3.8 | Fetal kidney | 58-11-4-C8-PU |
| ID1487 | new | 3.8 | Heart | 67-6-4-B12-PU |
| ID1488 | new | 3.8 | Fetal kidney | 58-7-3-B5-PU |
| ID1489 | new | 3.8 | Fetal kidney | 58-46-3-C6-PU |
| ID1490 | new | 3.7 | Dystrophic muscle | 29-2-4-D8-PU |
| ID1491 | new | 3.7 | Fetal kidney | 58-7-1-D10-PU |
| ID1492 | new | 3.7 | Kidney | 21-2-4-A11-PU |
| ID1493 | new | 3.6 | Fetal kidney | 58-45-3-B7-PU |
| ID1494 | new | 3.6 | Fetal kidney | 58-29-1-D7-PU |
| ID1495 | new | 3.6 | Fetal kidney | 58-16-3-B3-PU |
| ID1496 | new | 3.6 | Dystrophic muscle | 29-7-3-C3-PU |
| ID1497 | new | 3.6 | Fetal kidney | 58-42-3-C2-PU |
| ID1498 | new | 3.5 | Fetal kidney | 58-38-3-G8-PU |
| ID1499 | new | 3.5 | Dystrophic muscle | 29-6-2-B12-PU |
| ID1500 | new | 3.5 | Fetal kidney | 58-8-1-D1-PU |
| ID1501 | new | 3.5 | Fetal kidney | 58-24-1-H2-PU |
| ID1502 | new | 3.5 | Fetal kidney | 58-41-4-G9-PU |
| ID1503 | ext-est-not-vrt | 12.7 | Muscle | 27-22-3-H1-PU |
| ID1504 | ext-est-not-vrt | 10.5 | Fetal kidney | 58-29-1-F11-PU |
| ID1505 | ext-est-not-vrt | 8 | Fetal kidney | 58-14-2-B12-PU |
| ID1506 | ext-est-not-vrt | 7.7 | Fetal kidney | 58-5-1-C4-PU |
| ID1507 | ext-est-not-vrt | 7.1 | Fetal kidney | 58-37-4-C7-PU |
| ID1508 | ext-est-not-vrt | 6.7 | Muscle | 27-21-2-C8-PU |
| ID1509 | ext-est-not-vrt | 6.7 | Heart | 67-1-1-C8-PU |
| ID1510 | ext-est-not-vrt | 6.3 | Fetal kidney | 58-26-3-G6-PU |
| ID1511 | ext-est-not-vrt | 6.2 | Fetal kidney | 58-15-3-B12-PU |
| ID1512 | ext-est-not-vrt | 6 | Muscle | 27-5-2-G11-PU |
| ID1513 | ext-est-not-vrt | 6 | Fetal kidney | 58-8-1-H10-PU |
| ID1514 | ext-est-not-vrt | 5.8 | Fetal kidney | 58-38-4-D2-PU |
| ID1515 | ext-est-not-vrt | 5.6 | Fetal kidney | 58-53-2-E6-PU |
| ID1516 | ext-est-not-vrt | 5.6 | Fetal kidney | 58-52-2-C7-PU |
| ID1517 | ext-est-not-vrt | 5.5 | Fetal kidney | 58-34-2-E7-PU |
| ID1518 | ext-est-not-vrt | 5.4 | Fetal kidney | 58-4-1-A2-PU |
| ID1519 | ext-est-not-vrt | 5.2 | Fetal kidney | 58-11-1-D3-PU |
| ID1520 | ext-est-not-vrt | 5.2 | Fetal kidney | 58-34-3-C9-PU |
| ID1521 | ext-est-not-vrt | 5.2 | Fetal kidney | 58-35-4-H11-PU |
| ID1522 | ext-est-not-vrt | 4.6 | Fetal kidney | 58-3-4-H7-PU |
| ID1523 | ext-est-not-vrt | 4.5 | Fetal kidney | 58-25-1-F3-PU |
| ID1524 | ext-est-not-vrt | 4.5 | Fetal kidney | 58-4-4-A8-PU |
| ID1525 | ext-est-not-vrt | 4.4 | Fetal kidney | 58-11-1-C1-PU |
| ID1526 | ext-est-not-vrt | 3.9 | Muscle | 27-19-2-F5-PU |
| ID1527 | ext-est-not-vrt | 3.5 | Dystrophic muscle | 29-2-2-A2-PU |
| ID1528 | est-not-ext | 14.1 | Fetal kidney | 58-29-2-B9-PU |
| ID1529 | est-not-ext | 11.4 | Dystrophic muscle | 29-11-2-E4-PU |
| ID1530 | est-not-ext | 11.2 | Fetal kidney | 58-7-2-A7-PU |
| ID1531 | est-not-ext | 10.8 | Muscle | 27-22-3-G4-PU |
| ID1532 | est-not-ext | 9.9 | Fetal kidney | 58-9-1-G1-PU |
| ID1533 | est-not-ext | 9.7 | Dystrophic muscle | 29-8-1-H5-PU |
| ID1534 | est-not-ext | 9.6 | Fetal kidney | 58-40-1-F5-PU |
| ID1535 | est-not-ext | 9.5 | Fetal kidney | 58-6-4-G2-PU |
| ID1536 | est-not-ext | 9.2 | Fetal kidney | 58-25-2-E7-PU |
| ID1537 | est-not-ext | 8.9 | Fetal kidney | 58-48-1-A11-PU |
| ID1538 | est-not-ext | 8.8 | Fetal kidney | 58-35-2-B6-PU |
| ID1539 | est-not-ext | 8.5 | Kidney | 21-7-4-C7-PU |

TABLE II-continued

| SEQ. ID NO. | CATEGORY | VON HEIJNE SCORE | TISSUE SOURCE | INTERNAL DESIGNATION |
|---|---|---|---|---|
| ID1540 | est-not-ext | 8.4 | Fetal kidney | 58-45-1-E6-PU |
| ID1541 | est-not-ext | 8.1 | Fetal kidney | 58-39-1-A12-PU |
| ID1542 | est-not-ext | 8 | Fetal kidney | 58-46-1-C7-PU |
| ID1543 | est-not-ext | 7.9 | Dystrophic muscle | 29-12-3-E10-PU |
| ID1544 | est-not-ext | 7.9 | Fetal kidney | 58-17-2-D9-PU |
| ID1545 | est-not-ext | 7.9 | Fetal kidney | 58-52-3-B7-PU |
| ID1546 | est-not-ext | 7.6 | Fetal kidney | 58-24-3-E7-PU |
| ID1547 | est-not-ext | 7.6 | Heart | 25-8-4-B12-PU |
| ID1548 | est-not-ext | 7.6 | Dystrophic muscle | 29-4-4-D12-PU |
| ID1549 | est-not-ext | 7.4 | Muscle | 27-1-2-B3-PU |
| ID1550 | est-not-ext | 7.3 | Fetal kidney | 58-48-1-G3-PU |
| ID1551 | est-not-ext | 7.3 | Dystrophic muscle | 29-2-3-F8-PU |
| ID1552 | est-not-ext | 7.2 | Fetal kidney | 58-19-3-B3-PU |
| ID1553 | est-not-ext | 7 | Fetal kidney | 58-14-2-C4-PU |
| ID1554 | est-not-ext | 6.7 | Fetal kidney | 58-16-3-B6-PU |
| ID1555 | est-not-ext | 6.6 | Fetal kidney | 58-9-4-F6-PU |
| ID1556 | est-not-ext | 6.4 | Fetal kidney | 58-1-1-E3-PU |
| ID1557 | est-not-ext | 6.4 | Fetal kidney | 58-33-3-B4-PU |
| ID1558 | est-not-ext | 6.3 | Dystrophic muscle | 29-12-1-H1-PU |
| ID1559 | est-not-ext | 6.3 | Muscle | 27-9-3-A5-PU |
| ID1560 | est-not-ext | 6.2 | Muscle | 27-17-4-C12-PU |
| ID1561 | est-not-ext | 6.2 | Fetal kidney | 58-33-1-F1-PU |
| ID1562 | est-not-ext | 5.9 | Fetal kidney | 58-48-4-H2-PU |
| ID1563 | est-not-ext | 5.9 | Fetal kidney | 58-42-1-A6-PU |
| ID1564 | est-not-ext | 5.7 | Fetal kidney | 58-33-4-E1-PU |
| ID1565 | est-not-ext | 5.7 | Fetal kidney | 58-26-2-E12-PU |
| ID1566 | est-not-ext | 5.6 | Fetal kidney | 58-26-1-E12-PU |
| ID1567 | est-not-ext | 5.5 | Fetal kidney | 58-54-1-D11-PU |
| ID1568 | est-not-ext | 5.5 | Muscle | 27-9-2-F9-PU |
| ID1569 | est-not-ext | 5.4 | Fetal kidney | 58-30-2-H10-PU |
| ID1570 | est-not-ext | 5.3 | Fetal kidney | 58-29-1-H1-PU |
| ID1571 | est-not-ext | 5.3 | Kidney | 21-1-4-F2-PU |
| ID1572 | est-not-ext | 5.1 | Fetal kidney | 58-42-4-H7-PU |
| ID1573 | est-not-ext | 5 | Fetal kidney | 58-34-3-H10-PU |
| ID1574 | est-not-ext | 5 | Kidney | 21-7-3-B4-PU |
| ID1575 | est-not-ext | 4.9 | Fetal kidney | 58-4-2-D12-PU |
| ID1576 | est-not-ext | 4.8 | Fetal kidney | 58-31-2-C10-PU |
| ID1577 | est-not-ext | 4.7 | Fetal kidney | 58-37-3-C10-PU |
| ID1578 | est-not-ext | 4.7 | Fetal kidney | 58-1-1-D11-PU |
| ID1579 | est-not-ext | 4.6 | Fetal kidney | 58-52-1-A11-PU |
| ID1580 | est-not-ext | 4.3 | Fetal kidney | 58-4-3-E10-PU |
| ID1581 | est-not-ext | 4.3 | Heart | 67-6-4-F2-PU |
| ID1582 | est-not-ext | 4.2 | Fetal kidney | 58-49-3-G10-PU |
| ID1583 | est-not-ext | 4.1 | Dystrophic muscle | 29-10-3-B11-PU |
| ID1584 | est-not-ext | 4.1 | Heart | 25-5-4-A7-PU |
| ID1585 | est-not-ext | 4.1 | Fetal kidney | 58-33-2-C6-PU |
| ID1586 | est-not-ext | 4 | Heart | 25-7-3-D4-PU |
| ID1587 | est-not-ext | 3.9 | Heart | 67-1-3-B11-PU |
| ID1588 | est-not-ext | 3.9 | Fetal kidney | 58-23-1-G5-PU |
| ID1589 | est-not-ext | 3.7 | Fetal kidney | 58-6-1-B6-PU |
| ID1590 | est-not-ext | 3.7 | Dystrophic muscle | 29-6-2-H8-PU |
| ID1591 | est-not-ext | 3.7 | Fetal kidney | 58-43-4-B8-PU |
| ID1592 | est-not-ext | 3.6 | Muscle | 27-3-4-G9-PU |
| ID1593 | est-not-ext | 3.6 | Fetal kidney | 58-38-1-F10-PU |
| ID1594 | est-not-ext | 3.5 | Heart | 67-6-4-E7-PU |
| ID1595 | est-not-ext | 3.5 | Fetal kidney | 58-54-1-E6-PU |
| ID1596 | est-not-ext | 3.5 | Heart | 67-4-4-G7-PU |
| ID1597 | est-not-ext | 3.5 | Fetal kidney | 58-23-4-F4-PU |
| ID1598 | ext-vrt-not-genomic | 10.5 | Fetal kidney | 58-42-3-A12-PU |
| ID1599 | new | 14.3 | Substantia nigra | 47-39-4-A10-PU |
| ID1600 | new | 11.1 | Fetal brain | 57-9-4-C5-PU |
| ID1601 | new | 10.6 | Fetal brain | 57-19-1-B11-PU |
| ID1602 | new | 9.1 | Fetal brain | 57-7-1-G12-PU |
| ID1603 | new | 8.8 | Substantia nigra | 47-22-3-D2-PU |
| ID1604 | new | 8.7 | Fetal brain | 57-21-2-H11-PU |
| ID1605 | new | 8.4 | Substantia nigra | 47-37-3-F6-PU |
| ID1606 | new | 8.2 | Substantia nigra | 47-54-1-A8-PU |
| ID1607 | new | 8.2 | Substantia nigra | 47-15-1-E5-PU |
| ID1608 | new | 8 | Substantia nigra | 47-24-1-A6-PU |
| ID1609 | new | 7.8 | Fetal brain | 57-10-3-H10-PU |
| ID1610 | new | 7.7 | Substantia nigra | 47-17-1-D7-PU |
| ID1611 | new | 7.6 | Cerebellum | 55-9-4-A4-PU |
| ID1612 | new | 7.5 | Substantia nigra | 47-18-3-C2-PU |
| ID1613 | new | 7.4 | Fetal brain | 57-19-1-C8-PU |
| ID1614 | new | 7.4 | Substantia nigra | 47-1-4-C5-PU |
| ID1615 | new | 7.2 | Substantia nigra | 47-24-1-B5-PU |

TABLE II-continued

| SEQ. ID NO. | CATEGORY | VON HEIJNE SCORE | TISSUE SOURCE | INTERNAL DESIGNATION |
|---|---|---|---|---|
| ID1616 | new | 7.2 | Cerebellum | 55-6-2-A9-PU |
| ID1617 | new | 7.1 | Substantia nigra | 47-30-4-A8-PU |
| ID1618 | new | 6.9 | Fetal brain | 57-21-1-D5-PU |
| ID1619 | new | 6.9 | Substantia nigra | 47-4-2-C7-PU |
| ID1620 | new | 6.8 | Substantia nigra | 47-12-3-A8-PU |
| ID1621 | new | 6.8 | Substantia nigra | 47-7-4-E6-PU |
| ID1622 | new | 6.8 | Substantia nigra | 47-15-3-G3-PU |
| ID1623 | new | 6.7 | Fetal brain | 57-20-2-B5-PU |
| ID1624 | new | 6.6 | Substantia nigra | 47-2-2-E6-PU |
| ID1625 | new | 6.5 | Fetal brain | 57-25-1-G3-PU |
| ID1626 | new | 6.5 | Fetal brain | 57-7-4-B12-PU |
| ID1627 | new | 6.5 | Substantia nigra | 47-21-1-D9-PU |
| ID1628 | new | 6.4 | Substantia nigra | 47-31-2-H9-PU |
| ID1629 | new | 5.7 | Cerebellum | 55-1-3-D11-PU |
| ID1630 | new | 5.7 | Cerebellum | 55-7-2-A1-PU |
| ID1631 | new | 5.7 | Fetal brain | 57-28-3-C1-PU |
| ID1632 | new | 5.6 | Fetal brain | 57-9-4-D11-PU |
| ID1633 | new | 5.5 | Substantia nigra | 47-7-4-C10-PU |
| ID1634 | new | 5.5 | Fetal brain | 57-22-1-E11-PU |
| ID1635 | new | 5.4 | Fetal brain | 57-20-2-D9-PU |
| ID1636 | new | 5.4 | Substantia nigra | 47-39-3-E7-PU |
| ID1637 | new | 5.4 | Surrenals | 62-3-1-G5-PU |
| ID1638 | new | 5.4 | Fetal brain | 57-18-4-H5-PU |
| ID1639 | new | 5.4 | Fetal brain | 57-22-2-H8-PU |
| ID1640 | new | 5.3 | Fetal brain | 57-22-2-E12-PU |
| ID1641 | new | 5.3 | Fetal brain | 57-23-3-B8-PU |
| ID1642 | new | 5.2 | Fetal brain | 57-6-3-C5-PU |
| ID1643 | new | 5.2 | Substantia nigra | 47-7-1-D2-PU |
| ID1644 | new | 5.1 | Fetal brain | 57-7-2-G9-PU |
| ID1645 | new | 5.1 | Fetal brain | 57-10-3-D3-PU |
| ID1646 | new | 5.1 | Substantia nigra | 47-4-4-F2-PU |
| ID1647 | new | 5.1 | Fetal brain | 57-4-4-H6-PU |
| ID1648 | new | 5 | Substantia nigra | 47-10-2-G12-PU |
| ID1649 | new | 5 | Cerebellum | 55-10-3-E12-PU |
| ID1650 | new | 4.9 | Substantia nigra | 47-8-2-D1-PU |
| ID1651 | new | 4.9 | Fetal brain | 57-3-4-C9-PU |
| ID1652 | new | 4.9 | Substantia nigra | 47-14-1-C3-PU |
| ID1653 | new | 4.8 | Substantia nigra | 47-3-4-C8-PU |
| ID1654 | new | 4.8 | Substantia nigra | 47-15-1-B10-PU |
| ID1655 | new | 4.8 | Fetal brain | 57-26-3-A12-PU |
| ID1656 | new | 4.7 | Substantia nigra | 47-26-3-B10-PU |
| ID1657 | new | 4.7 | Substantia nigra | 47-26-1-B6-PU |
| ID1658 | new | 4.7 | Surrenals | 62-5-1-B8-PU |
| ID1659 | new | 4.6 | Substantia nigra | 47-15-4-H9-PU |
| ID1660 | new | 4.6 | Cerebellum | 55-2-4-D3-PU |
| ID1661 | new | 4.5 | Fetal brain | 57-6-1-B1-PU |
| ID1662 | new | 4.5 | Fetal brain | 57-26-4-E4-PU |
| ID1663 | new | 4.5 | Substantia nigra | 47-2-2-A7-PU |
| ID1664 | new | 4.5 | Substantia nigra | 47-55-2-B3-PU |
| ID1665 | new | 4.5 | Substantia nigra | 47-54-1-C9-PU |
| ID1666 | new | 4.4 | Cerebellum | 55-8-2-A2-PU |
| ID1667 | new | 4.4 | Substantia nigra | 47-4-2-H4-PU |
| ID1668 | new | 4.3 | Fetal brain | 57-27-3-B11-PU |
| ID1669 | new | 4.2 | Fetal brain | 57-22-4-D2-PU |
| ID1670 | new | 4.2 | Substantia nigra | 47-20-4-E2-PU |
| ID1671 | new | 4.2 | Substantia nigra | 47-2-3-H2-PU |
| ID1672 | new | 4.1 | Substantia nigra | 47-22-3-G5-PU |
| ID1673 | new | 4.1 | Fetal brain | 57-18-3-A5-PU |
| ID1674 | new | 4.1 | Fetal brain | 57-9-3-H7-PU |
| ID1675 | new | 4.1 | Surrenals | 62-5-2-B6-PU |
| ID1676 | new | 4 | Cerebellum | 55-12-1-E12-PU |
| ID1677 | new | 4 | Fetal brain | 57-20-1-A5-PU |
| ID1678 | new | 3.9 | Substantia nigra | 47-22-4-F6-PU |
| ID1679 | new | 3.8 | Fetal brain | 57-19-3-E1-PU |
| ID1680 | new | 3.8 | Substantia nigra | 47-18-3-G5-PU |
| ID1681 | new | 3.8 | Substantia nigra | 47-20-1-G3-PU |
| ID1682 | new | 3.8 | Fetal brain | 57-6-4-A1-PU |
| ID1683 | new | 3.8 | Fetal brain | 57-27-3-G10-PU |
| ID1684 | new | 3.7 | Substantia nigra | 47-2-4-C7-PU |

TABLE II-continued

| SEQ. ID NO. | CATEGORY | VON HEIJNE SCORE | TISSUE SOURCE | INTERNAL DESIGNATION |
| --- | --- | --- | --- | --- |
| ID1685 | new | 3.7 | Cerebellum | 55-6-1-E6-PU |
| ID1686 | new | 3.6 | Fetal brain | 57-4-4-F7-PU |
| ID1687 | new | 3.6 | Substantia nigra | 47-30-2-B1-PU |
| ID1688 | new | 3.6 | Substantia nigra | 47-29-1-F11-PU |
| ID1689 | new | 3.6 | Substantia nigra | 47-39-3-D4-PU |
| ID1690 | new | 3.5 | Substantia nigra | 47-15-2-G3-PU |
| ID1691 | new | 3.5 | Fetal brain | 57-18-3-E6-PU |
| ID1692 | new | 3.5 | Substantia nigra | 47-40-2-G6-PU |
| ID1693 | new | 3.5 | Fetal brain | 57-6-4-D7-PU |
| ID1694 | new | 3.5 | Substantia nigra | 47-55-4-A8-PU |
| ID1695 | ext-est-not-vrt | 9.8 | Substantia nigra | 47-39-4-B9-PU |
| ID1696 | ext-est-not-vrt | 9.2 | Cerebellum | 55-11-1-H5-PU |
| ID1697 | ext-est-not-vrt | 9 | Substantia nigra | 47-4-4-G1-PU |
| ID1698 | ext-est-not-vrt | 7.2 | Substantia nigra | 47-2-3-G9-PU |
| ID1699 | ext-est-not-vrt | 7.2 | Cerebellum | 55-10-3-F5-PU |
| ID1700 | ext-est-not-vrt | 5.6 | Fetal brain | 57-4-4-G6-PU |
| ID1701 | ext-est-not-vrt | 4.2 | Cerebellum | 55-7-1-D11-PU |
| ID1702 | ext-est-not-vrt | 3.7 | Substantia nigra | 47-19-2-F7-PU |
| ID1703 | ext-est-not-vrt | 3.7 | Substantia nigra | 47-1-4-D2-PU |
| ID1704 | ext-est-not-vrt | 3.6 | Cerebellum | 55-5-4-A6-PU |
| ID1705 | ext-est-not-vrt | 3.6 | Cerebellum | 55-4-4-H3-PU |
| ID1706 | ext-est-not-vrt | 3.5 | Cerebellum | 55-3-1-G6-PU |
| ID1707 | ext-est-not-vrt | 3.5 | Substantia nigra | 47-55-2-H2-PU |
| ID1708 | est-not-ext | 12.4 | Substantia nigra | 47-39-4-H8-PU |
| ID1709 | est-not-ext | 11.4 | Fetal brain | 57-26-4-A4-PU |
| ID1710 | est-not-ext | 11.1 | Substantia nigra | 47-2-3-D1-PU |
| ID1711 | est-not-ext | 9.2 | Substantia nigra | 47-4-1-E4-PU |
| ID1712 | est-not-ext | 9 | Substantia nigra | 47-40-4-G9-PU |
| ID1713 | est-not-ext | 8.8 | Fetal brain | 57-5-4-G3-PU |
| ID1714 | est-not-ext | 7.5 | Substantia nigra | 47-13-4-C1-PU |
| ID1715 | est-not-ext | 7.4 | Fetal brain | 57-20-4-E2-PU |
| ID1716 | est-not-ext | 7 | Substantia nigra | 47-24-4-H4-PU |
| ID1717 | est-not-ext | 6.9 | Substantia nigra | 47-26-2-B2-PU |
| ID1718 | est-not-ext | 6.8 | Substantia nigra | 47-11-1-A2-PU |
| ID1719 | est-not-ext | 6.4 | Fetal brain | 57-19-2-G8-PU |
| ID1720 | est-not-ext | 6.4 | Fetal brain | 57-19-4-H8-PU |
| ID1721 | est-not-ext | 6.3 | Substantia nigra | 47-39-2-A11-PU |
| ID1722 | est-not-ext | 6.2 | Fetal brain | 57-24-2-B4-PU |
| ID1723 | est-not-ext | 5.9 | Surrenals | 62-1-1-G3-PU |
| ID1724 | est-not-ext | 5.7 | Fetal brain | 57-2-4-H4-PU |
| ID1725 | est-not-ext | 5.6 | Fetal brain | 57-8-2-D3-PU |
| ID1726 | est-not-ext | 5.5 | Cerebellum | 55-11-4-G2-PU |
| ID1727 | est-not-ext | 5.4 | Substantia nigra | 47-24-1-B6-PU |
| ID1728 | est-not-ext | 5.4 | Substantia nigra | 47-55-3-B10-PU |
| ID1729 | est-not-ext | 5.4 | Surrenals | 62-8-1-B12-PU |
| ID1730 | est-not-ext | 5.3 | Substantia nigra | 47-39-1-C9-PU |
| ID1731 | est-not-ext | 5.3 | Fetal brain | 57-20-2-F1-PU |
| ID1732 | est-not-ext | 5.2 | Fetal brain | 57-25-1-F10-PU |
| ID1733 | est-not-ext | 5.2 | Fetal brain | 57-28-4-B12-PU |
| ID1734 | est-not-ext | 5.1 | Substantia nigra | 47-15-2-D12-PU |
| ID1735 | est-not-ext | 5.1 | Substantia nigra | 47-2-3-G3-PU |
| ID1736 | est-not-ext | 4.9 | Substantia nigra | 47-40-3-D8-PU |
| ID1737 | est-not-ext | 4.9 | Substantia nigra | 47-40-3-G11-PU |
| ID1738 | est-not-ext | 4.9 | Substantia nigra | 47-14-3-D2-PU |
| ID1739 | est-not-ext | 4.8 | Substantia nigra | 47-19-1-B7-PU |
| ID1740 | est-not-ext | 4.8 | Substantia nigra | 47-19-1-A3-PU |
| ID1741 | est-not-ext | 4.7 | Substantia nigra | 47-55-3-G2-PU |
| ID1742 | est-not-ext | 4.6 | Substantia nigra | 47-3-4-G7-PU |
| ID1743 | est-not-ext | 4.5 | Substantia nigra | 47-29-1-B7-PU |
| ID1744 | est-not-ext | 4.4 | Fetal brain | 57-21-4-G6-PU |
| ID1745 | est-not-ext | 4.3 | Substantia nigra | 47-2-1-E12-PU |
| ID1746 | est-not-ext | 4.3 | Substantia nigra | 47-9-4-D2-PU |
| ID1747 | est-not-ext | 4.3 | Fetal brain | 57-2-4-F8-PU |
| ID1748 | est-not-ext | 4.3 | Fetal brain | 57-18-1-D5-PU |
| ID1749 | est-not-ext | 4.2 | Substantia nigra | 47-8-4-D2-PU |
| ID1750 | est-not-ext | 4.1 | Substantia nigra | 47-17-3-H11-PU |
| ID1751 | est-not-ext | 3.9 | Fetal brain | 57-28-2-G6-PU |
| ID1752 | est-not-ext | 3.7 | Fetal brain | 57-27-3-G1-PU |
| ID1753 | est-not-ext | 3.7 | Substantia nigra | 47-37-4-G11-PU |
| ID1754 | est-not-ext | 3.7 | Surrenals | 62-11-3-A2-PU |
| ID1755 | ext-vrt-not-genomic | 10.9 | Surrenals | 62-10-2-E4-PU |
| ID1756 | ext-vrt-not-genomic | 8.9 | Substantia nigra | 47-14-3-H7-PU |

TABLE III

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID38 | MLLLLGLCLGLSLC | 1757 | -14 through -1 |
| ID39 | MENGGAGTLQIRQVLLFVLLGMSQA | 1758 | -26 through -1 |
| ID40 | MRGPEPGPGPQPTMEGDVLDTLEALGYKGPLLEEQALTKAAEGGLSSPEFSELCIWLGSQIKSLCNLEESITSAGRDDLESFQLEISGFLKEMACPYSVLISGDIKDRLKKKED CLKLLLFLSTELQA | 1759 | -126 through -1 |
| ID41 | MEKSWMLWNFVERWLIALASWSWALC | 1760 | -26 through -1 |
| ID42 | MQQTRTEAVAGAFSHCLGFCGMRLGLLLLARHWCIA | 1761 | -36 through -1 |
| ID43 | MEKGNAFLKNRLVVFLLLPLASGP | 1762 | -24 through -1 |
| ID44 | MFPFNQAGLPTLLMLIVFHAASMA | 1763 | -24 through -1 |
| ID45 | MTSRSLRRCCSCLRVTHNKEILASTVSLGVEGYMLGGGSRINSSNLNDGBEECSPDSLLVWKKKSLLLWMSSLPSLG | 1764 | -76 through -1 |
| ID46 | MWTASAMDFRTCIASXLPALCYVQACRALMIAASVLGLPAILLLTVLPCIXM | 1765 | -53 through -1 |
| ID47 | MGPPPTHIKYLHLNIYCNGKSTAPGIRSHSLGFALLSLSHPTCQA | 1766 | -45 through -1 |
| ID48 | MFCLLTFLAFTLLFA | 1767 | -16 through -1 |
| ID49 | MHCGSTPGLCPCWVPFLKCLLAVLSSLFA | 1768 | -29 through -1 |
| ID50 | MNLVCSALLLLGIVSS | 1769 | -16 through -1 |
| ID51 | MSVLDDRQRDILVVQKRHSSLEAAMLIGLLAWLQT | 1770 | -35 through -1 |
| ID52 | MGVNGRRLLIICHYLPLSLC | 1771 | -20 through -1 |
| ID53 | MKLRECPALRWSQLSQHKLECLLLYLAESSG | 1772 | -31 through -1 |
| ID54 | MDPRGILKAFPKRQKIHADASSKVLAKIPRREBGEAEEWLSSLRAHVRTGIRARAELFEKQIVQHGGQLCPAQGPVTHIVVDEGMDYERALRLRLPQLPPXCSA | 1773 | -109 through -1 |
| ID55 | MFWKLSLSLFLVAVLVKVAEA | 1774 | -21 through -1 |
| ID56 | MAFLGLFSLLVLQSMATG | 1775 | -18 through -1 |
| ID57 | MAFLGLFSLLVLQSMATG | 1776 | -18 through -1 |
| ID58 | MSFSLNFTLPANTTSSPVTGGKETDCGPSLGLAAGIPLLVATALLVALLFTLIHR | 1777 | -55 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID59 | MSTWYLALNKSYKNKDSVRIYLSLCTVSIKFYTYFHDIQTNCLTTWKHSRCRFYWAFGGSILQHSVDPLVLFLSLALLVTP | 1778 | -80 through -1 |
| ID60 | MAIGISLQLLCCIFTLVLQ | 1779 | -19 through -1 |
| ID61 | MQATSNLLNLLLSLFAGL | 1780 | -19 through -1 |
| ID62 | MMKWKPEDLGSVPCEAFSVTLLCGWPGSHWC | 1781 | -31 through -1 |
| ID63 | MQATSNLLNLLLSLFAGL | 1782 | -19 through -1 |
| ID64 | MASSHWNETTSVVQYLGFQVQKIYPFHDNWNTACFVILLLFIFTVVS | 1783 | -48 through -1 |
| ID65 | MLWFSGVGALAERYCRRSPGITCCVLLLNCSG | 1784 | -33 through -1 |
| ID66 | MLFLQMGKQSWTLIFFLNVTQLVRG | 1785 | -25 through -1 |
| ID67 | MELRXXPPGGREVQLLLGLCSPXXSL | 1786 | -27 through -1 |
| ID68 | MLWSLLSSSGSHFG | 1787 | -14 through -2 |
| ID69 | MDISGLIPGLVSTFILLSXSDHYGRKFPMILSSVGALATSVWLCLLCYFAFP | 1788 | -52 through -1 |
| ID70 | MXVFFSKNRFEMYFSLLLFVILLITSLIFC | 1789 | -30 through -1 |
| ID71 | MPVPACWISSSLSLLASHHSVSC | 1790 | -23 through -1 |
| ID72 | MCPVFSKQLLACGSLLPGLWQ | 1791 | -21 through -1 |
| ID73 | MALTIHGERMRPDWESPWITSSQAQSLSLGGSPSSRGPLVPRGEYLASCPEGVRSHSLLPRSLLPLSAWPPWAWH | 1792 | -76 through -1 |
| ID74 | MAARFRCGHLCVPEVPRGPASHAEGGGGRLSRKAAHQOLCWRAGGDGRGNFNPMNFLVAGTFASSCHSPPLLWSLPRILIASSLPTLSHP | 1793 | -92 through -1 |
| ID75 | MASTISAYKEKMKELSVLSLICSCFYTQP | 1794 | -29 through -1 |
| ID76 | MLQVYGKPVYQGHRSTLKKGPYLRFNSPSPKSRPQRPKVIERVKGTKVKSIRTQTDFYATKPKKMDSKMKHSVPVLPHGDQQYLFSPSREMPTFSGTLEGHLIPMAILLGQTQS | 1795 | -114 through -1 |
| ID77 | MSVLEISGMIMNRVNSHIPGIGYQIFGNAVSLILGLTPFVFRLSQATDLEQLTAHSASELYVIAFGSNEDVIVLSMVIISFVVRVSLVWIFFFLLCVAERTYKQRLLFAKLFGHLTSA | 1796 | -118 through -1 |
| ID78 | MCKGIKAGDTCEKLVGYSAVYRVCFGMACFFFIFCLLTLKINNSKSCRAHIHNGFWFKLLLLGAMCSG | 1797 | -69 through -1 |
| ID79 | MSDSAGGRAGLRRYPKLPVWVVEDHQEVLPFIYRAIGSKELPASNVSFLHFDSHPDLLIPVNMPADTVFDKETLFGELSIENWIMPAVYAGHFSHVVWFHPTWA | 1798 | -104 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID80 | MSSCRGQKVAGGLRVVSPFPLCQPAGEPSRGKMRSSCVLLTAIVALA | 1799 | -47 through -1 |
| ID81 | MIIPFKIKNLGGRVLLSGREMPPASVRAPDLAVALSLLPAWT | 1800 | -42 through -1 |
| ID82 | MVCSAPRKIVVRAFITIIFIYYAIKKRANEPAAYLMLKPEALILLLLAQKGPS | 1801 | -53 through -1 |
| ID83 | MTESSMKKLASTLLDAITDKDPLVQEQVCSALCSLGEVRP | 1802 | -40 through -1 |
| ID84 | MQETDCNKRWGRGLGGLWSETGRRFHCKSFVFLFHCTSGLSSC | 1803 | -43 through -2 |
| ID85 | MLLEVPWLSSTVSCAQG | 1804 | -17 through -1 |
| ID86 | MSGGRMQARCSQQSTWSPAFLAVAGPGWA | 1805 | -29 through -1 |
| ID87 | MLQMLWHFLASFFPRAGC | 1806 | -18 through -1 |
| ID88 | MYSHPVSSLVCLLAMGKGLG | 1807 | -20 through -1 |
| ID89 | MGRKEEDCSXWKKQTTNIRKTFIFMEVLGSGAFS | 1808 | -35 through -1 |
| ID90 | MMIAVFGNANDRNVLTLLPNQSLFSLARA | 1809 | -29 through -1 |
| ID91 | MFFELPLVVTAWFFGMCRS | 1810 | -19 through -1 |
| ID92 | MNHNIIICVMYIVPFLMTKCLIFCHSCKRGSFLLIVANVHFSQT | 1811 | -44 through -1 |
| ID93 | MSCGSAASLTGLCXCCLQALG | 1812 | -21 through -1 |
| ID94 | MQAVDNLTSAPGNTSLCTRDYKITQVLFPLLYTVLFFVGLIINGLA | 1813 | -46 through -1 |
| ID95 | MAAAMXLLCSSCCSWGPAAG | 1814 | -20 through -1 |
| ID96 | MDFIKDQSLSHRSVVKVLSLRKAQA | 1815 | -25 through -1 |
| ID97 | MTRPFWASCSTWATSRISCAFSLASSTA | 1816 | -28 through -1 |
| ID98 | MKSCAVSLTTAAVAFG | 1817 | -16 through -1 |
| ID99 | MSIHECACLSLSLICLRMSLS | 1818 | -21 through -1 |
| ID100 | MLSGLSFLSVFSLWC | 1819 | -15 through -1 |
| ID101 | MGLKDKSQAPASGLGVLRGQRSGSFISMPAPASGQXPEESRSPAPPVASRSQNRGYRPWHGPLWVHQSVRFGLYSILHFPFWVHG | 1820 | -85 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID102 | MSDQIKFIMDSLNKEPFRKNYNLITFDSLEPMQLLQVLSDVLA | 1821 | -43 through -1 |
| ID103 | MSPSCLHPDLWSMCLEVPSFTATDSVNCGCCLELATEPARNIRSTTRASLLRCSSFTSTRNSTGISALPPAAPMAWPSASLSTLPVPLTHSSVASLTATPSLA | 1822 | -104 through -1 |
| ID104 | MDLSFHLLLDPSSTQS | 1823 | -16 through -1 |
| ID105 | MPHFLDWFVXVYLIVISVLILVGFGAC | 1824 | -26 through -1 |
| ID106 | MSKLKVIPEKSLTNNSRIVGLLAQLEKINA | 1825 | -30 through -1 |
| ID107 | MMSASRLAGTLIPAMAFLSCVRP | 1826 | -23 through -1 |
| ID108 | MVDGTQLRGLTRMYQVPLXLDRDETLVRLRFTMVALVTVCCXLVAPLFC | 1827 | -49 through -1 |
| ID109 | MKQNFLVLNSVWYLISMLQMLAVIIT | 1828 | -26 through -1 |
| ID110 | MECQNSSLKKCLLVEKSLVKASYLIAPQTAASKKPFSIAEELIKPYLIVEMCLEVLGSSA | 1829 | -59 through -2 |
| ID111 | MHSSIKTKGSVMNLVALLEMCVC | 1830 | -23 through -1 |
| ID112 | MTVLPLEAISSLSSFVLG | 1831 | -18 through -1 |
| ID113 | MGTASRSNIARHLQTNLILFCVGAVGACTL | 1832 | -30 through -1 |
| ID114 | MNSSKEEMRELAALFYSVVVSTVSG | 1833 | -25 through -1 |
| ID115 | MSQDGGXGELKHMVMSFRVSELQVLLGFAGRNKSGRKHELLAKALHLLKSSC | 1834 | -52 through -1 |
| ID116 | MPCISLLGLLYNFVQVLCYLSIFCLGVLF | 1835 | -29 through -1 |
| ID117 | MKIAVLFCFFLLIF | 1836 | -15 through -1 |
| ID118 | MAKQKPHVLGSRVMPASCVSERRRKPSFQVSTWSSASLRGSWQ | 1837 | -43 through -1 |
| ID119 | MGFLYLKSVFDVSLG | 1838 | -15 through -1 |
| ID120 | MRMGPGRKRDFSPVPWSQYFESMEDVEVENETGKDTFRVYKSGSEGPVLLLHGGGHSALS | 1839 | -61 through -1 |
| ID121 | MIFLLYLLPSSEE | 1840 | -13 through -1 |
| ID122 | MRMGPGRKRDFSPVPWSQYFESMEDVEVENETGKDTFRVYKSGSEGPVLLLHGGGHSALS | 1841 | -61 through -1 |
| ID123 | MLSLLNLISILASIPS | 1842 | -16 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID124 | MGTTSNMVTTIHLMLLWPVHPLLVG | 1843 | -25 through -1 |
| ID125 | MGDPERPEAAGLDQDERSSSDTNESEIKSNEEPLLRKSSRRFVIFPIQYPDIWKMYKQAQASFWTAEEVDLSKDLPHWNKLKADEKYFISHILAFFAASDG | 1844 | -101 through -1 |
| ID126 | MDAGLFSLLPHPPCVG | 1845 | -16 through -1 |
| ID127 | MLITLTYLIQGESA | 1846 | -14 through -1 |
| ID128 | MYTGFRIEATLLTRVQCLCAIPFAFS | 1847 | -26 through -1 |
| ID129 | MYKQAQASFWTAEEVDLSKDLPHWNKLKADEKYFISHILAFFAASDG | 1848 | -47 through -1 |
| ID130 | MLIHLCSVKNLYQNRFLGLAAMASPSRN | 1849 | -28 through -1 |
| ID131 | MPCPTWTCLKSFPSPTSS | 1850 | -18 through -1 |
| ID132 | MEDLFSPSIXPPAPNISVPILLGWGLNLTLGQG | 1851 | -33 through -1 |
| ID133 | MAETKDAAQMLVTFKDVAVTFTREEWRQLDLAQRTLYREVMLETCGLLVSLG | 1852 | -52 through -1 |
| ID134 | MLILSQNIAQLEA | 1853 | -13 through -1 |
| ID135 | MLLGASAQGLWAHSWTCSCSA | 1854 | -21 through -1 |
| ID136 | MAAPLELSCWGGGWG | 1855 | -15 through -1 |
| ID137 | MSXVGIDLGFLNCYIAVARS | 1856 | -20 through -1 |
| ID138 | MEYSKXFVVFSTMFTASSP | 1857 | -19 through -1 |
| ID139 | MPMASSPPPSPHPQEPAPLLPSLPRLSLPFRLPWASTATA | 1858 | -40 through -1 |
| ID140 | MQHVXGHXPDPIAIMYVCPPCGHTTWALGLKFLSSSSQ | 1859 | -38 through -1 |
| ID141 | MGWEMTCIKSFFWARSHAGFLKCLLLSSLQ | 1860 | -30 through -1 |
| ID142 | MVFGGVCPSVTSIIAESLQGWNLVQLSFAATTPVLA | 1861 | -36 through -1 |
| ID143 | MHFITWSLLFLYQCSL | 1862 | -16 through -1 |
| ID144 | MSGASPIERTPMEEAPSSCPTSSCWPSVASPSSSWS | 1863 | -36 through -1 |
| ID145 | MEWAGKQRDFQVRAAPGWDHLASFPGPSLRLFSGSQA | 1864 | -37 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID146 | MIAFFDEDNPRKRRSYSFTQSAGILCQETTYSTPHTKLEKAKSPTADAKVVSLSLQTSSA | 1865 | -60 through -1 |
| ID147 | MGKSIXSLCSVXLKARLKGXLEAVHLCLRAQKRTALFCTLPCPVERG | 1866 | -48 through -1 |
| ID148 | MCLHMTLFRVPFTFS | 1867 | -15 through -1 |
| ID149 | MLNILKTLTSAALP | 1868 | -14 through -1 |
| ID150 | MRARVWPRSHGIPVPSFLSKSSLSHTPSPLLCLYHPVYT | 1869 | -40 through -1 |
| ID151 | MWNAVAIICNGSWCQTXSTSGLESLCLSLLIPGPKP | 1870 | -36 through -1 |
| ID152 | MRLGLFKISWARC | 1871 | -14 through -1 |
| ID153 | MPFAEDKTYKYICRNFSNFCNVDVVEILPYLPCLTA | 1872 | -36 through -1 |
| ID154 | MPGSSGLRFICKSRNHPQFGSFSGTDSLSFLPCPC | 1873 | -36 through -1 |
| ID155 | MDVTGDEEEIKQEINMLKKYSHHRNIATYYGAFIKNPPGMDDQLXLVMEFCGAGS | 1874 | -57 through -1 |
| ID156 | MIFGLYFVLAVKLFLVFLLNICKG | 1875 | -24 through -1 |
| ID157 | MRKKRVEELIVFPGEVTSFSSIKCSSWISSLASG | 1876 | -34 through -1 |
| ID158 | MPSSSLAELCLMQQDACLFSXFLAVSRH | 1877 | -28 through -1 |
| ID159 | MDLWSCLFPVMLMEPSKGLEDSEWKMALQMRNQLPCLVLG | 1878 | -40 through -1 |
| ID160 | MSGKGKCRPIALRRAVPLPTTSTLTSA | 1879 | -27 through -1 |
| ID161 | MTPKAIQKSSGLFCPSQA | 1880 | -18 through -1 |
| ID162 | MPDQFDQAVVLNQLRYSGMLETVRIRKAGYAVRRPFQDFYKRYKVLMRNLALPEDVRGKCTSLLQLYDASNS | 1881 | -72 through -1 |
| ID163 | MCLVSFFLELNVLQQ | 1882 | -15 through -1 |
| ID164 | MRSLACLTPCGHA | 1883 | -13 through -1 |
| ID165 | MHLLSNWANPASS | 1884 | -13 through -1 |
| ID166 | MWSGKWALVSPFAMLHSVWRLIPA | 1885 | -24 through -1 |
| ID167 | MKVHMHTKFCLICLLTFIFH | 1886 | -20 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID168 | MGRRHWVLTHSALSLFYTADTSHG | 1887 | -24 through -2 |
| ID169 | MAVFVVLLALVAGVLG | 1888 | -16 through -1 |
| ID170 | MAPLLLQLAVLGAALA | 1889 | -16 through -1 |
| ID171 | MPVTVTRTTITTTTTSSSGLGSPMIVGSPRALTQPLGLLRLLQLVSTCVA | 1890 | -50 through -1 |
| ID172 | MELVLVFLCSLLAPMVLA | 1891 | -18 through -1 |
| ID173 | MGPIWSSYYGNCRSLLFVMDASDPTQLSASCVQLLGLLSAEQLAEA | 1892 | -46 through -1 |
| ID174 | MSGGRAPAVLLGGVASLLLSFVVMPALLPVASRLLLLPRVLLTMASG | 1893 | -47 through -1 |
| ID175 | MALSCTLNRYLLLMAQEHLEFRLPEIXSLLLLFGGQFASS | 1894 | -40 through -1 |
| ID176 | MAARGVIAPVGESLRYAEYLQPSAKRPDADVDQQRLVRSLIAVGLGVAALAFA | 1895 | -53 through -1 |
| ID177 | MRMCAGSIYKSATQAVLGXLFLGGLCRG | 1896 | -28 through -1 |
| ID178 | MAERRRPLSPIPSXRRPSEPSRPPAAAGXRSLPRPGDEELQLPCAVHDLIFWRDVKKTGFVFGTTLIMLLSWQLSVS | 1897 | -78 through -1 |
| ID179 | MAAPVLLRVSVPRWERVARYAVCAAGILLSIYAYHVEREKERDPEHRALCDLGPWVKCSAALASRWGRGFGLLGSIFGKDGVLNQPNSVFGLIFYILQLLLGMTASAVA | 1898 | -109 through -1 |
| ID180 | MSFLQDPSFFTMGMWSIGAGALGAAALALLLANT | 1899 | -34 through -1 |
| ID181 | MASLLCCGPKLAACGIVLSAWGVIMLIMLGIFFNVHS | 1900 | -37 through -1 |
| ID182 | MILPYRMXSLFLHAVSSSFT | 1901 | -20 through -1 |
| ID183 | MATLVELPDSVLLEIFSYLPVRDRIRISRVCHRWKRLVDDRWLWRHVDLTLYTVRALAGRAWA | 1902 | -63 through -1 |
| ID184 | MKNACIVLPPTPPPSLQPSASLLAPNRFLFSCFCFLSHKFG | 1903 | -41 through -1 |
| ID185 | MAFGLQMFIQRKFPYPLQMSLLVAVAG | 1904 | -28 through -1 |
| ID186 | MYCKILVLMLHTELIRTDYSSVDQLLLNYPAEEGLGRERSLLWTPLLSPGSLR | 1905 | -53 through -1 |
| ID187 | MAVSHSVKERTISENSLILLQGLQG | 1906 | -26 through -1 |
| ID188 | MESGGRPSLCQFILLGTTSVVTA | 1907 | -23 through -1 |
| ID189 | MAALDLRAXWIRWSCCSCLGXLXGAGGETNGVERPGGGGLALARQGSLRDGRQVGRAPAVCFPHGAPGLPPRQRXXGGXPEVQGGESWCPRPRGGGASRTGLRRRKGPTKTPE PESSEAPQDPLNWFGILVPHSLRQAQA | 1908 | -139 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID190 | MAFLPSPAWWISLLPSLLSIC | 1909 | -21 through -1 |
| ID191 | MEPKVAELKQKIEDTLCPFGFEVYPFQVAWYNELLPPAFHLPLPGPTLA | 1910 | -49 through -1 |
| ID192 | MLVLRSGLTKALA | 1911 | -13 through -1 |
| ID193 | MSGGHLADLTLLFVLLLFSLLPA | 1912 | -23 through -1 |
| ID194 | MKPSRTPARLWMLPQQQAGAVVVAAPTERHPTHHMAGWLLGALTLLGLVTS | 1913 | -51 through -1 |
| ID195 | MGESIPLAAPVPVEQAVLETFFSHLGIFSYDKAKDNVEKEREANKSAGGSWLSLLAALAHLAAA | 1914 | -64 through -1 |
| ID196 | MQMSYAIRCAFYQLLLAALMLVAMLQLLYLSLLSGLHG | 1915 | -38 through -1 |
| ID197 | MLRAELKIAVVLFAFHLLLSFILG | 1916 | -24 through -1 |
| ID198 | MNHQQTLIGRLLCDLHGLSLSPPVANNVQALFRMLTPEAYSCLLILLLRTFLCSA | 1917 | -55 through -1 |
| ID199 | MIITAVVSISVTIFCFQTKVDFTSCTGLFCVLGIVLLVTG | 1918 | -40 through -1 |
| ID200 | MAAGGRMEDGSLDITQSIEDDPLLDAQLLPHHSLQAHFRPRFHPLPTVIIVNLLWFIHLVFVVLX | 1919 | -65 through -1 |
| ID201 | MSPCCMLLFVFGFVGG | 1920 | -16 through -1 |
| ID202 | MKLLLGIALLAYVAS | 1921 | -15 through -1 |
| ID203 | MDIIVPLIQLLVLLLTLPLHLMA | 1922 | -23 through -1 |
| ID204 | MEAASPSNSTGVERXADLMDADSLLLSLELASGSG | 1923 | -35 through -1 |
| ID205 | MIRQERSTSYQEAVRPALPSSKPCLLTSPAVLVKLLSSSASTS | 1924 | -43 through -1 |
| ID206 | MKLIDYGLSGYQBESAEVKAMDFITSTAILPLLFGCLGVFG | 1925 | -41 through -1 |
| ID207 | MRCLTTPMLLRALAQAARA | 1926 | -19 through -1 |
| ID208 | MSRFLNVLRSWLVMVSIIAMGNTLQSFRDHTFLYEKLYTGKPNLVNGLQARTFGIWTLLSSVIRCLC | 1927 | -67 through -1 |
| ID209 | MIFLTLSLDSRVSA | 1928 | -14 through -1 |
| ID210 | MQCFSFIKTMMILFNLLIFLCGAALLXVG | 1929 | -29 through -1 |
| ID211 | MAEFALEAVRXSYENSRPLQGSSACLLLCPTWTNP | 1930 | -35 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID212 | MATASPSVFLLMVNGQVES | 1931 | -19 through -1 |
| ID213 | MAGIKALISLSFGGAIGLMFLMLGCALP | 1932 | -28 through -1 |
| ID214 | MIGDILLFGTLLMNAGA | 1933 | -17 through -1 |
| ID215 | MKTMILTLSLFGSCIS | 1934 | -16 through -1 |
| ID216 | MDWRVPPSXXDPGHQDIPLPVTXXFISVVLSSLGIVLA | 1935 | -39 through -1 |
| ID217 | MAAAALPAWLSLQSRA | 1936 | -16 through -1 |
| ID218 | MAMVSAMSWVLYLWISACAMLLCHG | 1937 | -25 through -1 |
| ID219 | MGKEWGWQEMENGGAAPAWGAGPPVHPAPPVEKTLSWGCGFGLHSGPGGSGGVGLCRLLCLVRLFC | 1938 | -69 through -1 |
| ID220 | MLQTSNYSLVLSLQFLLLSYD | 1939 | -21 through -1 |
| ID221 | MWFEILPGLSVMGVCLLIPGLATA | 1940 | -24 through -1 |
| ID222 | MRPSLSGILADPLXLFPFSEG | 1941 | -22 through -1 |
| ID223 | MRESLSXRSWHLPASLMMAQXFIPAVA | 1942 | -27 through -1 |
| ID224 | MSGVVPTAPEQPAXEMENQTKPDPRPDAPPEYSSHXFTRTPWKQLSLHLLATRACYG | 1943 | -58 through -1 |
| ID225 | MWRYQFGWGVITRGPREIPFPPSLLASESLLPPLPDLVLTCTSLGFVTRVWMSLNLNELSLYSRTWVFTCLVFFCFG | 1944 | -77 through -1 |
| ID226 | MVKLLVAKILCMVGVFFFMLLGSSLLPVKI | 1945 | -29 through -1 |
| ID227 | MPVSIMCLIGLKANASS | 1946 | -17 through -1 |
| ID228 | MKVILLYIVLEKLVSRA | 1947 | -17 through -1 |
| ID229 | MAVTLSLLLGGRVCXPSLA | 1948 | -19 through -1 |
| ID230 | MLNQTSGRTSLLPELGVVTPAQG | 1949 | -23 through -1 |
| ID231 | MTSENLVQTAPKKKNKGKKGLEPSQSTAAAKVPKKAKTWIPEVHDQKADVSAWKDLFVPRPVLRALSFLGFSAPTIQA | 1950 | -79 through -1 |
| ID232 | MAAFGRQXXXWHXLIPLTWACMA | 1951 | -23 through -1 |
| ID233 | MSLTSSPKKRRSICFDRFLMPQSQSGPSSLGESYRTGVGFLIPEGWFLSGCPHGSSA | 1952 | -57 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID234 | MGELGNRSRCILFLSENPCLSESIFQSLXFCLSPPPSPS | 1953 | -39 through -1 |
| ID235 | MAELGLNEHHQNEVINIWMRFARSKRGLRLKTVDSCFQDLKESRLVEDTFTIDEVSEVLNGLQAVVHSEVESELINTAYTNVLLRQXFAQAEK | 1954 | -93 through -1 |
| ID236 | MVTLPSGTWAFSCPYLALVDGGMLGSAREDAHASVVSWAVGLLYAVAQG | 1955 | -49 through -1 |
| ID237 | MASASARGNQDKDAHFPPPSKQSLLFCPKXXLHIHRAEISKIMRECQEESFWKRALPFSLVSMLVTQG | 1956 | -68 through -1 |
| ID238 | MLLMKSILLKVVCVLCIYLKFKLMALIYVPDKNNTNNNILRYNHNEISIGISVQCHFILSLCVLCIVLT | 1957 | -69 through -1 |
| ID239 | MAQRLLLRRFLASVIS | 1958 | -16 through -1 |
| ID240 | MAASKVKQDMPPXGGYGPIDYKRNLPRRGLSGYSMLAIGIGTLIYGHWSIMKWNRERRLQIEDFEARIALLPLLQA | 1959 | -77 through -1 |
| ID241 | MRHLVTEELFPCSNLEDVVEDNSHSYFTLRITMACKGVPSTLLSLAILSHISTP | 1960 | -54 through -1 |
| ID242 | MSAEVKVTGQNQEQFLLLAKSAKGAALATLIHQVLEAPGVYVFGELLDMPNVRELAESXFASTFRLLXVFAYGTYA | 1961 | -76 through -1 |
| ID243 | MLLSIGMLMLSATQVXTILXVQLFAFLNLLPVEA | 1962 | -34 through -1 |
| ID244 | MGWEVVSLSYCGVSWG | 1963 | -16 through -1 |
| ID245 | MRECISVHVGQAGVQIGNACWELFCLEHGIQA | 1964 | -32 through -1 |
| ID246 | MAGPLQGGGAPALDLLRGLPRVSLA | 1965 | -25 through -1 |
| ID247 | MPAGVPMSTYLKMFAASXLAMCAGA | 1966 | -25 through -1 |
| ID248 | MAVQCVRLARRSLPALALSLRASP | 1967 | -24 through -1 |
| ID249 | MFSIISRSRACSMYFKENAKPSQLRLMHHYLSTPTSA | 1968 | -37 through -1 |
| ID250 | MKRLLPATSLAGPVLS | 1969 | -16 through -1 |
| ID251 | MLIITNPWPKYFDAAGRLTPEFSQRLTNKIRELLQQMERGLKSADXXDGTGYTGWAGIAVLYLHLYDVFG | 1970 | -70 through -1 |
| ID252 | MCATETVRAWLAQGSSSAGWG | 1971 | -21 through -1 |
| ID253 | MLLLATHPETVGQVTLRVXPVSLEVSIQMCAAAAAAFCLKXXGANT | 1972 | -46 through -1 |
| ID254 | MAASSATPAPXXSQRCGADAGSAARIVFRWGRGRRGARSPEGSGHHGRANSGLGGAQLQGGAX | 1973 | -64 through -1 |
| ID255 | MLRRPLAGLAAALGRA | 1974 | -17 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID256 | MDRPGFVAALVAGGVAG | 1975 | -17 through -1 |
| ID257 | MIVWFEGISMDLLTLLFQRRS | 1976 | -21 through -1 |
| ID258 | MRTFVHFALDALMFPARRA | 1977 | -20 through -1 |
| ID259 | MAAPPQLRALLVVNALLRKRRYHAAALAVLKGFRNGAVYGAKIRAPHALVMTFLFRNGSLQ | 1978 | -61 through -1 |
| ID260 | MPVDLGXALGLLPSLAKA | 1979 | -18 through -1 |
| ID261 | MNLFIMYMAGNTISIFPTMMVCMMAWRPIQALMAISATFKMLESSSQKFLQGLVYLIGNLMGLALAVYKCQS | 1980 | -72 through -1 |
| ID262 | MISLTDTQKIGMGLTGFGVFFLFFGMILFFDKALLAIGNVLFVAGLAFVIG | 1981 | -51 through -1 |
| ID263 | MAASGAPRILVDLLKLXVAPLAVFQMLKSMCAG | 1982 | -33 through -1 |
| ID264 | MASVSSATFSGHGARSLLQFLRLVGQ | 1983 | -26 through -1 |
| ID265 | MWYLAVLLVLFTLNIL | 1984 | -16 through -1 |
| ID266 | MFTFGRLFQIITVVTCLQFIQDCCIHSRQINSLLEXSSLSRC | 1985 | -42 through -1 |
| ID267 | MIQDRDRCAQAAAVAVGNLEPRGTPGPEDEAPCLPGCVGTLCQLDWWIWG | 1986 | -51 through -1 |
| ID268 | MKIIFPILSNPVPRRTVKILLCLLMIGYSQG | 1987 | -31 through -1 |
| ID269 | MVSRMVSTMLSGLLFWLASGWTPAFA | 1988 | -26 through -1 |
| ID270 | MTATLAAAADIATMVSGSSGLAXA | 1989 | -24 through -1 |
| ID271 | MSSWSRQRPKSPGGIQPHVSRTLFLLLLLAASAWG | 1990 | -35 through -1 |
| ID272 | MRVRIGLTLLLXAVLLSLASA | 1991 | -21 through -1 |
| ID273 | MFSHLPFDCVLLLLLLLTRS | 1992 | -21 through -1 |
| ID274 | MGPVRLGILLFLFLAVDEAWA | 1993 | -21 through -1 |
| ID275 | MKSLSLLAVALGLATA | 1994 | -17 through -1 |
| ID276 | MLLLTLXLLGGPTWA | 1995 | -16 through -1 |
| ID277 | MKIGILLSLLNSVISQTLMSCNWKQQMRRMKTILIILIXIWIWCLG | 1996 | -46 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID278 | MKASSGRCGLVRMLQVLLPFLLSLFPGALP | 1997 | -30 through -1 |
| ID279 | MIVDCVSSHLKKTGDGAKTFIIFLCHLLRGLHA | 1998 | -33 through -1 |
| ID280 | MAKALLFPSGRSVRVLYGAVNKERQXESVLNPACPPKANSKERRGPAVLGAELTQWSPTTAGSCCSSCTLCARSSSXVIAPSPLVPFTSGLTSLSWLLXASCS | 1999 | -104 through -1 |
| ID281 | MAASEAAVVSSPSLKTDTSPVLETAGTVAAMAATPSARAAAAVVAAAARTGSEARVSKAALATKLLSLSGVFA | 2000 | -73 through -1 |
| ID282 | MKVGVLWLISFFTFTDG | 2001 | -17 through -1 |
| ID283 | MEFGLSWIFLAAILKGVQC | 2002 | -19 through -1 |
| ID284 | MAEPGHSHHLSARVRGRTERRIPRLWRLLLWAGTAFQ | 2003 | -37 through -1 |
| ID285 | MTADPRKGRMGLQACLLGLFALILS | 2004 | -25 through -1 |
| ID286 | MLVDGPSERPALCFLLLAVAMSFF | 2005 | -24 through -1 |
| ID287 | MAAPLVLVLVVAVTVRA | 2006 | -17 through -1 |
| ID288 | MTAAIRRQRELSILPKVTLEAMNTTVMQGFNRSERCPRDTRIVQLVPPALYTVVFLTIGILLNTLALWVFVHIPSSSTFIIYLKNTLVADLXMTLMLPFKILS | 2007 | -102 through -1 |
| ID289 | MSSVLAASHPLVLSSNAGTPGISEKDNRDPAGSSIGVLTLSHLISG | 2008 | -46 through -1 |
| ID290 | MGLAMEHGGSYAPAGGSSRGCWYLRYFPLFVSLIQFLIILGLIVLFMVYG | 2009 | -50 through -1 |
| ID291 | MVEASLSVRHPEYNRPLLANDLMLIKLDESVSESDTIRSISIASQCPTAGNSCLVSGWGLLANG | 2010 | -64 through -1 |
| ID292 | MGGKQRDEDDEAYGKPVKYDPSPRGPIKNRSCTDVICCVLFLFILG | 2011 | -47 through -1 |
| ID293 | MQKASVLLFLAWVCFLFY | 2012 | -18 through -1 |
| ID294 | MSPVLHFYVRPSGHEGAASGHTRRKLQGKLPELQGVETELCYNVNWTAEALPSAEETKKLMWLFGCPYCWMMLLGSXGSFL | 2013 | -82 through -1 |
| ID295 | MDVTPRESLSILVVAGSGGHTTEILRLLGSLSNAYS | 2014 | -36 through -1 |
| ID296 | MMGVAKLTLLRVLNLPHNSIG | 2015 | -21 through -1 |
| ID297 | MDVTPRESLSILVVAGSGGHTTEILRLLGSLSNAYS | 2016 | -36 through -1 |
| ID298 | MVLLTMIARVADG | 2017 | -13 through -1 |
| ID299 | MVPVENTEGPSLLNQKGTAVETEGXGSRHPPWARGCGMFTFLSSVXA | 2018 | -47 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID300 | METFLEPNNKKLLFPVGRSWSCFA | 2019 | -24 through -1 |
| ID301 | MGFLWGLALPLFFC | 2020 | -15 through -1 |
| ID302 | MQSTSNHLWLLSDILGQGATA | 2021 | -21 through -1 |
| ID303 | MVEICAGSVLPPYSNC | 2022 | -16 through -1 |
| ID304 | MVAPVLETSHVFCCPNRVRGVLNWXSGPRGLLAFGTSCSVXXY | 2023 | -43 through -1 |
| ID305 | MDSLRKMLISVAMLGAXAGVGYALLVIVTPGERRKQEMLKEMPLQDPRSREEAARTQQLLLATLQEAATT | 2024 | -70 through -1 |
| ID306 | MRQTLPCIYFWGGLLPFGMLCASSTT | 2025 | -26 through -1 |
| ID307 | MADDLEQQSQGWLSSWLPTWRPTSMSQLKNVEARILQCLQNKFLARYVSLPNQNKIWTVTVSPEQNDRTPLVMVHGFGGGVGLWILNMDSLXARRTLHTXGLLGFGRXQG | 2026 | -110 through -1 |
| ID308 | MKVTGITILFWPLSMILLSDKIQS | 2027 | -24 through -1 |
| ID309 | MAAGRAQVPSSEQAWLEDAQVFIQKTLCPAVKEPNVQLTPLVIDCVKTVWLSQGRNQGSTLPLSYSFVSVQDLKTHQRLPCCSHLSWSSSAYQAWA | 2028 | -96 through -1 |
| ID310 | MSTCCWCTPGGAST | 2029 | -14 through -1 |
| ID311 | MPPAEDKTYKYICRNFSNFCXVDVVEILPLYLPCLTA | 2030 | -36 through -1 |
| ID312 | MAESEDRSLRIVLVGKTGSGKSATANTILGEEIFDSRIAAQAVTKNCQKASREWQGRDLLVDTPGLFDTKESLXTTCKEIXRCIISSCPGPHAIVLVLLLGRYTEE | 2031 | -107 through -1 |
| ID313 | MAQKPLRLLACGDVEGKFDILFNRVQAIQKXSGNFDLLXCVGNFFGSTQ | 2032 | -49 through -1 |
| ID314 | MESRKDITNQEELWKMKPRRNLEDDYLHKDTGETSMLKRPVLLHLHQTAHA | 2033 | -52 through -1 |
| ID315 | MESRKDITNQEEXWKMKPRRNLEDDYLHKDTGETSMLKRPVLLHLHQTAHA | 2034 | -52 through -1 |
| ID316 | MAATCEISNIFSNYFSAMYSSEDSTLASVPPAATFG | 2035 | -36 through -1 |
| ID317 | MRDCPGVEXILDCSXRQKTEGCRLQAGKECVDSPVEGGQSEAPPSLVSFAVSSEGTEQ | 2036 | -58 through -1 |
| ID318 | MERQSRVMSEKDEYQFQHQGAVELLVFNFLLILTILT | 2037 | -37 through -1 |
| ID319 | MKMASSLAFLLLNFNVSLLLVQLLTPCSA | 2038 | -29 through -1 |
| ID320 | MVFLPLKWSLATMSFLLSSLLALLTVSTPSWC | 2039 | -32 through -1 |
| ID321 | MESAAALHFSRPASLLLLLXCVHWS | 2040 | -26 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID322 | MEKIPVSAFLLLVALSYTLA | 2041 | -20 through -1 |
| ID323 | MGPWGEPELLVWRPEAVASEPPVPVGLEVKLGALVLLVLTLLCSL | 2042 | -46 through -1 |
| ID324 | MAPLLLQLAVLGAALA | 2043 | -16 through -1 |
| ID325 | MAMEGYWRFLXLLGSALLVGFLSVIFA | 2044 | -27 through -1 |
| ID326 | MAQSLALSLLILVLAFG | 2045 | -17 through -1 |
| ID327 | MEAMWLLCVALAVLA | 2046 | -15 through -1 |
| ID328 | MAPITTSREEFDEIPTVVGIFSAFGLVFTVSLFAWICC | 2047 | -38 through -1 |
| ID329 | MEGPRGWLVLCVLAISLA | 2048 | -18 through -1 |
| ID330 | MTAWEAMAPHVNPTLKDKALSPQQXXXTSPAPCXSNHHNKKHLILAFCAGVLLTLLLIAFIFL | 2049 | -63 through -1 |
| ID331 | MLCSLLLCECLLLXAGYA | 2050 | -18 through -1 |
| ID332 | MGHAMGLVXSLPVHCLTFA | 2051 | -19 through -1 |
| ID333 | MARCFSLVLLLTSIWT | 2052 | -16 through -1 |
| ID334 | MLLTRKQTCQLGILLSIHRQHSKDLQDIVATLGPRSATHPQPAIQVLAQLAFLSQISQ | 2053 | -59 through -1 |
| ID335 | MWAFSELPMPLLINLIVSLLGFVATVTL | 2054 | -28 through -1 |
| ID336 | MFKVIQRSVGPASLSLLTFKVYA | 2055 | -23 through -1 |
| ID337 | MAKSLLKTASLSGRTKLLHQTGLSLYSTSHGFYEEEVKKTLQQFPGGSIDLQKEDNGIGILTLNNPSRMNAFSGVMMLQLLEKVIELENWTEGKGLIVRGAKNTFSSGSDLNAVKSLGLQRLPLISVALVQGWALG | 2056 | -136 through -1 |
| ID338 | MTSFSTSAQCSTSDSACRISPGQINXVRPKLPLLKILHAAGAQG | 2057 | -44 through -1 |
| ID339 | MDTAEEDICRVCRSEGTPEKPLYHPCVCTGSIKXVHQECLVQWLKHSRKEYCELCKHRFAFTPIYSPDMPSRLPIQDIFAGLVTSIGTAIRYWFHYTLVAFAWLGVVPLTAC | 2058 | -112 through -1 |
| ID340 | MLIMLGIFFNVHS | 2059 | -13 through -1 |
| ID341 | MGGLWRPGWRCVPFCGWRMIHPGSPTRAAERVEPFLRPEWSGTGGAERGLRWLGTWKRCSLRARHPALQPPRRPKSSNPFTRAXEEERRRXNKTTLTYVAAVAVGMLXASYA | 2060 | -112 through -1 |
| ID342 | MAAQCVTKVALNVSCANLLDKDIGSKSDPLCVLFLNTSG | 2061 | -39 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID343 | MTGSNEFKINQPPEDGISSVKFSPNTSQFLLVSSWDTSVRLYDVPANSMRLKYQHTGAVLDCAFYDPTHA | 2062 | -70 through -1 |
| ID344 | MGKHLWYPGQASAHLCWCGSHCCST | 2063 | -25 through -1 |
| ID345 | MLAVSLTVXLLGA | 2064 | -13 through -1 |
| ID346 | MSSTLAKIAEIEAEMARTQKNKATAHHIGLLKARLAKLRRELITPKGGGGGPGEGFDMPRQVMLELDLLVFHLMG | 2065 | -76 through -1 |
| ID347 | MAAAVPKRMRGPAQAKLLPGSAIQALVGLARPLVLALLLVSAALS | 2066 | -45 through -1 |
| ID348 | MTPQSLLQTTLFLLSLLFIVQGAHG | 2067 | -25 through -1 |
| ID349 | MMVVGTGTSLALSSLLSLLLFAGMQIYSRQLASTEWLTIQGGLLGSGLFVFSLTAFNNLENLVFGKGFQAKIFPEILLCLLLALFASG | 2068 | -88 through -1 |
| ID350 | MDWTWRVFCLLAVAPGAHS | 2069 | -19 through -1 |
| ID351 | MRIANRTRFPSSPPLARGAGWTHGRGMMVVGTGTSLALXSLLSLLLFAGMQMYSRQLASTEWLTIQGGLLGSGLFVFSLTAFNNLENLVFGKGFQAKIFPEILLCLLLALFASG | 2070 | -113 through -1 |
| ID352 | MTSVSTQLSLVLMSLLLVLPVVEA | 2071 | -24 through -1 |
| ID353 | MTPLLTLIIVVLMGLPLAQA | 2072 | -20 through -1 |
| ID354 | MALLLALSLLVLWTSP | 2073 | -16 through -1 |
| ID355 | MGGLEPCSRLLLLPLLLAVSG | 2074 | -21 through -1 |
| ID356 | MEVPPPAPRSFLCRALCLFPRVFA | 2075 | -24 through -1 |
| ID357 | MDLRQFLMCLSLCTAFALS | 2076 | -19 through -1 |
| ID358 | MAGVRPLRGLRALCRVLLFLSQFCILSGG | 2077 | -30 through -1 |
| ID359 | MAAAWLQVLPVILLLGAHP | 2078 | -21 through -1 |
| ID360 | MRTLFNLLWLALACSPVHT | 2079 | -19 through -1 |
| ID361 | MDVLFVAIFAVPLILG | 2080 | -16 through -1 |
| ID362 | MAAAAWLQVLPVILLLLGAHP | 2081 | -21 through -1 |
| ID363 | MRTLFNLLXLALACSPVHT | 2082 | -19 through -1 |
| ID364 | MGSKVADLLYWKDTRTSGVVFTGLMVSLLCLLHFSIVSVA | 2083 | -40 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID365 | MAARWRFWCVSVTMVALLIVCDVPSASA | 2084 | -29 through -1 |
| ID366 | MEGESTSAVLSGFVLGALA | 2085 | -19 through -1 |
| ID367 | MFAPAVMRAFRKNKTLGYGVPMLLIVGGSFG | 2086 | -32 through -1 |
| ID368 | MAAAWXSGPSAPEAVTARLVGVLMFVSVTTGPWGAVATSAGGEESLKCEDLKVGQYICKDPKINDATQEPVNCTNYIAHVSCFPAPNITCKDSSGNETHFTGNEVGFFKPISCRNVNGYSYKVAVALSLFLGWLGA | 2087 | -136 through -1 |
| ID369 | MRTLFNLLMLALACSPVHT | 2088 | -19 through -1 |
| ID370 | MDGQKKNWKDKVVDLLYWRDIKTGVVFGASLFLLLSLTVFS | 2089 | -42 through -1 |
| ID371 | MVAPGLVLGLVLPLILWA | 2090 | -18 through -1 |
| ID372 | MSPSGRLCLLTIVGLILPTRG | 2091 | -21 through -1 |
| ID373 | MRIANRTRFSLPFLARGAGWTHGRGMMVVGTGTSLALSSLLSLLLFA | 2092 | -47 through -1 |
| ID374 | MVLGGCPVSYLLLCGQAALLLGNLLLLHCVSRSHS | 2093 | -35 through -1 |
| ID375 | MGSVLGLCSMASWIPCLCGSAPCLLCRCCPSGNNSTVTRLIYALFLLVGVCVA | 2094 | -53 through -1 |
| ID376 | MVLLHVLFEHAVGYALALLAKEVEEISLLQPQVEESVLNLGKFHSIVRLIVAFCPFASS | 2095 | -57 through -1 |
| ID377 | MSGGPAPAVLLGGVASLLLSFVMMPALLPVASRLLLLPRVLLTMASG | 2096 | -47 through -1 |
| ID378 | MVAPVWYLVAAALLVGFILFLTRSRG | 2097 | -26 through -1 |
| ID379 | MAVLAPLIALVYSVPRLSRWLAQPYYLLSALLSAAFLLVRKLPPLCHG | 2098 | -48 through -1 |
| ID380 | MVGEAGRDLRRRRXXAVTAXKMAVLAPLIALVYSVPRLSRWLAQPYYLLSALLSAAFLLVRKLPPLCHG | 2099 | -69 through -1 |
| ID381 | MEALGKLKQFDAYPKTLEDFRVKTCGGATVTIVSGLLMLLLFLSELQY | 2100 | -48 through -1 |
| ID382 | MAVLAPLIALVYSVPRLSRWLAQPYYLLSALLSAAFLLVRKLPPLCHG | 2101 | -48 through -1 |
| ID383 | MRCLTTPMLLRALAQAARA | 2102 | -19 through -1 |
| ID384 | MRCLTTPMLLRALAQAARA | 2103 | -19 through -1 |
| ID385 | MDFITSTAILPLLFGCLGVFG | 2104 | -21 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID386 | MHPAVFLSLPDLRCSLLLLVTWVFTPVTT | 2105 | -29 through -1 |
| ID387 | MASLGHILVFCVGLLTMAKA | 2106 | -20 through -1 |
| ID388 | MSGSSLFSALALSLLLVSGSLLP | 2107 | -23 through -1 |
| ID389 | MAVHDLIFWRDVKKTGFVFGTTLIMLLSLAAFSVIS | 2108 | -36 through -1 |
| ID390 | MKGSVECTXGWGHCAPSPLLWTLLLFAAPFG | 2109 | -32 through -1 |
| ID391 | MQCFSFIKTMMILFNLLIFLCGAALLAVG | 2110 | -29 through -1 |
| ID392 | MRGSVECTWGXGHCAPSPLLWTLLLFAAPFG | 2111 | -32 through -1 |
| ID393 | MALRLLKLAATSASA | 2112 | -15 through -1 |
| ID394 | MPSAFSVSSFPVSIPAVLTQTDWTEPWLMGLATFHALCVLLTCLSSRSYRLQIGHFLCLVILVYC | 2113 | -65 through -1 |
| ID395 | MALPHQEPKPGDLIEIFRLGYEHWALYIXDGYVIHLAPPSEYPGAGSSVFSVLSNSAEVKRERLEDVVGGCCYRVNNSLDHEYQPRPVEVIISSAKEMVGQKMKYSIVSRNCEHFVTQLRYGKSRCKQVEKAKVEVGVATALGILVVAGCSFA | 2114 | -154 through -1 |
| ID396 | MAASTSMVPVAVTAAVAPVLSINSDFSDLREIKKQLLLIAGLTRERGLLHSSKWSAELAFSLPALPLAEL | 2115 | -70 through -1 |
| ID397 | MEEGGNLGGLIKMVHLLVLSGAWG | 2116 | -24 through -1 |
| ID398 | MAGPAAAFPRLGALSGAAALGFASYGAHGAXPPDAYGKELFDKANKHHFLHSLALLGVPHCRKPLWAGLLLASGTTLFCTS | 2117 | -81 through -1 |
| ID399 | MGHRFLRGLLTLLLPPPPLYT | 2118 | -21 through -1 |
| ID400 | MELLQVTILFLLPPSICSSNS | 2119 | -20 through -1 |
| ID401 | MASSNTVLMRLVASAYSIA | 2120 | -19 through -1 |
| ID402 | MRSSCVLLTALVALA | 2121 | -15 through -1 |
| ID403 | MGIQTSPVLLASLGVGLVTLLGLAVG | 2122 | -26 through -1 |
| ID404 | MTLQWAAVATFLYAEIGLLIFCLPFIPPQRWQKIFSNVWGKIATFWNKAPLTIIILLIVLFLDAVRE | 2123 | -69 through -1 |
| ID405 | MPSEGRCWETLKALRSSDKGRLCYYRDWLLRREVSGGPGGRRPFRPLATETFSLAVGTFCSREPVQSNNLHLFLDFCVYIPLSWG | 2124 | -85 through -1 |
| ID406 | MTKLAQWLWGLAILGSTWVALTTG | 2125 | -24 through -1 |
| ID407 | MLLAWVQAFLVSNMLLAEAYG | 2126 | -21 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID408 | MAMHFIFSDTAVLLFHFWSVHSPAGMALSVLVLLLAVLYE | 2127 | -41 through -1 |
| ID409 | MKQVHQCIERCHVPLAQAQALVTSELEKPQDRLARCTMHCNDKAKDSIDAGXKELQVKQQLXVVXXSVLXTTCXS | 2128 | -75 through -1 |
| ID410 | MQMSYAIRCAFYQLLLAALMLVAMLQL | 2129 | -27 through -1 |
| ID411 | MMTQTCIILLIHTMQVCTT | 2130 | -19 through -1 |
| ID412 | MXXHLQTRPLFLTCLFWPLAAL | 2131 | -22 through -1 |
| ID413 | MAANYSSTXTRREHVKVKTSSQPGFLERLSETSGGMFVGLMAFLLSFYLIFT | 2132 | -52 through -1 |
| ID414 | MRGAHLTALEMLTAFASHIBA | 2133 | -21 through -1 |
| ID415 | MVHKPMMTQTCIILLIHTMQVCTT | 2134 | -24 through -1 |
| ID416 | MAGIKALISLSFGGAIGLMFLMLGCALP | 2135 | -28 through -1 |
| ID417 | MSLMPKMHLLFPLTLVRSFWS | 2136 | -21 through -1 |
| ID418 | MMKRAAAAAVGGALAVGAVPVVLSAMGFTGAGIAASSIAAKMMSAAAIANGGGVSAGSLVATLQSVGAAGLSTSSNILLASVGSVLG | 2137 | -87 through -1 |
| ID419 | MVTIILLLSCXFWA | 2138 | -14 through -1 |
| ID420 | MXKRAAAAAVGGALAVGAVPVVLSANGFTGAGIAASSIAAKMMSAAAIANGGGVSAGSLVATLQSVGAAGLSTSSNILLASVGSVSG | 2139 | -87 through -1 |
| ID421 | MSQDGGXGELKHMVMSFRVSELQVLLGXXGRNKSGRKHELLAKALHLLKSSCAPSVQMKIKELYRRRPPRKTLGPSDLSLLSLPPGTSP | 2140 | -89 through -1 |
| ID422 | MPXILLPVASRLLLLPRVLLTMASG | 2141 | -24 through -1 |
| ID423 | MVFSNNDEGLINKKLPKELLLRIFSFLDIVTLCRC | 2142 | -35 through -1 |
| ID424 | MVFSNNDEGLINKKLPKELLLRIFSFLDIVTLCRC | 2143 | -35 through -1 |
| ID425 | MASYFDEHDCEPSDPEQETRTNMLLELARSLFNRMDFEDLGLVVDWDHHLPPPAAKTVVENLPRTVIRGSQAELKCPVCLLEFEEEETAIEMPCHHLFHSSCILPWLSKTNS | 2144 | -112 through -1 |
| ID426 | MPLILSLQVCRPATL | 2145 | -15 through -1 |
| ID427 | MLGITSCSDQQAKEGEGLEGSSTGSSSGNHGGSGGGNHKPGCEKPGNEARGSGNLGFRTLRRLLGCLTLTLS | 2146 | -73 through -1 |
| ID428 | MARKALKLASWTSMALA | 2147 | -17 through -1 |
| ID429 | MAAAALPAWLSLQSRA | 2148 | -16 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID430 | MVKIAFNTPTAVQKEEARQDVEALLSRTVRTQILTGKELRVATQEKEGSSGRCMLTLXXLSFILA | 2149 | -65 through -1 |
| ID431 | MIGSGLAGSGAGGPSSTVTWCALXSNHVAATQASLLLSFVWMPALLP | 2150 | -48 through -1 |
| ID432 | MSGAQLXGFLFXVIVLTS | 2151 | -18 through -1 |
| ID433 | MSFFQLLMKRKELIPLVVFMTVAASGASS | 2152 | -29 through -1 |
| ID434 | MELAHSLLLNEEALA | 2153 | -15 through -1 |
| ID435 | MTSALTQGLERIPDQLGYIVLSEGAVLA | 2154 | -28 through -1 |
| ID436 | MRAAWPSGPXAPEAVTARLVGVLMFVSVTTG | 2155 | -31 through -1 |
| ID437 | MVLLTMIARVADG | 2156 | -13 through -1 |
| ID438 | MVLLTMIARVADG | 2157 | -13 through -1 |
| ID439 | MTSQPVPNETIIVLPSNVINFSQAEKPEPTNQGQDSLKKKHLHAEIKVIGTIQILCGMMVLSLGIXLASA | 2158 | -69 through -1 |
| ID440 | MASVVLALRTRTAVTSLLSPTPATA | 2159 | -25 through -1 |
| ID441 | MASVVLALRTRTAVTSLLSPTPATA | 2160 | -25 through -1 |
| ID442 | MMPSRTNLATGIPSSKVKYSRLSSTDDGYIDLQFKKTPPKIPYKAIALATVLFLIGA | 2161 | -57 through -1 |
| ID443 | MPLILSLQVCRPATL | 2162 | -15 through -1 |
| ID444 | MPLILSLQVCRPATL | 2163 | -15 through -1 |
| ID445 | MASSVGNVADSTEPTKRMLSFQGLAELAHREYQAGDFEAAERHCMQLWRQEPDNTGVLLLLSSIHFQC | 2164 | -68 through -1 |
| ID446 | MFGSAPQRPVAMTAQRDSLLWKLAGLLREXGDVVLSGCSTLSLLTPTLQQLNHVFELHLGPWGPGQTGFVALPSHPADSPVILQLFLFDVLQ | 2165 | -94 through -1 |
| ID447 | MSFIFEWIYNGFSSVLQFLGLYKKSGKLVFLGLDNAGKTTLLHMLKDRLGQHVPTLHPTSEELTIAGMTLQLLILVGTSKHVAFG | 2166 | -86 through -1 |
| ID448 | MDKPCGCPPGVCDHGTGDRRDPWYSTVGLLPVRA | 2167 | -35 through -1 |
| ID449 | MAAALKCLLTLGRWCPGLGVAPQARALAALVPGVTQ | 2168 | -36 through -1 |
| ID450 | MVARVWSLMRFLIKGSVAGGAVILVYDQELLGPSDKSQAALQKAGEVVPPAMXQFSQYVCQQTGLQIPQLPAPPKIYFPIRDSWXAGIMTVMSALSVAPSKA | 2169 | -102 through -1 |
| ID451 | MVNELQNLXSLQGSQA | 2170 | -16 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID452 | MLYMSLKYIRAFFFSIQPFLPCSS | 2171 | -24 through -1 |
| ID453 | MNLERVSNEEKLNLCRKYYLGGFAFLPLMLVNIFWFFREAFLVPAYTEQSQIKGYVWRSAVGFLFWVIVLTSWITIFQ | 2172 | -79 through -1 |
| ID454 | MAGELQGTQAPSLRGXGLTSQDSGVNPNNSXRGREAMASGSNWLSGVNVVLVMAYGSLVFVLLFIFVKRQ | 2173 | -70 through -1 |
| ID455 | MTGFLLPPASRGTRRSCSRSRKRQTRRRRNPSSFVASCPTLLPFACVPGASPTTLA | 2174 | -56 through -1 |
| ID456 | MEEXSXPLVEFVKVLCTNQVLITARA | 2175 | -26 through -1 |
| ID457 | MVRRLXXVVAFVAPGES | 2176 | -17 through -1 |
| ID458 | MAVPGVGLLTRLNLCARRRTRVQRPIVRLLSCPGTVA | 2177 | -37 through -1 |
| ID459 | MMAAVPPGLEPWNRVRIPKAGNRSAVTVQNPGAALDLCIAAVIKECHLVILSLKSQTLDA | 2178 | -60 through -1 |
| ID460 | MASLDRVKVLVLGDSGVGKSSLVHLLCCNQVLG | 2179 | -33 through -1 |
| ID461 | MVFPAKRFCLVPSMEGVRWAFSCCGTWLPSRA | 2180 | -31 through -1 |
| ID462 | MASKIGSRRWMLQLIMQLGSVLLTRC | 2181 | -26 through -1 |
| ID463 | MLSKGLKRKREEEEEKEPLAVDSWWLDPGHA | 2182 | -31 through -1 |
| ID464 | MDYSLAAALTLHGHWG | 2183 | -16 through -1 |
| ID465 | MSYITSQEMKCILHWFANWSGPQRERFLEDLVAKAVPEKLQPXLDSLEQLSVSGADDHLLSLXASYIFGISG | 2184 | -72 through -1 |
| ID466 | MPLLCQIEMEYLLLKWQMTMLQSMLCDLVSYPLLPLQQTKEANLDFPKIKVSSVTITPTRWFXLIVULMVVSFIAS | 2185 | -76 through -1 |
| ID467 | MWFEILPGLSVMGVCLLIPGLA | 2186 | -22 through -1 |
| ID468 | MEFKLEAHRIVSISLGKIYNSRVQRGGIKLHKNLLVSLVLRXPAKS | 2187 | -46 through -1 |
| ID469 | MAVLSKEYGFVLLTGAASFIMVAHLAINVSKARKKYKVEYPIMYSTDPENGHIFNCIQRAHQNTLEVYPXFLFFLAVGGVYHPRIASGLGLXLDCWT | 2188 | -97 through -1 |
| ID470 | MDGHWSAAFSALTVTAMSSWARRRSSSSRRIPSLPGSPVCWA | 2189 | -42 through -1 |
| ID471 | MAQRLLLRRFLASVIS | 2190 | -16 through -1 |
| ID472 | MASLKPAFVNYFFLLLEVSHLLLI | 2191 | -25 through -1 |
| ID473 | MNLERVSNEEKLNLCRKYYLGGFAFLPLMLVNIFWFFREAFLVPAYTEQSQIKGYVWRSAVGFLFWVIVLTSWITI | 2192 | -77 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID474 | MAQLGAVVAVASSFFCASLFS | 2193 | -21 through -1 |
| ID475 | MSLRNLWRDYKVLVFMVPLVGLIHL | 2194 | -25 through -1 |
| ID476 | MGMDGCKCLGVFCLLISIPTPSA | 2195 | -23 through -1 |
| ID477 | MAASQAVEEMRTAWFWGSLGFAMSILLTFPVTIPVMMPGTRXGFEXRXFRVDVHMDENSLEFDMVGIDAAIANAFRRILLAEVPTMAVEKVLVYNNTSIVQDEILAHRLGLIPIHA | 2196 | -118 through -1 |
| ID478 | MAASKVKQDMPPGGYGPIDYKRNLPRRGLSGYSMLAIGIGTLIYGHWSIMKWNRERRLQIEDFEARIALLPLLQA | 2197 | -77 through -1 |
| ID479 | MSGFLEGLRCSECIDWGEKRNTIASIAAGVLFFTGWWIIIDA | 2198 | -42 through -1 |
| ID480 | MMTQEPGIYTWPEKTRIICSACSSVPLPWTVLVFLTFLSIPSFV | 2199 | -44 through -1 |
| ID481 | MFLTALLWRGRIPG | 2200 | -14 through -1 |
| ID482 | MNQENPPYPGPGPTAPYPPYPPQMPGPXMGGPYPPPQGYPPQGYPQYGWQGGPQEPPKTTVYVVEDQRRDELGPSTCLTACWTALCCC | 2201 | -90 through -1 |
| ID483 | MASLEVSRSPRRSRRELEVRSPRQNKHSVLLPTYNERELPLIVWLLIVKSFSES | 2202 | -54 through -1 |
| ID484 | MCPTCLCAPSXXWG | 2203 | -14 through -1 |
| ID485 | MAAATGAVAASASGQAEG | 2204 | -19 through -1 |
| ID486 | MAAMSLLXRVSVTAVAA | 2205 | -17 through -1 |
| ID487 | MAGPLQGGGARALDLLRGLPRVSLA | 2206 | -25 through -1 |
| ID488 | MATATEQNVLVEMVQALYEAPAYHLILEGILILWIIRLLFS | 2207 | -41 through -1 |
| ID489 | MEDPNPEENMXQQDSPKERSPQSPGGNICHLGAPKCTRCLIITFADSKXXERHMKREHPADFVAQKLQGVLFICFTCARS | 2208 | -79 through -1 |
| ID490 | MNVIDHVRDMAAAGLHSNVRLLSSLLLTMSNN | 2209 | -32 through -1 |
| ID491 | MQNVINTVKGKALEVAEYLTPVLKESKFKETGVITPEEFVAAGDHLVHHCPTWQWATG | 2210 | -58 through -1 |
| ID492 | MATLTFSLRKPLQRSLIRPSHLPLCCFDWRLSHYYRLPPAVRLHQQRGGRPGRSSADHWHSGVPTRILPPAHRLLCIQRLPWLLLCRG | 2211 | -88 through -1 |
| ID493 | MEKPLFPLVPLHWFGFGYTALVVSGGIVGYVKTGSVPSLAAGLLFGSXA | 2212 | -49 through -1 |
| ID494 | MASTVVAVGLTIAAAGFA | 2213 | -18 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID495 | MVIRVYIASSSGSTAIKKKQQDVLGFLEANKIGFEEKDIAANEENRKWMRENVPENSRPAVQGPHAFRYKAFSFSRLLSQCRP | 2214 | -83 through -1 |
| ID496 | MSSRGHSTLPRTLMAPRMISEGDIGGIAQITSSLFLGRGSVA | 2215 | -42 through -1 |
| ID497 | MAAPGPALCLFDVDGTLT | 2216 | -18 through -1 |
| ID498 | MPLGARILFHGVFYAGGFA | 2217 | -19 through -1 |
| ID499 | MLLSIGMLMLSAT | 2218 | -13 through -1 |
| ID500 | MSLTSSSVRVEMIAAVTIAAGTAA | 2219 | -25 through -1 |
| ID501 | MSGSNGSKENSHNKARTSPYPGSKVERSQVPNEKVGWLVEWQDYKPVEYTAVSVLAGPRWA | 2220 | -61 through -1 |
| ID502 | MAISLRSSGISVKCLSKLWMRWTVTSTTRA | 2221 | -30 through -1 |
| ID503 | MSEVRLPPLRALDDFVLGSARLGGSGS | 2222 | -27 through -1 |
| ID504 | MKLVSATAWLEECWN | 2223 | -15 through -1 |
| ID505 | MKAISVSLLRLIKLLWFFSIVLYVPLLAVCCLHS | 2224 | -34 through -1 |
| ID506 | MGSLSGLRLAAGSCFRLCERDVSXSLRLTRSSDLKRINGFCTKPQESPGAPSRTYNRVPLHKPTDWQKKILIWSGRFKKEXXIPETVSLEMLXXAKNKMRVKISYLMIALTVVGCIFM | 2225 | -118 through -1 |
| ID507 | METLYRVPFLVLECPNLKLKKPWLHMPSAMTVYALVVVSYFLITGGIIYDVIVEPPSVGSMTDEHGHQRPVAFLAYRVNGQYIMEGLASSFLFTMGGLG | 2226 | -100 through -1 |
| ID508 | MLVLRSGLITKALA | 2227 | -13 through -1 |
| ID509 | MAAPLSVEVEFGGGAXSCLTVLRNIESLAWTGGTLG | 2228 | -36 through -1 |
| ID510 | MTHLIEYDRHRKSRLSPLQHLYLLPADHSRNAAERFPGAWFQPPTVDSEASAFVGGLPVIFWSWA | 2229 | -65 through -1 |
| ID511 | MAAALGQIWARKLLSVPWLLC | 2230 | -22 through -1 |
| ID512 | MAVESRVTQEEIKKEPEKPIDREKTCPLLLLVFTTNNG | 2231 | -38 through -1 |
| ID513 | MRLKYQHTGAVLDCAFYDPTHA | 2232 | -22 through -1 |
| ID514 | MALLFARSLRLCRWGAKRLGVASTEAQRGVSFKLXEKTAHSSLALFRDDTGVKYGLVGLEPTKVALNVERFREWAVVLADTAVTSG | 2233 | -86 through -1 |
| ID515 | MAAAAAGTXTSQRFFQSFSDALIDEDPQAALEELTKALEQKPDDAQYYCQRAYCHILLGNYCVAVADA | 2234 | -68 through -1 |
| ID516 | MAQLKYMENVGYAQEDRERMRHRNIVSLAQNLLNFMIGSILDLWQCFLMFYIGSSLNGTRG | 2235 | -60 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID517 | MSPAFRAMDVEPRAKGSFWSPLSTRSGGTHA | 2236 | −31 through −1 |
| ID518 | MADEELEALRRQRLAELQAKHGDPGDAAQQEAKHREAEMRNSILAQVLDQSARA | 2237 | −54 through −1 |
| ID519 | MSAAGARGLRATYHRLLDKVELMLPEKLRPLYNHPAGPRTVFFWAPIMKWGLVCAGLADMARP | 2238 | −63 through −1 |
| ID520 | MSNYSVSLVGPAPWGFRLQGGKDFNMPLTISSLKDGGKAAQANVRIGDVVLSIDGINAQGMTHLEAQNKIKGCTGXLNMTLQRASA | 2239 | −86 through −1 |
| ID521 | MANPKLLGLELSEAEAIG | 2240 | −18 through −1 |
| ID522 | MIIPLLEILIIIVLNEVLLFDVNSVYKALLCTLLLHFQNI | 2241 | −40 through −1 |
| ID523 | MDIQMANNFTPPSATPQGNDCDLYAHHSTARIVMPLHYSLVFIIGLVGNLLA | 2242 | −52 through −1 |
| ID524 | MLTIVKSPQKSYLFPSSMIGIGSLPSCWA | 2243 | −29 through −1 |
| ID525 | MVLVALILLHSALA | 2244 | −14 through −1 |
| ID526 | MAQHHLWILLLCLQTWPEAAG | 2245 | −21 through −1 |
| ID527 | MKDLWIFLLLVTAPRCILS | 2246 | −19 through −1 |
| ID528 | MAQHHLWILLLCLQTWPEAAG | 2247 | −21 through −1 |
| ID529 | MDWTWRFLFVVAAATGVQS | 2248 | −19 through −1 |
| ID530 | MSICFLGLLLLCLLPHRLA | 2249 | −19 through −1 |
| ID531 | MIGFLVLLILPLLSSLS | 2250 | −17 through −1 |
| ID532 | MQCLLSVLMAQFIXHFLSLLMSLLVSTVTMQ | 2251 | −31 through −1 |
| ID533 | MELGLSWIFFLATLKGVQC | 2252 | −19 through −1 |
| ID534 | MVSVSLALLSGWVGS | 2253 | −15 through −1 |
| ID535 | MPLPWSLALPLLLSWVAGGFG | 2254 | −21 through −1 |
| ID536 | MVSNFFHVIQVFEKSATLISKTEHIGFVIYSWXKSTTHLGSRRKFAISIYLSEVSLQKYDCPFSGTSFVVFSLFLICAMA | 2255 | −80 through −1 |
| ID537 | MRXFWFLMYPFRFHDCKQKYDLYISIAGWLIICLACVLFPLLRT | 2256 | −44 through −1 |
| ID538 | MVSLCCLFTCFFIPCIS | 2257 | −17 through −1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID539 | MDFFFLERSYWGKMILLLVTYSPIAYS | 2258 | -27 through -1 |
| ID540 | MTMRHNWTPDLSPLWVLLLCAHVVTL | 2259 | -26 through -1 |
| ID541 | MDNMSGGKVDEALVKSSCLHPWSKRNDVSMQCSQDILRMLLSLQPVLQ | 2260 | -48 through -1 |
| ID542 | MXLQGQRATGKVLIKIHKDTSQVPTAXGDASIAALVLWTLPGAQR | 2261 | -45 through -1 |
| ID543 | MTEHSLTHQGIPILVLILFPTSCVM | 2262 | -25 through -1 |
| ID544 | MYIGGLRFIFLTSLQLISS | 2263 | -19 through -1 |
| ID545 | MSVSLKHIHLFIIMSVLVFWNCSHLIFFSLIFLNLFA | 2264 | -38 through -1 |
| ID546 | MXXLGXXRFMVSFLSXPPLCSA | 2265 | -22 through -1 |
| ID547 | MDWTWYILVSVAAATGAHS | 2266 | -19 through -1 |
| ID548 | MISKFSSKAYSVRGLELFSLLPINPSPNSAIXVACVLSSLIAVNS | 2267 | -45 through -1 |
| ID549 | MVLLGAFGSCIKSFSLLFLIFSLNLNRG | 2268 | -28 through -1 |
| ID550 | MAARQAVGSGAQETCGLDRILEALKLLLSPGXSGS | 2269 | -35 through -1 |
| ID551 | MSTQKGLALFLMALGFSCI | 2270 | -19 through -1 |
| ID552 | MKDVEIIMIFHGYFLIVFFVFLCNC | 2271 | -25 through -1 |
| ID553 | MCFPEHRRQMYIQDRLDSVTRRARQGRICAILLLQSQCAYWA | 2272 | -42 through -1 |
| ID554 | MLVVKQCFSDSSILSTFVSWLSA | 2273 | -23 through -1 |
| ID555 | MIXLRDTAASLRLERDTRQLPLLTSALHGLQQ | 2274 | -32 through -1 |
| ID556 | MITMMLALISVCLF | 2275 | -14 through -1 |
| ID557 | MWLLTLVQCSDLCPS | 2276 | -15 through -1 |
| ID558 | MRVHLFPYLCQPSVLSNFLLFACLTMLLVKT | 2277 | -31 through -1 |
| ID559 | MIPLCFLILPYPVLS | 2278 | -15 through -1 |
| ID560 | MAGSRLPRQLFLQGVXASSCLLSXPSTRKSQA | 2279 | -32 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID561 | MYICFCLESFEIKCGFVLHLLAQDLVCC | 2280 | -28 through -1 |
| ID562 | MHFILHNLNAFTLLVWLSLS | 2281 | -20 through -1 |
| ID563 | MSFFPFNRSLNSNPHPNLLFPNIAPLFTLLPKSIP | 2282 | -35 through -1 |
| ID564 | MVVWVLEVRFLLDLHCFCSLAKT | 2283 | -23 through -1 |
| ID565 | MVCGWWTQGPVPGLCCPALGSAWS | 2284 | -24 through -1 |
| ID566 | MGRAFPSRHKTARFECALVSASLTTA | 2285 | -26 through -1 |
| ID567 | MGLKALCXXLLCVLFVSH | 2286 | -18 through -1 |
| ID568 | MMATQTLSIDSYQDGQQMQVVTELKTEQDPNCSEPDAEGVSPPPVESQTPMDVDKQAIYRHPLFPLLALLFEKCEQ | 2287 | -76 through -1 |
| ID569 | MSPSQLTCSVFLSGSVCLSFL | 2288 | -21 through -1 |
| ID570 | MLQALAPAHHLCSLKRSFCSLLCLRTQLFP | 2289 | -30 through -1 |
| ID571 | MLFLKYLMWRSLCRG | 2290 | -14 through -1 |
| ID572 | MALLAMHSWRWAAAAAFEKRRHSAILIRPLVSVSGS | 2291 | -37 through -1 |
| ID573 | MKAXAMFGAGDEDDTDFLSPSGGARLASLFGLDQXAAG | 2292 | -38 through -1 |
| ID574 | MLWLLRSLTDVSS | 2293 | -13 through -1 |
| ID575 | MTIFHVLIAHSSSFS | 2294 | -15 through -1 |
| ID576 | MHWQLLXGFCGSYSA | 2295 | -15 through -1 |
| ID577 | MTMMVMASFLPRNTMYTNTMNYSIFVFLLFFFSXLXY | 2296 | -37 through -1 |
| ID578 | MPSQTLSQPRISVLHGDLVPAGMAVQEIGAQMVLPCEVVSGSGLTREHLVTRLALCQSPRA | 2297 | -61 through -1 |
| ID579 | MSLRVHTLPTLLGAVVRPGCRELLCLLMITVTVGPGAS | 2298 | -38 through -1 |
| ID580 | MIYLTSLLLLGRWLTLTS | 2299 | -18 through -1 |
| ID581 | MNWNVRGTRGFLLCPLVCGLRR | 2300 | -22 through -1 |
| ID582 | MEQAALEVVSPLPRRCSVRSPVTTCCAKDLVCLTFITATTHE | 2301 | -42 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID583 | MIIPLPSLVGCWEGGNGKGLMVSDTTCWTLASSNVPSPSPAPTLGRGAPSHTPQKKPTIPGARHRPIILPKGLVQLHATXLALG | 2302 | -84 through -1 |
| ID584 | MSMRLSGERIYLLLEVWLPXLNPESVLHPIQTVHIALPGSLG | 2303 | -42 through -1 |
| ID585 | MGTLLLFCFMPVVINP | 2304 | -16 through -1 |
| ID586 | MVVLNPMTLGIYLQLFFLSIVS | 2305 | -22 through -1 |
| ID587 | MAPHTASFGVCPLLSVTRVVATEHWLFLASLSGIKT | 2306 | -36 through -1 |
| ID588 | MSYKWMPSLPCLLSFCTLCLV | 2307 | -20 through -1 |
| ID589 | MPLPTWAPTLAGFLLVLYVCLP | 2308 | -22 through -1 |
| ID590 | MNLYLLDWIGLKALIRG | 2309 | -17 through -1 |
| ID591 | MSCXVXDAXXRWAHXLLIGWXHLTQKVHPIALSHCVNMGTLLLFCFMPVVINP | 2310 | -54 through -1 |
| ID592 | MVPNLCGRQILAPQTFLLNLRA | 2311 | -22 through -1 |
| ID593 | MFSLIIFFPPSSP | 2312 | -14 through -1 |
| ID594 | MSAFYLSYSLLHCLLIVPILVEF | 2313 | -23 through -1 |
| ID595 | MAEAKLVQSLVAPQRXSAGVVLTMDGASA | 2314 | -30 through -1 |
| ID596 | MKGVGPEQLNDGAPSNEIEMTPCFFSEFLLLDVGVVNIVIKMSYNVLLTISTNASVLG | 2315 | -59 through -1 |
| ID597 | MLRKLSASNENLCLLSNPSHNEVYLIRCCESHQLFWVTASTPCRS | 2316 | -45 through -1 |
| ID598 | MYPLILLPLNPFVLQ | 2317 | -15 through -1 |
| ID599 | MLLRPSPGSPRGFVAVGLGQISA | 2318 | -23 through -1 |
| ID600 | MARPGATACGPAAHQCSA | 2319 | -18 through -1 |
| ID601 | MEPVSSLSLCIXXLEHLFT | 2320 | -19 through -1 |
| ID602 | MRPAGRWCSAAAWRSPLSA | 2321 | -19 through -1 |
| ID603 | MWLCAYVLFFFNGCLY | 2322 | -16 through -1 |
| ID604 | MLLLHRAVVLRLQQA | 2323 | -15 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID605 | MEMFGXXEKDFSSVEGVLXSLVPSMCFHVTNS | 2324 | -32 through -1 |
| ID606 | MQMHGWRMDPHSSEQLDLAHTLSREASLENNTALLGVHASFQMSVA | 2325 | -46 through -1 |
| ID607 | MASPRGTDYNQTPNTTMCYAVGTGVLTSRLARA | 2326 | -34 through -1 |
| ID608 | MAPILSSFKSLLKYHLLETSLSILLKPVTLHCLCPFPALFLS | 2327 | -42 through -1 |
| ID609 | MNRLSKHLIILVPWWLPPFVYT | 2328 | -22 through -1 |
| ID610 | MSSNKEQRSAVFVILFALITILILYSSNS | 2329 | -29 through -1 |
| ID611 | MDMKSNTGHGLFLGRQPSFSVRSMPGTPALAICQPHNPGPPMGTPTEDPSGCSFPCLFLSPQSFLVLS | 2330 | -68 through -1 |
| ID612 | MSEAGCKPSRPEHGSFLSLSSTLLLTSHH | 2331 | -29 through -1 |
| ID613 | MESGXGXVFLVALLRGVQC | 2332 | -19 through -1 |
| ID614 | MLCRLFTLLLLQSLLLG | 2333 | -17 through -1 |
| ID615 | MDLLHKNMKHLWFLLLVAGPRNVLS | 2334 | -26 through -1 |
| ID616 | MQAQAPVVVTQPCVGPGPAPQNSNWQTGMCDCFSDCGVCLCGTFCFPCLG | 2335 | -51 through -1 |
| ID617 | MKALCLLLLPVLGLLVSS | 2336 | -18 through -1 |
| ID618 | MSPSGRLCLLXIVGLXLPTXG | 2337 | -21 through -1 |
| ID619 | MLLAWVQAFLVSNMLLAEAYG | 2338 | -21 through -1 |
| ID620 | MLSESRGPPVQEHEAPVVLPPAGGGSQMGPVPAAXAGESGPGXVKPLETLXLTCSVSGGSIS | 2339 | -62 through -1 |
| ID621 | MTSGQAPASXQSPQALEDSGPVNISVSITLTLDPLKPFGGYSRNVTHLYSTILGHQIGLSGREAHEEINITFTLPTAWSSDDCALHGHCEQVVFTACMTLTASPGVFP | 2340 | -108 through -1 |
| ID622 | MLGGDHRALLLKIWLLQRPES | 2341 | -21 through -1 |
| ID623 | MRPRKAWAPVLAALSHSLMSLLDESSCQA | 2342 | -29 through -1 |
| ID624 | MVVWPCAVVLAQYLWFHRRSLPGKAILEIGAGVSLPGILAAKCGAEVILSDSSELPHCLEVCRQSCQMNNLPHLQVVGLTWG | 2343 | -82 through -1 |
| ID625 | MLNPAQXDTMPCEYLSLDAMEKWIIFGFILCHGILNTXATALNLWKLALQSSSCLS | 2344 | -56 through -1 |
| ID626 | MNAQASSRCHGVCLSVPSLPSIS | 2345 | -24 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID627 | MAKVQVNNVVLDNPSPYNPFQFEITPECIEDLSEDLEWKIIYVGSAESEEYDQVLDSVLVGPVPA | 2346 | -67 through -1 |
| ID628 | MADVEDGEETCALASHSGSSG | 2347 | -21 through -1 |
| ID629 | MWTCLLGDCGPPEA | 2348 | -14 through -1 |
| ID630 | MDWTWXVFCLLAVAPGAHS | 2349 | -19 through -1 |
| ID631 | MDNSWRLGPAIGLSAGQSQLLVSLLLLTRVQP | 2350 | -33 through -1 |
| ID632 | MXHLXFPLLLVAAPRWVLS | 2351 | -19 through -1 |
| ID633 | MPVPASWPHPPGPFLLLTLLLGLTEVAG | 2352 | -28 through -1 |
| ID634 | MKEYVLLLFLALCSA | 2353 | -15 through -1 |
| ID635 | MAQSLALSLLILVLAFG | 2354 | -17 through -1 |
| ID636 | MKKVLLLITAILAVAVG | 2355 | -17 through -1 |
| ID637 | MKKVLLLITAILAVAVG | 2356 | -17 through -1 |
| ID638 | MRIMLLFTAILAPSLAQS | 2357 | -18 through -1 |
| ID639 | MAWTVLLLGLLSHCTVS | 2358 | -17 through -1 |
| ID640 | MTILHTGXNPFRPSQRWTAPALLHHRPXTXPPSXHRSRCTEXVGIPXLLLQTLPASTX | 2359 | -58 through -1 |
| ID641 | MKHLWFFLLLLVAAPKXXLS | 2360 | -20 through -1 |
| ID642 | MLSYFLSSLVCGSLGLSNVSG | 2361 | -21 through -1 |
| ID643 | MGTQDPQAEQGLRIPLPGLLLSKHHHPAPELPALALLHAGHA | 2362 | -42 through -1 |
| ID644 | MMTIYALSNEFAFKINEEQLSXXPLXSVQLXHA | 2363 | -33 through -1 |
| ID645 | MRGAHLXALEMLTAFASHIRA | 2364 | -21 through -1 |
| ID646 | MNPESPQQLERQSTGPRTGTRRCLSKFTWCTSRMMTQTCIILLIHTMQVCTT | 2365 | -52 through -1 |
| ID647 | MMTQTCIILLIHTMQVCTT | 2366 | -19 through -1 |
| ID648 | MAGKGSSGRRPLLLGLLVAVATVHL | 2367 | -25 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID649 | MAGSPTCLTLIYILWQLTGSAA | 2368 | -22 through -1 |
| ID650 | MVGMVCFIILGLLICIQC | 2369 | -18 through -1 |
| ID651 | MXLLHSLSSGVRA | 2370 | -13 through -1 |
| ID652 | MTMAECPTLCVSSSPALWA | 2371 | -19 through -1 |
| ID653 | MVPLVAVVSGPRAQLFACLLRLGTQ | 2372 | -25 through -1 |
| ID654 | MSEMAELSELYEESSDLQMDVMPGEGDLPQMEVGSGSRELSLRPSRSGAQQLEEEGPMEEEAQPMAXQRGNGALLTGPTLGSSQA | 2373 | -86 through -1 |
| ID655 | MLIVSVLALIPXTT | 2374 | -15 through -1 |
| ID656 | MTCRGSCSYATRRSPSELSLLPSSLWVLA | 2375 | -29 through -1 |
| ID657 | MEAVVFVFSLLDCCA | 2376 | -15 through -1 |
| ID658 | MAATSGTDEPVSGELVSVAHALSLPAQSYG | 2377 | -30 through -1 |
| ID659 | MADEALFLLLHNEMVSG | 2378 | -17 through -1 |
| ID660 | MASMQKRLQKELLALQNDPPPGMTLNEKSVQNSITQWIVDMEGAPGTLYEGEKFQLLFKFSSRYPFDSPQVMFTGENIPVHPHVYSNGHICLSILTEDWSPALSVQSVCLSIISMLSSC | 2379 | -119 through -1 |
| ID661 | MKXMTGSENWKTKKVLMFCVTPPELET | 2380 | -27 through -1 |
| ID662 | MQHIVGVPHVLVRRGLLGRDLFMTRTLCSPGPS | 2381 | -33 through -1 |
| ID663 | MYHQSEALALASSQSHLLG | 2382 | -19 through -1 |
| ID664 | MSGQGLAGFFASVAMICAIASG | 2383 | -22 through -1 |
| ID665 | MPTGKQLADIGYKTFSTSMMLLTVYGGYLC | 2384 | -30 through -1 |
| ID666 | MFPVCLTVTAAVCG | 2385 | -14 through -1 |
| ID667 | MSVIFFACVVRVRDG | 2386 | -15 through -1 |
| ID668 | MLXGGLKMAPRGKRLSSTPLEILFFLNGWYNATYFLLELFIFLYKGVLLPYPTANLVLDVMLLLYLG | 2387 | -68 through -1 |
| ID669 | MIGGGRWDPPGAQAPSSQAFPRRPALTILIHLPGTEG | 2388 | -36 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID670 | MVRRVQPDRKQLPIVLRLLCLLPTGLP | 2389 | -28 through -1 |
| ID671 | MPLHYSLVFIIGLVGNLLA | 2390 | -19 through -1 |
| ID672 | MARGLGAPHWVAVGLLTWATLGLLVAGLGG | 2391 | -30 through -1 |
| ID673 | MVFVHLYLGNVLALLLFVHYSNG | 2392 | -23 through -1 |
| ID674 | MGMCFAAESDVQMFIAFLLCIFLICAALA | 2393 | -29 through -1 |
| ID675 | MAVRELCFSRQRQVLFLFWGVSLA | 2394 | -26 through -1 |
| ID676 | MRILQLILALATGLVGG | 2395 | -18 through -1 |
| ID677 | MRILQLILALATGLVGG | 2396 | -18 through -1 |
| ID678 | MRSCLWRCRHLSQGVQWSLLLAVLVFFLFA | 2397 | -30 through -1 |
| ID679 | MRILQXILALATGLVGG | 2398 | -18 through -1 |
| ID680 | MLEECGAGVDLGPGGVKFASETPNLLWLLLKLVSTXWA | 2399 | -38 through -1 |
| ID681 | MIACSIRELHRCLLLALVAESSS | 2400 | -23 through -1 |
| ID682 | MGPPSLVLCLLSATVFS | 2401 | -17 through -1 |
| ID683 | MPGPRVWGKYLWRSPHSKGCPGAMWWLLLWGVLQX | 2402 | -35 through -1 |
| ID684 | MHRPEAMLLLTLALLGGPTWX | 2403 | -22 through -1 |
| ID685 | MVSVSLALLSGWVGS | 2404 | -15 through -1 |
| ID686 | MHIFSICMXSELHKMKSLSLQASEKRSLVALVEEIVFLLLRVSPCLG | 2405 | -49 through -1 |
| ID687 | MKLWVSALLMAWFGVLS | 2406 | -17 through -1 |
| ID688 | MKVLISSLLLLLPLMLMSMVSS | 2407 | -22 through -1 |
| ID689 | MKVLISSLLLLLPLMLMSMVSS | 2408 | -22 through -1 |
| ID690 | MLLLLQLSLPSPTS | 2409 | -14 through -1 |
| ID691 | MLKMLSFKLLLLAVALG | 2410 | -17 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID692 | MHRPEAMLLLTLALLGXXXWA | 2411 | -22 through -1 |
| ID693 | MLKVSAVLCVCAAAWC | 2412 | -16 through -1 |
| ID694 | MKVGVLWLISFFTFTDG | 2413 | -17 through -1 |
| ID695 | MCIILLDLICLLFITA | 2414 | -16 through -1 |
| ID696 | MDCASISVKFTSMATMHDLSQFWASRGEVTNWMPVGQTSLPLFYLAFMVFGSFFPLISC | 2415 | -59 through -1 |
| ID697 | MTASPDYLVVLFGITAGATG | 2416 | -20 through -1 |
| ID698 | MVCVLVLAAAAGAVA | 2417 | -15 through -1 |
| ID699 | MKKTGDGGTLSTERIGGAALLSLLLKRMKMTLMIPLLLLTPITA | 2418 | -44 through -1 |
| ID700 | MELGCWTQLGLTFLQLLLISSLP | 2419 | -23 through -1 |
| ID701 | MRXKWKMGGMKYIFSLLFFLLLEGGXT | 2420 | -27 through -1 |
| ID702 | MRGATRVSIMLLLVTVSDC | 2421 | -19 through -1 |
| ID703 | MIAISAVSSALLFSLLCEAST | 2422 | -21 through -1 |
| ID704 | MIAISAVSSALLFSLLCEAST | 2423 | -21 through -1 |
| ID705 | MDPNGGCCTLLTLVLCVAVAYE | 2424 | -22 through -1 |
| ID706 | MEGEIYFQVFLSLFTFSTSLPSSLS | 2425 | -25 through -1 |
| ID707 | MYVVAMFGNCIVVFIVRTERSLHAPMYLFLCMLAAIDLALS | 2426 | -41 through -1 |
| ID708 | MRETXPLPKPLKDTAPSSHGVGSDSPSATRPWFLAPWCPGTQS | 2427 | -43 through -1 |
| ID709 | MDRPGSLSVFGSLPASLGTWLSSPAWLVDRPVRSAHPSANSTGVRMSVLVVLALRSLGRS | 2428 | -60 through -1 |
| ID710 | MHYFVAGKVILLFSYPSCCLC | 2429 | -22 through -1 |
| ID711 | MDLNSASTVLQVLTQATS | 2430 | -29 through -1 |
| ID712 | MSSCNFTHATFVLIGIPGLEKAHFWVGPPLLSMYVVAMFGNCIVVFIVRTERSLHAPMYLFLCMLAAIDLALS | 2431 | -73 through -1 |
| ID713 | MYRLSLIAGPGSYPVLRWGVWDIPSSLVQVTYHQPNLTTNLDLPLFFSCSISATHS | 2432 | -56 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID714 | MLVDGPSERPALCFLLLAVAMSFF | 2433 | -24 through -1 |
| ID715 | MPCSLTWRLPPRTCQXXGLXKSXLXXLLTPPPSYG | 2434 | -35 through -1 |
| ID716 | MVXWLVLFALQIYSYXSTRDQPASRXRLLFLFLTSIAEXCS | 2435 | -42 through -1 |
| ID717 | MARHGLPLLXXXSLPVGA | 2436 | -18 through -1 |
| ID718 | MVHLRTGLMLMSADRLRTLYYTVTILYILMYCSVCSS | 2437 | -37 through -1 |
| ID719 | MGILSTVTALTFARA | 2438 | -15 through -1 |
| ID720 | MELGCWTQLGLTFLQXLLISSLX | 2439 | -23 through -1 |
| ID721 | MELLRVCSFFLLCXSVFTDCKG | 2440 | -22 through -1 |
| ID722 | MIVRPRLNLTWFLLLPPGQCRA | 2441 | -22 through -1 |
| ID723 | MQFLFKMVALCCCLWKISG | 2442 | -19 through -1 |
| ID724 | MLKVSAVLCVCAAXXSQSLX | 2443 | -21 through -1 |
| ID725 | MSMQFLFKMVALCCCLWKISG | 2444 | -21 through -1 |
| ID726 | MAQHLWILLGSLSCRTS | 2445 | -17 through -1 |
| ID727 | MNKEXVSXERXAQVRLYLFSGFWTFXLG | 2446 | -28 through -1 |
| ID728 | MVLWRAKIXRNVPVTLSEENRSEGKVGPQAYKNYFRAGAHWIVFIFLLLNTAA | 2447 | -54 through -1 |
| ID729 | MLLXFFTSVLWLTSPSQP | 2448 | -18 through -1 |
| ID730 | MELISPTVIIILGCLALFLLLQ | 2449 | -22 through -1 |
| ID731 | MHGFEIISLKEESPLGKVSQGPLRNVTSGSSSPVTWLGLLSFQNLHC | 2450 | -47 through -1 |
| ID732 | MTWRHAPGKSLEWATVTDGGDKTFYAASVKGRFNVSRDNSKNTLFLHLSGLSAA | 2451 | -56 through -1 |
| ID733 | MLTSFFSLTANCQS | 2452 | -14 through -1 |
| ID734 | MLLCLLTPLFFMXPTGFS | 2453 | -18 through -1 |
| ID735 | MDDYEAVHSLFLSLLGLCPS | 2454 | -21 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID736 | MEWGKQWLVWLLLGHMVVS | 2455 | -19 through -1 |
| ID737 | MRRGKRLLESQSSSPKACLQLGFETELTQGVLMLVLIQA | 2456 | -39 through -1 |
| ID738 | MVAATEAALLESVVWLPCHG | 2457 | -20 through -1 |
| ID739 | MSWNPSVSLPLLSSWGSTA | 2458 | -19 through -1 |
| ID740 | MKRIQGILFLILLSLHLERRWT | 2459 | -22 through -1 |
| ID741 | MVQRLWVSRLLRHRKAQLXLXNLLTFGLEVCLAAG | 2460 | -35 through -1 |
| ID742 | MAAGVPFALVTSCSSVFS | 2461 | -18 through -1 |
| ID743 | MTVFLXFCFPRCHS | 2462 | -14 through -1 |
| ID744 | MXPNNFWQKLGRKKPRIFTCTQSSTGEAAVKAENLILLEVFVWNGLQG | 2463 | -48 through -1 |
| ID745 | MFRSDRMWXCHWKWKPSPLLFLFALYIMCVPHSVWG | 2464 | -36 through -1 |
| ID746 | MTQRSIAGPICNLKFVTLLVALSSELPFLGA | 2465 | -31 through -1 |
| ID747 | MIIPLLLLRSACN | 2466 | -14 through -1 |
| ID748 | MXSPLPVLLLSXNLNLIIQ | 2467 | -19 through -1 |
| ID749 | MLMCKMLKSQKNCQENXXIKIILFLKPMCSPQYLLTFLVFTXKLSS | 2468 | -46 through -1 |
| ID750 | MKKKSSPNQYLHSSLHXIRLFSFLHFSEEGVLLLAIDLKIIVILHCAASIIS | 2469 | -52 through -1 |
| ID751 | MFSCFFSTSLATSVSLEAQSCFA | 2470 | -23 through -1 |
| ID752 | MHHGLTPLLLGVHEQKQQVVKFLIKKKANLNALDRYGRTALILAVCCGSA | 2471 | -50 through -1 |
| ID753 | MSPCIYFFACFQALTSS | 2472 | -17 through -1 |
| ID754 | MAEMESSLEAXFSSSGAVSGASGFLPPARS | 2473 | -31 through -1 |
| ID755 | MAEMESSLEASFSSSGAVSGASGFLPPARS | 2474 | -31 through -1 |
| ID756 | MLVLGSPLLGPLLWHLSLILLKPLCLP | 2475 | -27 through -1 |
| ID757 | MHLLDLESMGKSSDGKSYVITGSWNPKSPHFQVNEETPKDKVLFMTTAVDLVIT | 2476 | -55 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID758 | MENLKDFVLFVFSSIPLTFL | 2477 | -21 through -1 |
| ID759 | MPQYCLSIFSLVLPVCRM | 2478 | -18 through -1 |
| ID760 | MVAPVLETSHVFCCPNRVRGVLNWSSGPRGLLAFGTSCSVVLY | 2479 | -43 through -1 |
| ID761 | MPIIDQVNPELHDFMQSAEVGTIFALSWLITWFGHXLS | 2480 | -38 through -1 |
| ID762 | METXCPCCCCCPCXGXGSLXXKPVYELQVQKSVTVQEGLCVLVPCSXSXX | 2481 | -49 through -1 |
| ID763 | MSPCIYFFACFXXLTSS | 2482 | -17 through -1 |
| ID764 | MGRGERRHYWGPKLVLKCLSFSXPSLP | 2483 | -27 through -1 |
| ID765 | MSQDGGXGELKHMVMSFRVSELQVLLGFAGRNKSGRKHELLAKALHLLKSSC | 2484 | -52 through -1 |
| ID766 | MHHRMNEMNLSPVGMEQLTSSSVSNALPVSGSHLGLAASPTHSAIPAPGLPVAIPNLGPSLSSLPSALS | 2485 | -69 through -1 |
| ID767 | MLHSDNIWNLFSLFSTSTT | 2486 | -19 through -1 |
| ID768 | MQPASPPARWSFHSAAGWSGGGQA | 2487 | -24 through -1 |
| ID769 | MCFSFLLAGSISHMFSQA | 2488 | -18 through -1 |
| ID770 | MYGFIIGLSILFHCSVCLFLC | 2489 | -21 through -1 |
| ID771 | MSFGXILTFRVSLLGCXLAININT | 2490 | -24 through -1 |
| ID772 | MAVYVGMLRLGRLCAGSSGVXG | 2491 | -22 through -1 |
| ID773 | MFNTIYLVISLVSIFFFWEVTNA | 2492 | -23 through -1 |
| ID774 | MALPPKGCGSLPLTTGSSWSLS | 2493 | -22 through -1 |
| ID775 | MFVFLSWASFLAPLLR | 2494 | -16 through -1 |
| ID776 | MXMKSANKITLLXHHLLSCSPLXPLGKS | 2495 | -28 through -1 |
| ID777 | MCNYNIYVLYNIGYLYHPKSFLLLFIVIPQTP | 2496 | -32 through -1 |
| ID778 | MAVAMVKLCERAGLPLLAAPLLRSLLP | 2497 | -27 through -1 |
| ID779 | MLNVRALRXPQWCAEYCLSIHYQHGGVICTQVHKQTVVQLALRVADEMDVNIGHEVGVIPPENCCTNETILRYCTDDMLQREMMSNPFLGSYGVIILDDIHERSIATDVLLGLLKDVLLA | 2498 | -122 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID780 | MHAGLERXSXQKALAGLCIGSTSYVHG | 2499 | -27 through -1 |
| ID781 | MLNGPFQHRNSRIMTHRSAEKTLLGSLSLWRWSAM | 2500 | -35 through -1 |
| ID782 | MRVKDPTKALPEKAKRSKRPTVPHDEDSSDDIAVGLTCQHVSHA | 2501 | -44 through -1 |
| ID783 | MPQKGLGLLGILSGDFSLLALSMLKGTG | 2502 | -28 through -1 |
| ID784 | MAWWNRPXXXLPQQPLXAEPTAEGEPHLPTGRXXTEANRFAYAALCGISLSQLFP | 2503 | -55 through -1 |
| ID785 | MLCFGDLLLSPWTVPVWS | 2504 | -19 through -1 |
| ID786 | MQENAHNLRLFKCLLIYFLGLAADTYF | 2505 | -27 through -1 |
| ID787 | MHTCSLPCLLFAQLLEFCSFPPDVPHNCAPIVSVRPPNIVAAFEGCSVATALFPPLCIS | 2506 | -59 through -1 |
| ID788 | MQQRGAAGSRGCALFPLLGVLFPQGVYI | 2507 | -28 through -1 |
| ID789 | MXXSIFISEKYGLCPSKTPIMKMLPSLILNRSLPTASSS | 2508 | -39 through -1 |
| ID790 | MAPDVSCFFWVLFSAGCKV | 2509 | -20 through -1 |
| ID791 | MEVAANCSLRVKRPLLDPRFEGYKXSLEPLPCYQLELDAAVAXVKLRDDQYTLEHMHAFGMYNYLHCDSWYQDSVYYIDTLGRIMNLTVMLDTAXG | 2510 | -96 through -1 |
| ID792 | MNVGTAHXXVNPNTRVMNSRGIWNLSYVLAIGLLHIVLLS | 2511 | -39 through -1 |
| ID793 | MENFNMYKNKSWWTLLSSSPSFM | 2512 | -23 through -1 |
| ID794 | MNVGTXHSEVNPNTRVMNSRGIWNLSYVLAIGLLHIVLLS | 2513 | -39 through -1 |
| ID795 | MAAASAVSVLLVAA | 2514 | -14 through -1 |
| ID796 | MAYSKASGSPVLSQAVPGENASHRRGSADLGSGSGLSWARLSQS | 2515 | -44 through -1 |
| ID797 | MKPRRNLEEDDYLHKDTGETSMLKRPVLLHLHQTAHA | 2516 | -37 through -1 |
| ID798 | MIICYDIPCAHMLVCPTIG | 2517 | -19 through -1 |
| ID799 | MYSSEDSTLASVPPAATFG | 2518 | -19 through -1 |
| ID800 | MGEDPXQPRKYKXKXELQGDXPPSSPTNDPTVKYETQPRFITATGGTLHMYQLEGLLNWLRFSWA | 2519 | -65 through -1 |
| ID801 | MFYVAMTKTHKRIRSLCNIHHGLFQFTQQLLGCLQCCWLQSG | 2520 | -42 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID802 | MVSPKDLPLVLLQDIKVPSSMTGSHAGNPHIERNDLPRHGSPQFFTGXTCASXNPSQCLA | 2521 | -60 through -1 |
| ID803 | MEFXSLFCLYFSCFL | 2522 | -15 through -1 |
| ID804 | MALHFQSLAELEXLCTHLYIGTDLTQRIEAEKALLELIDSPECLS | 2523 | -45 through -1 |
| ID805 | MRTLFGAVRAPFSSLTLLLITPSPSPL | 2524 | -27 through -1 |
| ID806 | MRHSLLKGISAQIVSAADKVDAGLPTAIAVSSLIAVGTSHG | 2525 | -41 through -1 |
| ID807 | MTLSCFIFFYISSLC | 2526 | -15 through -1 |
| ID808 | MILCFLLPHHRLQEA | 2527 | -15 through -1 |
| ID809 | MFSLFALNMPLGFC | 2528 | -14 through -1 |
| ID810 | MASSPGVAMHSLWATIHTSVWGVLPPPACSA | 2529 | -31 through -1 |
| ID811 | MSQEGAVPASAVPLEELSSWPEELCRRELPSVLPRLLSLSQHSES | 2530 | -45 through -1 |
| ID812 | MTRECPSPAPGPGAPLSGSVLAEAAVVPAVVLSIHA | 2531 | -36 through -1 |
| ID813 | MQELHLLWWALLLGLAQA | 2532 | -18 through -1 |
| ID814 | MGRQALLLLALCATGAQG | 2533 | -18 through -1 |
| ID815 | MGPSTPLLILFLLSWSGPLQG | 2534 | -21 through -1 |
| ID816 | MSCRELTHRPCSPHLLLLCPLSRGCCP | 2535 | -27 through -1 |
| ID817 | MGWTMRLVTAALLLGLMMVVTG | 2536 | -22 through -1 |
| ID818 | MKFLIFAFFGGVHLLSLCSGKVYA | 2537 | -24 through -1 |
| ID819 | MQCFSFIKTMMILFNLLIFLCGAALLAVG | 2538 | -29 through -1 |
| ID820 | MWAFSELPMPLLINLIVSLLGFVATVTL | 2539 | -28 through -1 |
| ID821 | MASSNTVLMRLVASAYSIA | 2540 | -19 through -1 |
| ID822 | MKFLIFAFFGGVHLLSLCSGKAIC | 2541 | -24 through -1 |
| ID823 | MADTTPNGPQGAGAVQFMMTNKLDTAIVIWLSRLFTVYCSALXVLPLLGLHEA | 2542 | -51 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID824 | MRFRHFXXIGXVLVLSVVXXAMA | 2543 | -24 through -1 |
| ID825 | MELGSCLEGGREAAEERGEPEVKKRRLLCVEFASVASCDA | 2544 | -40 through -1 |
| ID826 | MASPFSGALQLTDLDDFIGPSQECIKPVKVEKRAGSGVAKIREDDGSYFQINQDGXTRRLEKAKVSLNYCXACSGCITSAETVLITQQSHELKKVLDANKMAAPSQQRLVVVSVSPQSRA | 2545 | -122 through -1 |
| ID827 | MGPVPTAVAGAGSRLVRPSQTLSLTCAVSGGSLVAELLLGAGSG | 2546 | -44 through -1 |
| ID828 | MESGGRPSLCQFILLGTTSVVTA | 2547 | -23 through -1 |
| ID829 | MQVCRCIYIICFXLPPLFS | 2548 | -19 through -1 |
| ID830 | MAQRLLLRFLASVIS | 2549 | -15 through -1 |
| ID831 | MLFIFNFLFSPLPTPALICILIFGAAIFLWLITRPQPVLP | 2550 | -40 through -1 |
| ID832 | MYPKWEAPVTFCQLKREKDPPHPAHSPFLQPRFSHMLQLLPSKALC | 2551 | -46 through -1 |
| ID833 | MALYQRWRCLRLQGLQACRLHTAVVSTPPRWLAERLGLFEELWA | 2552 | -44 through -1 |
| ID834 | MGVPRPQPWAXGLLLFLLPGSLG | 2553 | -23 through -1 |
| ID835 | MAAAVPKRMRGPAQAKLLPGSAIQALVGLARPIVLALXLIVSAALS | 2554 | -45 through -1 |
| ID836 | MWLWEDQQGLLGPFSFLLVLLLVTRXRS | 2555 | -29 through -1 |
| ID837 | MNWELLLWLLVLCALLLLLVQLLRFLRA | 2556 | -28 through -1 |
| ID838 | MEKIPVSAFLLLVALSYTLA | 2557 | -20 through -1 |
| ID839 | MSNYTDAESSFSKQEIIRVAMEKIPVSAFLLLVALSYTLA | 2558 | -40 through -1 |
| ID840 | MQFXTWATSSSQPALWSLLLVSWAAMLRLRSKCALVTFFFILLLIFIAEVAA | 2559 | -53 through -1 |
| ID841 | MNWELLLWLLVLCALLLLLVHLLRFLPA | 2560 | -28 through -1 |
| ID842 | MTTFLPVPQMMAGFSGTFGNPPMESPSAWQTIHQPFIVSCLTLWSPGCWP | 2561 | -51 through -1 |
| ID843 | MASKGMRHFCLISEQLVXFSLLATAILG | 2562 | -28 through -1 |
| ID844 | MAAAAWLQVLPVILLLLGAHP | 2563 | -21 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID845 | MASPRTVTIVALSVALGLFFVFMGTIKLTPRLSKDAYSEMKRAXKSYVRALPLLKKMGINSILLRKSIGALEVACGIVMTLVPGRPKDVANFPLLLLVLAVLPFHQLVG | 2564 | -109 through -1 |
| ID846 | MPNLSFGGLDTNQMRVNFLSVDVCKLLLLCALHSHIYC | 2565 | -38 through -1 |
| ID847 | MGPPMLQEISNLFLILLMMGAIFTLAALKESLSTCIPAIVCLXXLLLLNVGQLLA | 2566 | -55 through -1 |
| ID848 | MXXFTDPSSVNEKKRREERERQNIVLWRQPLITIQYFSLEILVILKEWTSKLWHRXXIVVXFLLLLAXLIA | 2567 | -71 through -1 |
| ID849 | MPLLRGLLMXQVLCA | 2568 | -15 through -1 |
| ID850 | MKLLSLVAVVGCLLVPPAEA | 2569 | -20 through -1 |
| ID851 | MPALLPVASRLLLLPRVLLTMASG | 2570 | -24 through -1 |
| ID852 | MCLLLGATGVGKTLLVKRLQEVSSRDGKGDLGEPPPTRPTVGTNLTDIVAQRKITIRELGGCMGPIWSSYYGNCRSLLFVMDASDPTQLSAXXVQLLGLLSAEQLAEA | 2571 | -108 through -1 |
| ID853 | MELPAVNLESDSPRSLAADNLGLHCIRLLCLGQLHHPGLG | 2572 | -41 through -1 |
| ID854 | MAFLRKVYSILSLQVLLTTVTSTVFLYPESVRTFVHESPALILLFALGSLG | 2573 | -51 through -1 |
| ID855 | MYTYGNKQHNSPTWDDPTLAIALAANAWA | 2574 | -29 through -1 |
| ID856 | MQQIFIQQCRELNFWSREPWILVLALPLTVWP | 2575 | -32 through -1 |
| ID857 | MKAVLLALLMAGLAL | 2576 | -15 through -1 |
| ID858 | MGLQACLLGLFALILS | 2577 | -16 through -1 |
| ID859 | MRPGQVSLLGPDAVSVLGSGLGLSPGTSS | 2578 | -29 through -1 |
| ID860 | MINPSVPSKSNSHPFLSTVMFTSASLLLPMSTG | 2579 | -33 through -1 |
| ID861 | MSEKEXNFPPLPKFIPVKPCFYQNFSDEIPVEHQVLVKRIYRLWMFYCATLGVNLIACLAWWIGGGSG | 2580 | -68 through -1 |
| ID862 | MNPTKLIIKTILRLYFFLQLAHS | 2581 | -23 through -1 |
| ID863 | MASSSPDSPCSXXCFVSVPPASA | 2582 | -23 through -1 |
| ID864 | MXPVLAALAHVLCPYMAPGLCREPIRXLIAXILEPPGAMA | 2583 | -39 through -1 |
| ID865 | MNNLNDPPNWNIRPNSRADGGDGSRWNYALLVPMLGLAAFRWIWS | 2584 | -45 through -1 |
| ID866 | MLLLFLAALCSLFFFLSLQ | 2585 | -19 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID867 | MLFLGKVLIVCSTGLAGIMLLNYQQDYTVWVLPLIIVCLFAFLVAHC | 2586 | -47 through -1 |
| ID868 | MQGIPILTPVTTQSIAISIVLTVQGLLLLVHSFWFTVC | 2587 | -38 through -1 |
| ID869 | MQNFCHHLAICTVILFCVLLSLRPHTS | 2588 | -27 through -1 |
| ID870 | MPSFSKDLLTVPKLGTGHXXGKGSYDXALXLLLKCLMSNVVPECTMASSNTVLMRLVASAYSIA | 2589 | -64 through -1 |
| ID871 | MRGAHLTALEMLXAFASHIXA | 2590 | -21 through -1 |
| ID872 | MEVGLPAITLFLTSASSPVATTMDQEPVGGVERGEAVAASGXAAAAAFGESAGQMSNERGFENVELGVIGKKKKKVPRRVIHFVSGETMEEYSTDEDXVDGLEKXMFCLLLIRQNLPGVPTYGFTCFGLLHQLSQCVTS | 2591 | -139 through -1 |
| ID873 | MKELERQQKEVEERPEKDFTEKGSRNNPGLSAATLASLGGTSS | 2592 | -43 through -1 |
| ID874 | MSMGFMMLVLVILCIVTVCVT | 2593 | -21 through -1 |
| ID875 | MMELXLKXXTKXEXESACTEAYSQSDEQYACHLGCQNQLPFAELRQEQLMSLMPKMHLLFPLTIVRSFWS | 2594 | -70 through -1 |
| ID876 | MVSNASETSCLGLILLFASHLINQ | 2595 | -24 through -1 |
| ID877 | MPRKRKCDLRAVRVGLLLGGGGVYGSRPRFTPPGCRALSPWRVXQRRRCEMSTMFADTLLIVFISVCTALLA | 2596 | -73 through -1 |
| ID878 | MGMWSIGAGALGAAALALLLANT | 2597 | -23 through -1 |
| ID879 | MDVAFLEXLIKDDIERGRLPLLIVANAGTAA | 2598 | -31 through -1 |
| ID880 | MRTLFNLLMLALACSP | 2599 | -16 through -1 |
| ID881 | MNAQPGLXLDCTTRFLTXGQFICLQWALPHSEA | 2600 | -33 through -1 |
| ID882 | MGKEWGWQEMENGGAAPAWGAGPPVHPAPPPVEKTLSWGCGFGLHSGPGGSGGGVGLCRLLCLVRLFCC | 2601 | -69 through -1 |
| ID883 | MAAPSGGWNGVGASLWAALLLFATVRLSA | 2602 | -29 through -1 |
| ID884 | MIAIYGKNFCVSAKNAFMLLMRNIVRVVVLDKVTDLLLFFGKLLVVGG | 2603 | -48 through -1 |
| ID885 | MERNCKGSFGVIKEGDTDTXETKARRTVWEPRGRYSFRXTPRPAYPVEQCGFARRALELLEIRKHSPEVCEPPNIPVTSVLELIVASVCQS | 2604 | -91 through -1 |
| ID886 | MFVEYRKQLKLLLDRLAQVSPELLLASVRRVFSSTLQNWQTRFMEVEVAIRLLYMLAEEALPVSHG | 2605 | -66 through -1 |
| ID887 | MLLGTSNIIIFLIQWHGSVFQ | 2606 | -21 through -1 |
| ID888 | MXNRFATAFVXACVLSLIST | 2607 | -20 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID889 | MSLTSGFLRVSQG | 2608 | -13 through -1 |
| ID890 | MANFKGHALPGSFFLIIGLCWSVKYPLKYFSHTRKNSPLHYYQRLEIVEAAIRTLFSVTGILA | 2609 | -63 through -1 |
| ID891 | MQDTGSVVTPLHWFGFGYAALVASGGIIGYVKAGSVPSLAAGLLFGSLAGLGA | 2610 | -52 through -1 |
| ID892 | MEXGLKSADPRDGTGYTXXXXYCCALLTSLXCIWG | 2611 | -35 through -1 |
| ID893 | MASPSRRLQTKPVITCFKSVLLIYTFIFWITGVILLAVGIWG | 2612 | -42 through -1 |
| ID894 | MFSRELAPTRIGGASSGSRSGGTLISTAPLTTRVLNPTAQCFCLDCTLRRMQTHLSVSLLPCAGAWS | 2613 | -67 through -1 |
| ID895 | MSMAVETFGFFMATVGLLMLGVTLPNSYW | 2614 | -29 through -1 |
| ID896 | MEKIPVSXFLXLXXLSXXWP | 2615 | -20 through -1 |
| ID897 | MHSAEEPLXLAALRGARGHLPCCSRHHVGSLAPASVPAPGACLWVCEWETLLPGLILERPLVPSAEA | 2616 | -67 through -1 |
| ID898 | MAGQFRSYVWDPLLILSQIVLMQTVYYGSLGLWLALVDGLVRX | 2617 | -43 through -1 |
| ID899 | MAPKVFRQYWDIPDGTDCHRKAYSTTSIASVAGLTAAAYRVTLNPPGTFLEGVAKVGQYTFTAAAVGAVFGLTTCISA | 2618 | -78 through -1 |
| ID900 | MAAAAWLQVLPVILLLG | 2619 | -18 through -1 |
| ID901 | MEIYFIFCIIVPIAAATVYKSWCLLLILDMNVLYTDA | 2620 | -37 through -1 |
| ID902 | MSRYTSPVNPAVFPHLTVVLLAIGMFFTAWF | 2621 | -31 through -1 |
| ID903 | MRLAAEAHPGRTHTLFRRLKPFIMLSSSLPLLIWL | 2622 | -35 through -1 |
| ID904 | MLEHLXSLPTQMDYKGQKLAXQMFQGIILFSAIVGFIYG | 2623 | -39 through -1 |
| ID905 | MEYSKVLFCSFSNVLG | 2624 | -16 through -1 |
| ID906 | MASKIGSRRWMLQLIMQLGSVLLTRC | 2625 | -26 through -1 |
| ID907 | MEHYRKAGSVELLPAPSPMPQLPPDTLEMRVRDGSKIRNLLGLALGRLEGGSA | 2626 | -52 through -1 |
| ID908 | MNALMVLFNVTVVLIALTCLDGTTVS | 2627 | -26 through -1 |
| ID909 | MNWSIFEGLLSGVNKYSTAFGRIWLSLVFIFRVLVYLVTAERVWS | 2628 | -45 through -1 |
| ID910 | MIISLFIYIFXTCSNT | 2629 | -16 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID911 | MPRLNSLSALAELAVG | 2630 | -16 through -1 |
| ID912 | MTAGTLRTWLCCAGSWA | 2631 | -17 through -1 |
| ID913 | MLGRPCFHSPQRLLVILCVSVKAG | 2632 | -24 through -1 |
| ID914 | MDEARDNACNDMGKMLQFVLPVATQIQQ | 2633 | -28 through -1 |
| ID915 | MSPISIRELCALGSAPSSMWA | 2634 | -21 through -1 |
| ID916 | MTDLLSASPWALT | 2635 | -13 through -1 |
| ID917 | MSWSGLLHGLNTSLTCGPALVPRLWA | 2636 | -26 through -1 |
| ID918 | MADVINVSVNLEAFSQAISAIQA | 2637 | -23 through -1 |
| ID919 | MNVIDNVRDMAAAGLHSNVRLLSSLLLTMSNN | 2638 | -32 through -1 |
| ID920 | MTSACLAWTAVRPSAC | 2639 | -16 through -1 |
| ID921 | MNGSRTLTHSISDGQLQGGQSNSELFQQEXQTAPAQVPQGFNVFGMSSSSGASNS | 2640 | -55 through -1 |
| ID922 | MLGFFLFLSFVLMYDG | 2641 | -16 through -1 |
| ID923 | MMEERANLMHNMKLSIKVLLQSALSLG | 2642 | -27 through -1 |
| ID924 | MELEXIVSAALLAFVQT | 2643 | -17 through -1 |
| ID925 | MLRQIIGQAKKHPSLIPLFXFIGTGA | 2644 | -26 through -1 |
| ID926 | MVKETQYYDILGVKPSASPERSRPIGSWRSSTTRTRTRMRARSLNSYPRHMKCFQIQRKGMFMTKAESRQXKKEAQAAPASLHPWTSLTCSLVVVDG | 2645 | -98 through -1 |
| ID927 | MANLFIRKMVNPLLYLSRHTVKPRALSTXLFGSIRG | 2646 | -36 through -1 |
| ID928 | MAAAASRGXGAKLGLRXIRIHLCQRSPGSQG | 2647 | -32 through -1 |
| ID929 | MFPSCYLCYSLCGSILLSIFSAYNRLSLMLRIALTLIPSMLSRA | 2648 | -44 through -1 |
| ID930 | MSTQXGLSMHAHPQAYTPFIYLHARKRRGEIGDADSRFNDRYAHKSAQLXFLYFVCCIFQ | 2649 | -60 through -1 |
| ID931 | MKHFQDLPSSCSCSLISFTRG | 2650 | -21 through -1 |
| ID932 | MSQRSLCMDTSLDVYRXLIELNYLGTVSLTKCVLPHMIERKXXKIVTVNSILGIISVPLSIG | 2651 | -62 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID933 | MGSGSRLSKELLAEYQDLTFLTKQEILLAHRRFCELLPQEQRXXSRHFGHKCPSSRFSAFQSSRPTPSRSESAGSSPHPQPKTALALRTSWISSVCS | 2652 | −98 through −1 |
| ID934 | MWRLLARASAPLLRVPLSDSWALLPASA | 2653 | −28 through −1 |
| ID935 | MADHVQSLAQLENLCKQLYETTDTXXRSSXAEKALVEFTNSPDCLSKCQLLERGSSSYSQLLAATCLTKLVSRTNNPLPLEQRIDIRNYVLNXLATRPKLATFVTQALIQXYA | 2654 | −114 through −1 |
| ID936 | MAVHGLTVPLIVMSVFWGFVGFLVPWFIPKGPNRGVIITMLVTCSVCCYLFWLIA | 2655 | −55 through −1 |
| ID937 | MSTGQLYRMEDIGRFHSQQPGSLTPSSPTVGEIIYNNTRNTLGWIGGILMGSFQGTIA | 2656 | −58 through −1 |
| ID938 | MGWQRWCFHLQAEASA | 2657 | −17 through −1 |
| ID939 | MSVIFFACVVRVRDG | 2658 | −15 through −1 |
| ID940 | MAVTALAAXTWLGVWG | 2659 | −16 through −1 |
| ID941 | MSLSAFTLFLALIGGTSG | 2660 | −18 through −1 |
| ID942 | MSLSAFTLFLALIGGTSG | 2661 | −18 through −1 |
| ID943 | MSLSAFTLFLALIGGTSG | 2662 | −18 through −1 |
| ID944 | MVELMFPLLLLLPFLLYMA | 2663 | −20 through −1 |
| ID945 | MWLLYLLVPALFCRA | 2664 | −15 through −1 |
| ID946 | MKQILHPALETTANTLFPVLLFLVAGLLPSFP | 2665 | −32 through −1 |
| ID947 | MLKALFLTMLTLALVKS | 2666 | −17 through −1 |
| ID948 | MEKNPLAAPLLIWFHLDCVSS | 2667 | −22 through −1 |
| ID949 | MRVVTIVILLCFCKA | 2668 | −15 through −1 |
| ID950 | MDQFPESVTENFFEYDDLAEACYIGDIVVFGTVFLSIFYSVIFAIGLVGNLLVVFALTNSKKPKSVTDIYLLNLALSDLLFVATLPFWTHY | 2669 | −90 through −1 |
| ID951 | MGEASPPAPARRELLVLLLLSTLIVIPSAA | 2670 | −30 through −1 |
| ID952 | MAPQTLLPVLVLCVLLLQAQG | 2671 | −21 through −1 |
| ID953 | MWTLKSSLVLLLCLTCSYA | 2672 | −19 through −1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID954 | MLPLLLLPLLWGGSLQ | 2673 | -16 through -1 |
| ID955 | METGALRRPQLLPLLLLLCGPSQDQC | 2674 | -26 through -1 |
| ID956 | MERIVLTLCTLPLAVA | 2675 | -16 through -1 |
| ID957 | MMLPQWLLLLFLLFFFLFLLTRG | 2676 | -23 through -1 |
| ID958 | MKPVLPLQXLVVFCLALQLVPG | 2677 | -22 through -1 |
| ID959 | MFRQRQETAQRSTQSCRCPRDGLFFSLFSAPLASA | 2678 | -35 through -1 |
| ID960 | MGSSACEIAVGTKRLLLALPLALVLG | 2679 | -26 through -1 |
| ID961 | MSNQRLPLIFSLLFICFFGESFC | 2680 | -23 through -1 |
| ID962 | MLWFLSFLLALLSLNC | 2681 | -16 through -1 |
| ID963 | MLXISLEIXSFICCVIVLISLSWT | 2682 | -24 through -1 |
| ID964 | MVFRNCILFILTFFSHTFC | 2683 | -19 through -1 |
| ID965 | MLAACPLSPGCQS | 2684 | -13 through -1 |
| ID966 | MAWSPLFLTLITHCTVSWA | 2685 | -19 through -1 |
| ID967 | MLKSVLVSLCSWSPPLTS | 2686 | -18 through -1 |
| ID968 | MTSKXILVSFILAALSLSTTFS | 2687 | -22 through -1 |
| ID969 | MKSLSLXLAVXLGLATAVSA | 2688 | -20 through -1 |
| ID970 | MWAMESGHLLWALLFMQSLWP | 2689 | -21 through -1 |
| ID971 | MAQTWAXLLVMGSLPSASWS | 2690 | -20 through -1 |
| ID972 | MKCGFLAYLLITLLYVWPVINA | 2691 | -22 through -1 |
| ID973 | MRKPAAGFLPSLLKVLLLPLAPAAA | 2692 | -25 through -1 |
| ID974 | MRQSLLFLTSVVPFVLA | 2693 | -17 through -1 |
| ID975 | MELSQMSELMGLSVLLGLLALMATA | 2694 | -25 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID976 | MQDAPLSCLSPIKWSSVSSADSTEKSASAAGTRNLPPQFCLRQALRMKAAGILTLIGCLVTGVES | 2695 | -65 through -1 |
| ID977 | MALAFCLCMAEAILLFSPEHSLFFFCSRKARIRLHWAGQTLAILCAALGLGFIISSRTRSELPHLVSWHSWVGALTLLATAVQALCGLCLLCPRAA | 2696 | -96 through -1 |
| ID978 | MLRPPTCFPSXRVXGXKQLPQEIIXLVWSPXRDXIXLANTAGEVLLHRLASFHRVWS | 2697 | -57 through -1 |
| ID979 | MFMVLEVVVSRVTSSLAMLSDSFHMLSDVLALVVALVAERFA | 2698 | -42 through -1 |
| ID980 | MENQLWHNTVRCCNQYQESPHDAEDILLLLLGLIVLVNI | 2699 | -39 through -1 |
| ID981 | MLSXKITLLTLSPNSVCC | 2700 | -18 through -1 |
| ID982 | MEGPRGWLVLCVLAISLA | 2701 | -18 through -1 |
| ID983 | MKSLLFTLAVFMLLAQLVSG | 2702 | -20 through -1 |
| ID984 | MLKLILFSLLISIVC | 2703 | -16 through -1 |
| ID985 | MTPWCLACLGRRPLASLQWSLTLAWC | 2704 | -26 through -1 |
| ID986 | MTMRHNWTPDLSPLWVLLLCAHVVTL | 2705 | -26 through -1 |
| ID987 | MTGNNRDLFCATLSCMPATS | 2706 | -20 through -1 |
| ID988 | MTMRHNWTPDLSPLWVLLLCAHVVTL | 2707 | -26 through -1 |
| ID989 | MKPLLETLYLLGMLVPGGLG | 2708 | -20 through -1 |
| ID990 | MNQAPRLRAVCLWTLTSAAMSRGDNCTDLLALGIPSITQAWGLWVLLGAVTLLFLISLAAHLSQ | 2709 | -65 through -1 |
| ID991 | MHRQISFLLLRKPRKNWFCQNHVNLRKRYLLSILSSLTMVIC | 2710 | -42 through -1 |
| ID992 | MKQWLCWVLRLEGRQGLGVGEPRGLRLCLGALSAXTFVSFLHA | 2711 | -43 through -1 |
| ID993 | MRLGLCFWVPHRGEMSFSSHYSRGTWYQWDLSLLMLTLISWFRMCLPAVSTVELLFLFPILFIRS | 2712 | -66 through -1 |
| ID994 | MDFWEEYRRGDVPFSWCPIRSYLMSVCPVTGKVNLNHLVKVASARFLHQVTIFPFLYSVKANYCFLNFDVPQYAWEIHSFAAPSILIVIIVITITSACSA | 2713 | -101 through -1 |
| ID995 | MSTSSSSWDNLLESLSLSTVWNWIQA | 2714 | -27 through -1 |
| ID996 | MVFATIGFSLKSGLALGSAGLLWCLA | 2715 | -26 through -1 |
| ID997 | MVLLSGSVSVGVC | 2716 | -14 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID998 | MCSQKRAVSNQGLMDLGLCXLCXVXNVFA | 2717 | -29 through -1 |
| ID999 | MLIVLTLHSPSCDT | 2718 | -14 through -1 |
| ID1000 | MTRLCLPRPEAREDPIPVPPRGLGAGESGSPVRPPVSTWGPSWAQLLDSVLMLGALGLTIQ | 2719 | -62 through -1 |
| ID1001 | MVLTCLFLSLISTYP | 2720 | -15 through -1 |
| ID1002 | MLIPVFSFSLQLLSSSST | 2721 | -18 through -1 |
| ID1003 | MAAAXLSGPSAGSAAGVPGGTGGLSAVSSGPRLRLLLESVSGLLQP | 2722 | -47 through -1 |
| ID1004 | MHNWLFLFVFTFCNC | 2723 | -15 through -1 |
| ID1005 | MHVECFYFLSTALGSQA | 2724 | -17 through -1 |
| ID1006 | MSPGSALALLWSLPASDLG | 2725 | -19 through -1 |
| ID1007 | MALALGSIPSSIA | 2726 | -13 through -1 |
| ID1008 | MLAFLFCTLFSLVVHP | 2727 | -16 through -1 |
| ID1009 | MAQMPLTGSYQDLEYFLECMFLHLLYTLQTISSLSG | 2728 | -36 through -1 |
| ID1010 | MALLMGLWVRTVLQG | 2729 | -15 through -1 |
| ID1011 | MINHLYLAILIXSLKLITG | 2730 | -19 through -1 |
| ID1012 | MGRQGTLEIEGILCVITWLEANLGKQKDENHYYKKLSLLYLCSFPLPGTS | 2731 | -50 through -1 |
| ID1013 | MELTNKQTGTDRHEQVLRRVKQDKRISAWWCVLLEWSQG | 2732 | -39 through -1 |
| ID1014 | MAKRQNPTSVLGLLFSISDTWA | 2733 | -22 through -1 |
| ID1015 | MNVLPFSYYYILFCLSLQIFRVSLA | 2734 | -25 through -1 |
| ID1016 | MKCLKVNPFLFLVFNFFSYISXFLSPVCG | 2735 | -29 through -1 |
| ID1017 | MSWTVPVVRASQRVSSVGANXLCLGMALCPRQA | 2736 | -33 through -1 |
| ID1018 | MGFLXLMTLTTHVHS | 2737 | -15 through -1 |
| ID1019 | MLFRVLLIAQLFLGSG | 2738 | -16 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1020 | MRVPEDLASKILLPGCAPGSLPLSTSAPPLRG | 2739 | -32 through -1 |
| ID1021 | MFPHXETQVKCFWQGLRRSDLCLCQCILARA | 2740 | -31 through -1 |
| ID1022 | MKSLLFTLAVFMXLAQLVSG | 2741 | -20 through -1 |
| ID1023 | MHLYSCSCMRLLNVACCIPFSSS | 2742 | -23 through -1 |
| ID1024 | MRAPLVLSPLSYQCSS | 2743 | -16 through -1 |
| ID1025 | MQVPHLRVWTQVXDTFIGYRNLGFTSMCILFHCLLS | 2744 | -36 through -1 |
| ID1026 | MQKLMAVPMITRAQGGDTCTRQILWLMHQSFQKSNS | 2745 | -36 through -1 |
| ID1027 | MCXAGFXDHPRAARHARTSRHPLPWVCVSQXPAHRSLCLWPACLC | 2746 | -45 through -1 |
| ID1028 | MTSKPILVSFILAALSLS | 2747 | -18 through -1 |
| ID1029 | MHLLIFILTVHHTPS | 2748 | -15 through -1 |
| ID1030 | MLSSSLMVQLISQVYS | 2749 | -16 through -1 |
| ID1031 | MFSYILCMLFCLFS | 2750 | -14 through -1 |
| ID1032 | MLFLYYVTLAFSLLVLSES | 2751 | -19 through -1 |
| ID1033 | MLLSGLWLSSVKEC | 2752 | -14 through -1 |
| ID1034 | MVAFSVFCFSWLMSSSSP | 2753 | -18 through -1 |
| ID1035 | MVPLALGIGPPGCLQG | 2754 | -16 through -1 |
| ID1036 | MNLCMGVLLKVGTSRRCLCLLWFCTAMRPGGA | 2755 | -32 through -1 |
| ID1037 | MSLAKSLFLRVARG | 2756 | -14 through -1 |
| ID1038 | MRLPPFLPSATLLLSAES | 2757 | -18 through -1 |
| ID1039 | MSDRKRTKFSYVQLPCPISLLPRSFKRGQIPGPSAPPLLLLREELVTG | 2758 | -49 through -1 |
| ID1040 | MTPLGSGPPREASIAQVRGFSRTFFRVAFCFFPAFLVXVXS | 2759 | -41 through -1 |
| ID1041 | MRCSALFPLLSLLSC | 2760 | -15 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1042 | MLYDQYYLIISLLKLCSPCFI | 2761 | -21 through -1 |
| ID1043 | MANCFLSHKSQTILISKPALTQSHFTSPAGLFLTVEKSHLLTRLFFHWLSLVLCSFLSLRFCTLS | 2762 | -65 through -1 |
| ID1044 | MHGAGLTYLLFLPDWAAV | 2763 | -18 through -1 |
| ID1045 | MCCLSATLAFSGSFL | 2764 | -15 through -1 |
| ID1046 | MAELDLMAPGPLPRATAQPPAPLSPDSGLRGLLLQEALG | 2765 | -39 through -1 |
| ID1047 | MTLTHGNNILHLANFFLVACPLFGVCLX | 2766 | -28 through -1 |
| ID1048 | MVLRWLPWPRGSHS | 2767 | -14 through -1 |
| ID1049 | MKARLSGNLICFSFLGTLFHKSNS | 2768 | -24 through -1 |
| ID1050 | MSHVCLVPQTPSLCLG | 2769 | -16 through -1 |
| ID1051 | MYPASFVFKIPSTAYVVLTSVNLFIGING | 2770 | -29 through -1 |
| ID1052 | MSSSRKDHLGAXAQSPSRSSLWVTAPLVSA | 2771 | -30 through -1 |
| ID1053 | MASPAAATYLVQSSACCPA | 2772 | -19 through -1 |
| ID1054 | MNAAINTGPAPAVTKTETEVQNPDVLWDLDIPEARSHADQDSNPXAEFALLPCNLHXSWLHS | 2773 | -61 through -1 |
| ID1055 | MINLLVGNCIYLLGAIRASCMCRXMSFAKFGIFLVIFCSESFS | 2774 | -43 through -1 |
| ID1056 | MLCCGPLRFLLRDPGCLLA | 2775 | -19 through -1 |
| ID1057 | MRKTSFILLRMTVLPTLWT | 2776 | -19 through -1 |
| ID1058 | MWWKPAPEGVRVGLVLVXRALC | 2777 | -23 through -1 |
| ID1059 | MFNFLLGNSSCVYQ | 2778 | -14 through -1 |
| ID1060 | MKRGAFSNLNDSQLSASFLQPSLQANCPALDPAVSLSAPAFA | 2779 | -42 through -1 |
| ID1061 | MKSAKLGFLLRFFIFCSLNTLLLG | 2780 | -24 through -1 |
| ID1062 | MDILFPLHSVIGSHP | 2781 | -15 through -1 |
| ID1063 | MLKVFRAXHPKICHFGILILLSQRQWS | 2782 | -27 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1064 | MLVRNARRGSRGRSPWWRAGCLXWRKLAASWTLS | 2783 | −34 through −1 |
| ID1065 | MTKGHHHQHPLHPHPLFTLGLGYPIPTRL | 2784 | −29 through −1 |
| ID1066 | MTYHXIQFSERLHILFIVCLARG | 2785 | −23 through −1 |
| ID1067 | MSQPPLCSPPWKPLVKVSRNLKIRMSIPWPLSVLIYCGLSQPLTLG | 2786 | −46 through −1 |
| ID1068 | MFRSLTIAFFRDAMGFLLMFDLTSQ | 2787 | −25 through −1 |
| ID1069 | MVLTTLPLPSANSPVNMPTTGPNSLSYASSALSPCLX | 2788 | −37 through −1 |
| ID1070 | MQRNATFIHLQLAIRPSLLPTLPWLPSTRL | 2789 | −30 through −1 |
| ID1071 | MNILFCFHSFHPLFQ | 2790 | −15 through −1 |
| ID1072 | MLTNRNYFNFLFLVQLCILA | 2791 | −20 through −1 |
| ID1073 | MKLNPGQVPTWEEALCRFVGMQPCTA | 2792 | −26 through −1 |
| ID1074 | MLAGFRRSAPASQSLCLNLCPCSSSLL | 2793 | −27 through −1 |
| ID1075 | MKEGASFYLLFFLNDVPP | 2794 | −18 through −1 |
| ID1076 | MGLECCCPPHNLRVYIETLLLKLSSQSRT | 2795 | −29 through −1 |
| ID1077 | MQLCPFTSVLSIAASLLQCRL | 2796 | −21 through −1 |
| ID1078 | MDVTCCFDAVEGSDFRVCCHGCVSWLCLQMLQLLFKLNSTWCRA | 2797 | −44 through −1 |
| ID1079 | MRQGPGAPLHCFCFTLFSYSSS | 2798 | −22 through −1 |
| ID1080 | MHITLLGIWLTXRLQ | 2799 | −15 through −1 |
| ID1081 | MLYGSWVCLLSAGTAFE | 2800 | −17 through −1 |
| ID1082 | MLFFPLLSFRFLPSESLLKXXXXFLLGRRVVG | 2801 | −32 through −1 |
| ID1083 | MPVWAILGCWGTLSRG | 2802 | −16 through −1 |
| ID1084 | MGMSGKKHFPLSWDHIQGSTEATSQGILCGSLPGPSLC | 2803 | −38 through −1 |
| ID1085 | MASKILLNVQEEVTCPICLELLTEPLSLDCGHSLCRA | 2804 | −37 through −1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1086 | MYMVCLFFRLIFS | 2805 | -14 through -1 |
| ID1087 | MGAGGXREIRAAAASWLRAAEHSKLAGLMSPGLVPA | 2806 | -36 through -1 |
| ID1088 | MGSKCCKGGPDEDAVERQRRQKLLLAQLHHRKRVKAAGQIQAWWRGVLVRRTLLVAALRA | 2807 | -60 through -1 |
| ID1089 | MQQGHPHLSAGTLSIHSWQLLTSAQP | 2808 | -26 through -1 |
| ID1090 | MSRYEXGSSLLPPDHFSVYSFKXXSFFEAYSISDYATCCLSLFQWCAV | 2809 | -49 through -1 |
| ID1091 | MIYFIKINNKLLLLHHYLLLFITT | 2810 | -24 through -1 |
| ID1092 | MELLYLKVKRGQKDLSWALCLSQSGYY | 2811 | -27 through -1 |
| ID1093 | MTLAVTLSALGATG | 2812 | -14 through -1 |
| ID1094 | MLGPPLQPGSHGKVLAPQGSSGLTPPPCRCLITLPRSCRP | 2813 | -41 through -1 |
| ID1095 | MGNVCSCCLRARYQQLXLILVHFPAYS | 2814 | -27 through -1 |
| ID1096 | MLYGLGSGPRCVISCIHGVWC | 2815 | -21 through -1 |
| ID1097 | MHRIMTLIHLKALQQLQNKIHVPRMLPGPVTPLDSCPPSAHS | 2816 | -42 through -1 |
| ID1098 | MLFLVLFYSAIFL | 2817 | -13 through -1 |
| ID1099 | MVSLCVAALFPLQA | 2818 | -14 through -1 |
| ID1100 | MSSNLFYIPSILTLLA | 2819 | -17 through -1 |
| ID1101 | MGLLRKCFPVMLGGNTHIQITCIKQFILCLGTCRG | 2820 | -35 through -1 |
| ID1102 | MMLPLFCSPWESGG | 2821 | -14 through -1 |
| ID1103 | MAKLLSDLSVDSARC | 2822 | -15 through -1 |
| ID1104 | MCGYWVCWGHLLPARVST | 2823 | -18 through -1 |
| ID1105 | MKLSCAGCADTAILGLSTFLNLLS | 2824 | -24 through -1 |
| ID1106 | MIPFSGTVFSLGSCPAGPLSA | 2825 | -21 through -1 |
| ID1107 | MIPSSQPRFXNPACKQTVLLXDPAVSLSAPAFASA | 2826 | -35 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1108 | MAPTFLLISDSFLTS | 2827 | -15 through -1 |
| ID1109 | MISLIVLSLLGLGIKIQWCLS | 2828 | -19 through -1 |
| ID1110 | MACDSFLKDALPQELSQLXFLFPLVDMREDLLYFNTFLPRKVA | 2829 | -43 through -1 |
| ID1111 | MLLLNENLKAEIQKNEAQGSCILFLFCFESQNNRSKSIFPFLILHFFPQQIRK | 2830 | -53 through -1 |
| ID1112 | MISKYVHYSLTDLLLPFTFLSLKAFL | 2831 | -26 through -1 |
| ID1113 | MARTMGVPRACKAFCSLLSSFCALHFG | 2832 | -27 through -1 |
| ID1114 | MLICFLLPHHRLQEA | 2833 | -15 through -1 |
| ID1115 | MQDYVSHAVRRHCQCFFVCFSPKIYG | 2834 | -26 through -1 |
| ID1116 | MEFAHAAECVSFALNETHVLLNLALSHFNNC | 2835 | -31 through -1 |
| ID1117 | MGNQGFPYLSPSLSVQDLLAASWLPRDAPC | 2836 | -30 through -1 |
| ID1118 | MKYQMVSGSAQLASPLLPGATP | 2837 | -22 through -1 |
| ID1119 | MGPSTPLLILFLLSWSGPLQG | 2838 | -21 through -1 |
| ID1120 | MASLGHILVFCVGLLTMAKA | 2839 | -20 through -1 |
| ID1121 | MSGSSLPSALALSLLLVSGSLLP | 2840 | -23 through -1 |
| ID1122 | MMEVVVGNGVVALRGIPPRTSRKSSRKTRFCGERGSKQSGKCSPVGLAVVSLGGSRG | 2841 | -57 through -1 |
| ID1123 | MARCFSLVLLLTSIWT | 2842 | -16 through -1 |
| ID1124 | MGSRKCGGCLSCLLIPLALWS | 2843 | -21 through -1 |
| ID1125 | MGSRKCGGCLSCLLIPLALWS | 2844 | -21 through -1 |
| ID1126 | MMVMILFGVSFVFLTHC | 2845 | -17 through -1 |
| ID1127 | MSNTHTVLVSLPHPHPALT | 2846 | -19 through -1 |
| ID1128 | MXVYRLQTQEKPNTTVQVPAFLQELVDRDNSKFEEWCIEMAEMRXKVWIKEKQNTKRLRSCTKGYLLELSPMSLSLWNGCKSGWMNQQXPNLLIITLACVPMTSFT | 2847 | -106 through -1 |
| ID1129 | MFPVLGWILIAVVIIILLIFT | 2848 | -21 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1130 | MFSCCISVCLCPCLNKGQS | 2849 | -19 through -1 |
| ID1131 | MRLCLIMYCSFGTLSHLTYLLLLSPIKYP | 2850 | -29 through -1 |
| ID1132 | MGKGMVANLILGLLLLALLLPVQVSS | 2851 | -26 through -1 |
| ID1133 | MGSSGLLSLLVLFVLLANVQG | 2852 | -21 through -1 |
| ID1134 | MVLGGCPVSYLLLCGQAALLLGNLLLHCVSRSHS | 2853 | -35 through -1 |
| ID1135 | METGRLLSLSSLPIVLLG | 2854 | -18 through -1 |
| ID1136 | MAASLGQVLALVLVAALWG | 2855 | -19 through -1 |
| ID1137 | MHIKSIILEGFKSYAQRTEVNGFDPLFNAITGLNGSGKSNILDSICFLLGISNLSQVRA | 2856 | -59 through -1 |
| ID1138 | MSPSPRWGFLCVLFTAVHP | 2857 | -19 through -1 |
| ID1139 | MCSLLYPLVTFFLLCLCIAYWAST | 2858 | -24 through -1 |
| ID1140 | MLPFLFFSTLFSSIFT | 2859 | -16 through -1 |
| ID1141 | MVALNLIIVPCCAA | 2860 | -14 through -1 |
| ID1142 | MAARGVIAPVGESLRYAEYLQPSAKRPDADVDQQRLVRSLIAVGLGVAALAFA | 2861 | -53 through -1 |
| ID1143 | MIKLKLLSLLRPSLC | 2862 | -15 through -1 |
| ID1144 | MPSVNSAGLCVLQLTTAVTS | 2863 | -20 through -1 |
| ID1145 | MMLGLHFALFLLVSXYMIRS | 2864 | -20 through -1 |
| ID1146 | MALLLSVLRVLLG | 2865 | -13 through -1 |
| ID1147 | MLKSLWLSLVAWHWGEA | 2866 | -17 through -1 |
| ID1148 | MGIVTWLLXSFMSSA | 2867 | -15 through -1 |
| ID1149 | MAGIKALISLSFGGAIGLMFLMLGCALP | 2868 | -28 through -1 |
| ID1150 | MKKQKHQKLWCISVKLVTLSVPTSLA | 2869 | -26 through -1 |
| ID1151 | MDGIPMSMKNEMPISQLLMIIAPSLGFVLFALFVAFLLRG | 2870 | -40 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1152 | MGGFLHLPALSSSCLWTFPPMCVRIFSVPLPILTPKTINLIPVLAICSCLPGPGPA | 2871 | -57 through -1 |
| ID1153 | MSPSPRWGFLCVLFTAVHP | 2872 | -19 through -1 |
| ID1154 | MTSQPVPNETIIVLPSNVINFSQAEKPEPTNQGQDSLKKHLHAEXKVIGTIQILCGMMVLSLGIILASASFSPNFT | 2873 | -76 through -1 |
| ID1155 | MRALENDFFNSPPRKTVRFGGTVTEVLLKYKKGETNDFELLKNQLLDPDIKDDQIINWLLEFRSSVMYLTKDFEQLISILRLPWLNRSQT | 2874 | -91 through -1 |
| ID1156 | MVFPAKRFCLVPSMEGVRWAFSCGTWLPSRA | 2875 | -31 through -1 |
| ID1157 | MNCFQGTNASALEKDIGPEQFPINEHYFGLVNFGNTCYCNSVLQALYSCRPFRENVLAYKAQQKKKENLLTCLADLFHSIAT | 2876 | -82 through -1 |
| ID1158 | MAAALRVRXXXFGTRA | 2877 | -16 through -1 |
| ID1159 | MKLLTHNLLSSHVRG | 2878 | -15 through -1 |
| ID1160 | MGXFSRRTFCGRSGRSCRGQLVQVSRPEVSAGSLLLPAPQA | 2879 | -41 through -1 |
| ID1161 | MEGGVRLDLSACGETSGVAVSELPASETAALVPEGHGPGLRACALSLPDAPGASG | 2880 | -55 through -1 |
| ID1162 | MTLLSFAALTAAFS | 2881 | -14 through -1 |
| ID1163 | MAAATGDPGLSKLQFAPFSSA | 2882 | -21 through -1 |
| ID1164 | MFTSTGSSGLYKAPLSKSLLLVPSXLS | 2883 | -27 through -1 |
| ID1165 | MTSMTQSLREVIKAMTKARNFERVLGKITLVSAAPGKVIC | 2884 | -40 through -1 |
| ID1166 | MADFGISAGQFVAVVWDKSSPVEALKGLVDKLQALTGNEGRVSVENIKQLLQSAHKESSXDIILSGLVPGSTT | 2885 | -73 through -1 |
| ID1167 | MGILLGLLLLGHLT | 2886 | -14 through -1 |
| ID1168 | MFLTVKLLLGQRCSLKVSG | 2887 | -19 through -1 |
| ID1169 | MNVIDHVRDMAAAGLHSNVRLLSSLLLTMSNN | 2888 | -32 through -1 |
| ID1170 | MGTPSLSILLIGAPESPIPYFPYHSGTGRVLCPLLXAAAAP | 2889 | -41 through -1 |
| ID1171 | MVYHALDSPDDDYHALFVLCLLYAMS | 2890 | -26 through -1 |
| ID1172 | MFIVLSMWLCCGFE | 2891 | -14 through -1 |
| ID1173 | MVVVILSSXVPLAAM | 2892 | -15 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1174 | MLAECSSLLHPSVRG | 2893 | -15 through -1 |
| ID1175 | MQMARLLGLCAWARK | 2894 | -15 through -1 |
| ID1176 | MTPQYLPHGGKYQVLGDYSLAVVFPLHFSDLISVLYLIPKTLT | 2895 | -43 through -1 |
| ID1177 | MVVLRAGKKTFLPPLXRAFACRG | 2896 | -23 through -1 |
| ID1178 | MKREGGAAHLCSDSLPESQQ | 2897 | -20 through -1 |
| ID1179 | MVTCPGPSSGQPLSSMYTAGDRRGAPSLPYSLAACPCGSQG | 2898 | -41 through -1 |
| ID1180 | MQRQLALEVIVTLSETAA | 2899 | -18 through -1 |
| ID1181 | MGDYLLRGYRMLGETCADCGTILLQDKQRKIYCVACQELDSDVDKDNPALNAQAALSQAREHQLASASELPLGSRP | 2900 | -76 through -1 |
| ID1182 | MWLLYLLVPALFCRA | 2901 | -15 through -1 |
| ID1183 | MKLEFTEKNXXSFVLQNLNRQRKREYWDMALSVDNHVFFAHRNVLAAVSPLVRSLIS | 2902 | -58 through -1 |
| ID1184 | MMWRPSVLLLLLLRHGAQG | 2903 | -20 through -1 |
| ID1185 | MGKICKNWVSFLDNVLLILFLYGLCSG | 2904 | -28 through -1 |
| ID1186 | MLTVALLALLCASASGNA | 2905 | -18 through -1 |
| ID1187 | MVLLLCLSCLIFS | 2906 | -13 through -1 |
| ID1188 | MPVPALCLLWALAMVTRPASA | 2907 | -21 through -1 |
| ID1189 | MHLRGSHTYPSCPSSELRLDSLMQHHRQLLPLWVFLPLSLG | 2908 | -41 through -1 |
| ID1190 | MPVPASWPHLPSPFLLMTLLLGGLTG | 2909 | -26 through -1 |
| ID1191 | MAQRCVCVLALVAMLLLVFPTVS | 2910 | -23 through -1 |
| ID1192 | MDYLISFLLLLLLLP | 2911 | -16 through -1 |
| ID1193 | MATTVPDGCRNGLKSKYRLCDKAEAWGIVLETVATAGVVTSVAFMLTLPILVCKVQDSNRRKMLPTQFLFLLGVLGIFGLTFA | 2912 | -84 through -1 |
| ID1194 | MESGLSWLFLVIFIKGVQC | 2913 | -19 through -1 |
| ID1195 | MSGTSVLLHVAFLPGRFG | 2914 | -18 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1196 | MLQGLLPVSLLLSVAVS | 2915 | -17 through -1 |
| ID1197 | MHICHVSLLLQLCSS | 2916 | -15 through -1 |
| ID1198 | MIFADRTHSSAFTLMRSYSLLLCSLLFSFPFLC | 2917 | -33 through -1 |
| ID1199 | MAFLPSWVCVLVGSFSASLA | 2918 | -20 through -1 |
| ID1200 | MFLVSCVICTGSFA | 2919 | -14 through -1 |
| ID1201 | MKKTGDGGTLSTERIGGAALLSLLLKRNKMTLMIPLLLLTPITA | 2920 | -44 through -1 |
| ID1202 | MGFFLPHGISDAXILLAGWCPDTPA | 2921 | -25 through -1 |
| ID1203 | MWLRPGSCWSTREPRRAPRTSASLSSFLGPSAVCTLLSSHPASRC | 2922 | -46 through -1 |
| ID1204 | MSEGMVTLLTFSCLWTDDSFMSXLNVLFLLSLFCRLYHG | 2923 | -39 through -1 |
| ID1205 | MLILGLPLCRPLWI | 2924 | -14 through -1 |
| ID1206 | MYIYFFVLCXLSHFILLVLPCLIFS | 2925 | -25 through -1 |
| ID1207 | MDSRVSSPEKQDKENFVGVNNKRLGVCGWILFSLSFLLVIIT | 2926 | -42 through -1 |
| ID1208 | MCILFCVVLCLSPTSY | 2927 | -16 through -1 |
| ID1209 | MHRGDIETLLCLGSSCCQC | 2928 | -19 through -1 |
| ID1210 | MFLKSGAGLSSCLLPLCWL | 2929 | -19 through -1 |
| ID1211 | MANAIIKKPCAMPAQPHTGNLLMPPLVWVWLGLLPLFS | 2930 | -38 through -1 |
| ID1212 | MSPPPLLQPLLLLLPLLNV | 2931 | -19 through -1 |
| ID1213 | MIPIYQNKSQTDSHCSLSHKGLAFLKVWLILIGLFSLTGLVA | 2932 | -42 through -1 |
| ID1214 | MALPGIHLLSGSTCPGPCSC | 2933 | -20 through -1 |
| ID1215 | MPSETLWEIAKAEVEKRGINGXXGDGAEIALIPLFSTXAFA | 2934 | -41 through -1 |
| ID1216 | MEWLRPSQISFYPGYSKERLRLVLLCMSLTFLALSTL | 2935 | -37 through -1 |
| ID1217 | MKAIIHLTLLALLSVNTG | 2936 | -18 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1218 | MDVSASKPVAESWSPGSLPLALTLSLSTS | 2937 | −29 through −1 |
| ID1219 | MGVRVGVSLRAMCVFIQTALLGLPXAWA | 2938 | −28 through −1 |
| ID1220 | MIISIIPRSFFLLLCIPLTLL | 2939 | −22 through −1 |
| ID1221 | MTMQRSRSSSWTSCNSWTLVLMSPEWALL | 2940 | −29 through −1 |
| ID1222 | MITLPQTSSLLCSLMASISPTLT | 2941 | −23 through −1 |
| ID1223 | MLRTCYVLCSQAGPPSRGWQSLSFDGGAFHLKGTGELTRALLVLRLCAWPPLVTHGLLLQAWS | 2942 | −63 through −1 |
| ID1224 | MICSPFSGFAPCQALGTLGVGCHFFHLALG | 2943 | −30 through −1 |
| ID1225 | MCNPEEALXGLEVFSATLAMVNSLVLQPLLPAAPDPSDPWGRECLRLLQQLHKSSQQLWEVTEESLHSLQERLRYPDSTGLESLLLLRGADRVLQA | 2944 | −98 through −1 |
| ID1226 | MDKLIPSLSSQENRKASHTLHKARNKQHCGGFLLVIHWVMCPSLS | 2945 | −45 through −1 |
| ID1227 | MSXLLPVVLASPPVGHG | 2946 | −17 through −1 |
| ID1228 | MVLLTMIARVADG | 2947 | −13 through −1 |
| ID1229 | MFHIAFSEALPVDIFKTQPNCHEAFSMKAIHITRIRSGLCLLELLFVPLLCFL | 2948 | −53 through −1 |
| ID1230 | MMHCTPSGSAAVSLLTETVLPLAFP | 2949 | −25 through −1 |
| ID1231 | MTRPFWASCSTWATSRISCAFSLASSTA | 2950 | −28 through −1 |
| ID1232 | MVTHLIRGVVLQSCCLIQWPELSFS | 2951 | −26 through −1 |
| ID1233 | MYMWSKLLVAFRVFLGLFS | 2952 | −19 through −1 |
| ID1234 | MSSRNCFFPSFLFGLYSFRAVDS | 2953 | −23 through −1 |
| ID1235 | MYMNTCLYLHVYVLTCSG | 2954 | −18 through −1 |
| ID1236 | MSCRQPTPTQCSLLPNDNRVSTRGGDSAGRHRQVPQVALSASLPQCSLG | 2955 | −49 through −1 |
| ID1237 | MITGCTKPTAGVVVLQGSRA | 2956 | −20 through −1 |
| ID1238 | MGLDLILSFSSSSP | 2957 | −14 through −1 |
| ID1239 | MREDNEHERNVPSGVENVKEEGGDEDLSWGDEGCQVLRHRLRVCRKVGLLDRLCALTSLCSP | 2958 | −62 through −1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1240 | MGKPAGAVVSSWAXCSLG | 2959 | -18 through -1 |
| ID1241 | MQSTSNHLWLLSDILGQQATA | 2960 | -21 through -1 |
| ID1242 | MKKLRPSQEQLNCPEPQLADGRAGIRLLVTWLQPAPLLCLSGLELEPSA | 2961 | -49 through -1 |
| ID1243 | MWSHLNRLLFWSIFSSVTC | 2962 | -19 through -1 |
| ID1244 | MLALRDLGMGKREGEELIQAEARCLVETFQGTEGRPFDPSLLLAQATSNVVC | 2963 | -52 through -1 |
| ID1245 | MLSVGASTSLCGCLRQLRC | 2964 | -19 through -1 |
| ID1246 | MFQQMYVLLSQFLYPLAYP | 2965 | -19 through -1 |
| ID1247 | MTSHFCXIGFLSYTTS | 2966 | -16 through -1 |
| ID1248 | MICSLTPFRSLTNVLLSGSLLRSLC | 2967 | -25 through -1 |
| ID1249 | MEPPGRSSLPFSPPALTLTFLPPSPT | 2968 | -27 through -1 |
| ID1250 | MDKLKKVLSGQDTEDRSGLSEVVEASSLSWSTRIKGFIACFAIGILCSLLGTVLL | 2969 | -55 through -1 |
| ID1251 | MYSRHTVKLKQGLGMVCIFSLRLQA | 2970 | -25 through -1 |
| ID1252 | MYPSLLVDYFPSLLLYSLPLNIIG | 2971 | -24 through -1 |
| ID1253 | MATTVPDGCRNGLKSKYRLCDKAEAWGIVLETVATAGVVTSVAFMXTLPILVCKVQDSNRRKMLPTQFLFLLGVLG | 2972 | -77 through -1 |
| ID1254 | MRLQHLDHLFFSGVVLG | 2973 | -17 through -1 |
| ID1255 | MPLPKPSFSNNHLIRLITVAFGLYNPSLCHA | 2974 | -31 through -1 |
| ID1256 | MEPITFTARKHLLPNEVSVDFGLQLVGSLPVHSLTTMPMLPWWAEVRRLSRQSTRKEPVTXQXRLCVSPSGLRC | 2975 | -75 through -1 |
| ID1257 | MGCLWGLALPLFFFCWEVGVSGSSA | 2976 | -25 through -1 |
| ID1258 | MKQNTDPYLCHISLLDVTQQ | 2977 | -20 through -1 |
| ID1259 | MVTYFNFTFKPFCILASIIVPTLISLLSSPNTPSA | 2978 | -35 through -1 |
| ID1260 | MESGGRPSLCQXILLGTTSVVTA | 2979 | -23 through -1 |
| ID1261 | MEAQQAQKSAEQPEQKAATEVSXELSESQVHMMAAAVADGTRA | 2980 | -43 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1262 | MPLNSVIWFGSVXPCIS | 2981 | -17 through -1 |
| ID1263 | MLQQLDSISLRRRETANFLDFANLADLTLA | 2982 | -30 through -1 |
| ID1264 | MCYLAELSLTTFXXGYIVTSRATTTTLAIQPGLPFTTLSNLSLPSQT | 2983 | -48 through -1 |
| ID1265 | MSISLSLILLPIWINM | 2984 | -17 through -1 |
| ID1266 | MDRDLLRQSLNCHGSSLLLLRSEQQDNPHFRSLLGSAAEPARGPPPQHPLQGRKEKRVDNIEIQKFISKKADLLFALSWKSDAPA | 2985 | -86 through -1 |
| ID1267 | MVLATLVTXXNASCSFA | 2986 | -17 through -1 |
| ID1268 | MMIWKRLIILKVLLNQTCQT | 2987 | -20 through -1 |
| ID1269 | MDAGKAGQTLKTHCSAQRPDVCRMLSPFILSCCVYFCLWIPEDQLSWFAALVKCLPVLCLA | 2988 | -61 through -1 |
| ID1270 | MQQRGAAGSRGCALFPLLGVLFFQGVYI | 2989 | -28 through -1 |
| ID1271 | MLGTHIYVSLWIILFSSPHLIYWYVLLILSFP | 2990 | -32 through -1 |
| ID1272 | MSIYNLFLNLHGFLGHLLS | 2991 | -19 through -1 |
| ID1273 | MCMQVDLAFSPPPACVCMCTXSCYS | 2992 | -25 through -1 |
| ID1274 | MAPGEKESGEGPAKSALRKIRTATLVISLARG | 2993 | -32 through -1 |
| ID1275 | MEPKRGRMWXFEIEDSCIYQDIPSFVLLYPLLHLFYQHLCFP | 2994 | -42 through -1 |
| ID1276 | MEFCSVLQRCLFSFVTS | 2995 | -17 through -1 |
| ID1277 | MAESQIYVLLFFLLMKFS | 2996 | -18 through -1 |
| ID1278 | MQTNNACSLSSGPLQINA | 2997 | -18 through -1 |
| ID1279 | MGQNNASFHCPCLKVLMGLLCNQTAA | 2998 | -26 through -1 |
| ID1280 | MLPLLSVMWSPIAP | 2999 | -14 through -1 |
| ID1281 | MWLNCGGLQRWITCPPTPHGCRA | 3000 | -23 through -1 |
| ID1282 | MWQGCNCSQLSETAVDQEQLGVLTFILQRTTC | 3001 | -32 through -1 |
| ID1283 | MCLPHPQVVSSNPHILIFLLPTKMLVTLLASKSPSCP | 3002 | -37 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1284 | MHLAVLFXFSDCCRKXLSSGQLYSIVSSLSNEHVLSAGFDINTPDNLGRTCLHAAASGGNVECLNLLLSSGADL | 3003 | −74 through −1 |
| ID1285 | MSFQWCGWQWGLHDCFLSVFQVLS | 3004 | −24 through −1 |
| ID1286 | MKVHMHTKFCLICLLTFIFH | 3005 | −20 through −1 |
| ID1287 | MSFNLQSSKKLFIFLGKSLFSLLEA | 3006 | −25 through −1 |
| ID1288 | MDLMCRKVKHLLFFLLIVAAPRMVVS | 3007 | −26 through −1 |
| ID1289 | MELKSPEEEVVAALPEGMRPDSNLYGFPWELVICAAVVGFFAVLFFLMRSFX | 3008 | −52 through −1 |
| ID1290 | MELSDVTLIEGVGNEVMVVAGVVVLIALVLAWLSTYVA | 3009 | −39 through −1 |
| ID1291 | MIARRNPEPLRFLPDEARSLPPPKLTDPRLLYIGFLGYCSG | 3010 | −41 through −1 |
| ID1292 | MPPGPWESCFWVGGLILWLSVGSS | 3011 | −24 through −1 |
| ID1293 | MCARALLACSSRG | 3012 | −14 through −1 |
| ID1294 | MGDERPHYYGKHGTPQKYDPTFKGPIYNRGCTDIICCVFLLLAIVG | 3013 | −46 through −1 |
| ID1295 | MAQRLLLRRFLASVIS | 3014 | −16 through −1 |
| ID1296 | MESGGGRPSLCQFILLGTTSVVTA | 3015 | −23 through −1 |
| ID1297 | MALSSQIWAACLLLLLLLASLTSG | 3016 | −24 through −1 |
| ID1298 | MGVPRPQPWALGLLLFLLPGSLG | 3017 | −23 through −1 |
| ID1299 | MKVVPSLLLSVLLAQVWL | 3018 | −18 through −1 |
| ID1300 | MLSITVLAALLACASS | 3019 | −16 through −1 |
| ID1301 | MLGITVLAALLACASS | 3020 | −16 through −1 |
| ID1302 | MAGNGESEPDRLHLLTGHRVKGEFQLLLPLLSLPVTTP | 3021 | −38 through −1 |
| ID1303 | MLWLVLLLLPTLK | 3022 | −14 through −1 |
| ID1304 | MAPQSLPSSRMAPLGMLLGLLMAACFTFC | 3023 | −29 through −1 |
| ID1305 | MMLHSALGLCLLLVTVSSNLAIA | 3024 | −23 through −1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1306 | MCTGKCARCVGLSLITLCLVCIVANA | 3025 | -26 through -1 |
| ID1307 | MDIIVPLIQLLVLLLTLPLHLMA | 3026 | -23 through -1 |
| ID1308 | MPFIVLFSFFNIALC | 3027 | -15 through -1 |
| ID1309 | MQQRGLAIVALAVCAALHA | 3028 | -19 through -1 |
| ID1310 | MRKTRLWGLLWMLFVSELRA | 3029 | -20 through -1 |
| ID1311 | MVGAMWKVIVSLVLLMPGPCDG | 3030 | -22 through -1 |
| ID1312 | MIHLRIIQRCYMAGLENKKNVVFEAKQICIGIILVLPFIRC | 3031 | -40 through -1 |
| ID1313 | MAGSPTCLTLIYILWQLTGSAA | 3032 | -22 through -1 |
| ID1314 | MGKKGKVGKSRRDKFYHLAKETGYRSRSAFKLIQLNRRFQFLQKARALLDLCAAPXGWL | 3033 | -59 through -1 |
| ID1315 | MPLSDFILALKDNPYFGAGFGLVXVGTALALA | 3034 | -32 through -1 |
| ID1316 | MEFGLSWVFLVAIIKGVQC | 3035 | -19 through -1 |
| ID1317 | MILRKRSCSLFSSLPIFLTWA | 3036 | -21 through -1 |
| ID1318 | MKNGLMFVKLVNPCSG | 3037 | -16 through -1 |
| ID1319 | MEAVVFVFSLLDCCA | 3038 | -15 through -1 |
| ID1320 | MTGFLLPPASRGTRRSCSRSRKRQTRRPNPSSFVASCPTLLPFACVPGASXTTLA | 3039 | -56 through -1 |
| ID1321 | MCGNTMSVPLLTDAATVSG | 3040 | -19 through -1 |
| ID1322 | MXXXXERRTSPHVMADQSSTRNEDFLKKTWSLWRLQWLKDASC | 3041 | -43 through -1 |
| ID1323 | MFLLNCIVAVSQN | 3042 | -14 through -1 |
| ID1324 | MLLVSAAPLGFGQG | 3043 | -14 through -1 |
| ID1325 | MLRIALTLIPSMLSRA | 3044 | -16 through -1 |
| ID1326 | MTLGGRLPGLRCSVPGVAA | 3045 | -19 through -1 |
| ID1327 | MAFTLXSLLQAALL | 3046 | -14 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1328 | MRPLAGGLLKVVFMVFASLXA | 3047 | -21 through -1 |
| ID1329 | MFEEPEWAEAAPVAAGLGPVIS | 3048 | -22 through -1 |
| ID1330 | MHIYTGIKYIALYNIIYVCGIQG | 3049 | -23 through -1 |
| ID1331 | MMWRPSVLLLLLLLRHGAQG | 3050 | -20 through -1 |
| ID1332 | MERPLCSHLCSCLAMLALLSPLSLA | 3051 | -25 through -1 |
| ID1333 | MIHLGHILFLLLLPVAAA | 3052 | -18 through -1 |
| ID1334 | MAVKLGTLLLALALGLAQPASA | 3053 | -22 through -1 |
| ID1335 | METLGALIVLEFLLLSPVEA | 3054 | -20 through -1 |
| ID1336 | MLLPLLLSSLLGGSQA | 3055 | -16 through -1 |
| ID1337 | MLWLLFFLVTAIHA | 3056 | -14 through -1 |
| ID1338 | MAGSPSRAAGRRLQLPLLCLFLQGATA | 3057 | -27 through -1 |
| ID1339 | MKNPWTCLAILCPGPVLSPPCSGPXLALALLLVLPLLWP | 3058 | -39 through -1 |
| ID1340 | MPSWIGAVILPLLGLLLSLPAGA | 3059 | -23 through -1 |
| ID1341 | MLLHWVRSQXXSDXKLWLSLLVPSCLCA | 3060 | -28 through -1 |
| ID1342 | MKYLRHRRPNATLILAIGAFTLLFSLLVSPPTC | 3061 | -34 through -1 |
| ID1343 | MPGPRVWGKYLWRSPHSKGCPGAMWWLLLWGVLQA | 3062 | -35 through -1 |
| ID1344 | MCGPAMFPAGPWPRVRVVQVLWALLAVLLASWRLWA | 3063 | -37 through -1 |
| ID1345 | MHRRKLPLTNKRQLQKXLSKFIFSDELFRNILFSLRTLRMILSLLLLSTALNILA | 3064 | -55 through -1 |
| ID1346 | MKLWVSALLMAWFGVLS | 3065 | -17 through -1 |
| ID1347 | MQLPLALCLVCLLVHTAFR | 3066 | -19 through -1 |
| ID1348 | MLCIHXXRIIQDSFIALKILLCSVAVXLSPS | 3067 | -31 through -1 |
| ID1349 | MGGFFPPTEVREVCANQGAAHNPDRLPFLSLFWPWAPG | 3068 | -38 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1350 | MKLFYNQLVSETKHDFAHLMILLLFSPCWM | 3069 | -30 through -1 |
| ID1351 | MPSESPPLLFFHILFHSCFS | 3070 | -20 through -1 |
| ID1352 | MSSMWSEYTIGGVKIYFPYKAYPSQLAMMNSILRGLNSKQHCLLESPTGSGKSLALLCSALAWQQSLS | 3071 | -68 through -1 |
| ID1353 | MALFLELFLNSYSLLFVRFLGFVSCLQS | 3072 | -28 through -1 |
| ID1354 | MNEDEKEMKEILMAGSSLSAGVSG | 3073 | -24 through -1 |
| ID1355 | MGSFLLGGIIPLIXXLSLCLC | 3074 | -21 through -1 |
| ID1356 | MLQVATTNYLELAREVKPVCLLCSGCSCAWS | 3075 | -31 through -1 |
| ID1357 | MFCLAPFFLALCFPKSTS | 3076 | -18 through -1 |
| ID1358 | MSESRFQPQNQGGSLQLPLQCLLCCISPPVFC | 3077 | -32 through -1 |
| ID1359 | MPKHCHSFITSSCLLGLLHLSSQ | 3078 | -23 through -1 |
| ID1360 | MCLLFXFIXFPFLFPFSFS | 3079 | -19 through -1 |
| ID1361 | MASERXPNRPXCLLVASGXAEGVSA | 3080 | -25 through -1 |
| ID1362 | MPPDYKLGGSYLLAFQLVFLRATSG | 3081 | -25 through -1 |
| ID1363 | MRRISLTSSPVRLLLXLXLLIALE | 3082 | -25 through -1 |
| ID1364 | MTFLLLLFXNAGRS | 3083 | -14 through -1 |
| ID1365 | MRTVVLTMKASVIEMFLVLLVTGVHS | 3084 | -26 through -1 |
| ID1366 | MSSPLLVEQSSTKSPKSWSWSFLAFSCISLLFIFFSIANS | 3085 | -40 through -1 |
| ID1367 | MYLFCLFSVSKTIPLLLLFFHLSFL | 3086 | -25 through -1 |
| ID1368 | MIVCLLILKFLSPAET | 3087 | -16 through -1 |
| ID1369 | MDKSIKSSIIWSLILCFLFILHTHT | 3088 | -25 through -1 |
| ID1370 | MFFIFINGFTLLLMTLAMKPRHPIFDLLLLLXXSNQ | 3089 | -36 through -1 |
| ID1371 | MCPSLEEAPSVKGTLPCSGQQQPFPFGASNIPLLLGRSRKVARGAPVLWPFLTWINPALS | 3090 | -60 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1372 | MLQDLLSALWFCHPCCL | 3091 | -17 through -1 |
| ID1373 | MMDLRPLLSLAAYLSGPHQ | 3092 | -19 through -1 |
| ID1374 | MEMPPCLLPGLPLVRTSFS | 3093 | -19 through -1 |
| ID1375 | MTVELWLRLRGKGLANLHVTRGVXG | 3094 | -25 through -1 |
| ID1376 | MSIEDFVNRSILILLLCSSPPDRV | 3095 | -24 through -1 |
| ID1377 | MRIHYLLFALLFLFLVPVPG | 3096 | -20 through -1 |
| ID1378 | MCLLTALVTQVIS | 3097 | -13 through -1 |
| ID1379 | MMGNPGLALVAGTPPSRS | 3098 | -18 through -1 |
| ID1380 | MNHLMPLTVLHSVLEMLRTPRTPPWPCVSLLWAPRXFA | 3099 | -38 through -1 |
| ID1381 | MGHVVFGDIKNSLLXLRASQLSEG | 3100 | -24 through -1 |
| ID1382 | MAGGRRDYSQLFGRGPGRLSRARASVVRWSPRATACPAPPSLLPDLKRQELVSRIECCGRGPVGATADFFLSLLXSVSETPG | 3101 | -81 through -1 |
| ID1383 | MFWXGSLWCFHSFISFSLS | 3102 | -19 through -1 |
| ID1384 | MAWPNVFQXGSLLSQFXXHHVVVFLLTFFSYSLLHA | 3103 | -36 through -1 |
| ID1385 | MILRNLWILAVGLSLPSSS | 3104 | -19 through -1 |
| ID1386 | MLTVNDVRFYRNVRSNHFPFVRLCGLLHLWLKVFS | 3105 | -35 through -1 |
| ID1387 | MNLKPGLPCNLFLNLCILAXPFS | 3106 | -23 through -1 |
| ID1388 | MMQGEAHPSASLLDRTIKMRKETEARKVVLAWGLLNVSMA | 3107 | -40 through -1 |
| ID1389 | MMNQTHPXXLLILAHITQS | 3108 | -19 through -1 |
| ID1390 | MGLPERRGLVLLLSLAEILF | 3109 | -20 through -1 |
| ID1391 | MWGLEEDRSYQGLRPLCWALLYNCFSSS | 3110 | -28 through -1 |
| ID1392 | MLCRDGSACVPRSRRLPLPAAVPAHGPMADXXDSARGCVVFEDVFVYPSREEWELLDDAQRLLYHDVMLENFALLASLGIAFSRS | 3111 | -85 through -1 |
| ID1393 | MLITRLQSGIDFAIQLDESTDIGSCTTLLVYVRYAWQDDFLEDFLCFLNLTSHLSG | 3112 | -56 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1394 | MESPQLHCILNSNSVACSFAVGAGFLAPLSCLAFLVLD | 3113 | -38 through -1 |
| ID1395 | MSNKYIKPSMSPGNTDHLFLLFPRSCSS | 3114 | -28 through -1 |
| ID1396 | MVELKQLGPRSFFFLFLLPPXPP | 3115 | -24 through -1 |
| ID1397 | MPYVTIPYIIVYSLILPALFFFPLHC | 3116 | -26 through -1 |
| ID1398 | MPPLAAVMGSLPLLLCMDLPHSVLS | 3117 | -25 through -1 |
| ID1399 | MLQIPERREFLFLGFPSNSWP | 3118 | -21 through -1 |
| ID1400 | MFVHFLITLFCCCVVVG | 3119 | -18 through -1 |
| ID1401 | MACFGEKRHAKSCLLHLRCLQLYWA | 3120 | -25 through -1 |
| ID1402 | MVDRDENILLKQIYSPLSLALQSSCCLC | 3121 | -28 through -1 |
| ID1403 | MKVKPPFVSVSLCVCDCVRG | 3122 | -20 through -1 |
| ID1404 | MISSCGVKYLFSHASLFFMVGSTGSLILLTSCFYTLVSS | 3123 | -39 through -1 |
| ID1405 | MGGGIAESFLCNFLVSLSLS | 3124 | -20 through -1 |
| ID1406 | MDALERGSLRNEQALVIYAGLAYFLCCQGVIFG | 3125 | -33 through -1 |
| ID1407 | MEYLFQQPGHSRGEARAAASLETLSSLWFLPLPTHVYT | 3126 | -39 through -1 |
| ID1408 | MVSSMLITILSFIFA | 3127 | -15 through -1 |
| ID1409 | MPLFTMNLVSALASSAXG | 3128 | -18 through -1 |
| ID1410 | MICKHYCIKKNNLDYLNRMVYSAQLKLILLLHCSIRVFF | 3129 | -39 through -1 |
| ID1411 | MKIPVWHKTCFLKSESFSPDNLSVSLPCRPSQVPSQGQGKSFLLLQLIHEDKA | 3130 | -53 through -1 |
| ID1412 | MGAAVFFGCTFVAFXPAFA | 3131 | -19 through -1 |
| ID1413 | MVGGLDPPGRRRFQKGFDWRNLMSSCWLAPLADG | 3132 | -34 through -1 |
| ID1414 | MSKMPVFASLLVVSCFYQISG | 3133 | -21 through -1 |
| ID1415 | MXVTQLLPFSSPDSA | 3134 | -15 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1416 | MGKAWQEMRVEWGADKGNVRSSFHFLPWALGAMA | 3135 | -34 through -1 |
| ID1417 | MKVMMRKRKKKDQCLPGICRSLKRRKSPRSPGMKVIRLSQFLLKCWP | 3136 | -47 through -1 |
| ID1418 | MTFSFFCFFPGFKPLLFHYFLFXSFSIXTLLWGLNC | 3137 | -36 through -1 |
| ID1419 | MAGGMKVAVSPAVGPGPWGSGVGGGGTVRLLLILSGCLVYG | 3138 | -41 through -1 |
| ID1420 | MVEMTGVWQCQAEAVKGLPPLLSCSCPPPLLG | 3139 | -32 through -1 |
| ID1421 | MQITPGSAAGLLPLLGNAPG | 3140 | -21 through -1 |
| ID1422 | MLLSTWLLLTLQNSVFT | 3141 | -17 through -1 |
| ID1423 | MAFHSYWGKSLQSFKTFMRVCIVLALCHTSRP | 3142 | -32 through -1 |
| ID1424 | MKLRFTLLPLVLHSQS | 3143 | -16 through -1 |
| ID1425 | MMIILGFAFCPGHFRFNFIPFLVIYSFVLS | 3144 | -30 through -1 |
| ID1426 | MNRVPADSPNMCLICLLSYIALGAIHA | 3145 | -27 through -1 |
| ID1427 | MDLFLNLPLVIGTIP | 3146 | -15 through -1 |
| ID1428 | MXXNHRNKKSIHFPLCTTIPSXMXKSCTLPLQRTWDXXPSFVHWXQARLQSPPXSHLVXLSVIRSTLVLSQCLC | 3147 | -73 through -1 |
| ID1429 | MSFIALVYSSLSFQ | 3148 | -14 through -1 |
| ID1430 | MVFDTLKSRIVLFLNSXPPIIC | 3149 | -22 through -1 |
| ID1431 | MLEMEMTWLRLCDECSRWGMASAWGRGGKLLGAQVALHPRNCSKAKIFLFSILLMSLRT | 3150 | -59 through -1 |
| ID1432 | MDDLMLFFLGALCRESG | 3151 | -17 through -1 |
| ID1433 | MVLGALNLPSQELPTLLLPVGAPG | 3152 | -25 through -1 |
| ID1434 | MLVSKIQTFVSFLSIPVLG | 3153 | -19 through -1 |
| ID1435 | MCNPVAHTFRGVHEHHANLLSTGLNILGTQA | 3154 | -31 through -1 |
| ID1436 | MQCWILLWEACTGRCQA | 3155 | -17 through -1 |
| ID1437 | MTGYPWANSITTVLCILGCHGNLCC | 3156 | -25 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1438 | MVSCDVXSYVIFTALFLXLHSVA | 3157 | -24 through -1 |
| ID1439 | MKSFDKKLFAIFLMCLKSIG | 3158 | -20 through -1 |
| ID1440 | MFGAGDEDTDFLSPSGGARLASLFGLDQXAXG | 3159 | -33 through -1 |
| ID1441 | MVLTLGESMPVLVGRRFLSLSAADGXDX | 3160 | -28 through -1 |
| ID1442 | MVIELTSVFQAMIWSQG | 3161 | -17 through -1 |
| ID1443 | MESTLGAGIVIAEALQNQLAWLENVWLMXXLXXXIPXILFLFYFPAAYYA | 3162 | -50 through -1 |
| ID1444 | MIIVSELGTPTGVLVGVFLSTFLYC | 3163 | -25 through -1 |
| ID1445 | MNWNVRGTRGFLLCPLVCGLRR | 3164 | -22 through -1 |
| ID1446 | MLRCGGRGLLLGLAVAAAA | 3165 | -19 through -1 |
| ID1447 | MILLMIVFSIFLLL | 3166 | -14 through -1 |
| ID1448 | MSLLFIFRSILISC | 3167 | -14 through -1 |
| ID1449 | MPLISKVLIQLSQAFWA | 3168 | -17 through -1 |
| ID1450 | MDTSSVGGLELTDQTPVLLGSTAMATSLT | 3169 | -29 through -1 |
| ID1451 | MDTGESFSPHTSCRGHWRILLLTHVPPWILE | 3170 | -31 through -1 |
| ID1452 | MPYLDPYITQPIIQIERKLVLLSVLKEPVSR | 3171 | -31 through -1 |
| ID1453 | MDTSSVGGLELTDQTPVLLGSTAMATSLT | 3172 | -29 through -1 |
| ID1454 | MHVLFNIVTTNXXNHFGLLDFVVQCCDS | 3173 | -28 through -1 |
| ID1455 | MPPQSCCCSKTAYWLSFMSWAQS | 3174 | -22 through -1 |
| ID1456 | MSCVFFHFLQGGLG | 3175 | -14 through -1 |
| ID1457 | MSISLSSLILLPIWINMAQI | 3176 | -20 through -1 |
| ID1458 | MTALNLVAPFSDGDSGSVSLASFCNAVVLSPVFQ | 3177 | -34 through -1 |
| ID1459 | MWSRPVQVLGLLATCQH | 3178 | -17 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1460 | MRYRLRIQITTSLNQILLFLLISC | 3179 | -24 through -1 |
| ID1461 | MPFFSNQPTQVSVLLFFCCSPLYSP | 3180 | -25 through -1 |
| ID1462 | MRVKDPTKALPEKARSKRPTVPHDEDSDDIAVGLTCQHVSHA | 3181 | -44 through -1 |
| ID1463 | MVSLGYYLIFVLYLWLCFMQISEEKLIEEHTGTYLTSSSPLCQL | 3182 | -44 through -1 |
| ID1464 | MSLTSRXXIMXTIKIQNISITKVLCCLLIATPTFF | 3183 | -35 through -1 |
| ID1465 | MXAEAAGVVSTSVAAAVA | 3184 | -18 through -1 |
| ID1466 | MWIMSSCLALTYTNS | 3185 | -15 through -1 |
| ID1467 | MPRGVYNSNALVLVTRGSSS | 3186 | -20 through -1 |
| ID1468 | MIEPCEKMKHYDMNWFLCMYECFFFHLLETEFLLPCVHPFSVIA | 3187 | -44 through -1 |
| ID1469 | MAMWNRPCQXLPQQPLVAEPTAEGEPHLPTGRELTEANRFAYAALCGISLSQXFP | 3188 | -55 through -1 |
| ID1470 | MEQVCLLVSYAVDSAAG | 3189 | -17 through -1 |
| ID1471 | MRKISHCLHCWPESGATLRCWASTPVSG | 3190 | -28 through -1 |
| ID1472 | MCINDHIIKLLHPCGSITLTSS | 3191 | -22 through -1 |
| ID1473 | MRCRVALQCGLTIPALX | 3192 | -17 through -1 |
| ID1474 | MTVRYGKFLSLLKDGAENDLTWVLKHCERFLKQQQTSIKSSLLCLQGNYAGHDMFVSSLFMIMLGDKEKTFQFLHQFSRLLTSAFLWLPRLHI | 3193 | -93 through -1 |
| ID1475 | MAFDVSCFFWVVLFSAGCKV | 3194 | -20 through -1 |
| ID1476 | MLTRLVLSAHLSSTTSPPWTHA | 3195 | -22 through -1 |
| ID1477 | MRYFQGPSPYSEIEIELCDHVYSFQGLCVNLLLGFEPVIS | 3196 | -40 through -1 |
| ID1478 | MXXKRTHXXXSVFNGLVYAAGGRNAEGSLASLECYVPSTNQ | 3197 | -41 through -1 |
| ID1479 | MFLKVQSQSFYXPYRDCLNFHKSTYLLFFHLLLNDFFT | 3198 | -38 through -1 |
| ID1480 | MQPLKIIFYLSVSIWILIIYTPQCNS | 3199 | -27 through -1 |
| ID1481 | MWRTTARVAACTAAAPLQA | 3200 | -19 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1482 | MEAATTLHPGPRPALPLGARARWASSCLHPSARS | 3201 | -34 through -1 |
| ID1483 | MQGVRGPVSFSWSTTMLCPVIFPPSNCWK | 3202 | -29 through -1 |
| ID1484 | MXXFSFXLLFXXFXFFRQ | 3203 | -18 through -1 |
| ID1485 | MLLLSEALSESVRLLFRFSVIMA | 3204 | -23 through -1 |
| ID1486 | MALISLPCTTAFPLLSS | 3205 | -17 through -1 |
| ID1487 | MSEEEAAQIPRSSVWEQDQQNVVQRVVALPLVRATCT | 3206 | -37 through -1 |
| ID1488 | MAAAAAGAAASGLPGPVAQGLKEALVDTLTGLLSPVQEVRAAAEEQIKVLEVTEEFGVHLAELTVDPQGALA | 3207 | -72 through -1 |
| ID1489 | MNSGGGFGLGLGFGLTPTSVIQVTNLSSAVTSEQMRTLFSFLGEIEELRLYPPDNAPLAFSSXVCYVKFRDPSSVGVAQHLTNTVFIDRXLXSCSLCRRLVSRFXXXYLNFCPVCYC | 3208 | -117 through -1 |
| ID1490 | MIEMLIFLDCVLS | 3209 | -13 through -1 |
| ID1491 | MHPFLAAHGPAFHKGYKHSTINIVDIYPMMCHILGLKPHPNNGTFGHTKCLLVDQWCINLPEAIAIVIGSLLVLTMLTC | 3210 | -79 through -1 |
| ID1492 | MIWPMSASVATLWS | 3211 | -14 through -1 |
| ID1493 | MGIDIFYPSHIPDFHPIHLFIYLVFVECLLC | 3212 | -31 through -1 |
| ID1494 | MKELNQKLTNKNNKIEDLEQEIKIQKQKETLQEEITSLQSSVQEYEERNXKIKQLLVKTKKELADSKQAETDHLIIQASLKGELEA | 3213 | -87 through -1 |
| ID1495 | MGNTLKEMQDVQGALQCYTRAIQINPAFADAHSNLASIHKDSGNIPEAIASYRTALKLKPDFPDAYCNLAHCLQIVCDWTDYDERMKKLVSIVADQLEKNRLLLCILIIVCYI | 3214 | -113 through -1 |
| ID1496 | MLILADTRRVQGGTLGLIPAVLNRVHVAYAIPSIPSLFC | 3215 | -39 through -1 |
| ID1497 | MLVGIYPCVFLFPLISNTSS | 3216 | -20 through -1 |
| ID1498 | MFLAPSLLITKLLTGSESPDGNPPALGRPLLLQGACPCLIFL | 3217 | -42 through -1 |
| ID1499 | MDPSASKSCLFYLQKVSG | 3218 | -18 through -1 |
| ID1500 | MSLTASGPRAAWERVGGLHTWGANIPTAPDSQRWLCLQAYLASFS | 3219 | -46 through -1 |
| ID1501 | MKYQMVSGSAQLASPLLPGATP | 3220 | -22 through -1 |
| ID1502 | MNGTFPGTYVYLVAYGDLRIFGCFWGLMYXWLLLG | 3221 | -35 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1503 | MGPSTPLLILFLLSWSGPLQG | 3222 | -21 through -1 |
| ID1504 | MKFISTSLLLMLLVSSLSPVQG | 3223 | -22 through -1 |
| ID1505 | MNYQYGFNMVMSHPHAVNEIALSLNNKNPRTKALVLELLAAVCLVRG | 3224 | -47 through -1 |
| ID1506 | MAQSIHMYAARVQWGLVMCFLSYFGTFA | 3225 | -28 through -1 |
| ID1507 | MGSGYSHSLHLFHLLIRPXQG | 3226 | -21 through -1 |
| ID1508 | MARCFSLVLLLTSIWT | 3227 | -16 through -1 |
| ID1509 | MAMRYNRLTVLAGAMLALGLMTCLSVLFGYATS | 3228 | -33 through -1 |
| ID1510 | MPQQPVEQGSPLLRQLLLPLPPFSFP | 3229 | -26 through -1 |
| ID1511 | MPSRSPFTWSHLCWRAGRCPRWRACLSSSSVRMCSPAAPSRFGALGXSARRWPRRDADTWCAPQGVMRASLLPMLLGSWA | 3230 | -80 through -1 |
| ID1512 | MSHTEVKLKIPFGNKLLDAVCLVPNKSLTYGIILTHGASG | 3231 | -40 through -1 |
| ID1513 | MELGSCLEGGREAAEBEGEPEVKKRRLLCXEFXSVASCDA | 3232 | -40 through -1 |
| ID1514 | MGRTYIVEETVGQYLSNINLQGKAFVSGLLIGQCSS | 3233 | -36 through -1 |
| ID1515 | MGSRKCGGCLSCLLIPLALWS | 3234 | -21 through -1 |
| ID1516 | MGSRKCGGCLSCLLIPLALWS | 3235 | -21 through -1 |
| ID1517 | MWWFQQGLSFLPSALVIWTSA | 3236 | -21 through -1 |
| ID1518 | MFNASTFTDWSSSIFFVTFKSKKSAGLPLIFSLWCSGVLL | 3237 | -41 through -1 |
| ID1519 | MKMASSLAFLLLNFHVSLLLVQLLTPCSA | 3238 | -29 through -1 |
| ID1520 | MHILQLLTTVDDGIQAIVHCPDTGKDIWNLLFDIVCHEFCQS | 3239 | -42 through -1 |
| ID1521 | MSDQIKFIMDSLNKEPFRKNYNLITFXSLEPMQLLQVLSDVLA | 3240 | -43 through -1 |
| ID1522 | MATSSQXRQLLSDYGPPSLGYTQGTGNSQXPQSKYAELLAIIXELGKEIRPMYAGSKSAMERLKRGIIHAXGLVRECLA | 3241 | -79 through -1 |
| ID1523 | MRLLGAAAVAALGRG | 3242 | -15 through -1 |
| ID1524 | MAQRLLLRRFLASVIS | 3243 | -16 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1525 | MFRLNSLSALAELAVG | 3244 | -16 through -1 |
| ID1526 | MSGSNGSKENSHNKARTSPYPGSKVERSQVPNEKVGMLVEWQDYKPVEYTAVSVLAGPRWA | 3245 | -61 through -1 |
| ID1527 | MRTTLMFSLTAQWXTS | 3246 | -16 through -1 |
| ID1528 | MSDLLLLGLIGGLTLLLLLTLLAFA | 3247 | -25 through -1 |
| ID1529 | MEGTEMGARPGGHPXKKWSFLWSLALWLPLALS | 3248 | -32 through -1 |
| ID1530 | MXFLRKVXSILSLQVLLTTVTSTVFLYPESVRTFVXESPALILLFALGSLGLIFA | 3249 | -55 through -1 |
| ID1531 | MAATLGPLGSWQQWRRCLSARDGSRMLLLLLLGSGQG | 3250 | -38 through -1 |
| ID1532 | MSSWMYLGYPIVTSNTTCLKLISSSFPQILPFLLFPPVNA | 3251 | -41 through -1 |
| ID1533 | MAPGVIIIQLCLLLLPSCSLS | 3252 | -21 through -1 |
| ID1534 | MRHGFIQQQFSLTAFSXXXXIFTLXXLSQLLSSAAPKHTAAPTALPCLQGQQLNSLSLGTSELSCVLASSCLSTKTDPSGLSLSLGASAPVQC | 3253 | -93 through -1 |
| ID1535 | MFQNIQKCLNVPFVRGYHVFYINLNAVILIIFLSFLPFINS | 3254 | -41 through -1 |
| ID1536 | MSLSQRGFPVLALFLSGSLA | 3255 | -20 through -1 |
| ID1537 | MAARWRFWCVSVTMVVALLIVCDVPSASA | 3256 | -29 through -1 |
| ID1538 | MFAPAVMRAFRKNKTLGYGVPMLLLIVGGSFG | 3257 | -32 through -1 |
| ID1539 | MELPSGPGPERLFDSHRLPGDCFLLLVLLLYAPVGFC | 3258 | -37 through -1 |
| ID1540 | MAQSQGWVXRYXKAFCKGFFVAVPVAVTFLDRVACVARVEGASMQPSLNPGGSXSSDVVXXNHWKVRNFEVHRGDIVSLVLLTVTPSXRQ | 3259 | -90 through -1 |
| ID1541 | MSSAAADHWAWLLVLSFVFGCNV | 3260 | -23 through -1 |
| ID1542 | MNLFKTNHVFFLLLLAHIIA | 3261 | -20 through -1 |
| ID1543 | MPALLPVASRLLLLPRVLLTMASG | 3262 | -24 through -1 |
| ID1544 | MIGSGLAGSGGAGGPSSTVTWCALFSNHVAATQASLLLSFVMPALLPVASRLLLLPRVLLTMASG | 3263 | -66 through -1 |
| ID1545 | MPALLPVASRLLLLPRVLLTMASG | 3264 | -24 through -1 |
| ID1546 | MEASWGSFNAERGWYVSVQQPEEAEAEELSPLLSNELHRQRSPGVSFGLSVFNLMNAIMGSGILGLAYVMANTGVFGFSFLLLTVALLASYS | 3265 | -92 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1547 | MPSSFFLLLRFFLRIDG | 3266 | -17 through -1 |
| ID1548 | MKRTHLFIVGIYFLSSCRA | 3267 | -19 through -1 |
| ID1549 | MGDKIWLPFPVLLLAALPPVLLP | 3268 | -23 through -1 |
| ID1550 | MPHSSLHPSIPCPRGHGAQKAALVLLSACLVTLMGLG | 3269 | -37 through -1 |
| ID1551 | MGAWGRGWPWEERQGHHLLLLLLPAPTLK | 3270 | -29 through -1 |
| ID1552 | MGQCGITSSKTVLVFLNLIFWGAAGILCYVGAVFITYDDYDHFFEDVYTLIPAVVIIAVRALLFIIGLIGCCAT | 3271 | -75 through -1 |
| ID1553 | MPXAFSVSSFPVSIPAVLTQTDWTEPWLMGLATFHALCVLLTCLSSRSYRLQIGHFLCLVILVYC | 3272 | -65 through -1 |
| ID1554 | MLLSLFFPLRISL | 3273 | -14 through -1 |
| ID1555 | METGERARLILIVLQLLLRIRR | 3274 | -23 through -1 |
| ID1556 | MCGXXFSLPCLRLFLVVTCYXLLLLHKEILGCSSVCQLCTG | 3275 | -41 through -1 |
| ID1557 | MNPVTESPSCLFSPPSESALASQLALSASCDQRAPFSLAGVXSXXPRLASRQVAPPFGSRACCFLSAFSPTLT | 3276 | -73 through -1 |
| ID1558 | MSRSSKVVLGLSVLLTAATVA | 3277 | -21 through -1 |
| ID1559 | MGIQTSPVLLASLGVGVLVTLLGLAVG | 3278 | -26 through -1 |
| ID1560 | MYPSYLLIXPPIPSQFLKQCXPPTLSDPFLPLALRSLDVLLLSSAXLVXXS | 3279 | -51 through -1 |
| ID1561 | MEQKHRXELEQLKLXTKENKILLLXTFQTWCLR | 3280 | -33 through -1 |
| ID1562 | MMTAPVLAAQTLKFLTLLQKSNA | 3281 | -23 through -1 |
| ID1563 | MDSAACAAAATPVPALALAXAPDLAQA | 3282 | -27 through -1 |
| ID1564 | MASLGLQLVGYILGLLGLLGTLVA | 3283 | -24 through -1 |
| ID1565 | MASLGLQLVGYILGLLGLLGTLVA | 3284 | -24 through -1 |
| ID1566 | MLCSLLLCECLLLVAGYA | 3285 | -18 through -1 |
| ID1567 | MASRLCGGALWYVCPCPSGAWM | 3286 | -22 through -1 |
| ID1568 | MTSALTQGLERIPDQLGYIVLSEGAVLA | 3287 | -28 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1569 | MASPSRRLQTKPVITCFKSVLLIXTXIXWITGVILLAVGIWG | 3288 | -42 through -1 |
| ID1570 | MADAASQVLLGSGLTILSQP | 3289 | -20 through -1 |
| ID1571 | MSRNLRTALIFGGFISLIGA | 3290 | -20 through -1 |
| ID1572 | MPHGLWCFHLVVLSLYS | 3291 | -17 through -1 |
| ID1573 | MSLVAVFLSCGLIS | 3292 | -14 through -1 |
| ID1574 | MMKRAAAAVGGALAVGAVPVVLS | 3293 | -24 through -1 |
| ID1575 | MAVIVDKPMFYDMKKVWEGYPIQSTIPSQYWYMIELSFYWSLLFSIASDVKRKDFKEQIIHHVATILISFSWFANYIRA | 3294 | -81 through -1 |
| ID1576 | MIISLFIYIFLTCSNT | 3295 | -16 through -1 |
| ID1577 | MAAELVEAKNMVMSFRVSDLQMLLGFVGRSKS | 3296 | -32 through -1 |
| ID1578 | MTGLSMXGGGSXXGDVXPXYYGKXGPLRXLPEPSGPLPPSSGLSQPQVHALCPLSPLVTT | 3297 | -60 through -1 |
| ID1579 | MQMYSRQLASXEWLTIQGGLLGXGLXXXSLT | 3298 | -31 through -1 |
| ID1580 | MASLEVSRSPRRSRRELEVRSPRQNKYSVLLPTYNERENLPLIVWLLVKSFSES | 3299 | -54 through -1 |
| ID1581 | MDKDSQGLLDSSLMASGTAS | 3300 | -20 through -1 |
| ID1582 | MGLLTFGYIEXXXKTEHNPDHHSCLAVSWEAAGCHG | 3301 | -36 through -1 |
| ID1583 | MGLYAAVAGVLAGVES | 3302 | -16 through -1 |
| ID1584 | MGLYAAAAGVLAGVESRQGSIKGLVYSSNFQNVKQLYALVCETQRYSAVLDAVIASAGLLDA | 3303 | -62 through -1 |
| ID1585 | MGAQHTALLLNTEVRWLSRGKVLVRLFELRRELLVFMDSAFRLSDCLTNSSWLLRLAYLADIFT | 3304 | -64 through -1 |
| ID1586 | MSLRNLWRDYKVLVVMVPLVGLIHL | 3305 | -25 through -1 |
| ID1587 | MVLRSLVEYSQDVLAHPVSEEHLPDVSLIGEFSDPAELGKLLQLVLIGCAIS | 3306 | -51 through -1 |
| ID1588 | MIHGFCLAPTTSA | 3307 | -13 through -1 |
| ID1589 | MXCPRTWCLACVEASPG | 3308 | -17 through -1 |
| ID1590 | MADVEDGEETCALASHSGSSG | 3309 | -21 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1591 | MFKVAAPPMLIXXIIMFLLIIVCGSP | 3310 | -26 through -1 |
| ID1592 | MDFWDPAVFXMCLWSLRNLFS | 3311 | -21 through -1 |
| ID1593 | MSPAGKHNSESKFTFFVALDGSVPLLSLSHSIGI | 3312 | -34 through -1 |
| ID1594 | MHWALVCVGLHTEGPWG | 3313 | -17 through -1 |
| ID1595 | MFGAAARSADLVLLEKNLQAAHGYAQEDRERNHRXIVSLXQNLLNFMIGSILDLMQCFLWFYIGSSLNGTRG | 3314 | -72 through -1 |
| ID1596 | MAARWRFWCVSVTMVALLIVCDVPSA | 3315 | -27 through -1 |
| ID1597 | MVVLLLQPSMIQEVWT | 3316 | -16 through -1 |
| ID1598 | MLHLHXSCLCFRSWLPAMLAVLLSLAPSASS | 3317 | -31 through -1 |
| ID1599 | MRVRIGLTLLLCAVLLSLASA | 3318 | -21 through -1 |
| ID1600 | MGLHLRPYRVGLLPDGLLFLLLLMLLA | 3319 | -28 through -1 |
| ID1601 | MATLSFVFLLLGAVSWPPASA | 3320 | -21 through -1 |
| ID1602 | MFLFLSPATPVLPPSLDSRDLLPHLFWGRAGSSSSPALSPVLCLRGLVSLAFQ | 3321 | -54 through -1 |
| ID1603 | MWAMESGHLLWALLFMQSLWP | 3322 | -21 through -1 |
| ID1604 | MTHYRNILGLLCCVLATMA | 3323 | -19 through -1 |
| ID1605 | MKLLLLASLIERSS | 3324 | -15 through -1 |
| ID1606 | MARNQALVCLPSFQNAFIPVEDLPTSFXLFLALCASFS | 3325 | -38 through -1 |
| ID1607 | MPNESWQIPCGKQEAETLFNFQSLLLLFYSFYVLA | 3326 | -35 through -1 |
| ID1608 | MQTTFIDVTVDQHVAKSNDHLSVLVLLICLVSSYLP | 3327 | -36 through -1 |
| ID1609 | MALGEEKAEAEASXDTKAQSYGRGSCRERELDIPGPMSGEQPPRLEAEGGLISPVWGAEXYLPLLAGLGLTLA | 3328 | -73 through -1 |
| ID1610 | MTSLYLKHLLCISPFVPPTSG | 3329 | -21 through -1 |
| ID1611 | MTDSPNAHGLALTTKWMPAVSLNLTYYLPSWYLCLATLTLFHTSFS | 3330 | -47 through -1 |
| ID1612 | MASSHWNETTSVYQYLGFQVQKIYPFHDNWNTACFVILLLFIFTVVS | 3331 | -48 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1613 | MSLLFVFCLECSIFLLNMWVACLLS | 3332 | -25 through -1 |
| ID1614 | MFVVTVLLLLPLVAFITL | 3333 | -18 through -1 |
| ID1615 | MNRSCRNTGIIYALQFLFIVFA | 3334 | -22 through -1 |
| ID1616 | MTQTTWGAPTRASNHPLPAMLTLSLLLAWVTLTHL | 3335 | -35 through -1 |
| ID1617 | MLKXXAVLCVCAAAWC | 3336 | -16 through -1 |
| ID1618 | MISAHCNLHLLGSSISPASA | 3337 | -20 through -1 |
| ID1619 | MXXKACRTLAWLPXPFLPFLLSLPLDQT | 3338 | -28 through -1 |
| ID1620 | MAVKRLGLLLVFLPHPQRG | 3339 | -19 through -1 |
| ID1621 | MQAVDNLTSAPGNTSLCTRDYKITQVLFPLLYTVLFFVGLITNGLAMRIFFQIRSKSNFIIFLKNTVISDLLMILTPFKILS | 3340 | -83 through -1 |
| ID1622 | MWTLPSLSASFQPFLGSLRPSHILWFFLPSLXCPEC | 3341 | -36 through -1 |
| ID1623 | MSLTDVPMSLLLFQPSSHSATG | 3342 | -22 through -1 |
| ID1624 | MDWSLAFLLVSLYWSHM | 3343 | -17 through -1 |
| ID1625 | MYLLILFMVGRIIP | 3344 | -15 through -1 |
| ID1626 | MNKPPWEESWGQNQLSGEPATWSLCISPLPGREPSLLVVSCCLLFHQA | 3345 | -48 through -1 |
| ID1627 | MLLIELTWMLSFLILLSIDSLVSG | 3346 | -24 through -1 |
| ID1628 | MKLQRSPAPRIECSAILRRAERLVWNDVCSESQSQSRDSCLLGAAWASRLRT | 3347 | -52 through -1 |
| ID1629 | MVIFTLCVFTLPFLCA | 3348 | -16 through -1 |
| ID1630 | MWGALPVLVVGTWSSQGQA | 3349 | -19 through -1 |
| ID1631 | MTRLVCGFLQISLSLA | 3350 | -16 through -1 |
| ID1632 | MNFLLPLLLHHLTFH | 3351 | -15 through -1 |
| ID1633 | MLSARDRRDRHPEGVVAELQGPAVDKAFLTSHKGILLETELALTLIIFICXTASISA | 3352 | -58 through -1 |
| ID1634 | MLTMSVTLSPLRS | 3353 | -13 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1635 | MFXPVALIFPISVSDPTIHPITQAQNLESXLQSFFLLISSVRPISQ | 3354 | -46 through -1 |
| ID1636 | MLLFPFPGETVSLHHPCMCAVLRSWLAASS | 3355 | -31 through -1 |
| ID1637 | MPLKNLFSVGLMDPYNLLKKHVLVVVCYLSWRVSS | 3356 | -35 through -1 |
| ID1638 | MAMAQKLSHLLPSLRQVIQ | 3357 | -19 through -1 |
| ID1639 | MIAPTLKGTPSSSAPLAIVALAPHSVQK | 3358 | -28 through -1 |
| ID1640 | MCLFPVSPCPAYSFSSEXXGAVLLLVESLCLVFNLLS | 3359 | -37 through -1 |
| ID1641 | MKIAVLFCFLLLIF | 3360 | -15 through -1 |
| ID1642 | MCSPRSPLNLSLVPVGAVLLSSLPISP | 3361 | -27 through -1 |
| ID1643 | MGLHISLIKFLLANGPHIPSHQRPFEPKGEKSCRIEVVTLPLTSHCLA | 3362 | -48 through -1 |
| ID1644 | MKTTYVIFMQSKALLTLYVFVASSMQ | 3363 | -26 through -1 |
| ID1645 | MNALVFLIFLRFINI | 3364 | -15 through -1 |
| ID1646 | MQLGPLHTVSTPFFCWGFLLTGHSLSHS | 3365 | -29 through -1 |
| ID1647 | MGRGWERTVCSLGWRGGPDPLSWATCWSGARSRHTRVSSIVNGYVGSVCCCCVGPLRG | 3366 | -57 through -1 |
| ID1648 | MPEAVEQSAHLFVTWSSQRALS | 3367 | -22 through -1 |
| ID1649 | MPGTHTFTFKSCWLIALSVPLVFW | 3368 | -24 through -1 |
| ID1650 | MLLLTFKWFLFCLIGLDLLCQV | 3369 | -22 through -1 |
| ID1651 | MATTGRRQAEPPPVRPAHSRPPPVPGSSSLGLAGLMSPVPNLHLLLPLTTP | 3370 | -52 through -1 |
| ID1652 | MVPFIYLQAHFTLCSG | 3371 | -16 through -1 |
| ID1653 | MFFSFLLTINLVSL | 3372 | -14 through -1 |
| ID1654 | MWPGRECKNWGLLCFASECTT | 3373 | -21 through -1 |
| ID1655 | MLTPFSLEEKLLECHYVLAKLAGACLLLTLRQPPTHS | 3374 | -37 through -1 |
| ID1656 | MKRIKSMMGKVEHIKIKGEKQRSRHVKIVFVGLIFLKSSA | 3375 | -40 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1657 | MQSALCLFCKICPFTHG | 3376 | -17 through -1 |
| ID1658 | MMHNIIVKELIVTFFLGITVVQMLISVTGLKGVEAQNGSESEVFVGKYETLVFYWPSLLCLAFLLGRFL | 3377 | -69 through -1 |
| ID1659 | MSNCLQNFLKITSTRLLCSRLCQQLRS | 3378 | -27 through -1 |
| ID1660 | MSGXGLFLRTTAAARA | 3379 | -16 through -1 |
| ID1661 | MNPLHKHCAAGPLTWLHLLLSHLKS | 3380 | -25 through -1 |
| ID1662 | MPKDKRGARHNSPHFSFAVLRVLHLPALT | 3381 | -29 through -1 |
| ID1663 | MTIHVLRKCCQMGRLNNEWLPGLVIPLCVSRQLLTGART | 3382 | -39 through -1 |
| ID1664 | MQAASFGRGPNGLDNWGIAALLGLLQLRFK | 3383 | -30 through -1 |
| ID1665 | MSPSLGDRCSSWLHLVSHLESISGPLLNIPENLLLCCHRCTNC | 3384 | -43 through -1 |
| ID1666 | MSGAEPTTFIRYFLLPCLINLAIG | 3385 | -24 through -1 |
| ID1667 | MVYDYFISQQLLFSFLLSTIPT | 3386 | -22 through -1 |
| ID1668 | MLFLCSCSLSLNQL | 3387 | -14 through -1 |
| ID1669 | MFFLMVLLFRSNKWT | 3388 | -15 through -1 |
| ID1670 | MLPLQGLCTCYFLHLEPLSHVTTSLASSS | 3389 | -29 through -1 |
| ID1671 | MYFYGLTFHFFLLLNTILLFG | 3390 | -21 through -1 |
| ID1672 | MRWNLFFFCILRNQTKLWASQGSLQDAQS | 3391 | -29 through -1 |
| ID1673 | MFIAALFTMAKTWN | 3392 | -14 through -1 |
| ID1674 | MPGXKHFLRVFRXSAXRSVGYXXKPGTSRASLWVXLPXXXVIAS | 3393 | -44 through -1 |
| ID1675 | MRLESPDENFAVVQEHAIHHIDGPLRRFLLLEVHEPVALGPLFVTGHFA | 3394 | -49 through -1 |
| ID1676 | MAGSPDREVLLPTVLRGSYC | 3395 | -20 through -1 |
| ID1677 | MHVSMLEGFDENLDVQGELILQDAFQVWDPKSLIRKGRERHLFLFEISLVFS | 3396 | -52 through -1 |
| ID1678 | MNVGTAHSEVNXNTRVMXXRGIWLSYVLAIGLLHIVLLS | 3397 | -39 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1679 | MLSFVXAIXXYIPTNS | 3398 | -16 through -1 |
| ID1680 | MDEYSWWCHVLEVVKGQMPTFINITLWLGSLC | 3399 | -32 through -1 |
| ID1681 | MRRKGQGHLAFIFLIQIWKTCLS | 3400 | -23 through -1 |
| ID1682 | MFLISGHVHLIYNILFLAVSSFSMP | 3401 | -25 through -1 |
| ID1683 | MTPRILSEVQFSAFCPYWTIARILERVGSACFRLELCAAIVGYFVLDVRTFLFIVVCVICVTLN | 3402 | -64 through -1 |
| ID1684 | MCSLLSGWGQLLRC | 3403 | -14 through -1 |
| ID1685 | MLFSFCFPVHFWNPSSLFPPSSVVSLIPNFSASGLCA | 3404 | -37 through -1 |
| ID1686 | MTWLRILFVIGSXL | 3405 | -15 through -1 |
| ID1687 | MSSTYCGNSSAKMSVNEVSAFSLSLEQKTGFAFVGILCIFLGLLIIRC | 3406 | -48 through -1 |
| ID1688 | MTDIWLTMLSMIVGATCY | 3407 | -18 through -1 |
| ID1689 | MXXCWIYAFISLGYILG | 3408 | -17 through -1 |
| ID1690 | MFIRTLKTTVLPFMRTAPQLALSWVPPXCRV | 3409 | -31 through -1 |
| ID1691 | MRTGAEMRTNSSVLIFCLLPYIYH | 3410 | -24 through -1 |
| ID1692 | MIVIPSWLENEGLELGFSHRTFA | 3411 | -23 through -1 |
| ID1693 | MLKKEIAHHSPSLVSCPVCTTKYRTLRLLRVISVFLSFLPSYP | 3412 | -43 through -1 |
| ID1694 | MTXPSRAQTVDXGIAKHCAYSLPGVALTLG | 3413 | -30 through -1 |
| ID1695 | MPFRLLIPLGLLCSLLAPMVLA | 3414 | -21 through -1 |
| ID1696 | MXLVLVFLCSLLAPMVLA | 3415 | -18 through -1 |
| ID1697 | MALRRPPRLRLCARLPDFFLLLLFRGCLIG | 3416 | -30 through -1 |
| ID1698 | MGGNGSTCKPDTERQGTLSTAAPTTSPAPCLSNHHNKKHLILAFCAGVLLTLLLIAFIFL | 3417 | -60 through -1 |
| ID1699 | MGTADSDEMAPEAPQHTHIDVHIHQESALAKLLLTCCSA | 3418 | -39 through -1 |
| ID1700 | MSLLSFLFARVNLG | 3419 | -14 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1701 | MARSPLRRRGRPTWSLSTPRPGSPTSSSRSRWCCPARLTLTSG | 3420 | -43 through -1 |
| ID1702 | MKIITTLLLACHLQLEVG | 3421 | -19 through -1 |
| ID1703 | MLMPVVGRGNGIPQTVSEWLRLLPFLGVLALLGYLAV | 3422 | -37 through -1 |
| ID1704 | MDRLGSFSNDPSDKPPCRGCSSYLMEPYIKCAECGPPPFFLCLQCFTRG | 3423 | -49 through -1 |
| ID1705 | MSDVNVSALPIKNSGHIYNKNISQKDCDCLHVVEPMPVRGPDVEAYCLRCECKYEERSSVTIKVTIIYLSILGLLLLYMVYLTL | 3424 | -87 through -1 |
| ID1706 | MAXCRRCRSQRRSHCCQDRRLRRPRLTLWRHHTALSLSLSMAPPNP | 3425 | -46 through -1 |
| ID1707 | MTRLGGKGGQQFPPGQKIISKDILALTALSVXRKXS | 3426 | -36 through -1 |
| ID1708 | MKGWGWLALLLGALLGTAWA | 3427 | -20 through -1 |
| ID1709 | MHRLLCLLLLFGGGDP | 3428 | -16 through -1 |
| ID1710 | MLWRQLIYWQLLALFFLPFCLC | 3429 | -22 through -1 |
| ID1711 | MRLLLLIVAASAMVRS | 3430 | -17 through -1 |
| ID1712 | MSSGXELMPGAALLVLLGVAASLC | 3431 | -25 through -1 |
| ID1713 | MTKEIFFFTXTELVCENKELCSSPRWRNAIQKSNFSKVTSFFMSCHHFKGLAPLPHVYTQGNCRPISCLGLTLMPFASS | 3432 | -78 through -1 |
| ID1714 | MTTDIGCLYFRALCLPRGAWG | 3433 | -21 through -1 |
| ID1715 | MVPSLVIPDLTCLFLFLNLRWS | 3434 | -22 through -1 |
| ID1716 | MALRLLKLAATSASA | 3435 | -15 through -1 |
| ID1717 | MWGNKFGVLLFLYSVLLTKG | 3436 | -20 through -1 |
| ID1718 | MYTFRKLSPYLNKIVFVCSSVLGQSWG | 3437 | -27 through -1 |
| ID1719 | MESRVLLRTFCLIFGLGAVWG | 3438 | -21 through -1 |
| ID1720 | MLVLKKHSVNIAAQTCFKFNFIFRILIFLGFFLGLFH | 3439 | -37 through -1 |
| ID1721 | MDVKCPGCYKITTVFSHAQTVVLCVGCSTVLC | 3440 | -32 through -1 |
| ID1722 | MCIILSVLHALPAGIA | 3441 | -16 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1723 | MLVVEASSVRLASSEVTSWSIIVTPSASTPIISLSAGPLRTPSHSKTWLLGALEPASE | 3442 | -60 through -1 |
| ID1724 | MYSFPTTVVEEILSLSLQLIAPPTVSC | 3443 | -27 through -1 |
| ID1725 | MLMLLPLRSLLALVRE | 3444 | -16 through -1 |
| ID1726 | MVPLVAVVSGPPAQLFACLLRLGTQ | 3445 | -25 through -1 |
| ID1727 | MDNRFATAFVIACVLSLIST | 3446 | -20 through -1 |
| ID1728 | MPEYCGNEVTPTEAAQAPEVTYEAEEGSLWTLLLTSLDGHLL | 3447 | -42 through -1 |
| ID1729 | MNRVLCAPAAGAVRA | 3448 | -15 through -1 |
| ID1730 | MAFTFAAFCYMLALLLTAALIFF | 3449 | -23 through -1 |
| ID1731 | MXXXXEXLLAFHHDCEA | 3450 | -17 through -1 |
| ID1732 | MGPYNVAVPSDVSHARFYFLFHRPLRLLNLLILIEG | 3451 | -36 through -1 |
| ID1733 | MMNFRQRMGWIGVGLYLLASAAA | 3452 | -23 through -1 |
| ID1734 | MLFASGGFXVKLYDIEQQQIRNALENIRKEMKLLEQAGSLKGSLSVEEQLSLISGCPNIQEAVEGAMHIQECVPEDLELKKKIFAQLDSIIDESSDLKRFXFLSHAFXVVCWLGPCEA | 3453 | -118 through -1 |
| ID1735 | MQCFLGGLGLCSLPLSPSAVCP | 3454 | -22 through -1 |
| ID1736 | MSSFLLSFSQSLS | 3455 | -13 through -1 |
| ID1737 | MLTASLAFQLVDG | 3456 | -13 through -1 |
| ID1738 | MYXRRELSILCILSAFNFLVCLSLG | 3457 | -25 through -1 |
| ID1739 | MGLSAMDTSIVFGVSWVMLVYS | 3458 | -22 through -1 |
| ID1740 | MYFWRDVAVSLDTLWALPRQQPGLGNNRVLGLLSGTNKDYKGQKLAEQMFQGIILFSAIVGFIYG | 3459 | -65 through -1 |
| ID1741 | MHWGKRWXLXXGGLLICXLXIGTATP | 3460 | -26 through -1 |
| ID1742 | MAXRYNRLTVLAGAXLALGLXTCLSVLFG | 3461 | -29 through -1 |
| ID1743 | MGFTGFFTATCFISKVFMTCILCRPPISS | 3462 | -29 through -1 |
| ID1744 | MIMYLFVICVIFEIIRNYAFSILIVLLPVLFFSLK | 3463 | -35 through -1 |

TABLE III-continued

| SEQ. ID NO. OF NUCLEIC ACID ENCODING A POLYPEPTIDE CONTAINING A SIGNAL SEQUENCE | SIGNAL PEPTIDE SEQUENCE | SEQ. ID NO. OF POLYPEPTIDE CONTAINING A SIGNAL PEPTIDE | LOCATION OF SIGNAL PEPTIDE IN POLYPEPTIDE SEQUENCE |
|---|---|---|---|
| ID1745 | MSTVGLXHFPXPLTRICPAPWGLRLWEKLTLLSPGIA | 3464 | -37 through -1 |
| ID1746 | MLALAXHLSTVES | 3465 | -13 through -1 |
| ID1747 | MLLSIGMLMLXATQVYTILTVQLFAFLNLLPVEA | 3466 | -34 through -1 |
| ID1748 | MSTVGLFHFPTPLTRICPAPWGLRLWEKLTLLSPGIA | 3467 | -37 through -1 |
| ID1749 | MELTIFILRLAIYILTFPLYLLNFLGLWSWICK | 3468 | -33 through -1 |
| ID1750 | MSLLHGNKNCVTIRPTGQPLNGDLLLYLCCMINIHH | 3469 | -37 through -1 |
| ID1751 | MSFNISYFIAFPNLSQA | 3470 | -17 through -1 |
| ID1752 | MKLKXNVLTIILLPVHLLIT | 3471 | -20 through -1 |
| ID1753 | MAALVTVLFTGVRR | 3472 | -14 through -1 |
| ID1754 | MASVGECPAPVPVKDKKLLEVKLGELPSWILMRDFSPSGIFG | 3473 | -42 through -1 |
| ID1755 | MLALLVLVTVALASA | 3474 | -15 through -1 |
| ID1756 | MRIISRQIVLLFSGFWGLAMG | 3475 | -21 through -1 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07393663B2). An electronic copy of the "Sequence Listing" will also be available from the USPTO upon request and payment of the fee set forth in 37 CFR 1.19(b)(3).

We claim:

1. A purified and isolated nucleic acid sequence encoding a polypeptide comprising amino acids −26 to −1 of SEQ ID NO: 2259 fused in frame to the 5' end of a polynucleotide sequence encoding a heterologous polypeptide.

2. The purified and isolated nucleic acid sequence of claim 1, wherein said nucleic acid sequence comprises nucleotides 170 to 247 of SEQ ID NO: 540.

3. A method of making a cDNA encoding a human secreted protein wherein said method comprises die steps of:
    a) contacting a collection of mRNA molecules from human cells with a primer comprising at least 15 consecutive nucleotides of a sequence complementary to a sequence of SEQ ID NO: 540;
    b) hybridizing said primer to an mRNA in said collection;
    c) reverse transcribing said hybridized primer to make a first cDNA strand from said mRNA;
    d) making a second cDNA strand complementary to said first cDNA strand; and
    e) isolating the resulting cDNA encoding said polypeptide comprising said first cDNA strand and said second cDNA strand.

4. A method of making a cDNA encoding a human secreted protein comprising the steps of:
    a) obtaining a cDNA comprising a sequence of SEQ ID NO: 540;
    b) contacting said cDNA with a detectable probe comprising at least 15 consecutive nucleotides of said sequence of SEQ ID NO: 540 or a sequence complementary thereto under conditions which permit said probe to hybridize to said cDNA;
    c) identifying a cDNA which hybridizes to said detectable probe; and
    d) isolating said cDNA which hybridizes to said probe.

5. A method of making a cDNA encoding a human secreted protein comprising the steps of:
    a) contacting a collection of mRNA molecules from human cells with a first primer capable of hybridizing to the polyA tail of said mRNA;
    b) hybridizing said first primer to said polyA tail;
    c) reverse transcribing said mRNA to make a first cDNA strand;
    d) making a second cDNA strand complementary to said first cDNA strand using at least one punier comprising at least 15 nucleotides of a sequence SEQ ID NO:540; and
    e) isolating the resulting cDNA comprising said first cDNA strand and said second cDNA strand.

6. A method of making a polypeptide comprising the steps of:
    a) introducing into a host cell or organism a nucleic acid sequence encoding a polypeptide comprising amino acids −26 to −1 of SEQ ID NO: 2259 fused in frame to the 5' end of a polynucleotide sequence encoding a heterologous polypeptide
    b) providing conditions that allow for the expression and secretion of said polypeptide by said host cell, organism, or tissue.

7. The method of claim 6, wherein said nucleic acid is operably linked to a promoter.

8. The method of claim 6, further comprising the recovery of said expressed and secreted polypeptide.

9. The method of claim 8, wherein the step of isolating the expressed and secreted protein comprises purifying the secreted protein from the supernatant, the culture medium or the cell extract of said host cell, organism, or tissue.

10. The method of claim 6, wherein said nucleic acid encodes a polypeptide comprising amino acids −26 to −1 of SEQ ID NO: 2259.

11. A vector comprising a nucleic acid encoding a polypeptide comprising amino acids −26 to −1 of SEQ ID NO: 2259 fused in frame to the 5' end of a polynucleotide sequence encoding a heterologous polypeptide.

12. A purified and isolated nucleic acid sequence encoding a polypeptide comprising:
    a) amino acids −1 to 29 of SEQ ID NO: 2259; or
    b) amino acids −26 to 29 of SEQ ID NO: 2259.

13. The purified and isolated nucleic acid sequence of claim 12, wherein said nucleic acid sequence encodes amino acids 1 to 29 of SEQ ID NO: 2259.

14. The purified and isolated nucleic acid sequence of claim 12, wherein said nucleic acid sequence encodes amino acids −26 to 29 of SEQ ID NO: 2259.

15. The purified and isolated nucleic acid sequence of claim 14, wherein said nucleic acid sequence comprises nucleotides 170 to 334 of SEQ ID NO: 540.

16. A vector comprising a nucleic acid sequence encoding a polypeptide comprising:
    a) amino acids 1 to 29 of SEQ ID NO: 2259; or
    b) amino acids −26 to 29 of SEQ ID NO: 2259.

17. The vector of claim 16, wherein said nucleic acid sequence encodes amino acids 1 to 29 of SEQ ID NO: 2259.

18. The vector of claim 16, wherein said nucleic acid sequence encodes amino acids −26 to 29 of SEQ ID NO: 2259.

19. The vector of claim 16, wherein said nucleic acid sequence comprises nucleotides 170 to 334 of SEQ ID NO: 540.

20. A method of making a polypeptide comprising:
    a) introducing into a host cell or organism a nucleic acid sequence encoding a polypeptide comprising:
        i) amino acids 1 to 29 of SEQ ID NO: 2259; or
        ii) amino acids −26 to 29 of SEQ ID NO: 2259; and b) providing conditions tat allow for the expression and secretion of said polypeptide by said host cell, organism, or tissue.

21. The method of claim 20, wherein said nucleic acid is operably linked to a promoter.

22. The method of claim 20, wherein said nucleic acid encodes amino acids 1 to 29 of SEQ ID NO: 2259.

23. The method of claim 22, wherein said nucleic acid sequence is operably linked to a promoter.

24. The method of claim 20, wherein said nucleic acid encodes amino acids −26 to 29 of SEQ ED NO: 2259.

25. The method of claim 24, wherein said nucleic acid sequence is operably linked to a promoter.

26. The method of claim 25, wherein the step of isolating the expressed and secreted protein comprises purifying the secreted protein from the supernatant, the culture medium or the cell extract of said host cell, organism, or tissue.

27. The method of claim 20, further comprising the recovery of said expressed and secreted polypeptide.

* * * * *

UNITED STATES PATENT AND TRADEMARK OFFICE
CERTIFICATE OF CORRECTION

| | |
|---|---|
| PATENT NO. | : 7,393,663 B2 |
| APPLICATION NO. | : 10/631441 |
| DATED | : July 1, 2008 |
| INVENTOR(S) | : Jean-Baptiste Dumas Milne Edwards, Aymeric Duclert and Bruno Lacroix |

It is certified that error appears in the above-identified patent and that said Letters Patent is hereby corrected as shown below:

Column 2,
Line 62, "operably lining" should read --operably linking--.

Column 5,
Line 6, "Further, polyeptides" should read --Further, polypeptides--.

Column 6,
Line 5, "5-carboxymethylarninomethyluracil" should read
--5-carboxymethylaminomethyluracil--.

Column 8,
Line 11, "determing" should read --determining--.
Line 25, "flumes" should read --frames--.

Column 10,
Line 11, "next tote" should read --next to the--.

Column 12,
Line 37, "oat least" should read --of at least--.

Column 16,
Line 26, "minimnum" should read --minimum--.

Column 19,
Line 12, "indentical" should read --identical--.

Column 26,
Line 3, "fingal" should read --fungal--.
Line 50, "BlueScrit" should read --BlueScript--.

Column 27,
Line 11, "geneII" should read --geneII--.

Column 29,
Line 46, "fingal" should read --fungal--.

UNITED STATES PATENT AND TRADEMARK OFFICE
CERTIFICATE OF CORRECTION

| | | |
|---|---|---|
| PATENT NO. | : 7,393,663 B2 | |
| APPLICATION NO. | : 10/631441 | |
| DATED | : July 1, 2008 | |
| INVENTOR(S) | : Jean-Baptiste Dumas Milne Edwards, Aymeric Duclert and Bruno Lacroix | |

It is certified that error appears in the above-identified patent and that said Letters Patent is hereby corrected as shown below:

Column 33,
Line 53, "amibiguities" should read --ambiguities--.
Line 60, "amibiguity" should read --ambiguity--.
Line 63, "amibiguity" should read --ambiguity--.

Column 36,
Line 10, "Proc. Nail. Aca. Sctl." should read --Proc. Natl. Acad. Sci.--.

Column 37,
Line 38, "liner" should read --inner--.
Line 48, "using Die Terminator" should read --using a Die Terminator--.
Line 59, "EcoRi" should read --EcoRI--.

Column 38,
Line 15, "primer walling" should read --primer walking--.
Line 30, "polyadenyaltion" should read --polyadenylation--.

Column 45,
Line 16, "intitiation site, an intiating" should read --initiation site, an initiating--.
Line 29, "polpypeptide" should read --polypeptide--.

Column 49,
Line 22, "Herrrann et al." should read --Herrmann et al.--.

Column 51,
Line 37, "allergenic cardiac" should read --allogeneic cardiac--.

Column 55,
Line 28, "tendinitis" should read --tendonitis--.
Lines 59-60, "(endotheliun)" should read --(endothelium)--.

Column 56,
Line 2, "cytokinc" should read --cytokine--.
Line 31, "Wiley-Intersciece" should read --Wiley Interscience--.
Line 42, "activities. inhibins are" should read --activities. Inhibins are--.
Line 47, "the Inhibin α" should read --the inhibin α--.

UNITED STATES PATENT AND TRADEMARK OFFICE
CERTIFICATE OF CORRECTION

| | | |
|---|---|---|
| PATENT NO. | : 7,393,663 B2 | Page 3 of 5 |
| APPLICATION NO. | : 10/631441 | |
| DATED | : July 1, 2008 | |
| INVENTOR(S) | : Jean-Baptiste Dumas Milne Edwards, Aymeric Duclert and Bruno Lacroix | |

It is certified that error appears in the above-identified patent and that said Letters Patent is hereby corrected as shown below:

Column 59,
Line 7, "ischemic-reperfusioninury" should read --ischemia-reperfusion injury--.

Column 61,
Line 60, "81: 39984002" should read --81: 3998-4002--.

Column 74,
Lines 23-24, "by adding antiserum-producing" should read --by adding fluorescein- or enzyme-conjugated antibody against the immunoglobulin class of the antiserum-producing--.

Column 78,
Line 15, "Ranaiah Nagaraja" should read --Ramaiah Nagaraja--.

Column 80,
Line 21, "vector and filsed" should read --vector and fused--.

Column 82,
Line 31, "antiserurn-producing" should read --antiserum-producing--.

Column 87,
Line 28, "5' postion" should read --5' position--.
Line 33, "bding the coding" should read --binding the coding--.

Column 88,
Line 48, "avalilabe from" should read --available from--.

Column 89,
Line 23, "ribozyrne capable" should read --ribozyme capable--.

Column 94,
Line 63, "are as defmed" should read --are as defined--.

Column 95,
Line 23, "of the polypeptides the polypeptides of" should read --of the polypeptides of--.

UNITED STATES PATENT AND TRADEMARK OFFICE
CERTIFICATE OF CORRECTION

| | | |
|---|---|---|
| PATENT NO. | : 7,393,663 B2 | |
| APPLICATION NO. | : 10/631441 | |
| DATED | : July 1, 2008 | |
| INVENTOR(S) | : Jean-Baptiste Dumas Milne Edwards, Aymeric Duclert and Bruno Lacroix | |

It is certified that error appears in the above-identified patent and that said Letters Patent is hereby corrected as shown below:

Column 96,
Lines 45-46, "may be determiined" should read --may be determined--.

Column 106,
Line 6, "detennine" should read --determine--.

Column 224,
Table III, SEQ ID NO. ID621, "MTSGQAPASXQSPQALEDSGPVNISVSITLT LDPLKPFGGYSRNVTHLYSTILGHQIGLSGREAHEEINITFTLPTAWSSDD CALHGHCEQVVFTACMTLTASPGVFP" should read --MTSGQARASXQSPQALEDSGPVNISVSITLTLDPLKPFGGYSRNVTH LYSTILGHQIGLSGREAHEEINITFTLPTAWSSDDCALHGHCEQVVFTA CMTLTASPGVFP--.

Column 254,
Table III, SEQ ID NO. ID951, "MGEASPPAPARRELLVLLLLLSTLVIPSAA" should read --MGEASPPAPARRHLLVLLLLLSTLVIPSAA--.

Column 277,
Table III, SEQ ID NO. ID1201, "MKKTGDGGTLSTERIGGAALLSLLLK RNKMTLMIPLLLLTPITA" should read --MKKTGDGGTLSTERIGGAALLSLLLKRMKMTLMIPLLLLTPITA--.

Column 279,
Table III, SEQ ID NO. ID1225, "MCNPEEAALXGLEEVFSATLAMVNSLV LQPLLPAAPDPSDPWGRECLRLLQQLHKSSQQLWEVTEESLHSLQERLR YPDSTGLESLLLLRGADRVLQA" should read --MCNPEEAALXGLEEVFS ATLAHVNSLVLQPLLPAAPDPSDPWGRECLRLLQQLHKSSQQLWEVTE ESLHSLQERLRYPDSTGLESLLLLRGADRVLQA--.

Column 282,
Table III, SEQ ID NO. ID1256, "MEPITFTARKHLLPNEVSVDFGLQLVGSLPVH SLTTMPMLPWWAEVRRLSRQSTRKEPVTXQXRLCVSPSGLRC" should read --MEPITFTARKHLLPNEVSVDFGLQLVGSLPVHSLTTMPM LPWVVAEVRRLSRQSTRKEPVTXQXRLCVSPSGLRC--.

UNITED STATES PATENT AND TRADEMARK OFFICE
CERTIFICATE OF CORRECTION

PATENT NO. : 7,393,663 B2
APPLICATION NO. : 10/631441
DATED : July 1, 2008
INVENTOR(S) : Jean-Baptiste Dumas Milne Edwards, Aymeric Duclert and Bruno Lacroix It is certified that error appears in the above-identified patent and that said Letters Patent is hereby corrected as shown below:

Column 293,
Table III, SEQ ID NO. ID1375, "MTVELWLRLRGKGLANLHVTRGVXG"
    should read --MTVELWLRLRGKGLAMLHVTRGVXG--.

Column 329,
Line 24, "die steps of" should read --the steps of--.
Line 59, "punier comprising" should read --primer comprising--.

Column 330,
Line 38, "-1 to 29" should read --1 to 29--.

Column 331,
Line 1, "tat allow" should read --that allow--.

Signed and Sealed this

Thirtieth Day of December, 2008

JON W. DUDAS
*Director of the United States Patent and Trademark Office*